United States Patent
Koenig et al.

(10) Patent No.: US 11,389,360 B2
(45) Date of Patent: Jul. 19, 2022

(54) LINKAGE MECHANISMS FOR MOUNTING ROBOTIC ARMS TO A SURGICAL TABLE

(71) Applicant: Verb Surgical Inc., Santa Clara, CA (US)

(72) Inventors: Karen Shakespear Koenig, San Jose, CA (US); Joan Savall, Palo Alto, CA (US); Pablo E. Garcia Kilroy, Menlo Park, CA (US); Bernard Fai Kin Siu, San Jose, CA (US); Thomas D. Egan, Marblehead, MA (US)

(73) Assignees: Verb Surgical Inc., Santa Clara, CA (US); Maquet GmbH, Rastatt (DE)

( * ) Notice: Subject to any disclaimer, the term of this patent is extended or adjusted under 35 U.S.C. 154(b) by 182 days.

(21) Appl. No.: 15/706,112

(22) Filed: Sep. 15, 2017

(65) Prior Publication Data
US 2018/0078440 A1     Mar. 22, 2018

Related U.S. Application Data

(60) Provisional application No. 62/395,807, filed on Sep. 16, 2016.

(51) Int. Cl.
*A61G 13/10*     (2006.01)
*A61G 13/12*     (2006.01)
(Continued)

(52) U.S. Cl.
CPC ............ *A61G 13/101* (2013.01); *A61B 34/30* (2016.02); *A61B 90/50* (2016.02); *A61G 13/105* (2013.01);
(Continued)

(58) Field of Classification Search
CPC ................ A61G 13/101; A61G 13/105; A61G 13/1285; A61G 13/129; A61G 2210/50;
(Continued)

(56) References Cited

U.S. PATENT DOCUMENTS

| 5,855,583 A | * | 1/1999 | Wang | A61B 34/70 606/139 |
| 5,876,325 A | * | 3/1999 | Mizuno | A61B 34/37 600/102 |

(Continued)

FOREIGN PATENT DOCUMENTS

| CN | 102006834 | 4/2011 |
| CN | 104783900 A | 7/2015 |

(Continued)

OTHER PUBLICATIONS

Written Opinion of the International Search Authority dated Nov. 16, 2017 for WO Application No. PCT/US17/051805.

(Continued)

*Primary Examiner* — Peter M. Cuomo
*Assistant Examiner* — Morgan J McClure
(74) *Attorney, Agent, or Firm* — Womble Bond Dickinson (US) LLP

(57) ABSTRACT

In some embodiments, an apparatus can include a surgical table and an adapter coupled thereto. The adapter includes an interface structure, a first link member coupled to a second link member, and a third link member coupled to a fourth link member. The first link member and the third link member are each pivotally coupled to the interface mechanism at a shared first pivot joint. The second link member and the fourth link member are each coupleable to a robotic arm. The first link member and the second link member collectively provide for movement of the first robotic arm in at least one of a lateral, longitudinal or vertical direction relative to the table top. The third link member and the fourth link member collectively provide for movement of the second robotic arm in at least one of a lateral, longitudinal or vertical direction relative to the table top.

24 Claims, 88 Drawing Sheets

(51) Int. Cl.
*A61B 90/50* (2016.01)
*A61B 34/30* (2016.01)
*A61B 90/57* (2016.01)

(52) U.S. Cl.
CPC ....... *A61G 13/129* (2013.01); *A61G 13/1285* (2013.01); *A61B 2034/302* (2016.02); *A61B 2090/571* (2016.02); *A61G 2210/50* (2013.01)

(58) Field of Classification Search
CPC ......... A61B 34/70; A61B 34/57; A61B 34/32; A61B 34/30; A61B 2017/00305; A61B 2017/00477; A61B 2090/571; A61B 90/50; A61B 2034/302
See application file for complete search history.

(56) References Cited

U.S. PATENT DOCUMENTS

| | | | |
|---|---|---|---|
| 6,246,200 B1* | 6/2001 | Blumenkranz | B25J 9/1689 128/DIG. 7 |
| 6,788,018 B1 | 9/2004 | Blumenkranz | |
| 7,027,892 B2* | 4/2006 | Wang | A61B 17/11 414/2 |
| 7,979,157 B2* | 7/2011 | Anvari | A61G 13/10 700/245 |
| 8,738,181 B2* | 5/2014 | Greer | A61B 34/37 700/264 |
| 9,119,653 B2* | 9/2015 | Amat Girbau | A61B 34/37 |
| 9,119,655 B2* | 9/2015 | Bowling | A61B 34/20 |
| 10,022,192 B1* | 7/2018 | Ummalaneni | A61B 6/0457 |
| 10,145,747 B1* | 12/2018 | Lin | A61B 34/32 |
| 10,492,874 B2* | 12/2019 | Hasegawa | B25J 9/1666 |
| 2006/0149418 A1 | 7/2006 | Anvari | |
| 2006/0161136 A1* | 7/2006 | Anderson | A61B 90/57 606/1 |
| 2007/0137371 A1* | 6/2007 | Devengenzo | A61B 34/37 74/490.01 |
| 2007/0293734 A1* | 12/2007 | Coste-Maniere | A61B 34/10 600/300 |
| 2008/0218770 A1* | 9/2008 | Moll | A61B 34/71 356/614 |
| 2009/0041565 A1* | 2/2009 | Rodriguez Y Baena | A61B 34/70 414/431 |
| 2009/0046146 A1 | 2/2009 | Hoyt | |
| 2010/0069920 A1* | 3/2010 | Naylor | A61B 34/71 606/130 |
| 2010/0152749 A1* | 6/2010 | von Pechmann | A61B 90/50 606/130 |
| 2010/0217991 A1 | 8/2010 | Choi | |
| 2010/0286712 A1* | 11/2010 | Won | A61B 34/30 606/130 |
| 2012/0277764 A1* | 11/2012 | Cooper | A61B 90/10 606/130 |
| 2013/0041219 A1* | 2/2013 | Hasegawa | A61B 34/76 600/109 |
| 2013/0269109 A1 | 10/2013 | Yu | |
| 2013/0310639 A1* | 11/2013 | Omori | A61B 1/00149 600/102 |
| 2014/0018960 A1 | 1/2014 | Itkowitz | |
| 2014/0249546 A1* | 9/2014 | Shvartsberg | B25J 18/005 606/130 |
| 2015/0119637 A1* | 4/2015 | Alvarez | A61M 25/0012 600/102 |
| 2015/0150635 A1* | 6/2015 | Kilroy | B25J 15/0286 606/130 |
| 2015/0190201 A1 | 7/2015 | Olson | |
| 2016/0037998 A1 | 2/2016 | Kawashima et al. | |
| 2016/0157942 A1* | 6/2016 | Gombert | A61B 34/30 606/130 |
| 2016/0220324 A1 | 8/2016 | Tesar | |
| 2016/0296294 A1* | 10/2016 | Moll | A61G 13/06 |
| 2016/0331477 A1* | 11/2016 | Yu | A61G 7/0755 |
| 2017/0071685 A1* | 3/2017 | Crawford | A61B 34/20 |
| 2018/0078439 A1* | 3/2018 | Cagle | A61G 13/101 |
| 2018/0279992 A1* | 10/2018 | Frankel | F16M 13/027 |
| 2018/0362060 A1* | 12/2018 | Schaller | B62B 3/10 |
| 2019/0216555 A1* | 7/2019 | DiMaio | B25J 9/126 |
| 2019/0216576 A1* | 7/2019 | Eyre | A61B 90/50 |
| 2019/0223291 A1* | 7/2019 | Seow | H02K 5/20 |
| 2019/0223966 A1* | 7/2019 | Holop | A61B 34/71 |
| 2019/0239889 A1* | 8/2019 | Stokes | A61B 34/30 |

FOREIGN PATENT DOCUMENTS

| | | |
|---|---|---|
| DE | 102013111935 A1 | 4/2015 |
| KR | 101448201 | 10/2014 |
| WO | 2010/068005 A2 | 6/2010 |
| WO | 2018/053281 A1 | 3/2018 |
| WO | 2018067611 | 4/2018 |

OTHER PUBLICATIONS

Outgoing—ISA/210—International Search Report dated Nov. 16, 2017 for WO Application No. PCT/US 17/051805.
International Preliminary Report on Patentability for International Application No. PCT/US2017/051805 dated Mar. 28, 2019, 12 pages.
Examination Report for Australian Application No. 2017326014 dated Apr. 16, 2019, 3 pages.
Office Action for Chinese Application No. 201780003865.5 dated Apr. 14, 2020, 25 pages.
Non-Final Office Action for U.S. Appl. No. 15/706,087 dated Sep. 16, 2019, 28 pages.
Final Office Action for U.S. Appl. No. 15/706,087 dated Mar. 16, 2020, 19 pages.
Office Action for Korean Application No. 10-2019-7006149 dated Aug. 20, 2020, 17 pages.
Extended European Search Report for European Application No. 17851615.9 dated Apr. 20, 2020, 14 pages.
Examiner's Report for Canadian Application No. 3035245 dated Feb. 10, 2020, 4 pages.
Notice of Reasons for Rejection for Japanese Application No. 2019-512243 dated Feb. 25, 2020, 10 pages.
Decision to Grant a Patent of the Japanese Patent Office dated Dec. 25, 2020 for related Japanese Patent Application No. 2019-512243.
Search Report of the Chinese Patent Office dated Apr. 5, 2020 for related Chinese Patent Application No. 201780003865.5.
Non-Final Office Action of the U.S. Patent Office dated Oct. 27, 2020 for related U.S. Appl. No. 15/706,087.
Office Action of the Canadian Patent Office dated Nov. 19, 2020 for related Canadian Patent Application No. 3035245.
Office Action of the Chinese Patent Office dated Jan. 5, 2021 for related Chinese Patent Application No. 201780003865.5.
Examination Report No. 1 of the Australian Patent Office dated Aug. 20, 2021 for related Australian Patent Application No. 2020202497.
Notice of Allowance of the U.S. Patent Office dated Sep. 1, 2021 for related U.S. Appl. No. 15/706,087.
Notice of Allowance of the U.S. Patent Office dated May 4, 2021 for related U.S. Appl. No. 15/706,087.
Decision on Rejection of the Chinese Patent Office dated Jun. 24, 2021 for related Chinese Patent Application No. 201780003865.5.
Notice of Allowance of the U.S. Patent Office dated Nov. 3, 2021 for related U.S. Appl. No. 15/706,087.
Office Action of the BR Patent Office dated Feb. 14, 2022 for related BR Patent Application No. 112019004179-6.
Office Action of the BR Patent Office dated Feb. 22, 2022 for related BR Patent Application No. 112019004179-6.

* cited by examiner

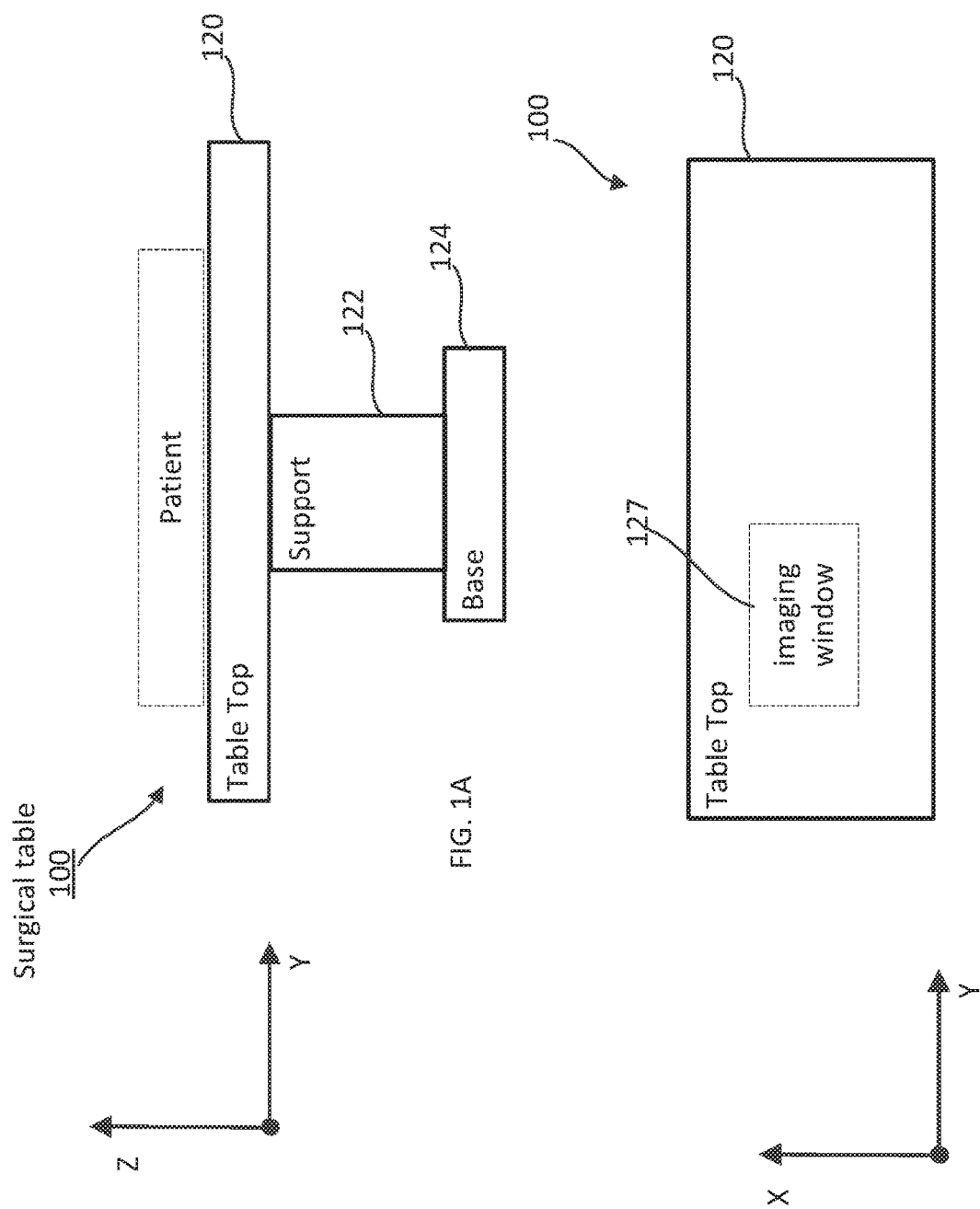

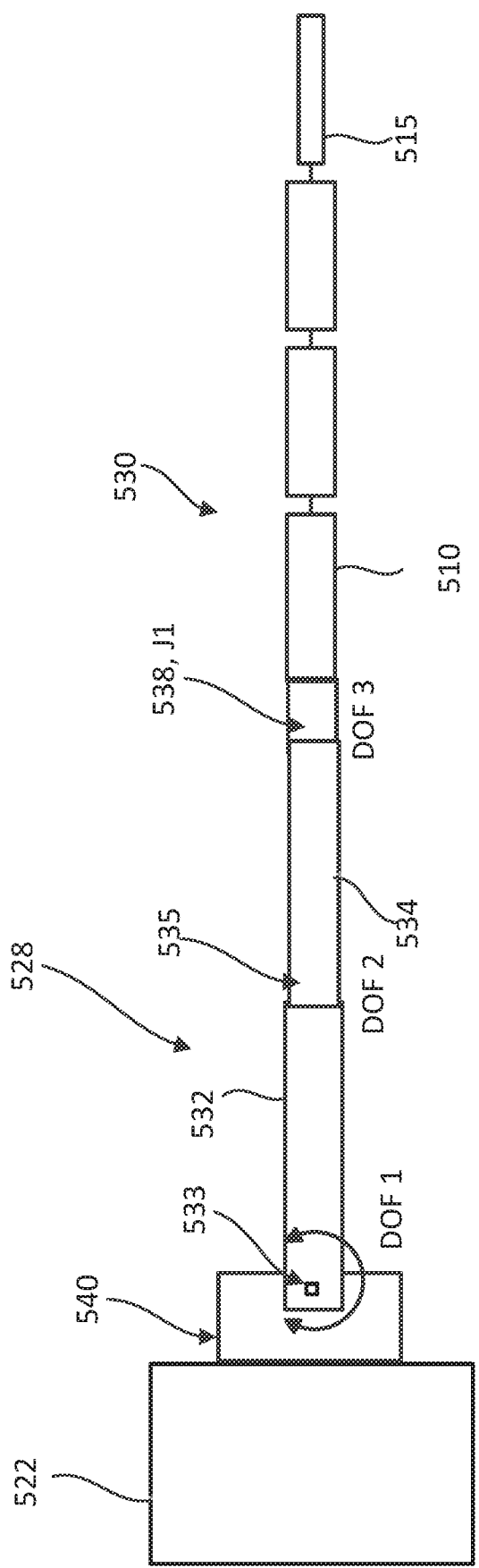
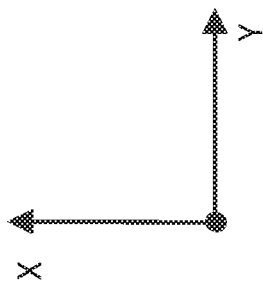
FIG. 3B

| DOF 1 | DOF 2 | DOF 3 |
|---|---|---|
| rotational | rotational | rotational |
| Z-axis rotation | X-Y plane rotation | X-Y plane rotation |

| DOF 1 | DOF 2 | DOF 3 | DOF 4 |
|---|---|---|---|
| rotational | rotational | rotational | rotational |
| Z-axis rotation | Z-axis rotation | X-Y plane rotation | X-Y plane rotation |

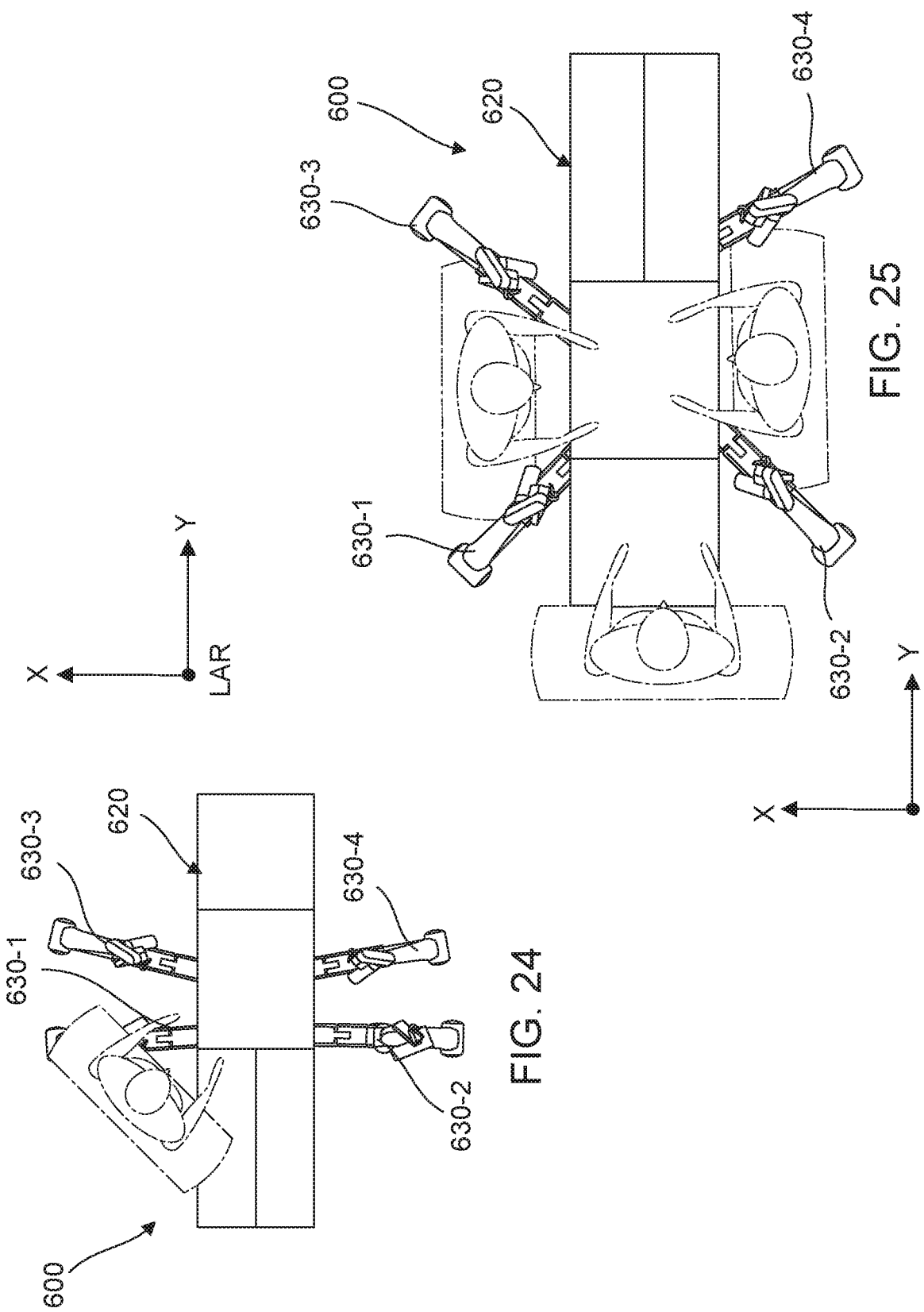

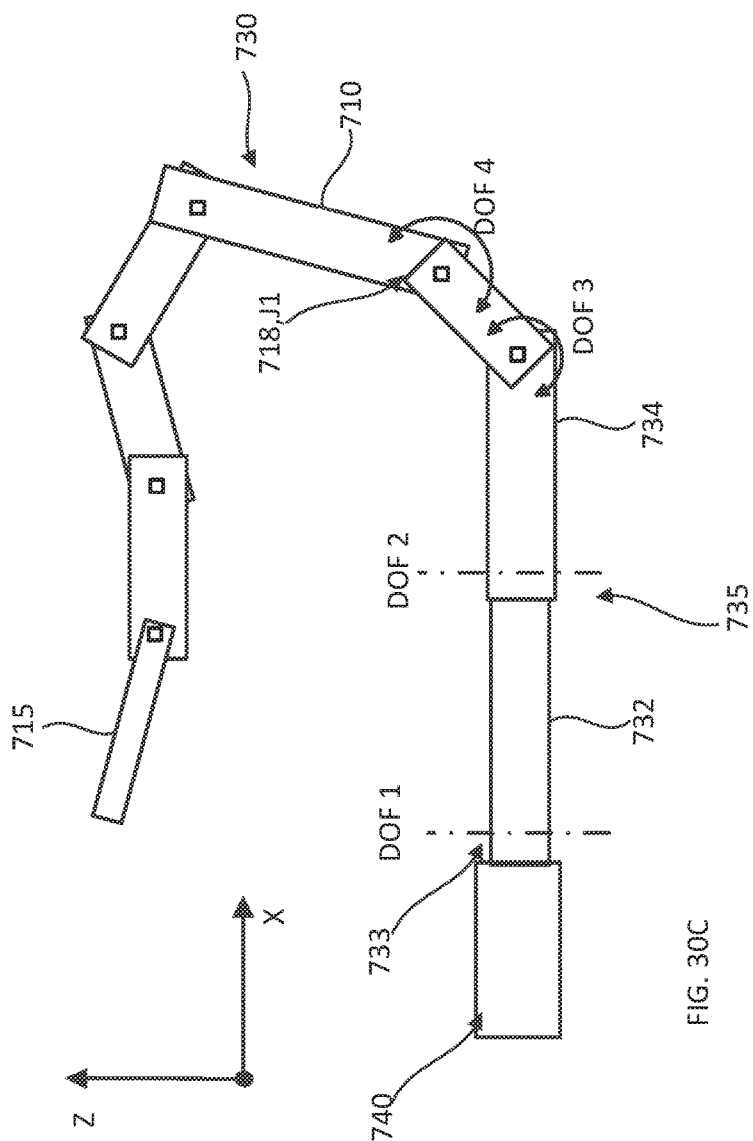

| DOF 1 | DOF 2 | DOF 3 | DOF 4 | DOF 5 |
|---|---|---|---|---|
| rotational | rotational | rotational | rotational | rotational |
| Z-axis rotation | Z-axis rotation | variable | variable | X-Y plane rotation |

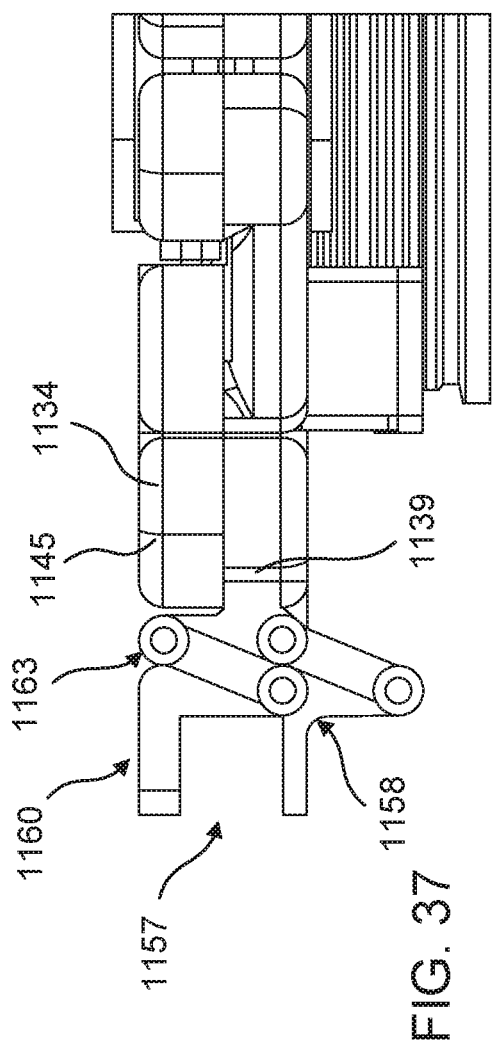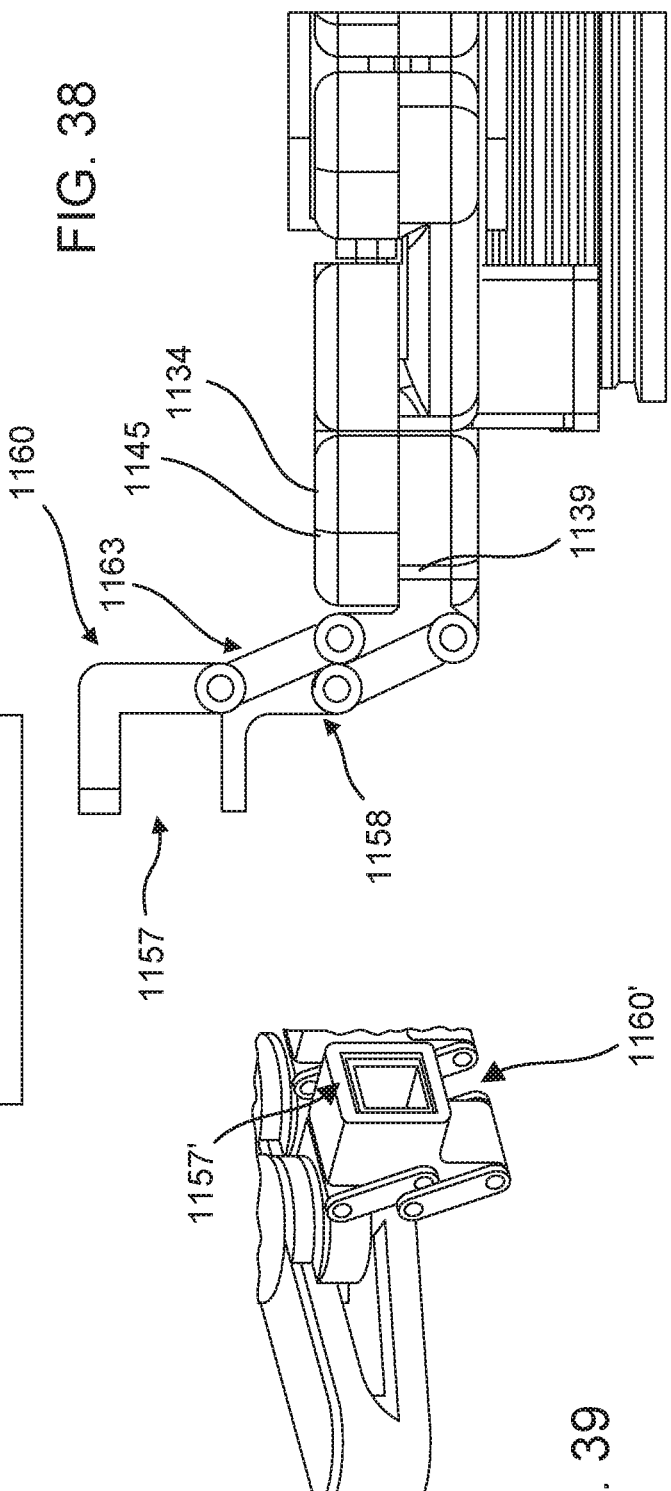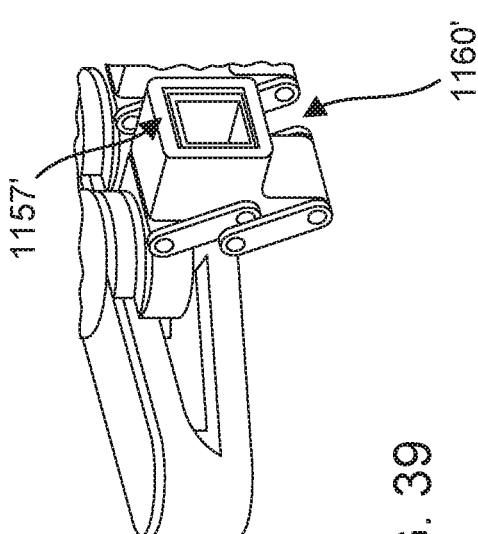

| DOF 1 | DOF 2 | DOF 3 | DOF 4 | DOF 5 |
|---|---|---|---|---|
| rotational | rotational | rotational | rotational | rotational |
| Z-axis rotation | Z-axis rotation | Z-axis rotation | X-Y plane rotation | X-Y plane rotation |

| DOF 1 | DOF 2 | DOF 3 | DOF 4 |
|---|---|---|---|
| rotational | rotational | rotational | rotational |
| Z-axis rotation | Z-axis rotation | Z-axis rotation | X-Y plane rotation |

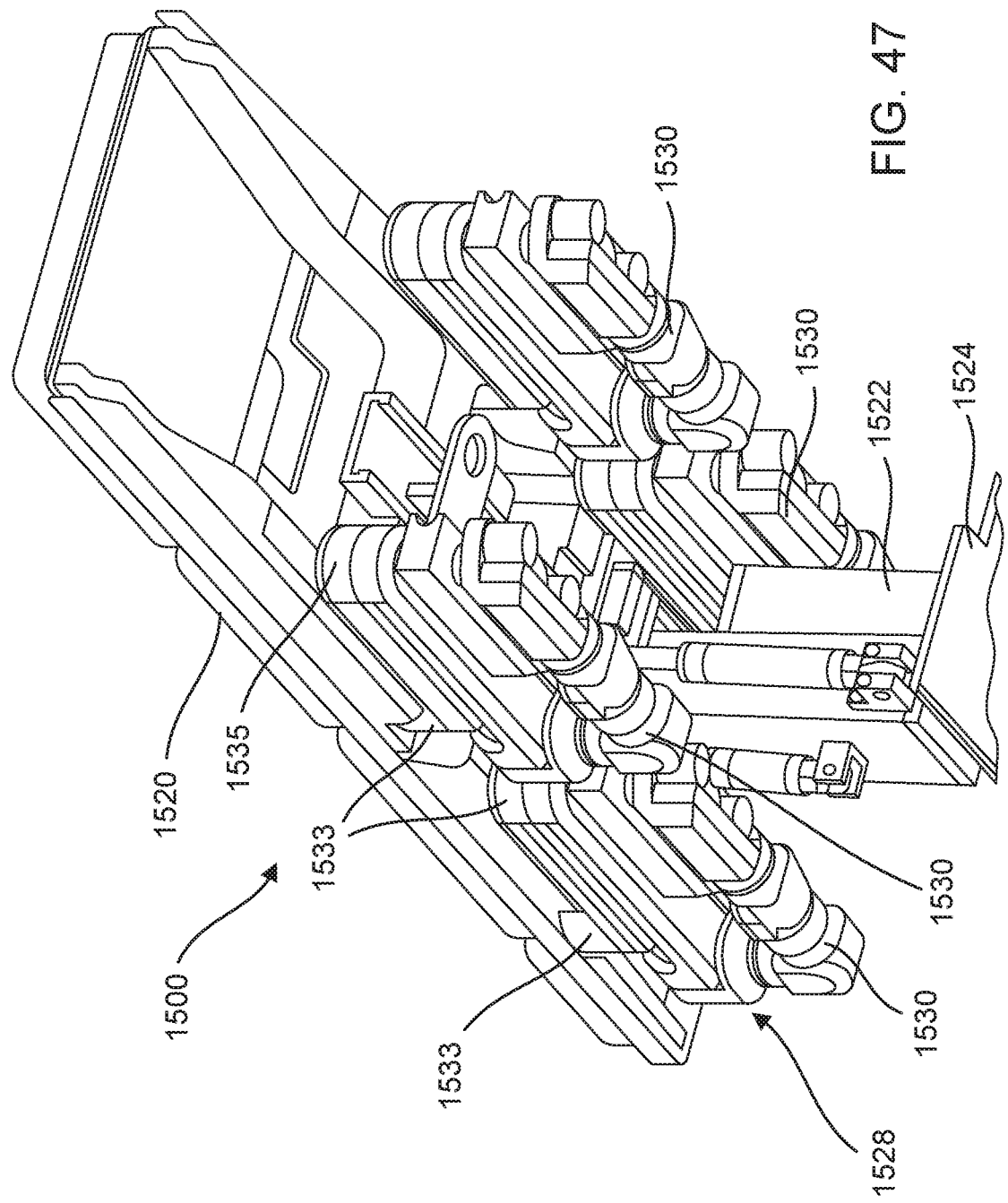

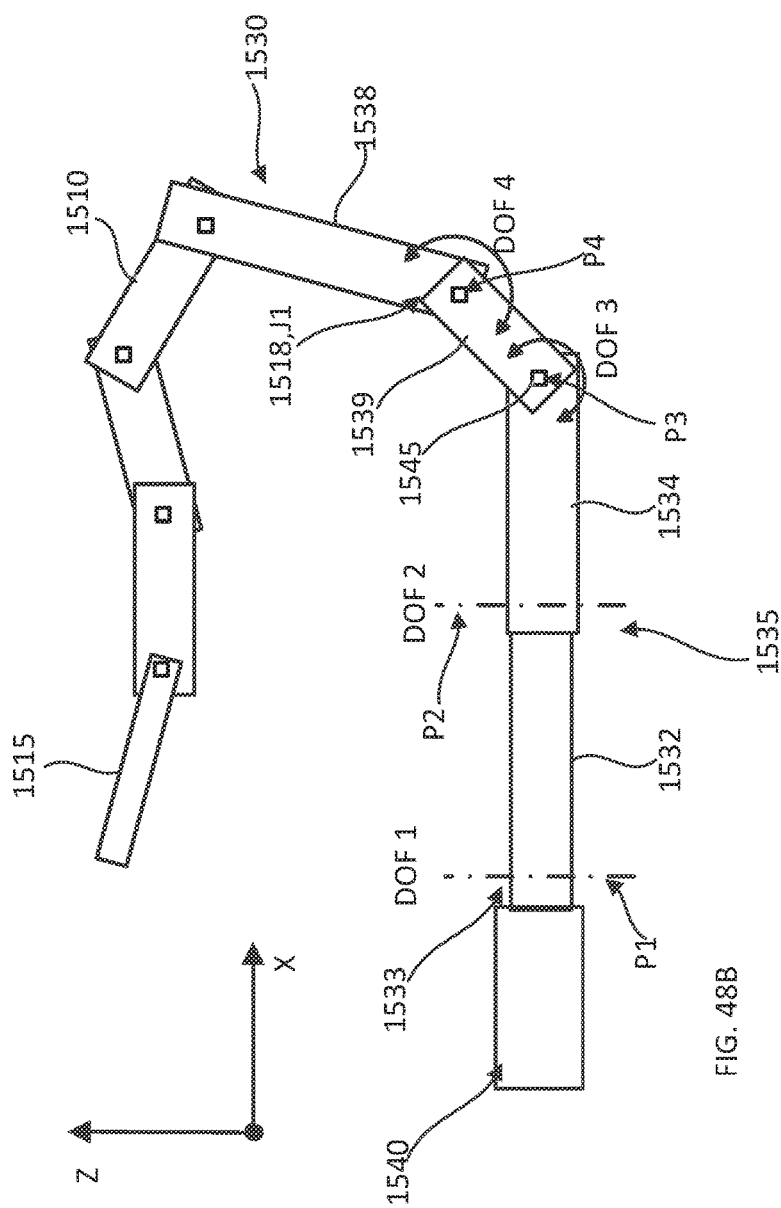

| DOF 1 | DOF 2 | DOF 3 | DOF 4 |
|---|---|---|---|
| rotational | rotational | rotational | rotational |
| Z-axis rotation | X-Y plane rotation | variable | X-Y plane rotation |

| DOF 1 | DOF 2 | DOF 3 | DOF 4 |
|---|---|---|---|
| rotational | rotational | rotational | rotational |
| Z-axis rotation | X-Y plane rotation | X-Y plane rotation | X-Y plane rotation |

| DOF 1 | DOF 2 | DOF 3 | DOF 4 | DOF 5 | DOF 6 |
|---|---|---|---|---|---|
| rotational | rotational | rotational | rotational | rotational | rotational |
| Z-axis rotation | Z-axis rotation | Z-axis rotation | X-Y plane rotation | X-Y plane rotation | X-Y plane rotation |

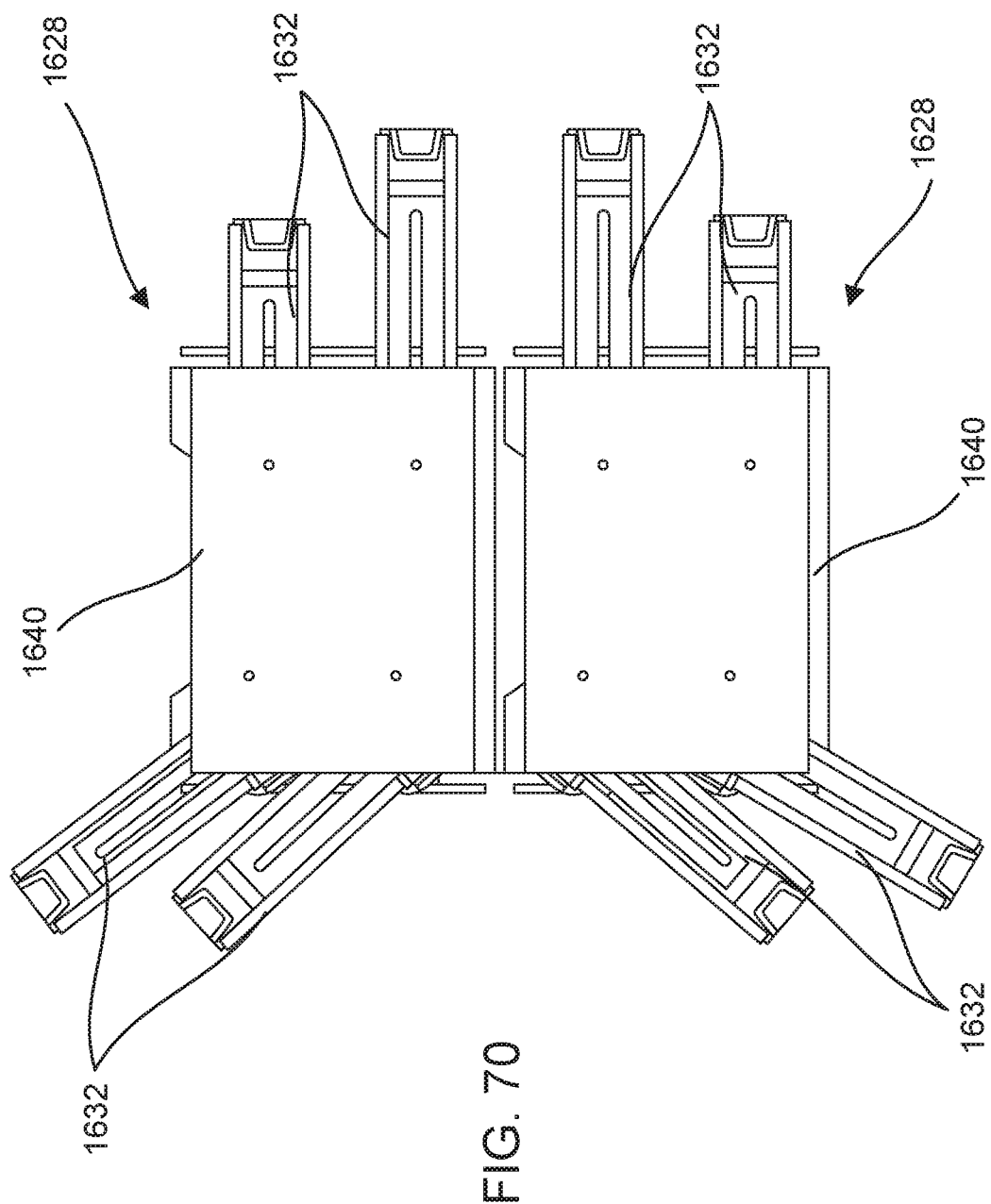

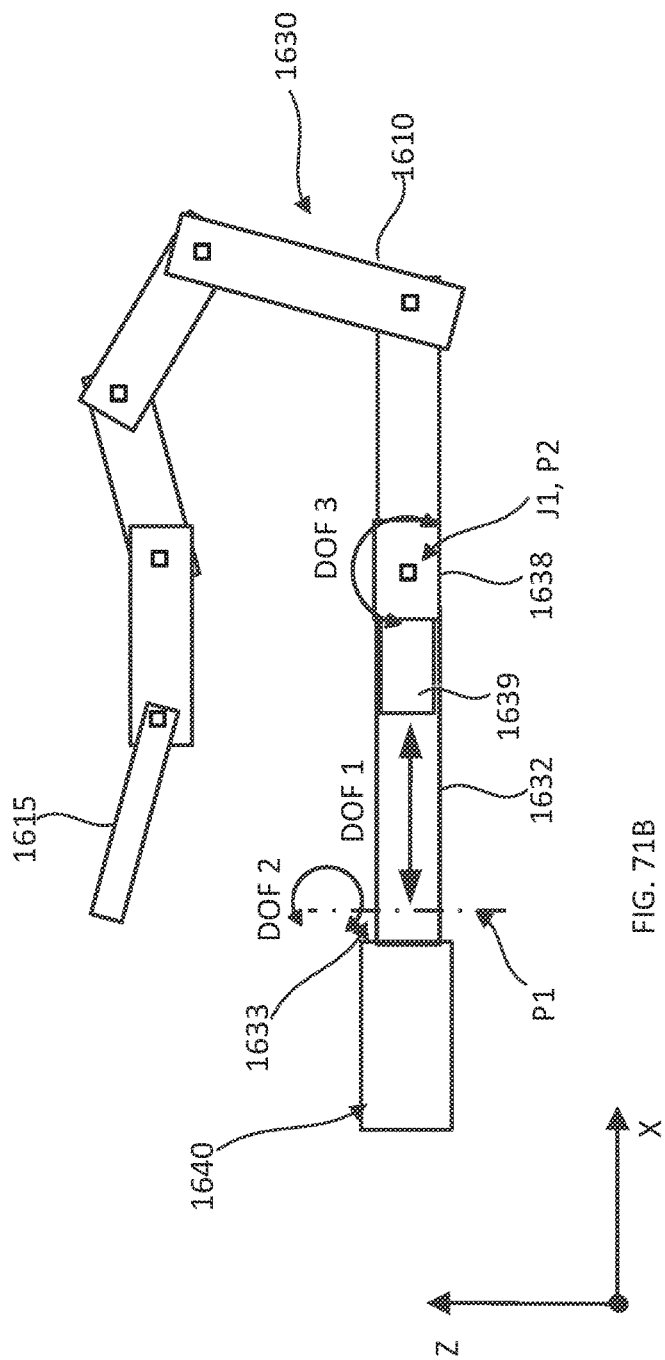

LINKAGE MECHANISMS FOR MOUNTING ROBOTIC ARMS TO A SURGICAL TABLE

CROSS-REFERENCE TO RELATED APPLICATIONS

This application claims priority to and the benefit of U.S. Provisional Patent Application Ser. No. 62/395,807, filed Sep. 16, 2016.

BACKGROUND

Embodiments described herein relate to apparatus and methods for a surgical table with robotic arms that can be moved between multiple different positions relative to the surgical table, such as, for example, a stowed position, an operating position and a parked position.

SUMMARY

Apparatus and methods for providing a robotic surgical system including a surgical table having a table top on which a patient can be disposed are described herein. In some embodiments, an apparatus includes a surgical table and robotic arms coupled, or coupleable to, the surgical table, with each robotic arm supporting a medical instrument or tool, such as a surgical instrument, tool driver, and/or imaging device. The surgical table includes a base, a pedestal and a table top coupled to the pedestal. Each of the robotic arms may be coupled to at least one of the table top, the pedestal or the base. Each robotic arm provides two or more links between the proximal end of the arm (at which the arm is coupled to the table) and the distal end of the arm (at which the arm is coupled to the medical instrument). The links are coupled to each other, and may be coupled to the table and to the medical instrument, by a joint that provides one or more degrees of freedom of relative movement between the links coupled by the joint, and correspondingly one or more degrees of freedom of relative movement between the distal end of the robotic arm and the surgical table. In some embodiments, the robotic arm can be releasably coupled to the surgical table. In some embodiments, the robotic arm can include a releasable coupling at a location between its proximal end and its distal end, such that the proximal portion of the robotic arm can be coupled to the surgical table and the distal portion of the robotic arm can be removed from the proximal portion. In some embodiments, the proximal portion of the robotic arm can be implemented as an adapter, which may be fixedly coupled to the surgical table. The adapter can include a table interface structure, a first link member pivotally coupled to the table interface structure at a first joint, and coupled to a second link member of the adapter at a second joint. The second link member can also be coupled to a robotic arm via a coupling. The first joint is configured to allow the first link member to rotate about a first axis defined in a vertical direction relative to the table top, and the second joint is configured to allow the second link member and a robotic arm coupled thereto to move in a vertical direction relative to the table top. The first link member and the second link member collectively provide for movement of the robotic arm in at least one of a lateral, longitudinal or vertical direction relative to the table top.

BRIEF DESCRIPTION OF THE DRAWINGS

FIGS. 1A and 1B are a schematic side view and a schematic top view, respectively, of a surgical table, according to an embodiment.

FIGS. 3B and 3C are a schematic top view and side view, respectively, of the adapter and a robotic arm of FIG. 3A illustrating the degrees of freedom between the joints of the adapter and robotic arm; and FIG. 3D is a table listing the type of degree of freedom of each of the joints.

FIGS. 20-24 are each a top view of the surgical table and adapter of FIGS. 12A and 12B shown in various different operating positions.

FIG. 25 is a top view of the surgical table and adapter of FIGS. 12A and 12B with four robotic arms coupled thereto and shown in a parked position.

FIGS. 30B and 30C are a schematic top view and side view, respectively, of the adapter and a robotic arm of FIGS. 27-30A illustrating the degrees of freedom between the joints of the adapter and robotic arm; and FIG. 30D is a table listing the type of degree of freedom of each of the joints.

FIG. 37 is a side view of the adapter of FIG. 36, with the portion of the adapter in a folded position.

FIG. 38 is a side view of the adapter of FIG. 35, with a coupling portion of the adapter in an operating or extended position.

FIG. 39 is a perspective view of a portion of the adapter of FIG. 35 with an alternative coupling portion.

FIGS. 46A and 46B are a schematic top view and side view, respectively, of the adapter and a robotic arm of FIGS. 41-45, illustrating the degrees of freedom between the joints of the adapter and robotic arm.

FIG. 47 is a bottom perspective view of an adapter according to another embodiment coupled to a surgical table, and four robotic arms coupled thereto and in a stowed or folded position.

FIGS. 48A and 48B are a schematic top view and side view, respectively, of the adapter and a robotic arm of FIG. 47, illustrating the degrees of freedom between the joints of the adapter and robotic arm; and FIG. 48C is a table listing the type of degree of freedom of each of the joints.

FIG. 70 is top view of two adapters of FIG. 65, each with two link members extended and two link members extended and rotated.

FIGS. 71A and 71B are a schematic top view and side view, respectively, of the adapter and a robotic arm of FIGS. 65-70, illustrating the degrees of freedom between the joints of the adapter and robotic arm; and FIG. 71C is a table listing the type of degree of freedom of each of the joints.

DETAILED DESCRIPTION

Figure 1C:
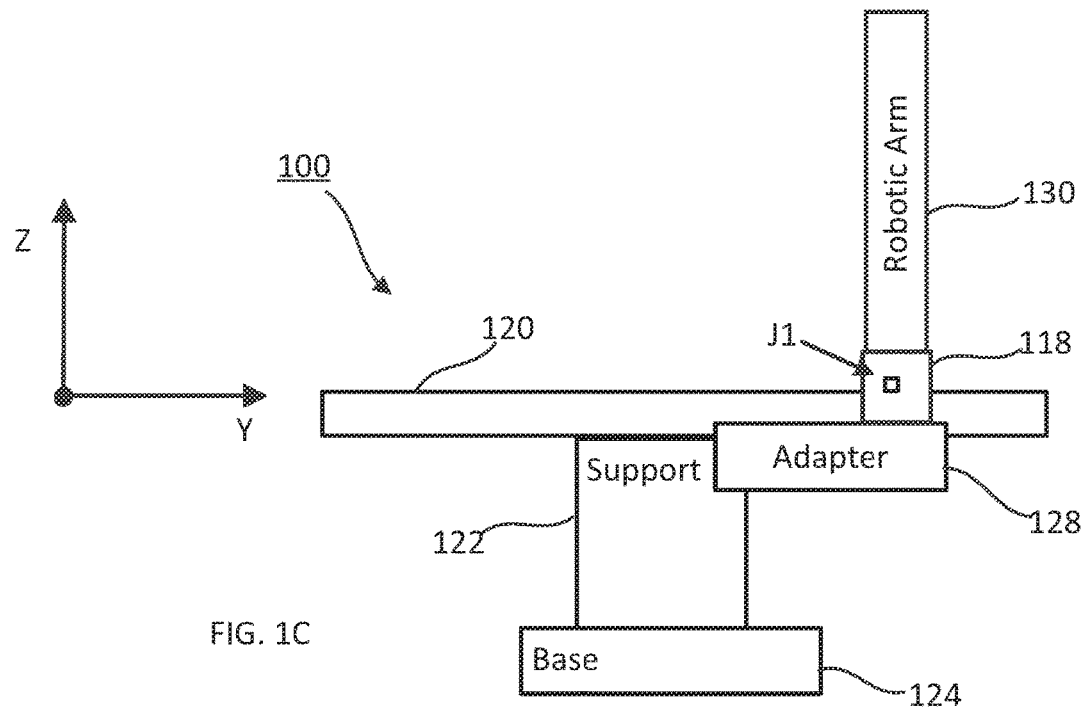
FIGS. 1C and 1D are a schematic side view and a schematic top view, respectively, of the surgical table of FIGS. 1A and 1B with an adapter and robotic arm coupled thereto.

Apparatus and methods for providing a robotic surgical system including a surgical table having a table top on which a patient can be disposed are described herein. In some embodiments, an apparatus includes a surgical table and robotic arms coupled, or coupleable to, the surgical table, with each robotic arm supporting a medical instrument, such as a surgical tool, tool driver, and/or imaging device. The surgical table includes a base, a pedestal and a table top coupled to the pedestal. Each of the robotic arms may be coupled to at least one of the table top, the pedestal or the base. Each robotic arm provides two or more links between the proximal end of the arm (at which the arm is coupled to the table) and the distal end of the arm (at which the arm is coupled to the medical instrument). The links are coupled to each other, and may be coupled to the table and to the medical instrument, by a joint that provides one or more degrees of freedom of relative movement between the links coupled by the joint, and correspondingly one or more degrees of freedom of relative movement between the distal end of the robotic arm and the surgical table. The links and corresponding degrees of freedom allow for movement of the distal end of the robotic arm about and/or along the X, Y, and/or Z axes, to a desired location relative to the table top and/or a patient disposed thereon and/or a desired target portion of the anatomy of a patient disposed thereon.

In some embodiments, an apparatus includes a surgical table having a patient table top, an adapter coupled to the surgical table, and one or more robotic arms coupled to the adapter. In some embodiments, an apparatus can include a surgical table having a patient table top and an adapter/robotic arm assembly coupled to the surgical table. For example, the adapter and robotic arm can be an integral mechanism or component. Each of the adapter and the robotic arms, or an adapter/robotic arm assembly, can include one or more links to allow for movement of the adapter and/or arms about and/or along the X, Y, and/or Z axes, to a desired location relative to the table top and/or a patient disposed thereon and/or a desired target portion of the anatomy of a patient disposed thereon.

In some embodiments, the robotic arm can be releasably coupled to the surgical table. In some embodiments, the robotic arm can include a releasable coupling between its proximal end and its distal end, such that the proximal portion of the robotic arm can be coupled to the surgical table and the distal portion of the robotic arm can be removed from the proximal portion. In some embodiments, the proximal portion of the robotic arm can be implemented as an adapter, which may be fixedly coupled to the surgical table. The adapter can include a table interface structure or mechanism, a first link member pivotally coupled to the interface structure at a first joint, and a second link member coupled to the first link member at a second joint. In some embodiments, the second link member can be pivotally coupled to the first link member at the second joint. The second link member is also configured to be coupled to a robotic arm at a coupling that includes a coupling portion of the second link member and a coupling portion at a proximal or mounting end portion of the robotic arm. The robotic arm also includes a target joint at the mounting end portion of the robotic arm. In some embodiments, the target joint is included with the coupling portion at the mounting end portion of the robotic arm.

The robotic arm can be used to perform a surgical procedure on a patient disposed on the surgical table. The first joint can provide for rotational motion of the first link member about a vertical z-axis relative to a table top of the surgical table and movement of the first link member and the second link member in lateral and longitudinal directions (also referred to herein as x-direction and y-direction) relative to the table top of the surgical table. The second joint can provide a lift mechanism to allow for vertical movement (e.g. movement closer to, above, and/or further above, the table top of the surgical table) of the second link member and the mounting end portion of a robotic arm coupled thereto. The collective movement of the first link member and the second link member allows for the adapter and a robotic arm when coupled thereto to move between a variety of different positions relative to the surgical table. For example, the adapter and robotic arm can be moved to a stowed position, and various operating positions where the target joint of the robotic arm can be placed at a target location to perform a particular surgical procedure on a patient disposed on the table top of the surgical table. The motion of the first link member and the second link member also provides for movement of the adapter and robotic arm to various parked or clearance positions in which the adapter and robotic arm are disposed such that access to the patient is not obstructed. For example, it may be desirable to move the adapter and robotic arm during a surgical procedure to provide clearance for equipment such as an imaging device and/or to provide clearance for additional medical personnel in, for example, an emergency during the procedure. In some cases, an operating position can also be a parked position.

As shown schematically in FIGS. 1A-1B, a surgical table 100 includes a table top 120, a table support 122 and a table base 124. The table top 120 has an upper surface on which a patient can be disposed during a surgical procedure, as shown schematically in FIG. 1A. The table top 120 is disposed on the support 122, which can be, for example, a pedestal, at a suitable height above the floor. The support 122 (also referred to herein as pedestal) may provide for movement of the table top 120 in a desired number of degrees of freedom, such as translation in the Z axis (height above the floor), Y axis (along the longitudinal axis of the table), and/or X axis (along the lateral axis of the table), and/or rotation about the Z, Y, and/or X axis. The table top 120 may also include multiple sections that are movable relative to each other along/about any suitable axes, e.g., separate sections for each of the torso, one or both legs, and/or one or both arms, and a head support section. Movement of the table top 120 and/or its constituent sections may be performed manually, driven by motors, controlled remotely, etc. The support 122 for the table top may be mounted to the base 124, which can be fixed to the floor of the operating room, or can be movable relative to the floor, e.g., by use of wheels on the base. In some embodiments, the height of the support 122 can be adjusted, which together with, for example, the motion (e.g., axial (longitudinal) or lateral motion) of the table top 120, can allow for the table top 120 to be positioned at a desired surgical site at a certain height above the floor (e.g., to allow surgeon access) and a certain distance from the support pedestal 120. This also can allow robotic arms (arms 130 discussed below) coupled to the table 100 to reach a desired treatment target on a patient disposed on the table top 120.

As shown in FIG. 1B, the surgical table 100 may also include a radio-translucent window 127 that is without intrusion by radio-opaque components of the table 100 (e.g., an adapter or robotic arm both discussed below) during a surgical procedure to allow the ability to image (e.g., x-ray or another suitable imaging modality) a patient disposed on the table 100 through the window 127.

Figure 1D:
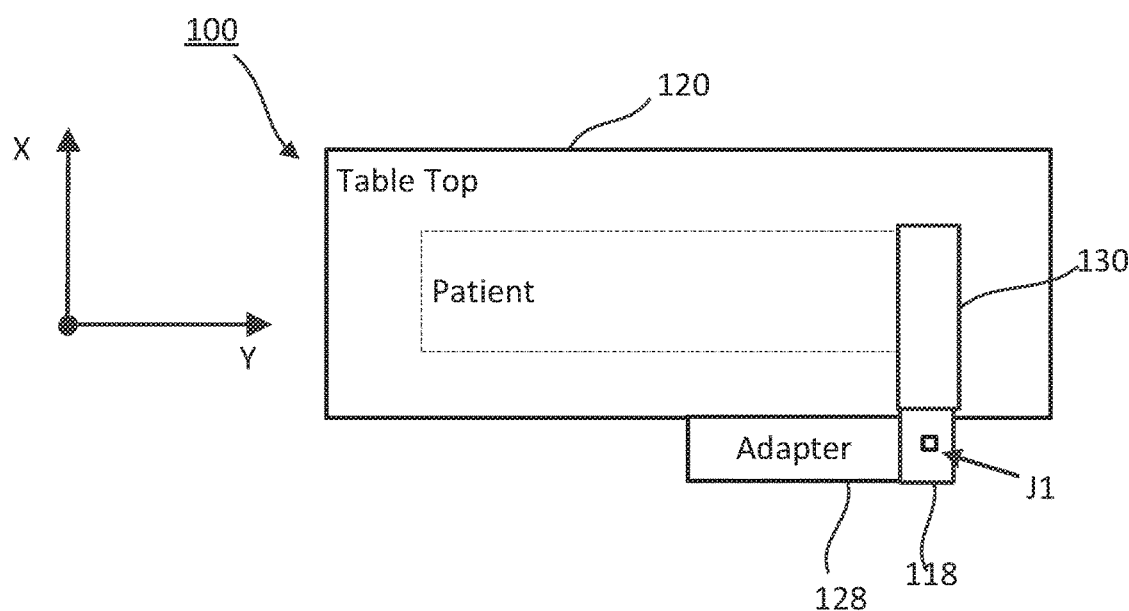

In a robotically assisted surgical procedure, one or more robotic arms 130 can be disposed in a desired operative position relative to a patient disposed on the table top 120 of the surgical table 100 (also referred to herein as "table"), as shown schematically in FIGS. 1C and 1D. The robotic arm(s) can be used to perform a surgical procedure on a patient disposed on the surgical table 100. In particular, the distal end of each robotic arm can be disposed in a desired operative position so that a medical instrument coupled to the distal end of the robotic arm can perform a desired function. The following description is for embodiments in which the connection between the surgical table and the distal end of the robotic arm (and thus the position and orientation of the medical instrument at the distal end of the robotic arm relative to the patient), is implemented with an adapter 128 and robotic arm(s) 130 coupled to the adapter 128. The adapter 128 can be separate from, but engageable with, or coupleable to, the surgical table 100, or can be fixedly attached to the surgical table 100. The adapter 128 can be coupled to, for example, the support 122, the table base 124 and/or the table top 120 of the table 100. However, as discussed in more detail below, the distinction between an adapter and robotic arm can be disregarded, and the connection between the surgical table and the distal end of the robotic arm can be conceptualized and implemented as a series of links and joints that provide the desired degrees of freedom for movement of the medical instrument, i.e. at the distal end of the connection. The connection may include a releasable coupling at any one or more link(s) or joint(s) or any location along the series of links and joints.

As described herein, the position and movement of the adapter 128, its constituent components and the robotic arms 130 are described in reference to X, Y and Z axes which can be defined relative to a top surface of the table top 120 of the surgical table 100 and in particular in reference to a top surface of the torso section of the table top 120. As used herein, the top surface refers to a top surface of the table top structure without any pads. Also as described herein, in some embodiments, the various sections of the table top 120 can move relative to each other (e.g., can be tilted or angled relative to each other) and/or the table top 120 can be moved (e.g., tilted, angled) relative to the support pedestal 122 and/or the base 124 of the surgical table 100. In some embodiments, it is contemplated that the adapter 128 and robotic arms 130 coupled thereto can move with the torso section of the table top 120 such that the frame of reference to the X, Y and Z axes for various embodiments remains relative to the top surface of the table top 120. In some embodiments, the adapter 128 and robotic arms 130 can be coupled to the support pedestal 122 of the table 100 and when the table top 120 is moved relative to the support 122, the positioning of the adapter 128 and arms 130 can be coordinated with the movement of the table top 120.

Figure 1E:
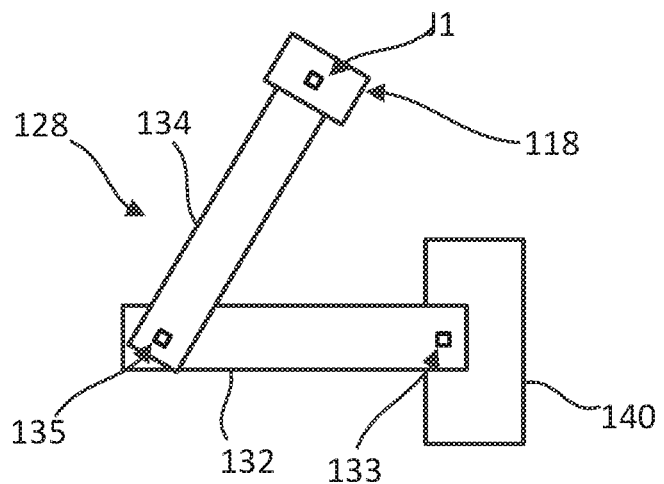
FIG. 1E is a schematic side view of an adapter, according to an embodiment, shown in an extended or use configuration.
Figure 1F:
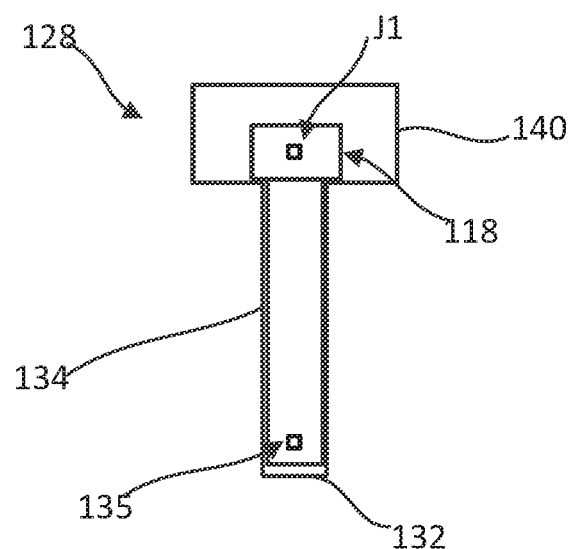
FIG. 1F is a schematic side view of the adapter of FIG. 1E, shown in a collapsed or folded configuration.

As shown schematically in FIGS. 1E and 1F, the adapter 128 can include a table interface structure or mechanism 140, and one or more link members. In this example embodiment, the adapter 128 includes a first link member 132 coupled to the interface structure 140 at a first joint 133, and a second link member 134 coupled to the first link member 132 at a second joint 135. In some embodiments, the first link member 132 can be pivotally coupled to the table interface structure 140 at the first joint 133. In some embodiments, the first link member 132 can be coupled to the table interface structure 140 with a joint that provides for linear motion. In some embodiments, the second link member 134 can be pivotally coupled to the first link member at the second joint. Other types of coupling joints for the first joint 133 and the second joint 135 can alternatively be used. Thus, various different types of coupling joints (e.g., linear, rotational) can be used between the link members of the adapter to achieve a desired movement and reach of the adapter. The second link member 134 is also coupleable to a robotic arm 130 at a coupling 118 (also referred to herein as "coupling joint"). The adapter 128 can be moved between various extended configurations for use during a surgical procedure as shown in FIG. 1E, and various folded or collapsed configurations for storage when not in use, as shown in FIG. 1F.

In some embodiments, the adapter 128 can include more than two link members. For example, an adapter can include a third link member (not shown) coupled to the second link member 134 between the second link member 134 and the coupling 118 to the robotic arm 130. In other embodiments, more than three link members can be included. The number and size of link members can vary such that the adapter 128 can provide a longer or shorter reach to extend the robotic arm 130 (e.g., the target joint J1 discussed below), for example, further above the patient, for larger patients. It can also be used to extend the position of the robotic arm 130 further under the table top 120 when the arm 130 is moved to a position on an opposite side of the table 100 as described in more detail below (e.g., the arm is moved to the opposite side to have three arms on one side of the table).

In accordance with various embodiments, each robotic arm 130 may be permanently, semi-permanently, or releasably coupled to the adapter 128 via the coupling 118. The coupling 118 can include a variety of different coupling mechanisms, including a coupling portion (not shown) on the adapter 128 that can be matingly coupled to a coupling portion (not shown) on the robotic arm. Each robotic arm 130 can be coupled at a fixed location on the table 100 or can be coupled such that the robotic arm 130 can be movable to multiple locations relative to the table top 120 and/or a patient disposed on the table top 120 as described in more detail herein. For example, the robotic arm 130 can be moved relative to the table top 120 and/or a specific target treatment location on the patient. In some embodiments, the axial motion (e.g., in the Y-axis direction) of the table top 120 can assist in allowing the arms 130 (and therefore, the medical instrument or tool coupled to the distal end of the arm) to reach the desired anatomy on the patient or provide clearance for access to the patient as needed. In some embodiments, the combination of vertical movement of the support pedestal 122, axial movement of the table top 120 and movement of, for example, the first link member 132 and the second link member 134, allows for placement of the robotic arms 130 in a position where it can reach the anatomy of the patient at the required height over the floor.

Some structural requirements for the adapter 128 can include providing a rigid support of the robotic arm 130 while maintaining adjustability for pre-operative and intra-operative position changes of the robotic arm 130. In some embodiments, the table adapter 128 can include a means of holding or locking the adapter 128 at a fixed position to withstand, for example, the effects of gravity, inertial effects due to robotic arm motion, and/or to withstand accidental bumps from a user or another part of the robotic system (including other robotic arms or table motion). The table adapter 128 can also include one or more sensors for measuring the spatial position of the adapter 128 and/or angles and displacements of various joints and coupling points of the adapter 128.

In some embodiments, the table adapter 128 can have a bending stiffness, for example, greater than 180 kN/m, with a range, for example, of 18 kN/m to 1800 kN/m. In some embodiments, the table adapter 128 can have a torsional stiffness greater than 800 N-m/deg, with a range of 80 N-m/deg to 8000 N-m/deg. The table adapter 128 can also include actuators to move the joints, such as motors, gearboxes, harmonic drives, pneumatic or hydraulic pistons and linkages. For example, the table adapter 128 can include force or torque sensors at the joints to detect loads applied, for example, by the user, by inertia, gravity, or accidental collision of the arms.

Structural elements of the table adapter 128 may be formed with various materials such as, for example, steel, stainless steel, aluminum, titanium, carbon fiber, or other strong and rigid materials that are resistant to chemicals. Structural elements of the table adapter 128 may also include materials to provide damping, such as, for example, rubber or viscoelastic coatings of the links. Structural stiffness of the adapter 128 can be important to minimize errors in controlling the position of the robotic arm(s), and also to reduce amplitude of unwanted vibrations.

Figure 1G:
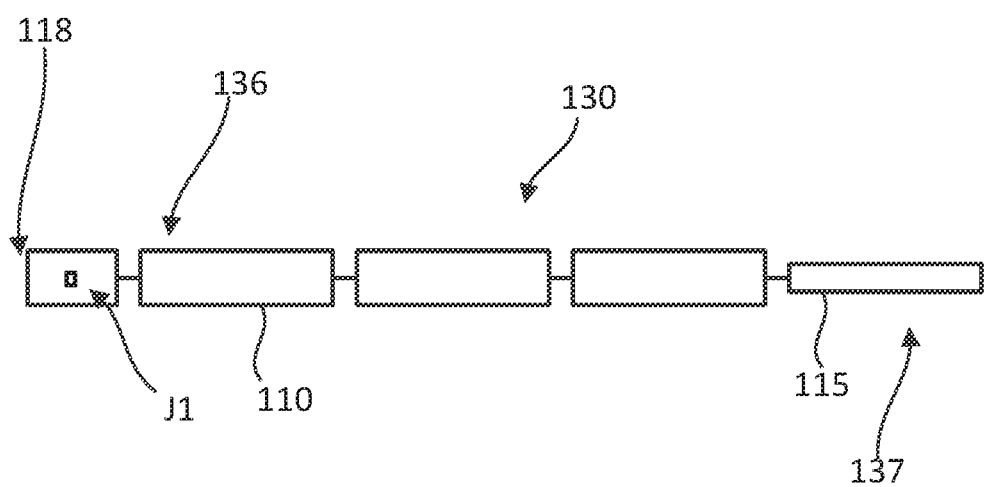
FIG. 1G is a schematic side view of a robotic arm, according to an embodiment, shown in an extended or use configuration.
Figure 1H:
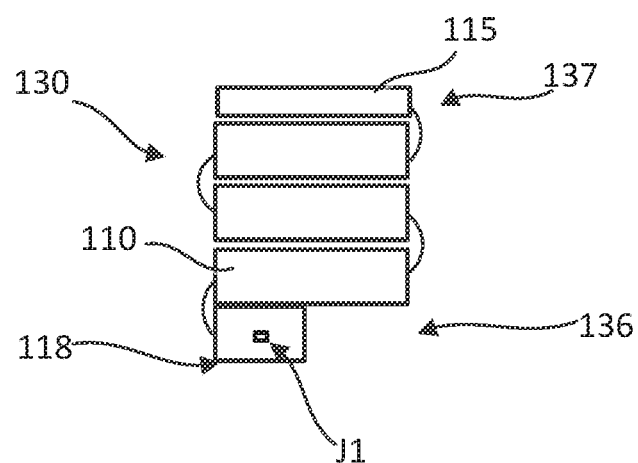
FIG. 1H is a schematic side view of the robotic arm of FIG. 1G, shown in a collapsed or folded configuration.

As shown schematically in FIGS. 1G and 1H, each robotic arm 130 can include a distal end portion 137 and a proximal end portion 136. The distal end portion 137 (also referred to herein as "operating end") can include or have coupled thereto a medical instrument or tool 115. The proximal end portion 136 (also referred to herein as the "mounting end portion" or "mounting end") can include the coupling portion to allow the robotic arm 130 to be coupled to the adapter 128 of the table 100. The robotic arm 130 can include two or more link members or segments 110 coupled together at joints that can provide for translation along and/or rotation about one or more of the X, Y and/or Z axes (shown, for example, in FIGS. 1A-1D). The coupling portion of the robotic arm 130 to couple the robotic arm 130 to the coupling portion of the adapter 128 at the coupling 118 can be disposed at the distal or mounting end 136 of the arm 130 and may be coupled to a segment 110 or incorporated within a segment 110. The robotic arm 130 also includes a target joint J1 disposed at or near the mounting end 136 of the robotic arm 130 that can be included within the coupling portion of the coupling 118 or disposed on a link or segment 110 of the robotic arm 130 coupled to the coupling portion. The target joint J1 can provide a pivot joint to allow a distal segment of the robotic arm 130 to pivot relative to the adapter 128. The robotic arm 130 can be moved between various extended configurations for use during a surgical procedure, as shown in FIG. 1G, and various folded or collapsed configurations for storage when not in use, as shown in FIG. 1H. As described in more detail below, the first joint 133 and the second joint 135 of the adapter 128 can provide for movement of the robotic arm 130 along and/or about the X, Y, and/or Z axes.

More specifically, in some embodiments, the first joint 133 can provide for rotational motion of the first link member 132 relative to the interface structure 140 about a vertical z-axis (shown in FIGS. 1C and 1D) relative to the table top 120, and thus for movement of the first link member 132 and second link member 134 in lateral and longitudinal directions (also referred to herein as x-direction and y-direction) relative to the table top 120 of the surgical table 100. The second joint 135 can provide a lift mechanism to allow for vertical movement of the second link member 134 and therefore, movement of the coupling 118 between the second link member 134 and the robotic arm 130 coupled thereto. The second joint 135 can be, for example, a pivotal coupling or other type of coupling that provides for vertical movement of the second joint and therefore a robotic arm coupled thereto. Such vertical movement, whether produced by rotational movement of the second link member 134 relative to the first link member 132, can produce movement of the coupling 118 closer to and/or further above, the table top 120 of the surgical table 100. In some embodiments, in which the lift mechanism includes a pivotal or rotary joint, the joint can provide for vertical motion as well as reach capabilities of the adapter 128. For example, the links coupled at the pivotal joint can be extended to a substantially linear position relative to each other to extend a length of the adapter 128 (i.e., the link members). This allows for additional reach capability to extend the adapter 128 and robotic arm 130 to a desired location relative to a patient disposed on the table top 120, including reaching to the opposite side of the table top 120. In addition, if the links are disposed about the pivotal joint at a substantial angle, up to 90 degrees, the height (Z-axis) of the arm can be maximized.

The collective motion of the first link member 132 and the second link member 134 of the adapter 128 can provide for movement of the coupling 118, and therefore, movement of a robotic arm 130 coupled thereto along and/or about the X, Y, and/or Z axes. For example, the target joint J1 of the robotic arm 130 can be moved to various target treatment locations relative to the table 100 to perform a variety of different surgical procedures on a patient disposed thereon. The collective motion of the first link member 132 and the second link member 134 also allows the adapter 128 and robotic arm 130 to move between a variety of different positions relative to the surgical table 100 including stowed positions, operating positions and parked or clearance positions.

Figure 2A:
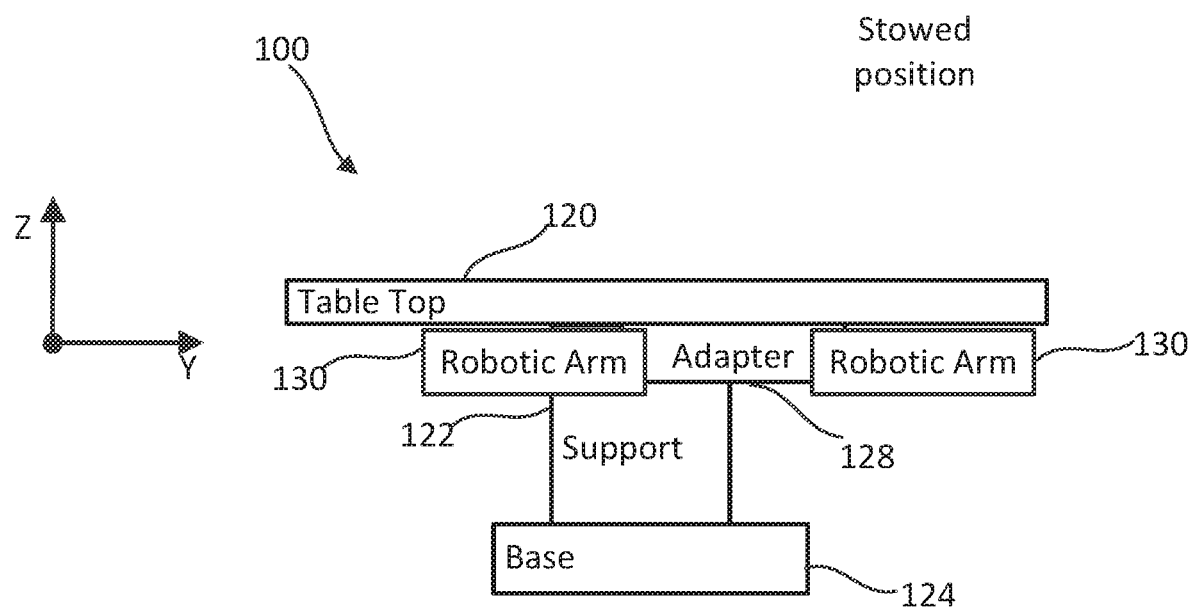
FIG. 2A is a schematic illustration of the surgical table, adapter and three robotic arms of FIGS. 1A-1H, shown in a stowed position.
Figure 2B:
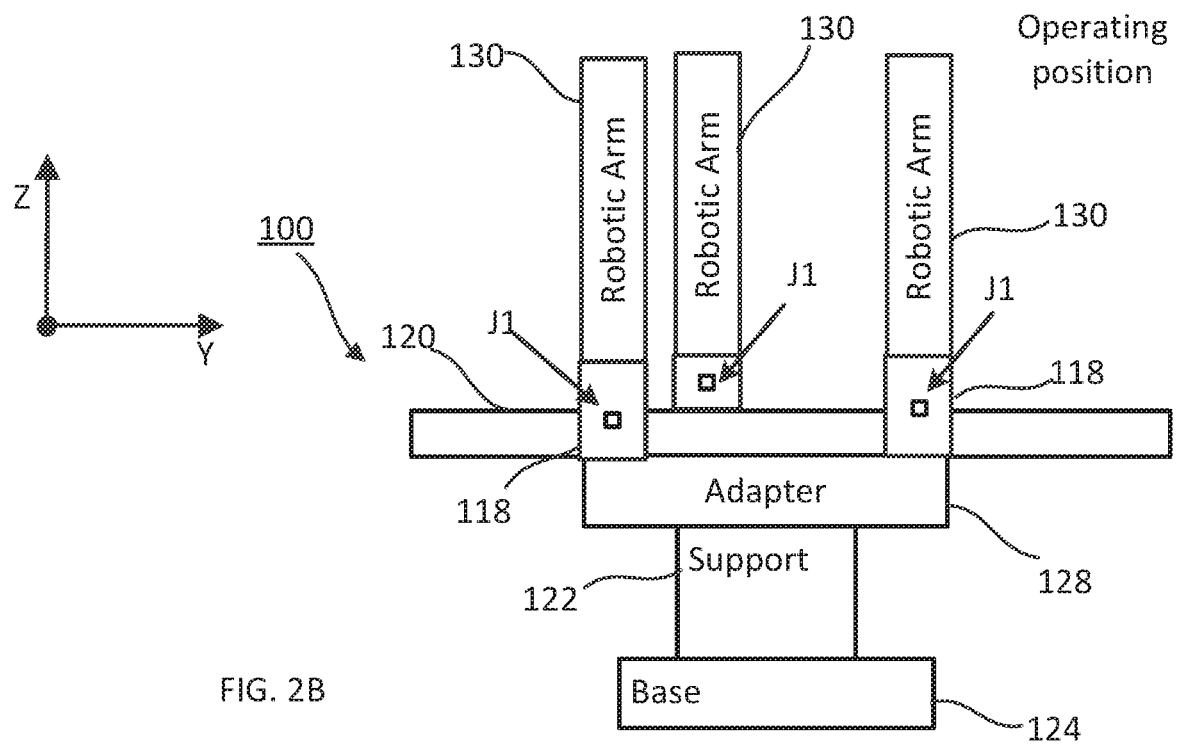
FIG. 2B is a schematic illustration of the surgical table, adapter and three arms of FIG. 2A shown in an operating position with the robotic arms in a ready configuration.
Figure 2C:
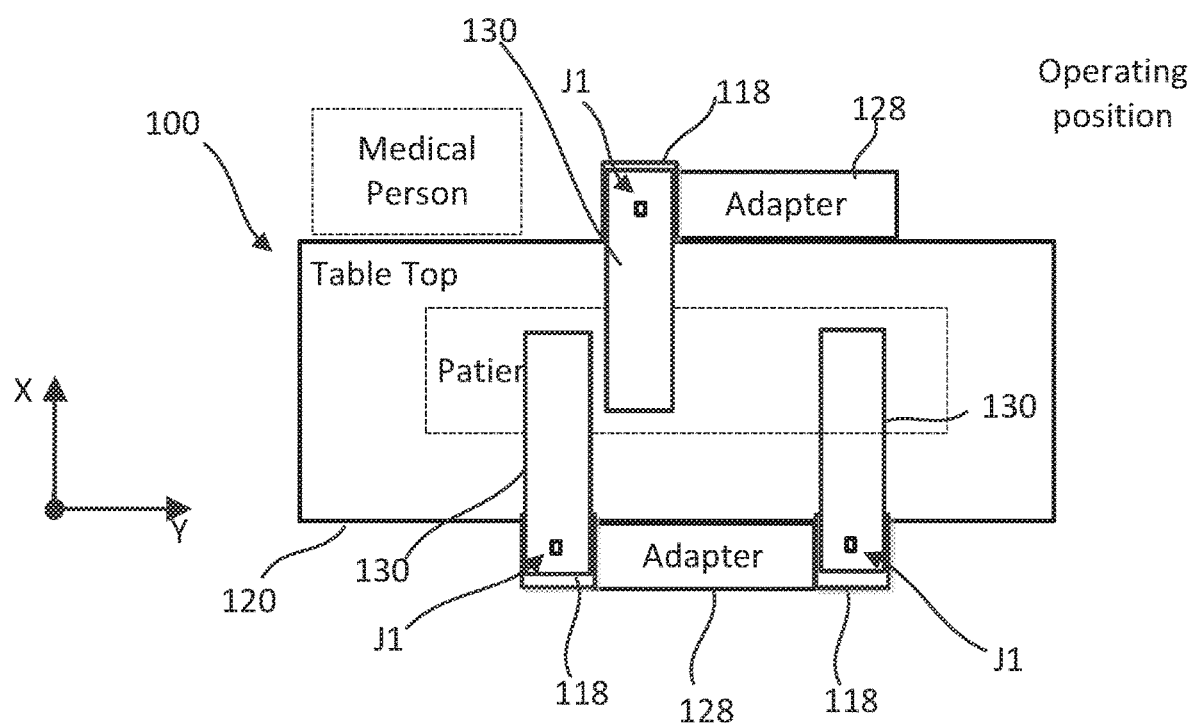
FIG. 2C is a schematic illustration of the surgical table, adapter and three arms of FIG. 2A shown in an operating position with the robotic arms in a treatment configuration.
Figure 2D:
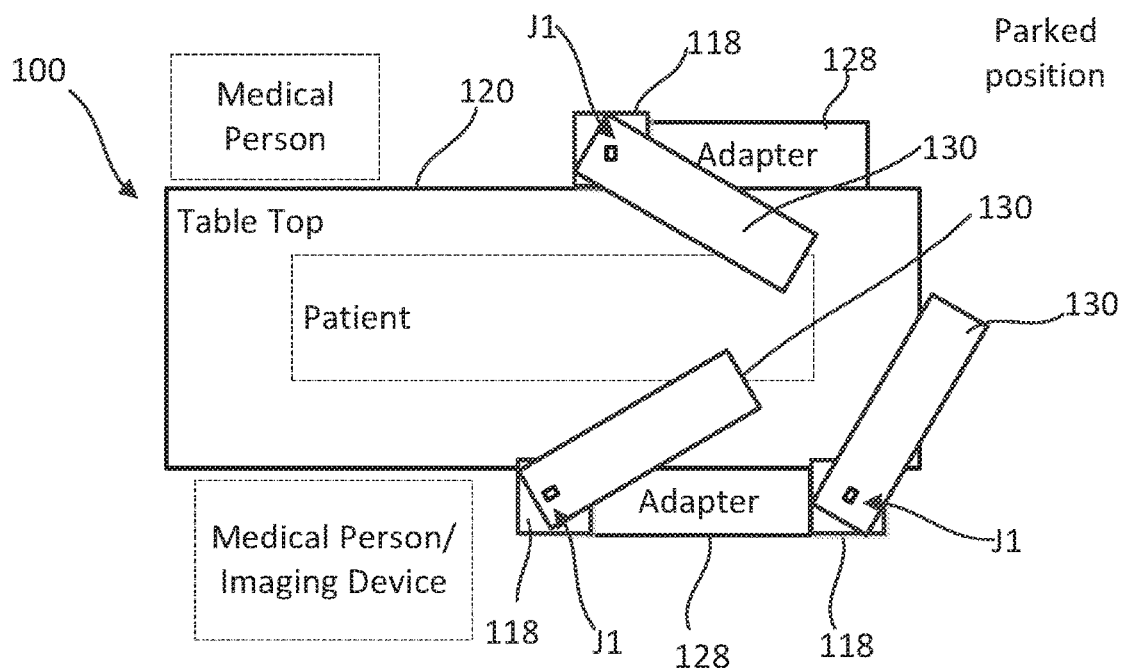
FIG. 2D is a schematic illustration of the surgical table, adapter and three arms of FIG. 2A, shown in a parked position.

For example, adapter 128 and robotic arm 130 can be moved to a stowed position to, for example, provide clearance and access to the table top as shown in FIG. 2A, and various operating positions as shown in FIGS. 2B and 2C, in which the target joint J1 is disposed at a target location to perform a particular surgical procedure. In some embodiments, it may be desirable to dispose the target joint J1 above the table top 120 and above a sterile plane for the surgical procedure. The sterile plane can be defined, for example, by the table top 120. For example, the sterile plane can be defined at a bottom surface of the table top 120 or at a top surface of the table top 120 (e.g., a top surface of the torso section of the table top 120). The adapter 128 can provide for movement and positioning of the robotic arms 130 to operating positions, while also leaving space for medical personnel such as a surgical assistant to stand near the patient on the table top 120 during a surgical procedure, such as for example, near the patient's torso or head as shown in FIGS. 2C and 2D. The location of the robotic arms 130 and medical personnel will depend on the particular surgical procedure to be performed.

To secure the table adapter 128 at various locations used during pre-operative setup and/or during surgery, the various joints and/or coupling locations may utilize braking or locking mechanisms. For example, braking mechanisms may provide the ability to hold position at any point in the range of motion of the joint. Braking mechanisms may include, for example, disc-caliper-style, drum-roller-style, or other friction-based mechanisms. Locking mechanisms may provide the ability to hold position at any number of discrete positions, but may not allow for continuous adjustment. Locking mechanisms can include, for example, disengaging-toothed, disengaging-pinned, or ball-detent, or other discrete position style locking mechanisms. In some embodiments, braking or locking mechanisms can prevent motion in an unpowered state and be biased towards a stopped or locked position via a spring or other mechanism. In some embodiments, in a powered state, braking or locking mechanisms may optionally release or engage depending on the desired state of the system.

The motion of the first link member 132 and the motion of the second link member 134 also provides for movement of the adapter 128 and robotic arm 130 to various parked or clearance positions in which the adapter 128 and robotic arm 130 are disposed such that access to the patient is not obstructed, as shown in FIG. 2D. For example, it may be desirable to move the robotic arm 130 during a surgical procedure to provide clearance for equipment such as an imaging device and/or to provide clearance for additional medical personnel in, for example, an emergency during the procedure. The robotic arm 130 can then be moved back to the operating position to continue the surgical procedure.

As described above for FIGS. 2A-2D, during the course of a surgical procedure it may be desirable to move the robotic arms 130 relative to the table top 120 and patient, i.e. move the robotic arm 130 along and/or about the X, Y, and/or Z axes, between two or more positions. For example, the robotic arms 130 can be moved from a stowed position to various operating positions and various parked positions relative to the table top 120 as described above. In the stowed positions, as shown, for example, in FIG. 2A, the robotic arms 130 can be disposed to allow for clearance to, for example, move a patient to the table top 120 from, for example, a gurney. In some instances, it may only be necessary to provide clearance on one side of the table top 120 (e.g., along the torso portion of the table top). Thus, one or more of the robotic arms 130 on one side of the table top 120 can be moved to an operating position, leaving one side clear for moving the patient to the table top 120. In other cases, it may be desirable to provide clearance on both sides of the table top 120. For example, in some cases, medical personnel may need to use straps to pull the patient from a gurney onto the table top 120. In such a case, both sides of the table top 120 should be clear of obstructions. In addition, it may be desirable to provide clearance at the head rest section of the table top 120, to provide clearance for anesthesia to be administered to the patient (e.g., clearance for anesthesiologists, equipment, and/or nurse, etc.). For example, a clearance region can be defined at an angle of 35° from a bottom of the head rest outwardly and away from the torso portion of the table top on both the left and right side of the table top.

With the patient disposed on the table top 120, the adapter 128 and arms 130 can be moved from the stowed position to an operating position where the target joint J1 is disposed at a target treatment location relative to the table top 120. For example, as shown in FIG. 2B, the adapter 128 and arms 130 are disposed in an operating position with the target joint J1 at a target location and the arms 130 are in a ready configuration relative to the table top 120. As shown in FIG. 2C, the adapter 128 and robotic arms 130 are in the operating position and the robotic arms 130 are also in a treatment configuration with a distal end 137 of the arms 130 (e.g., with the tool 115 coupled thereto) disposed within a treatment region. During the surgical procedure, it may also be desirable to provide for access to the patient by at least one medical staff near or at the side of the patient as shown in FIG. 2B. In some instances, as shown in FIG. 2D, it may be desirable to move the arms 130 and adapter 128 from an operating position (e.g., as in FIGS. 2B and 2C) to a parked position. In the parked position, the adapter 128 and robotic arms 130 do not obstruct access to the patient disposed on the table top 120. This allows clearance to position other devices and/or medical personnel and/or to accommodate various sized patients. For example, it may be desirable to provide access for an imaging device and/or to provide access to medical staff in the operating room, for example, during a medical emergency. In one example, to facilitate surgery on obese patients, e.g., for bariatric surgical procedures, the robotic arm(s) 130 can be moved relative to the table 100 to a position spaced laterally further away from the longitudinal axis (y-axis) of the surgical table 100, thus accommodating a wider patient.

The various parked or clearance positions of the robotic arm(s) 130 may be enabled by moving the robotic arm(s) 130 about and/or along the X, Y, and/or Z axes, to a desired clearance location relative to the table top 120, with the robotic arm(s) 130 remaining attached to, and/or in some cases being separated from the surgical table 100. Thus, the arms 130 can be moved laterally away from the surgical table 100, longitudinally along the table top 120 and/or raised vertically relative to the table top 120, to provide access, for example, for an imaging device and/or medical staff. The robotic arms 130 can be moved in a variety of different manners depending on the particular configuration of the adapter 128 and/or the coupling 118 between the robotic arm 130 and the adapter 128.

As described above, the table 100 may include or have coupled thereto multiple robotic arms 130 via the adapter 128. The coupling 118 and adapter 128 provide the ability to move the robotic arms 130 to various positions relative to the table top 120 and to move the location of target joint J1 to various desired target treatment locations relative to the table top 120 depending on the particular surgical procedure to be performed. The adapter 128 can also provide for movement of the robotic arms 130 such that the window 127 is free of obstructions to allow for imaging of the patient through the window 127. In some embodiments, the adapter 128 and/or the robotic arm(s) 130 can be moved manually by a user of the surgical table between the various positions. In some embodiments the adapter 128 and/or the robotic arm(s) 130 can be coupled to a system to allow for automated controls. For example the adapter and/or robotic arms can be coupled to a drive motor(s) that can be controlled and operated by a user (e.g., medical professional).

As described above, the links (of the adapter 128 and/or the robotic arm 130) are coupled to each other, and may be coupled to the table 100 and to the medical instrument 115, by a joint that provides one or more degrees of freedom of relative movement between the links coupled by the joint, and correspondingly one or more degrees of freedom of relative movement between the distal end of the robotic arm 130 and the surgical table 100. The links and corresponding degrees of freedom allow for movement of the distal end of the robotic arm (and medical instrument 115) about and/or along the X, Y, and/or Z axes, to a desired location relative to the table top and/or a patient disposed thereon and/or a desired target portion of the anatomy of a patient disposed thereon.

Figure 2E:
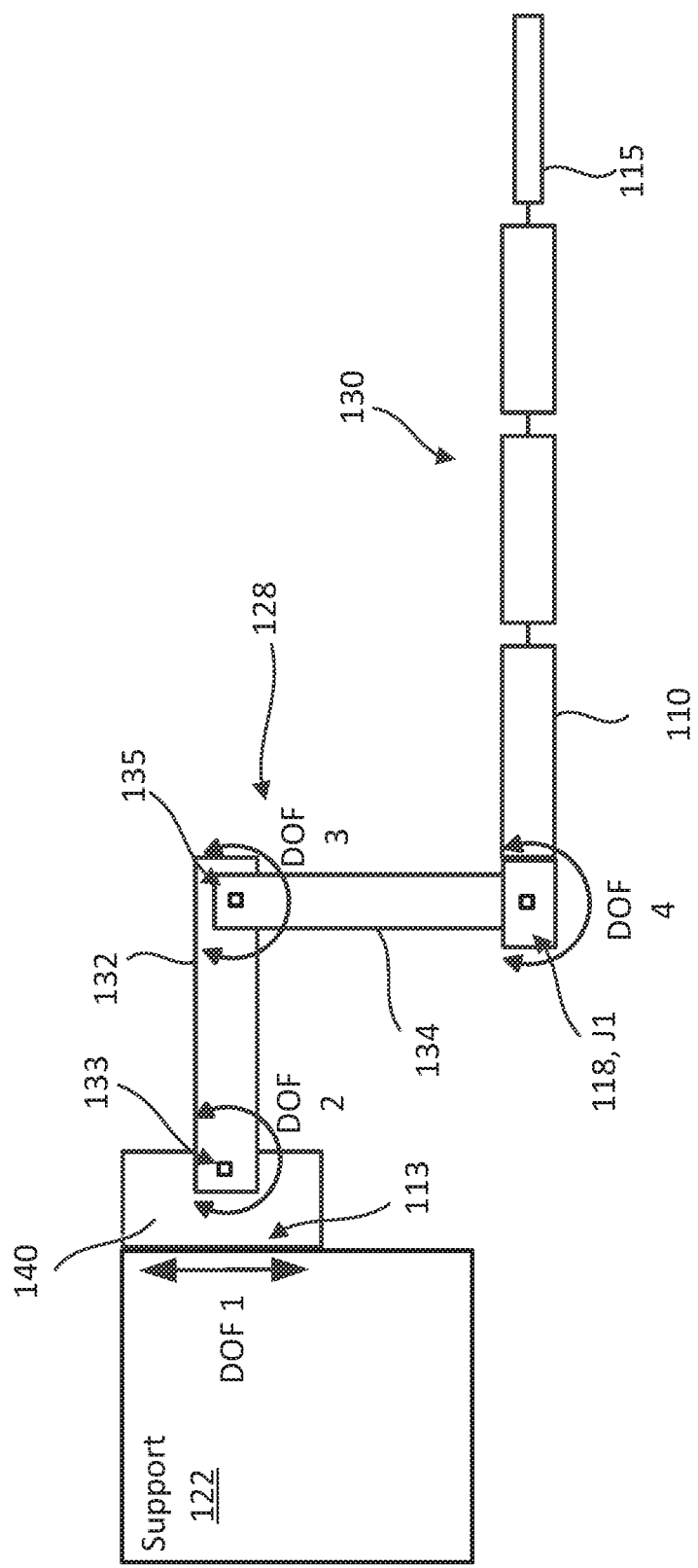
FIG. 2E is a schematic illustration of a top view of a portion of the surgical table, adapter and robotic arm of FIGS. 1A-1H, illustrating degrees of freedom associated with the joints of the adapter.

FIG. 2E is a top view of a portion of support 122, adapter 128 and a robotic arm 130 illustrating example degrees of freedom associated with the joints of the adapter 128 and/or robotic arm 130.

As shown in FIG. 2E, and as described above, the first link member 132 can be coupled to the interface mechanism 140 at a joint 133 and the second link member 134 can be coupled to the first link member 132 at a joint 135. The robotic arm 130 can be coupled to the second link member 134 at a coupling joint 118 and each of the links 110 of the robotic arm 130 can be coupled to each other at a joint. As shown in this example, the J1 joint of the robotic arm 130 coincides with the coupling joint 118. In some embodiments, the adapter 128, and more particularly, the interface mechanism 140 can be movably coupled to the surgical table (e.g., to the support 122) at a coupling joint 113 such that a first degree of freedom DOF 1 is provided at the coupling joint 113. In the example of FIG. 2E, the coupling joint 113 provides for linear movement between the interface mechanism 140 and the surgical table, i.e. translation parallel to the X axis. In other embodiments, the coupling joint can provide pivotal or rotational movement of the interface mechanism 140 relative to the surgical table. In other embodiments, the interface mechanism 140 is fixedly coupled to the surgical table, and thus, does not move relative to the surgical table.

As also shown in FIG. 2E, a second degree of freedom DOF 2 is provided at the joint 133 between the first link member 132 and the interface mechanism, and a third degree of freedom DOF 3 is provided at the joint 135 between the first link member 132 and the second link member 134. A fourth degree of freedom DOF 4 is provided at the joint 118, J1 between the second link member 134 and a link 110 of the robotic arm 130. In this example, each of DOF 2, DOF 3, and DOF 4 are shown as rotation about the Z axis.

Figure 2F:
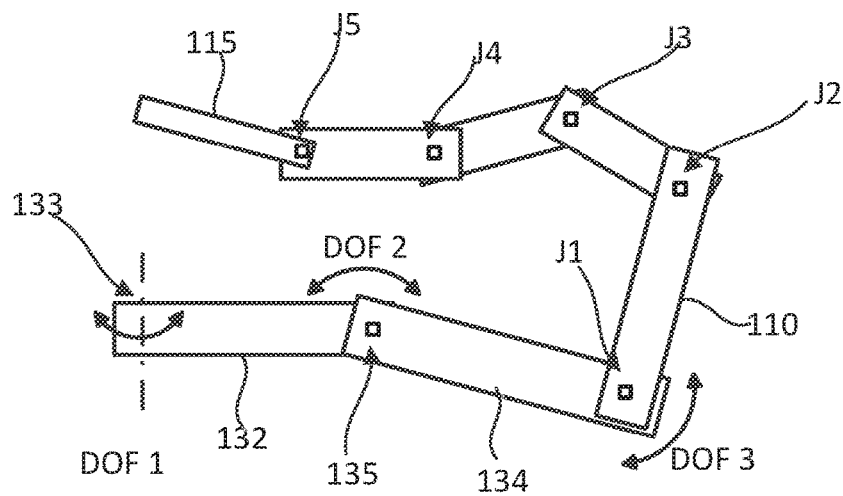
FIG. 2F is a schematic illustration of a side view of the adapter and a robotic arm of FIG. 2E illustrating degrees of freedom associated with the joints of the adapter and the robotic arm.

FIG. 2F is another example schematic illustration of the adapter 128 and robotic arm 130 demonstrating the degrees of freedom associated with various joints. FIG. 2F also illustrates various joints J2, J3, J4 between links 110 of the robotic arm 130 and a joint J5 between a link 110 and the medical instrument 115. In this example, a first degree of freedom DOF 1 is provided at joint 133 between the first link member 132 and the interface mechanism (not shown) of the adapter 128, a second degree of freedom DOF 2 is provided at joint 135 between the first link member 132 and the second link member 134, and a third degree of freedom DOF 3 is provided between the second link member 134 and the robotic arm 130 at the J1 joint.

As described above, the robotic arm 130 or a portion thereof can be releasably coupled to the adapter 128 and/or portions (e.g., links) of the robotic arm 130 can be incorporated into the adapter 128. Thus, the connection between the surgical table and the distal end of the robotic arm 130 can be conceptualized and implemented as a series of links and joints that provide the desired degrees of freedom for movement of the medical instrument 115 at the distal end of the connection. The connection may include a releasable coupling at any one or more link(s) or joint(s) or any location along the series of links and joints.

Figure 2G:
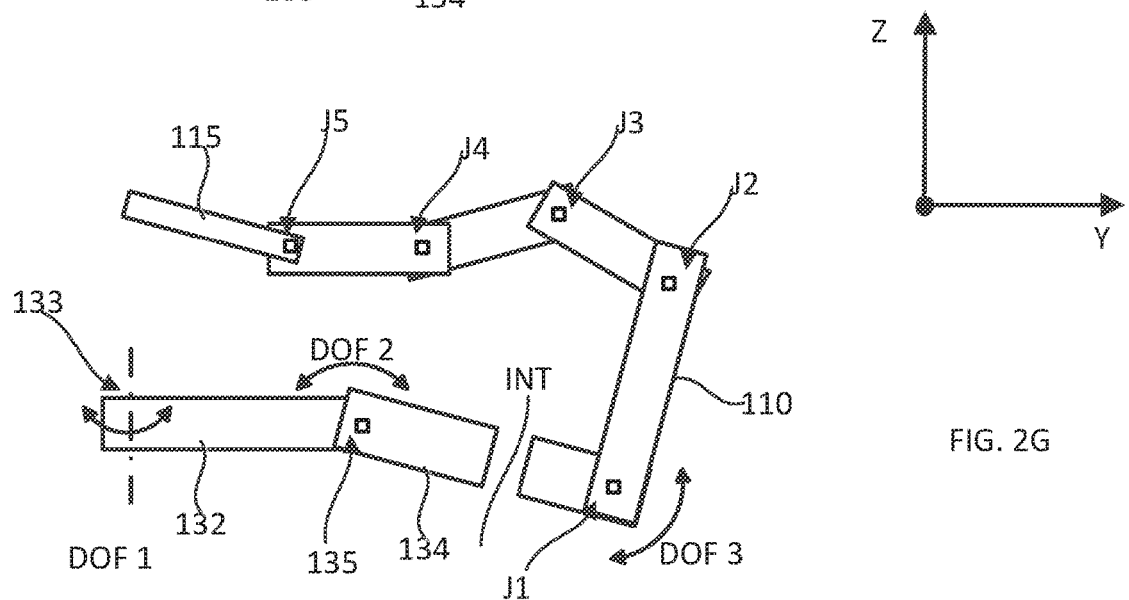
FIGS. 2G and 2H are each a schematic illustration of a side view of the adapter and robotic arm of FIG. 2F illustrating degrees of freedom and an example releasable coupling location between a link of the adaptor and/or robotic arm.
Figure 2H:
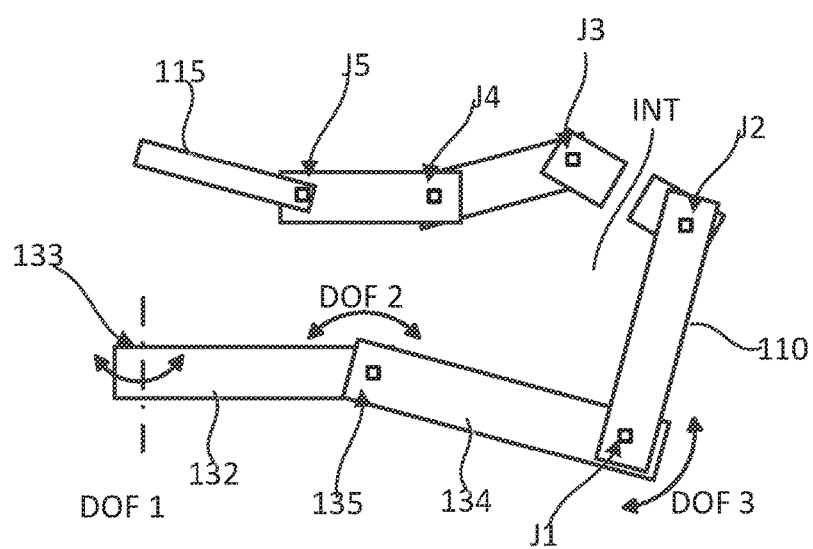

FIGS. 2G and 2H illustrate two different example locations for the releasable coupling described above. It should be understood that FIGS. 2G and 2H illustrate only two examples, and that the releasable coupling can be provided at various different locations along the series of links and joints that are illustrated in this example as including an adapter and a robotic arm 130, though as noted above this distinction can be considered as arbitrary. As shown in FIG. 2G, a releasable coupling can be provided at an interface location INT between a portion of the robotic arm 130 (e.g., at a link 110) and the second link member 134. The example of FIG. 2H illustrates the releasable coupling at an interface INT between the joint J2 and the joint J3 of the robotic arm 130. Thus, in the example of FIG. 2H, a portion of the links 110 of the robotic arm 130 are incorporated with the adapter 128.

The various degrees of freedom of the links of the adapter 128 and/or robotic arm 130 provide for movement of the robotic arm 130 and therefore, a medical instrument 115 disposed at a distal end thereof to be moved to a variety of different positions and orientations relative to the table top 120 to perform various different procedures on a patient disposed thereon. The adapters 128 described herein can also provide for variations on the number of robotic arms 130 that are coupled to the table to use for a particular procedure, and to position robotic arms 130 on one or both sides of the table top 120. For example, in some procedures, it may be desirable to position two robotic arms 130 on one side of the table top 120 and two robotic arms 130 on an opposite side of the table top 120. In other procedures, it may be desirable to position three robotic arms 130 on one side of the table top 120 and one robotic arm 130 on an opposite side of the table top 120. Although many of the embodiments described herein describe the use of four robotic arms 130, it should be understood that the number of robotic arms 130 to be used for a particular surgery can vary and more or less than four robotic arms 130 can be used. Various specific example embodiments are described herein demonstrating the movement and location of the robotic arms relative to the table top 120 within a treatment area or treatment "cloud" for various different procedures.

Each of the embodiments described herein can include the same or similar features as the surgical table, adapter, and robotic arms described with respect to FIGS. 1A-2H.

FIGS. 3A-8 illustrate a surgical table and an adapter according to another embodiment. A surgical table 500 includes a table top 520, a support 522 (also referred to herein as pedestal) and a base 524 (see FIGS. 4 and 6). As described above for previous embodiments, the support 522 can be mounted to the base 524, which can be fixed to the floor of an operating room, or can be movable relative to the floor. The table top 520 includes a head section 516, a torso section 517 and a leg section 519. The table top 520 can also include an arm section(s) (not shown). The table top 520 has a top surface on which a patient can be disposed. The support 522 can provide for movement of the table top 520 in a desired number of degrees of freedom as described above for previous embodiments. Also as described above, movement of the table top 520 and/or its constituent sections may be performed manually, driven by motors, controlled remotely, etc. The surgical table 500 can also include a radio-translucent window (not shown) as described for previous embodiments.

Figure 3A:
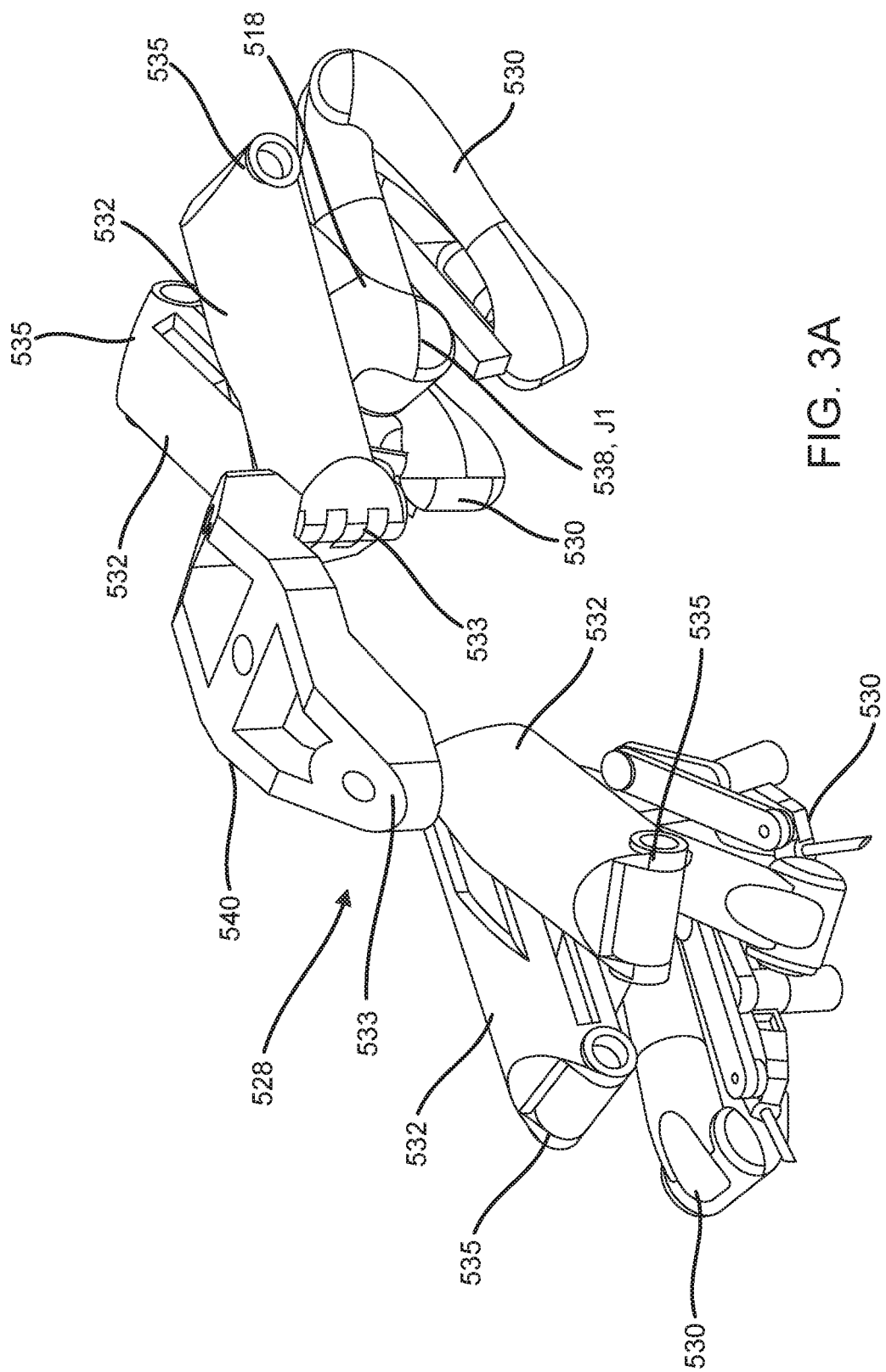
FIG. 3A is a perspective view of an adapter, according to another embodiment, with four robotic arms coupled thereto.

A table adapter 528 (also referred to herein as "adapter") can be coupled to the surgical table 500 and is shown in FIG. 30 with four robotic arms 530 attached thereto. The adapter 528 includes a table interface mechanism 540 (a portion of which is shown in FIG. 3A) that can be coupled to the support 522 and/or the table top 520. In some embodiments, the adapter 528 can be coupled to the support 522 such that the adapter 528 can move vertically up and down relative to the support 522 as described above.

The adapter 528 further includes multiple first link members 532 that are each pivotally coupled to the table interface mechanism 540. In this embodiment, two first link members 532 are coupled to the interface mechanism at a single shared first joint 533 on each side of the interface mechanism 540. Multiple second link members 534 are each coupled to one of the first link members 532 at a second joint 535. The second joint 535 provides the lift mechanism for moving the second link member 534 vertically. In this embodiment, the second joint 535 includes a pivotal coupling between the first link member 532 and the second link member 534. The first link member 532 and the second link member 534 can be moved between an extended configuration for use during a surgical procedure as shown, for example, in FIGS. 6-9, and a folded or collapsed configuration for storage when not in use, as shown, for example, in FIGS. 4 and 5.

Each of the second link members 534 can also be coupled to a robotic arm 530 at a coupling 518. The coupling 518 includes a coupling portion (not shown) on the second link member 534 that can be coupled to a coupling portion 538 at a mounting end of a robotic arm 530. As with the previous embodiment, in this embodiment, the coupling portion 538 includes the target joint J1. In this embodiment, the robotic arms 530 are fixedly or semi-fixedly coupled to the adapter 528. In this embodiment, the adapter 528 can accommodate four arms 530 (i.e., the adapter 528 can include four first link members 532 and four second link members 534). Each robotic arm 530 can be configured the same as or similar to, and function the same as or similar to, the robotic arms 130 described above and thus, specific details regarding the robotic arms are not discussed with respect to this embodiment. For example, as described above for robotic arms 130, the robotic arms 530 can include multiple links or segments coupled together to allow the robotic arm 530 to move between an extended configuration for use during a surgical procedure, and a folded or collapsed configuration for storage when not in use. The movement of the first link member 532 and the second link member 534 can provide for movement of the robotic arm 530 (and the target joint J1) along and/or about the X, Y, and/or Z axes as described in more detail below.

Figure 4:
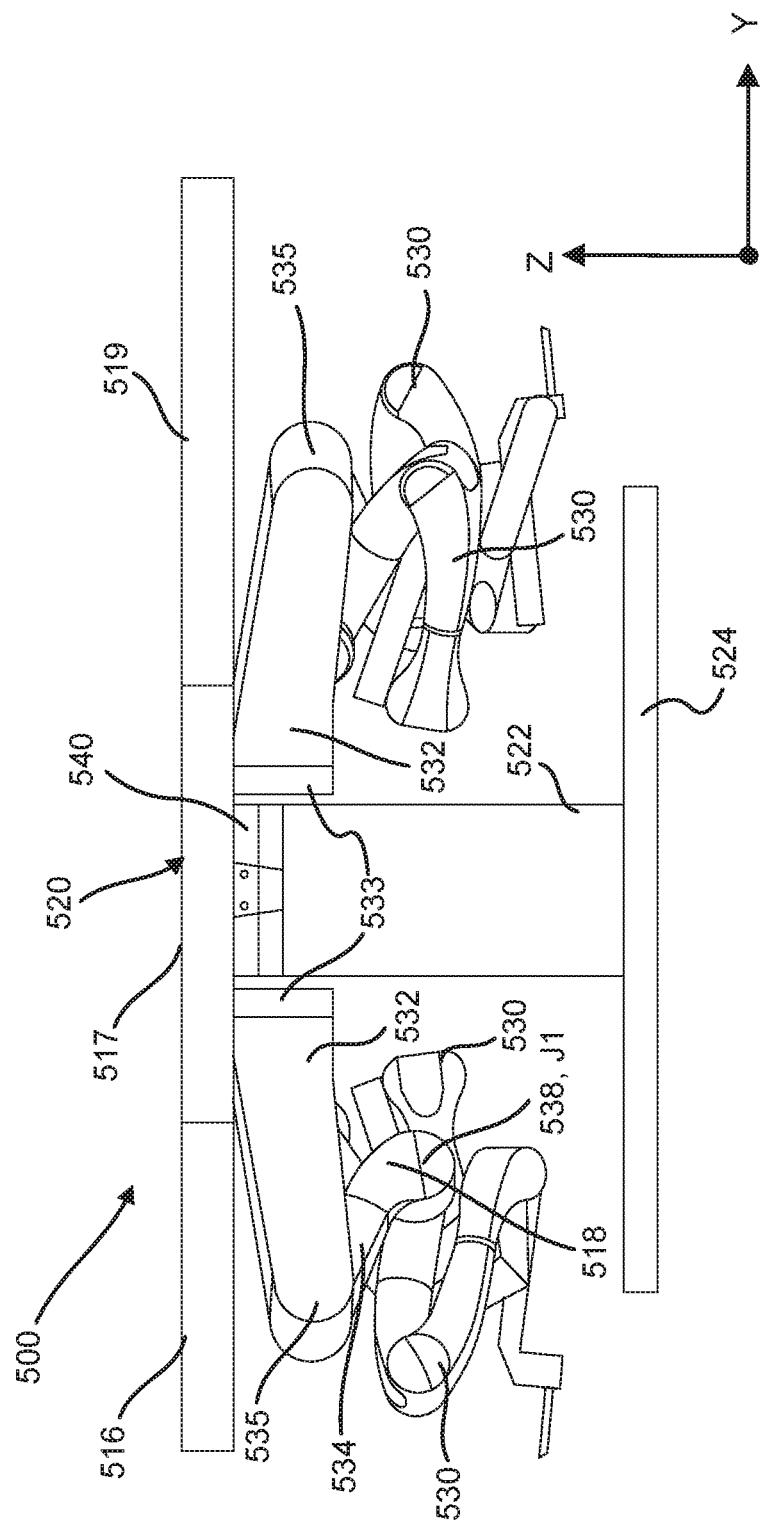
FIG. 4 is a side view of a surgical table and the adapter and robotic arms of FIG. 3A shown in a stowed position.
Figure 5:
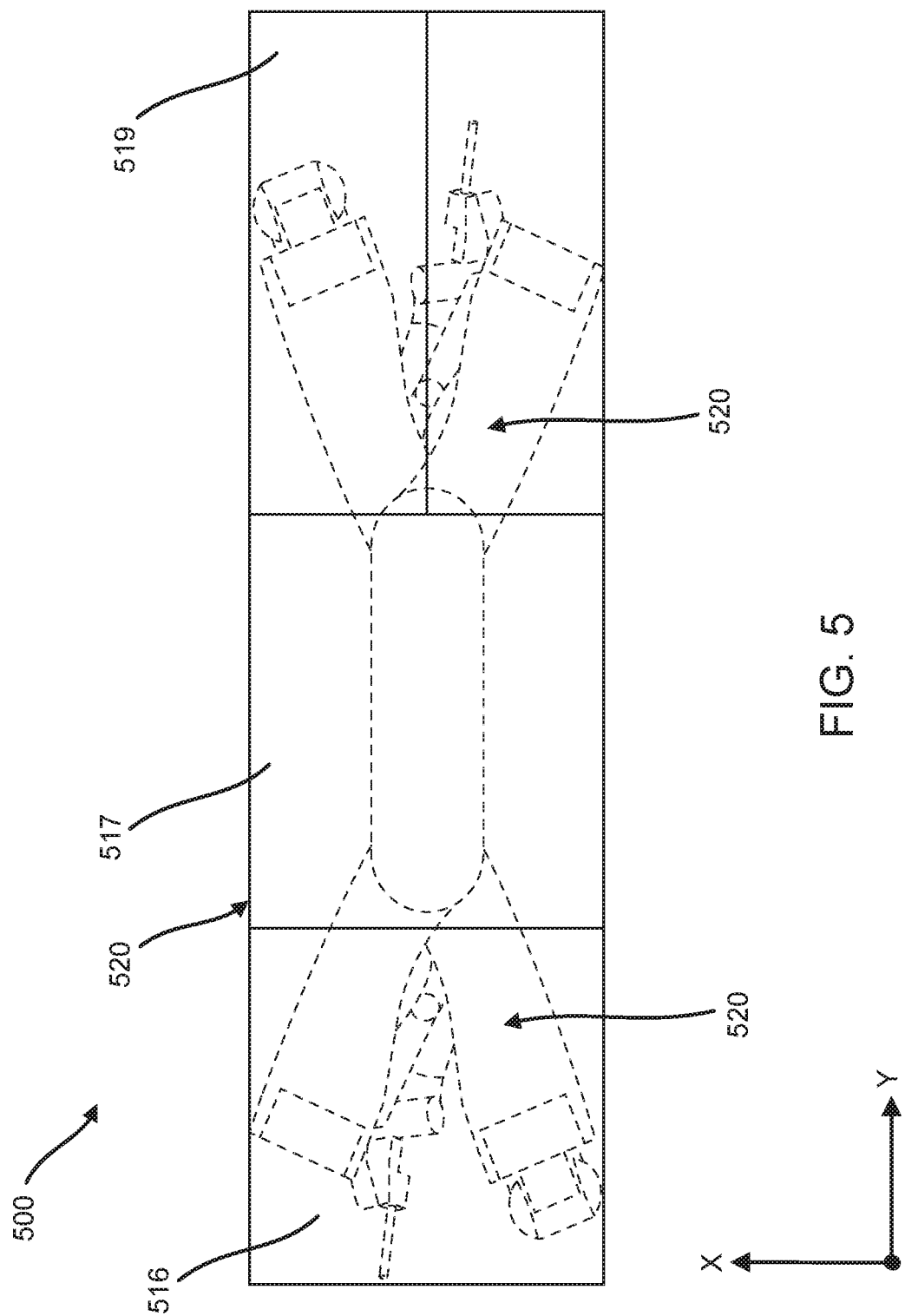
FIG. 5 is top view of the surgical table with the table top shown partially transparent and the adapter of FIG. 4 shown in the stowed position.

More specifically, as with the previous embodiments, the first joint 533 can provide for rotational motion of the two first link members 532 coupled thereto relative to the table interface structure 540 (and table 500) about a vertical z-axis (shown in FIG. 4) relative to a top surface of the table top 520 (e.g., a top surface of the torso section 517), and movement of the first link members 532 and second link members 534 in lateral and longitudinal directions (also referred to herein as x-direction and y-direction) relative to a top surface of the table top 520 of the surgical table 500 (see, e.g., X-Y axes in FIG. 5). As described above, the second joint 535 can provide the lift mechanism to allow for vertical movement of the second link member 534 and the coupling 518 between the second link member 534 and the robotic arm 530. Thus, the motion of the first link member 532 and the second link member 534 of the adapter 528 can provide for movement of a robotic arm 530 coupled thereto along and/or about the X, Y, and/or Z axes to position the target joint J1 at a desired treatment location relative to the table top 520.

Figures 3C, 3D:
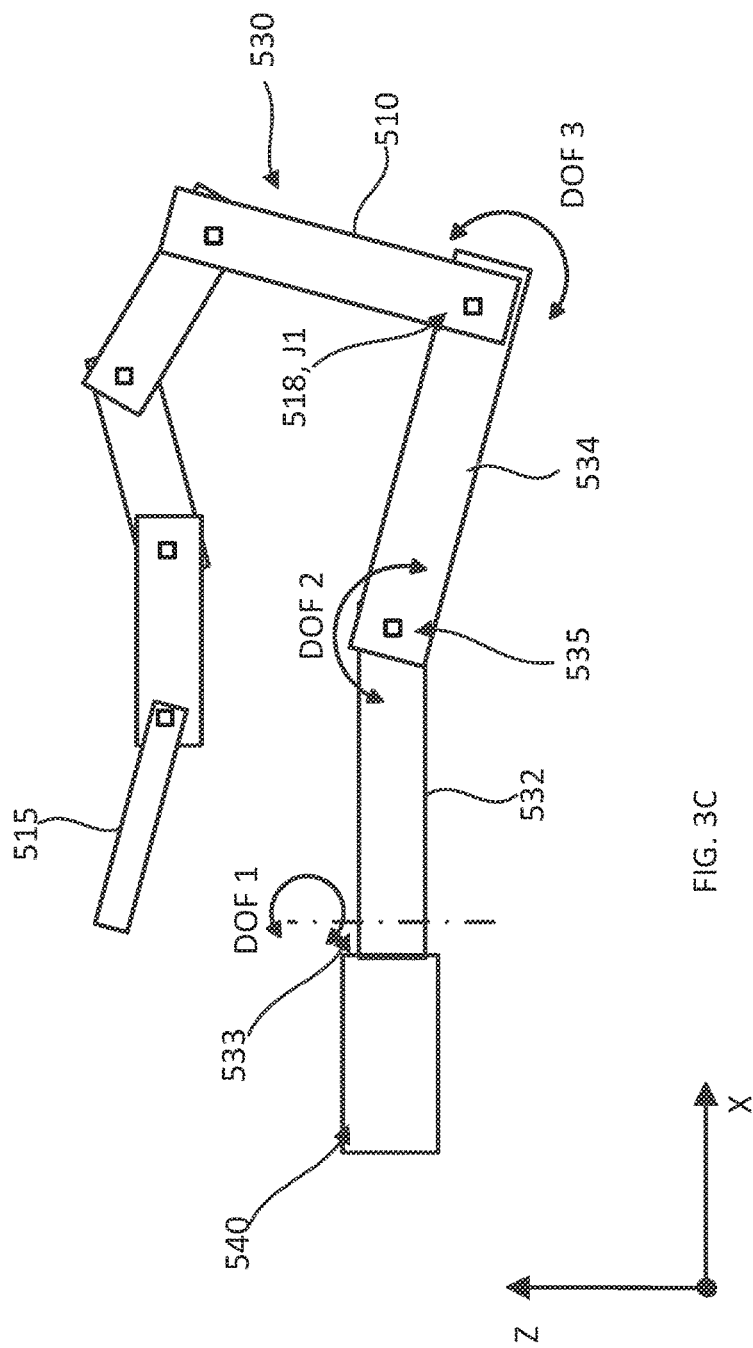

FIGS. 3B and 3C are schematic illustrations of the various degrees of freedom provided by the joints of the adapter 528 and robotic arm 530, and FIG. 3D is a table listing the type of degree of freedom (e.g., rotational, linear) associated therewith. As shown in FIGS. 3B and 3C, and as described above, the interface mechanism 540 is coupled to the support 522 of the table 500 and the first link members 532 are pivotally coupled to the interface mechanism 540 at joint 533. The pivotal joint 533 of the first link members 532 to the interface mechanism 540 allows the first link members 532 to rotate about the z-axis and provide a first degree of freedom DOF 1 at joint 533, i.e., Z-axis rotation. The joint 535 between the first link member 532 and the second link member 534 is also a rotational or pivotal joint that can pivot about a horizontal axis, i.e. an axis lying in the X-Y plane and thus provide a second degree of freedom DOF 2 (best shown in the side view illustration of FIG. 3C) that is X-Y plane rotation. Similarly, the joint J1 at the coupling 518 is also a pivotal joint that can pivot about a horizontal axis and provide a third degree of freedom DOF 3 (best shown in the side view illustration of FIG. 3C) that is X-Y plane rotation. Although not labeled in FIGS. 3B and 3C, the various joints between links 510 of the arm 530 and a medical instrument 515 disposed on the distal end of the robotic arm 530 can provide additional motion of the arm relative to a patient (e.g., a target treatment location on the patient) disposed on the table 500, and therefore, additional degrees of freedom.

Figure 32:
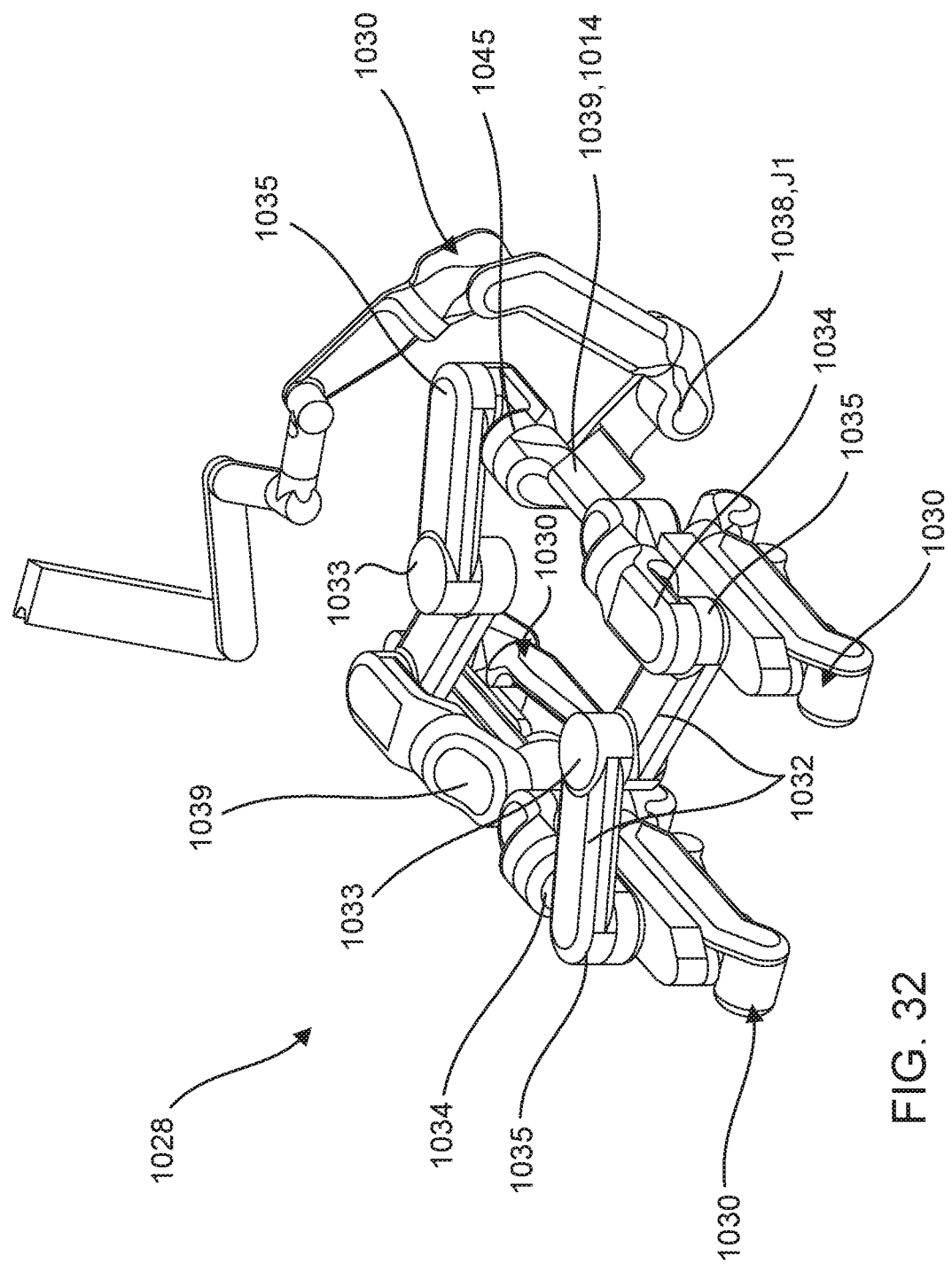
FIG. 32 is an end perspective view of the adapter and robotic arms of FIG. 32, with one of the robotic arms in an operating or extended position.

The collective motion of the first link members 532 and the second link members 534 allows the adapter 528 and robotic arms 530 to move between a variety of different positions relative to the surgical table 500 during a surgical procedure. For example, adapter 528 and robotic arms 530 can be moved to a stowed as shown, for example, in FIGS. 4 and 32). As shown in FIG. 4, two arms 530 are disposed beneath the head section 516 and two arms 530 are disposed beneath the leg section 519 of the table top 520.

As with the previous embodiment, the arms 530 and the link members 532 and 534 can be moved to the stowed position via the first joint 533 and the second joint 535. For example, the arms 530 and the second links 534 can be lowered via the second joint 535. The first links 532, second links 534 and the arms 530 can then be pivoted to the ends via the first joints 533. The arms 530 can be further folded via the joints between the links/segments of the arms 530. Similarly, the first link member 532 and the second link member 534 can be further folded or collapsed. The arms 530 and adapter 528 are thus in a folded or collapsed configuration in the stowed position.

Figure 6:
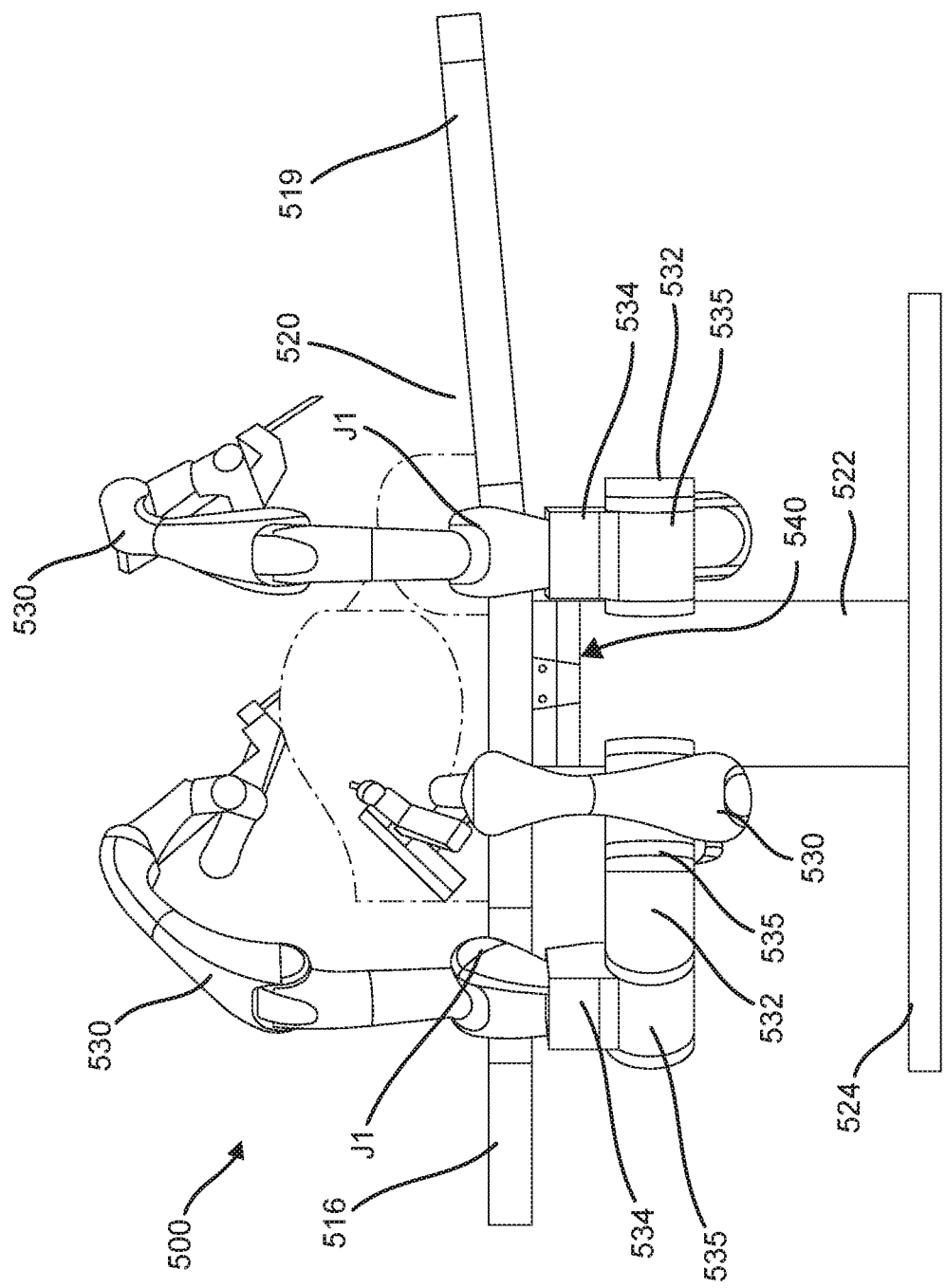
FIG. 6 is a side view of the surgical table, adapter and arms of FIG. 4 shown in an operating position with three arms on one side of the table and one arm on the opposite side of the table.
Figure 7:
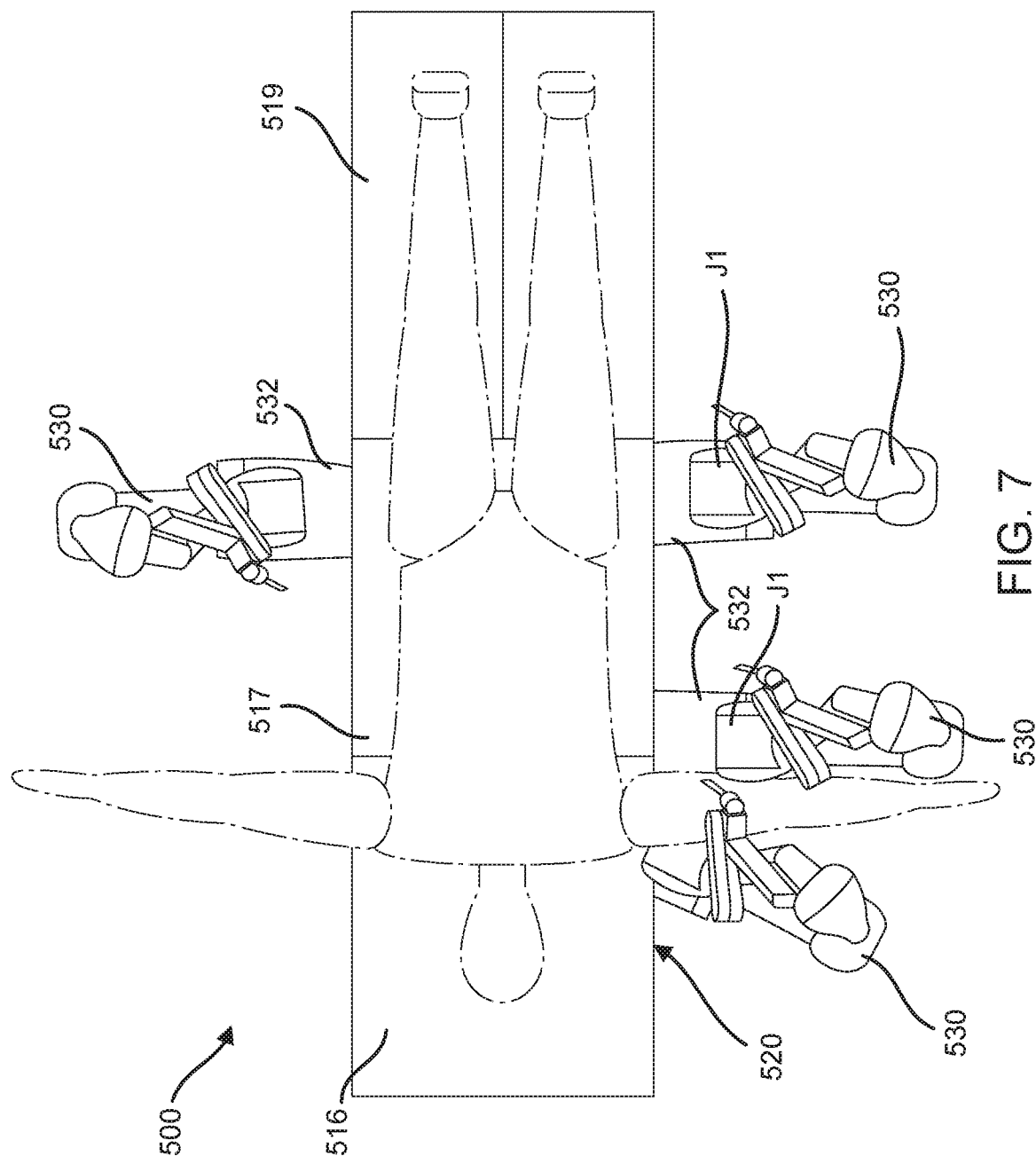
FIG. 7 is a top view of the surgical table, adapter and arms of FIG. 6 shown in an operating position with three arms on one side of the table and one arm on the opposite side of the table.

The adapter 528 and arms 530 can also be moved from the stowed position to various operating positions in a similar manner by moving the arms 530 via the first joints 533 and the second joints 535. FIGS. 6-9 illustrate the robotic arms 530 and adapter 528 in various different operating positions for particular surgical procedures. FIGS. 6 and 34 illustrate an example operating position that includes three arms 530 on one side of the table 500 and one arm 530 on the opposite side of the table 530. To achieve this configuration, one arm from the pair of arms 530 coupled to the adapter 528 on one side of the table 500 can be pivoted via the first joint 533 to the other side of the table. For example, from the stowed configuration, the arms can be pivoted out from under the table top 520 and then upward using the second pivot joint 535. Such a configuration may be used to perform, for example, a prostatectomy procedure.

Figure 8:
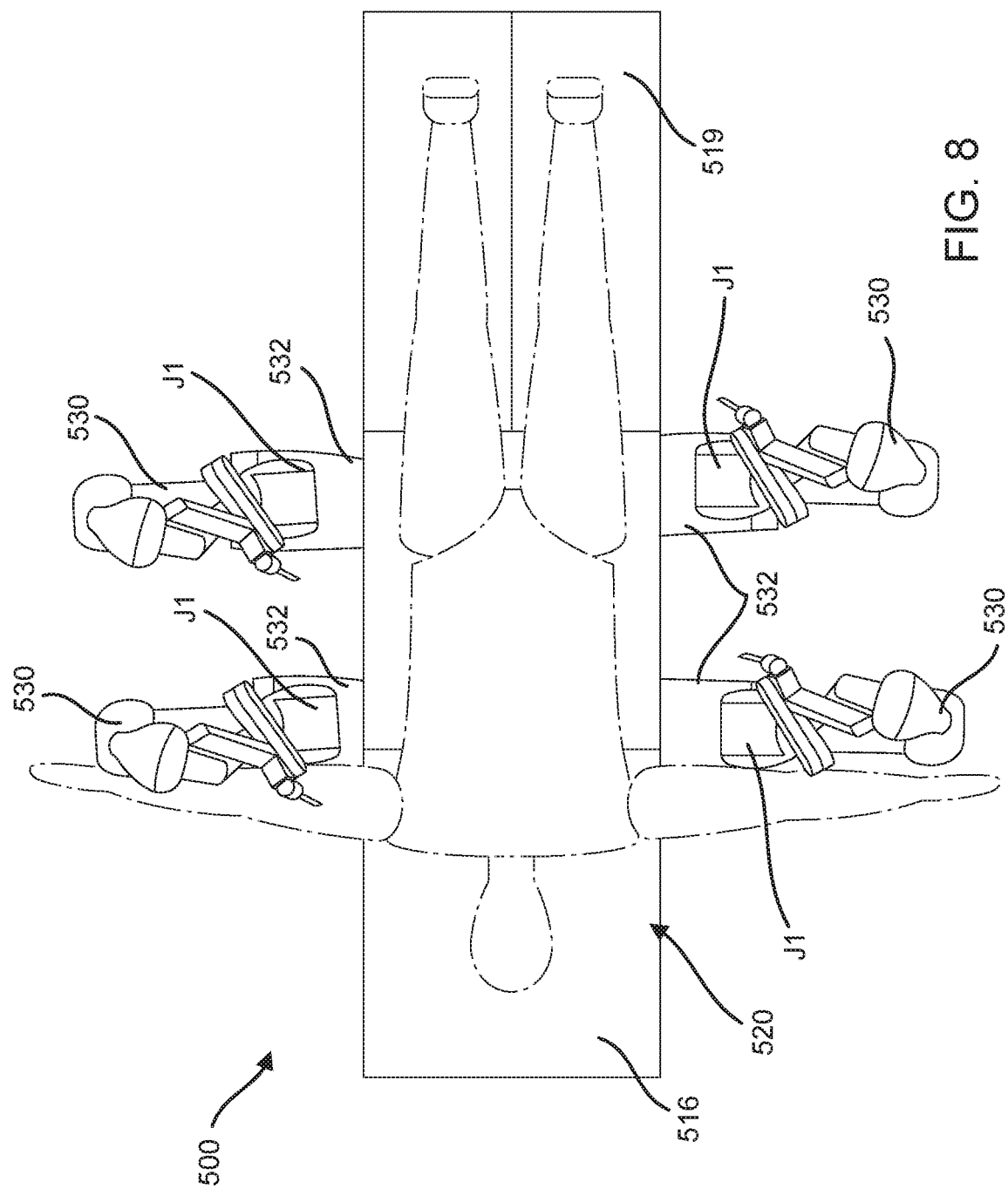
FIG. 8 is a top view of the surgical table, adapter and arms of FIG. 6 shown in an operating position with two arms on each side of the table.
Figure 9:
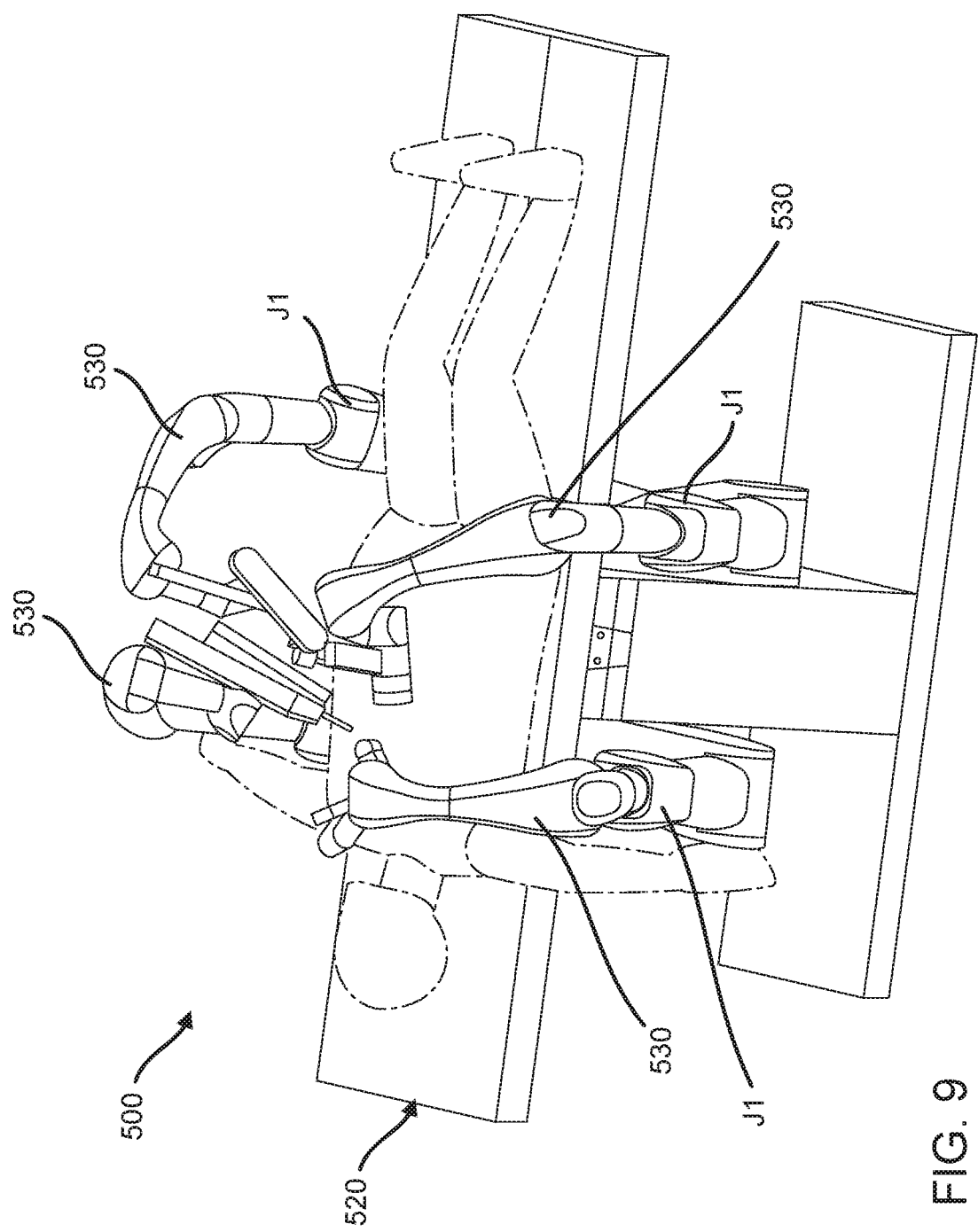
FIG. 9 is a side perspective view of the surgical table, adapter and arms of FIG. 8 shown in an operating position with two arms on each side of the table.

FIGS. 8 and 9 illustrate an example operating position that includes two arms 530 on each side of the table 500. Such an operating position may be used to perform, for example, a LAR procedure. FIG. 8 illustrates the arms 530 in a ready configuration on the sides of the table top 520, and FIG. 9 illustrates the arms 530 in a treatment configuration with the distal ends of the arms 530 (with medical instrument thereon) disposed in a treatment zone above the patient. Also, although not shown, as described above, in the operating positions it may be desirable to have space for a medical person (e.g., a surgical assistant, physician) to be located near the patient. Thus, the arms 530 can be positioned to accommodate such a situation. In each of the operating positions, the target joint J1 for each arm 530 is positioned at a target location relative to the table top 520 such that a distal end of the arm 530 (e.g., with medical instrument thereon) can be disposed in a desired treatment zone and can be maneuvered within a range of motion in a treatment region or zone.

Figure 10:
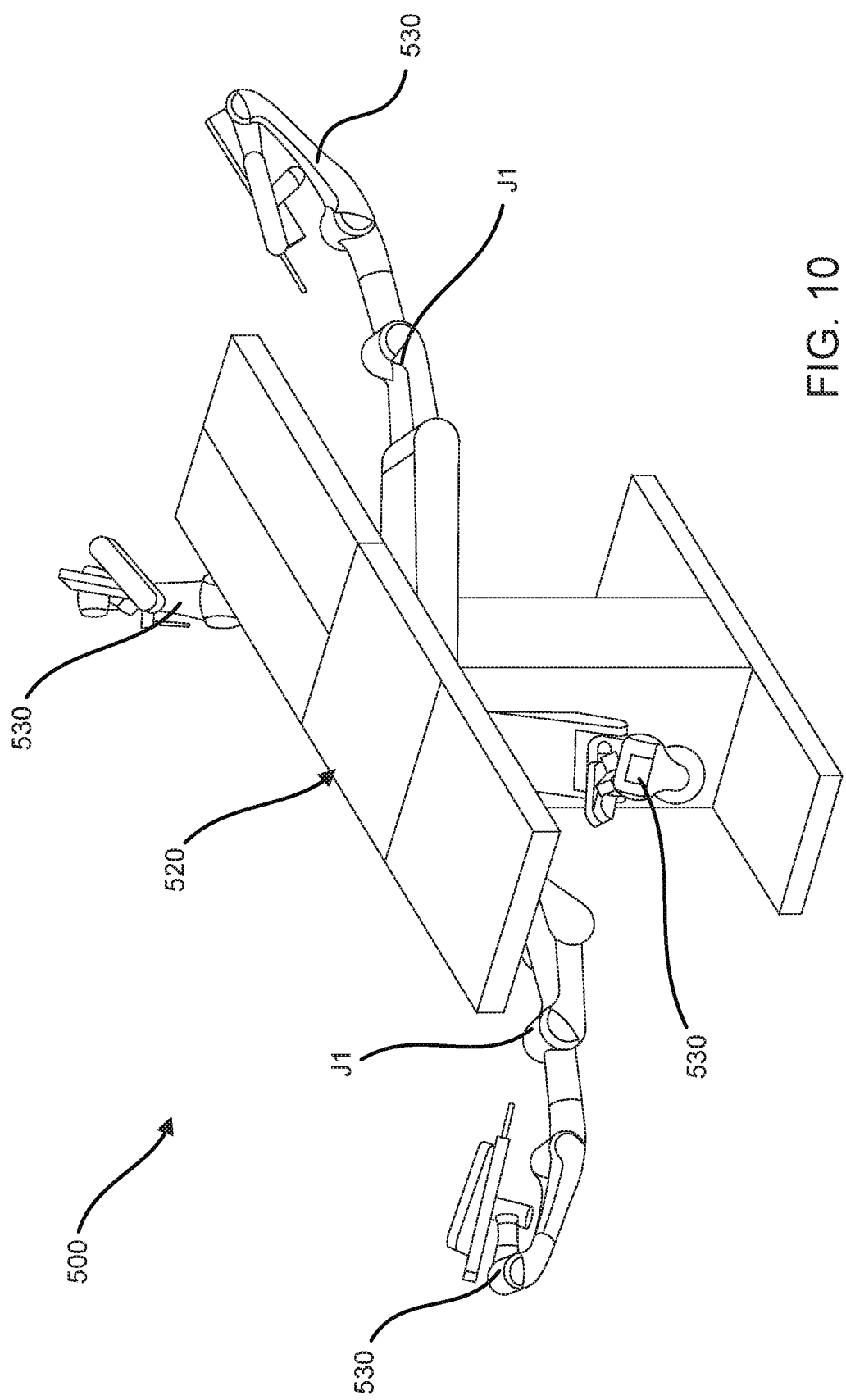
FIGS. 10 and 11 are a side perspective view and a top view, respectively, of the surgical table and arms of FIG. 8 shown in a parked position.
Figure 11:
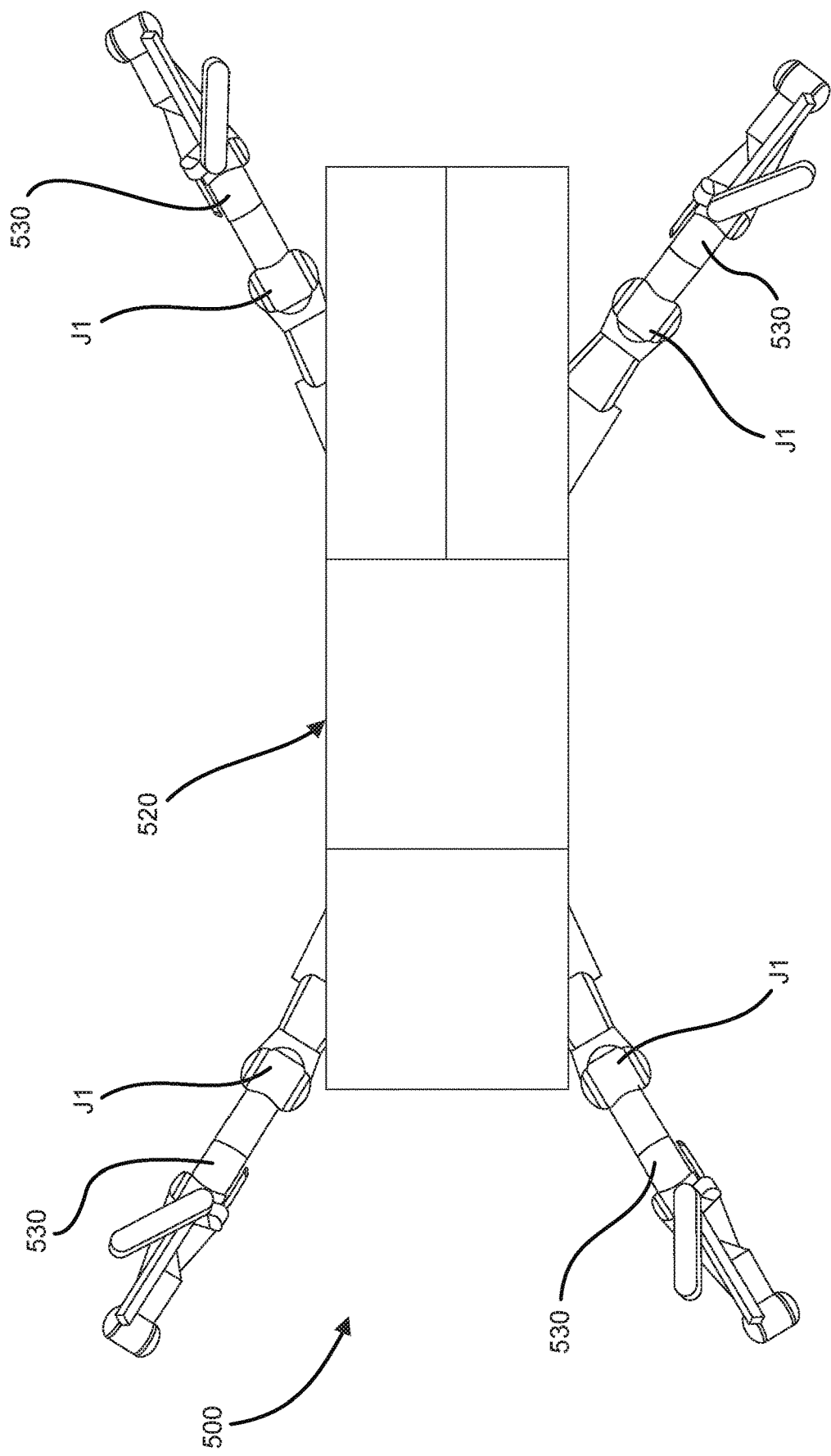

As described above, during a surgical procedure, the adapter 528 and arms 530 can also be moved to a parked position to provide clearance, for example, medical staff to access the patient or to provide clearance for other devices such as an imaging device. FIGS. 10 and 11 illustrate an example parked position in which the arms 530 are disposed out of the way of the sides of the table 500 to provide clearance for medical personnel or other equipment. When the need for the clearance has passed, the arms 530 can then be placed back into the operating position with the target joints J1 disposed at the target treatment locations relative to the table top 520.

FIGS. 12A-26 illustrate a surgical table and an adapter according to another embodiment. A surgical table 600 includes a table top 620, a support 622 (also referred to herein as pedestal) and a base 624 (see, e.g., FIG. 19). As described above for previous embodiments, the support 622 can be mounted to the base 624, which can be fixed to the floor of an operating room, or can be movable relative to the floor. The table top 620 includes a head section 616, a torso section 617 and a leg section 619. The table top 620 can also include an arm section(s) (not shown). The table top 620 has a top surface on which a patient can be disposed. The support 622 can provide for movement of the table top 620 in a desired number of degrees of freedom as described above for previous embodiments. Also as described above, movement of the table top 620 and/or its constituent sections may be performed manually, driven by motors, controlled remotely, etc. The surgical table 600 can also include a radio-translucent window (not shown) as described for previous embodiments.

Figure 12A:
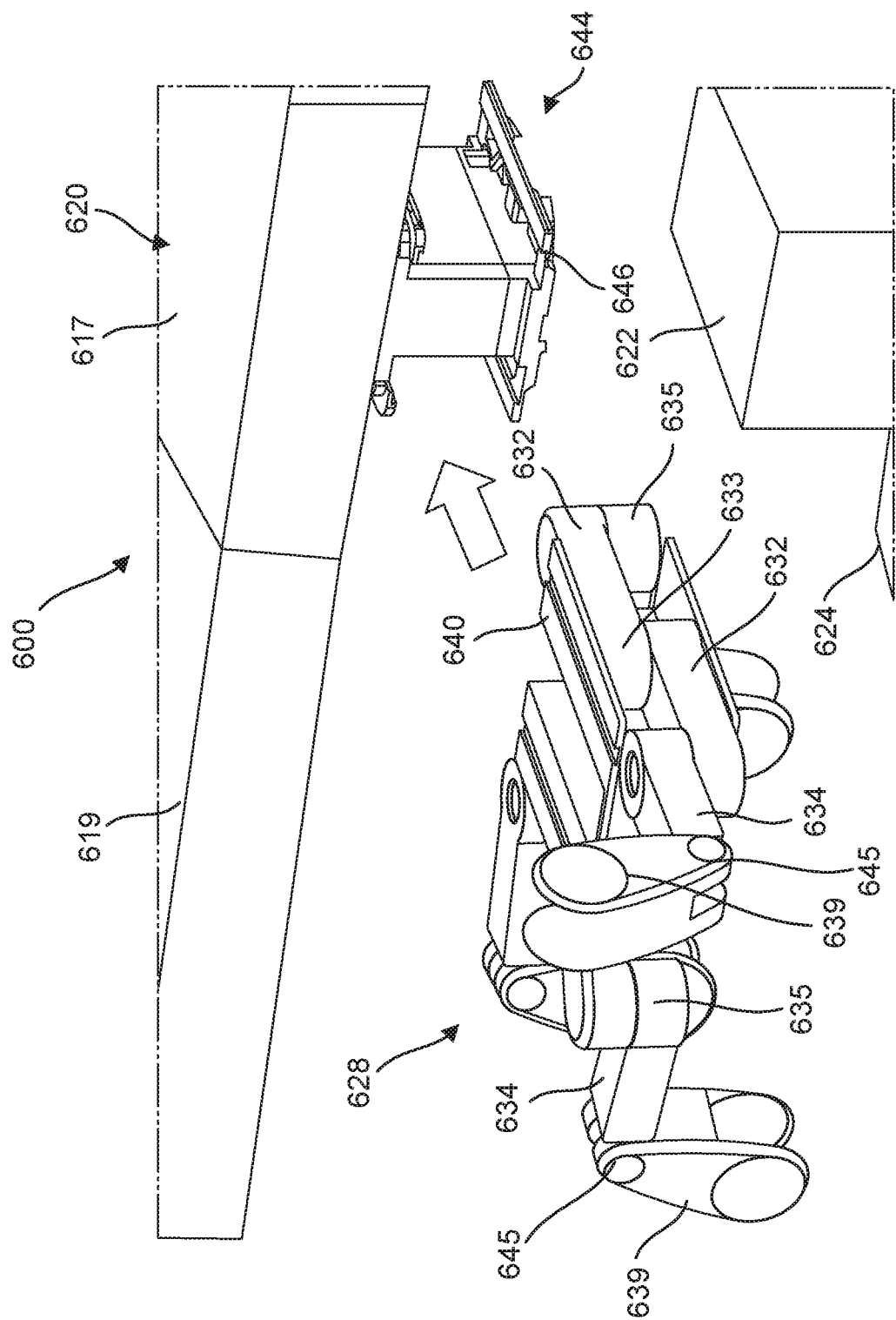
FIG. 12A is an exploded view of a portion of a surgical table and an adapter according to another embodiment.
Figure 12B:
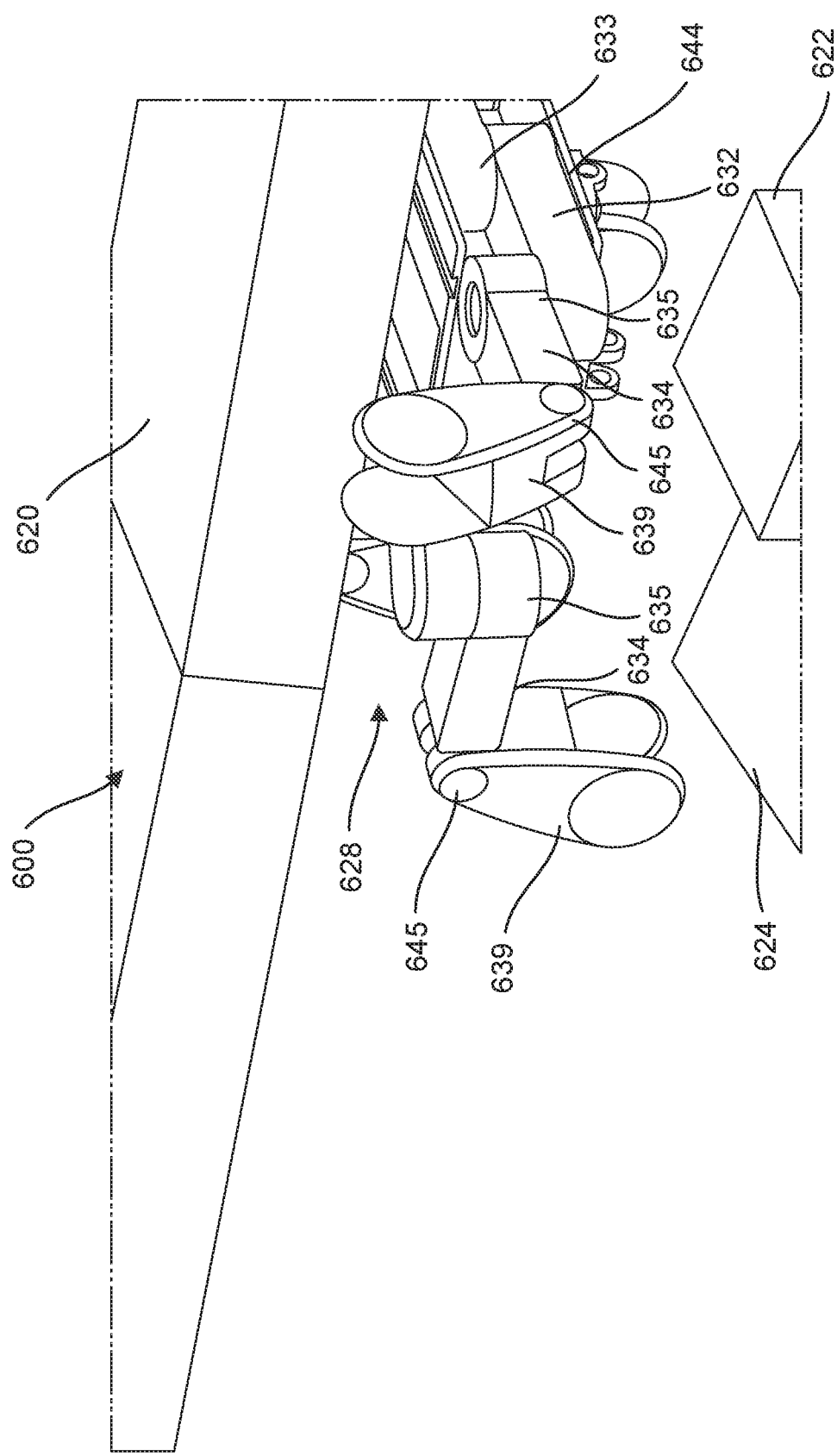
FIG. 12B is an exploded view of a portion of the surgical table and an adapter of FIG. 12A with the adapter coupled to the surgical table.
Figure 13:
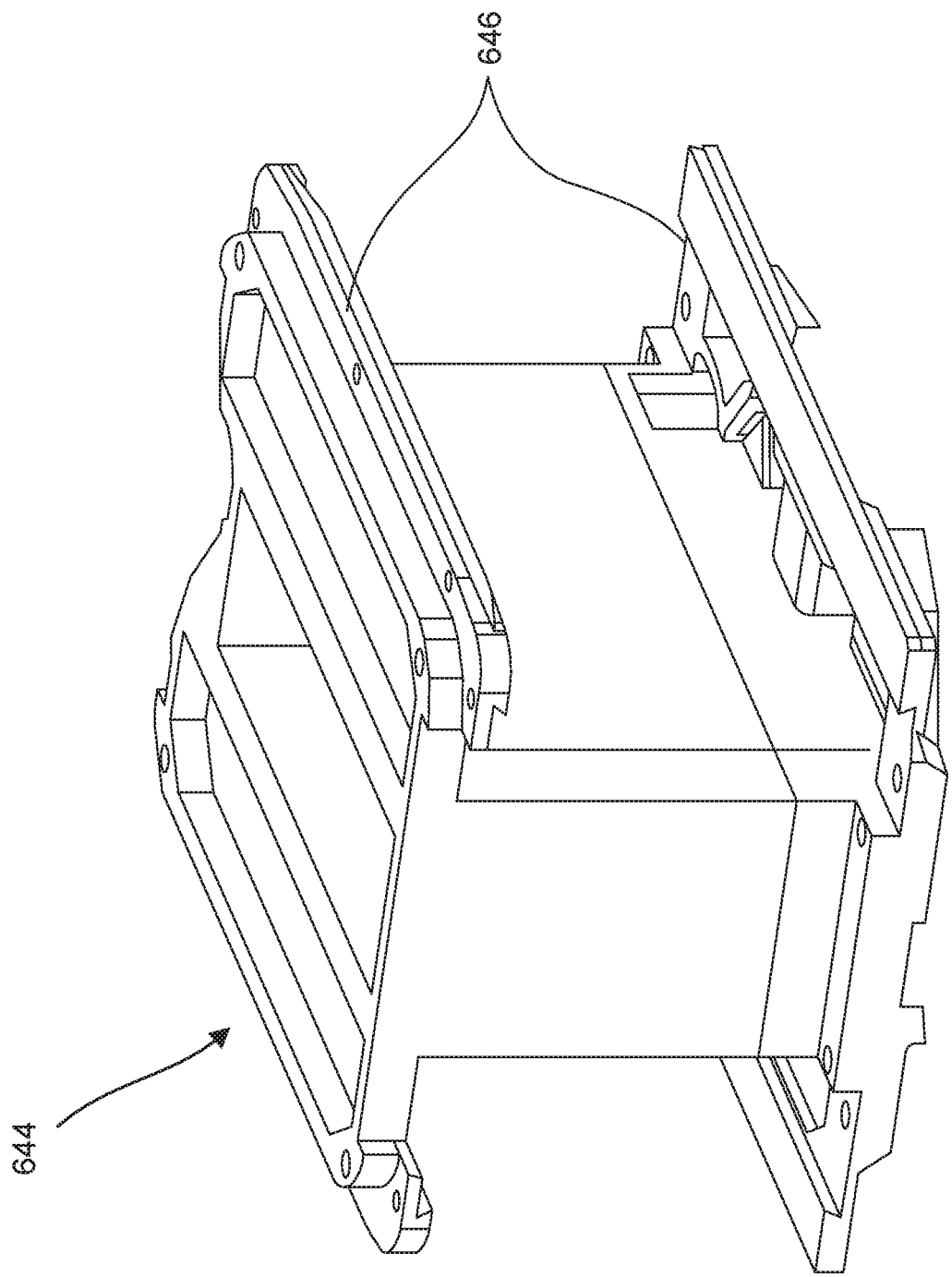
FIG. 13 is a perspective view of a column mount for coupling the adapter of FIGS. 12A and 12B to the surgical table.
Figure 14:
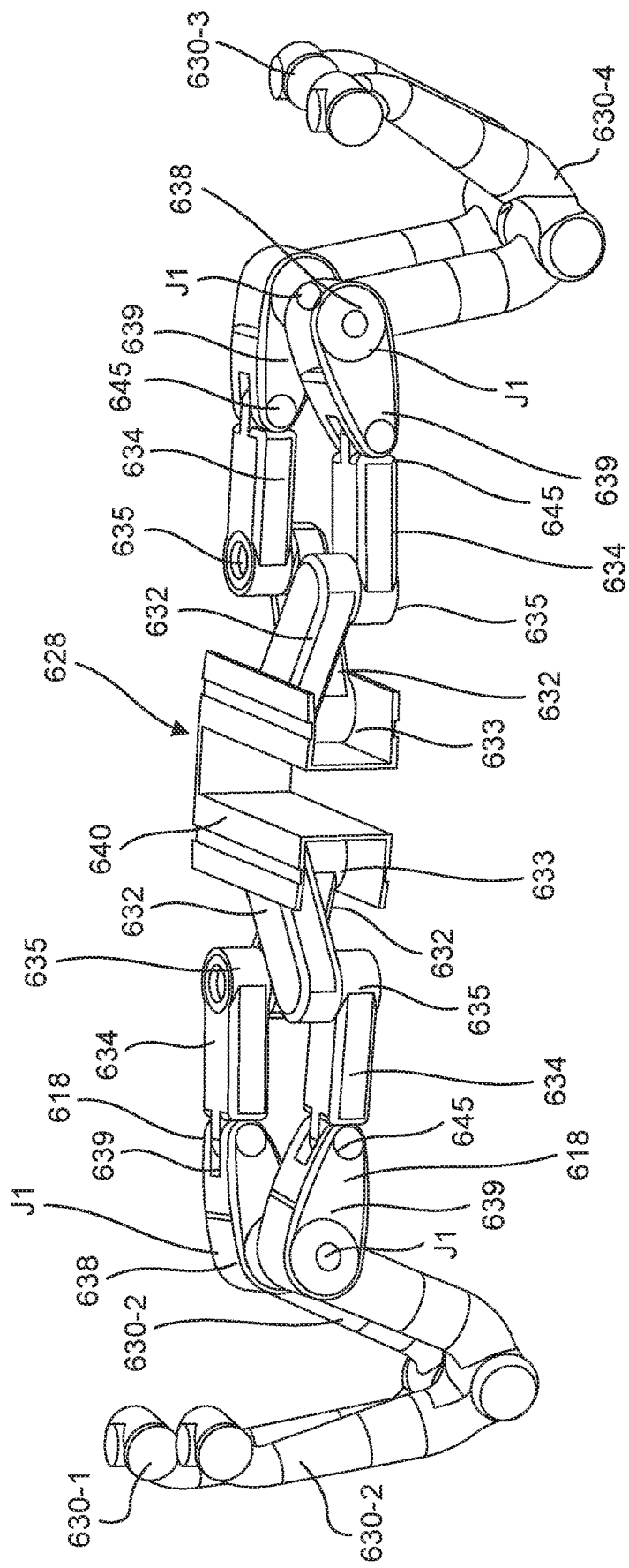
FIG. 14 is a perspective view of the adapter of FIGS. 12A and 12B with four robotic arms coupled thereto.
Figure 15:
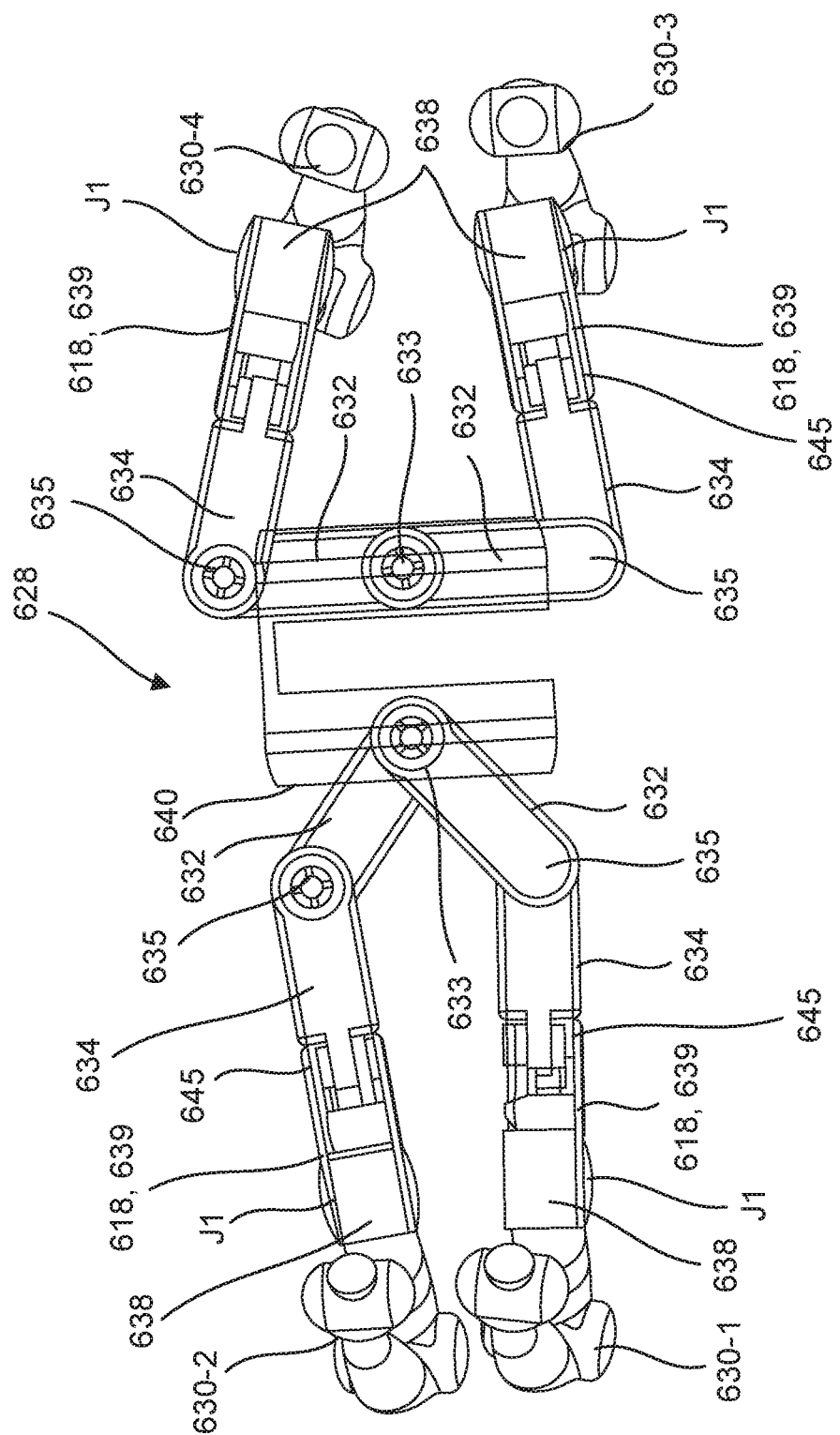
FIG. 15 is a bottom view of the adapter and robotic arms of FIG. 14.

As shown in FIGS. 12A and 12B, a table adapter 628 (also referred to herein as "adapter") can be coupled to the surgical table 600 via a column mount 644 (see also FIG. 13) that is coupled to the support 622. The adapter 628 includes a table interface mechanism 640 (as best shown in FIGS. 14 and 15) that can be slidably received between rails 646 of the column mount 644 to couple the adapter 628 to the support 622. The adapter 628 further includes multiple first link members 632 that are each pivotally coupled to the table interface mechanism 640. As with the previous embodiment, two first link members 632 are coupled to the interface mechanism 640 at a single shared first joint 633 on each side of the interface mechanism 640. In this embodiment, the adapter 628 is coupled to the table 600 such that the shared first joints 633 are disposed at the ends of the table 600 beneath the head section 616 and the leg section 619. In addition, in some embodiments, the location of the first joint 633 can be moved laterally (in the X-axis direction) within the rails 646 of the column mount 644.

The adapter 628 also includes multiple second link members 634 that are each coupled to one of the first link members 632 at a second joint 635. The second joint 635 provides the lift mechanism for moving the second link member 634 vertically. In this embodiment, the second joint 635 includes a pivotal coupling between the first link member 632 and the second link member 634. The first link member 632 and the second link member 634 can be moved between an extended configuration for use during a surgical procedure as shown, for example, in FIGS. 20-27, and a folded or collapsed configuration for storage when not in use, as shown, for example, in FIGS. 18 and 19.

Each of the second link members 634 can also be coupled to a robotic arm 630 at a coupling 618 (see, e.g., FIGS. 14-17). The coupling 618 includes a coupling portion 639 pivotally coupled to the second link member 634 at a coupling joint 645. The coupling portion 639 is also pivotally coupled to a coupling portion 638 at a mounting end of a robotic arm 630. The coupling portion 639 is effectively a third link member of the adapter 628. The pivotal coupling of the coupling portion 639 (e.g., third link member) to the second link member 634 allows the coupling portion 639 to extend the reach (e.g., a collective length of the link members) of the adapter 628 and the arm 630 coupled thereto as shown, for example, in FIG. 17. In this embodiment, a target joint J1 is defined at the pivotal coupling between the coupling portion 639 and the coupling portion 638. In this embodiment, the robotic arms 630 are fixedly or semi-fixedly coupled to the adapter 628. In this embodiment, the adapter 628 can accommodate four arms 630 (i.e., the adapter 628 can include four first link members 632 and four second link members 634). The four arms are labeled 630-1, 630-2, 630-3, 630-4 in FIGS. 14, 15, 19-24 (collectively referred to as arms 630). Each robotic arm 630 can be configured the same as or similar to, and function the same as or similar to, the robotic arms 130 described above and thus, specific details regarding the robotic arms are not discussed with respect to this embodiment. For example, as described above for robotic arms 130, the robotic arms 630 can include multiple links or segments coupled together to allow the robotic arm 630 to move between an extended configuration for use during a surgical procedure, and a folded or collapsed configuration for storage when not in use. In this embodiment, the movement of the first joint 633, the second joint 635 and the coupling joint 645 between the second link member 634 and the coupling portion 639 can provide for movement of the robotic arm 630 (and the target joint J1) along and/or about the X, Y, and/or Z axes as described in more detail below.

More specifically, as with the previous embodiments, the first joint 633 can provide for rotational motion of the two first link members 632 coupled thereto relative to the table interface structure 640 (and table 600) about a vertical z-axis (shown in FIG. 18) relative to a top surface of the table top 620 (e.g., the top surface of the torso section 617), and movement of the first link members 632 and second link members 634 in lateral and longitudinal directions (also referred to herein as x-direction and y-direction) relative to the top surface of the table top 620 of the surgical table 600 (see, e.g., X-Y axes in FIGS. 20-52). As described above, the second joint 635 can provide the lift mechanism to allow for vertical movement of the second link member 634 and the coupling 618 between the second link member 634 and the robotic arm 630. Further, as described above, the location of the first joints 633 can be moved laterally within the column mount 644. Also as described above, the coupling joint 645 provides additional movement capabilities for moving the robotic arms 630. Thus, the motion of the first link member 632 and the second link member 634 of the adapter 628 can provide for movement of a robotic arm 630 coupled thereto along and/or about the X, Y, and/or Z axes to position the target joint J1 at a desired treatment location relative to the table top 620.

Figure 16A:
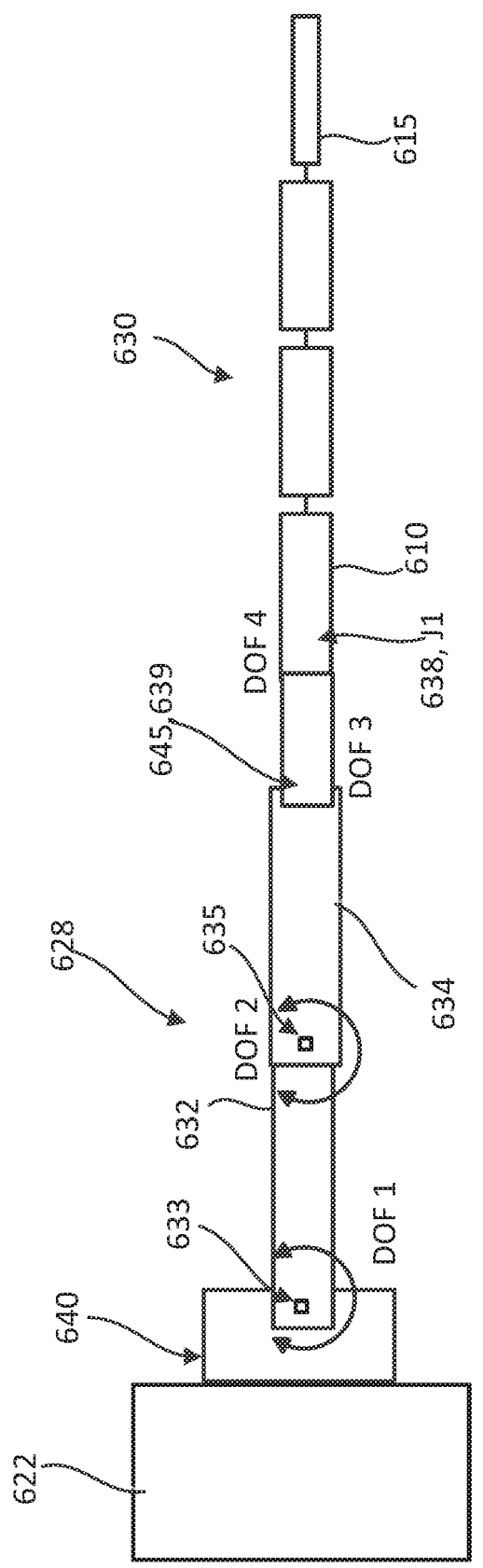
FIGS. 16A and 16B are a schematic top view and side view, respectively, of the adapter and a robotic arm of FIGS. 14 and 15 illustrating the degrees of freedom between the joints of the adapter and robotic arm.
Figures 16B, 16C:
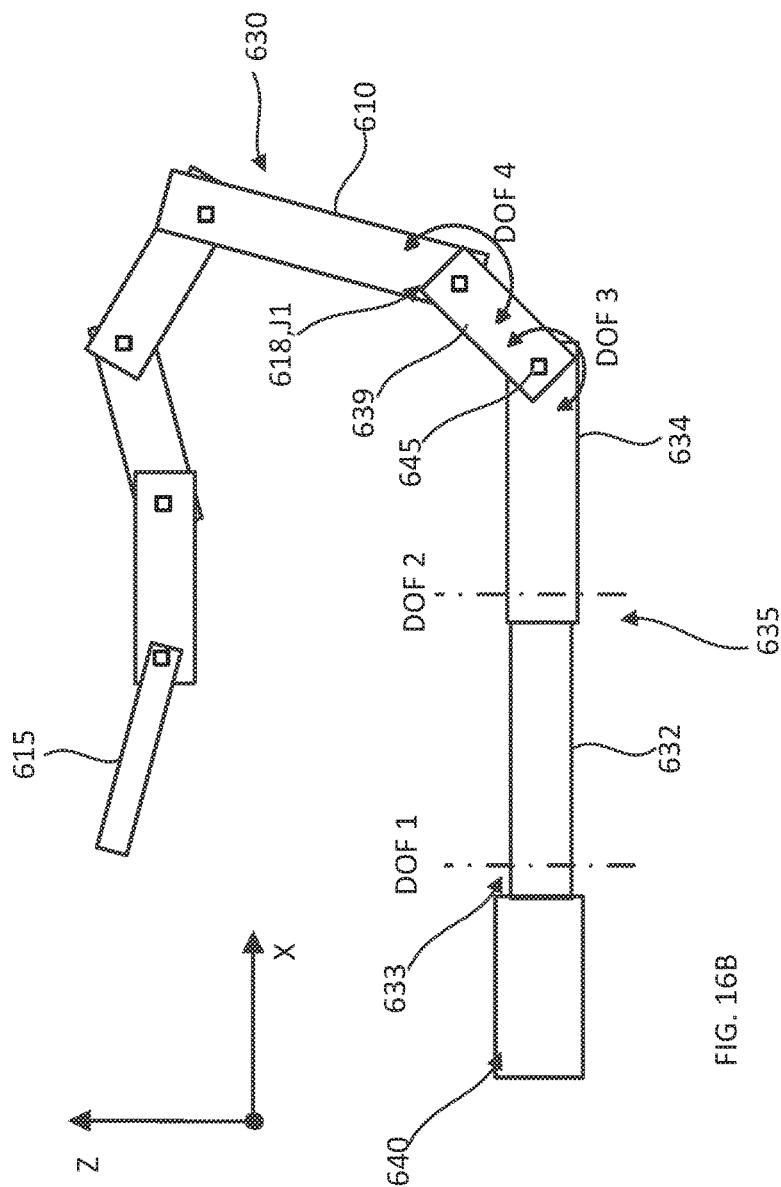
FIG. 16C is a table listing the type of degree of freedom of each of the joints.
Figure 17:
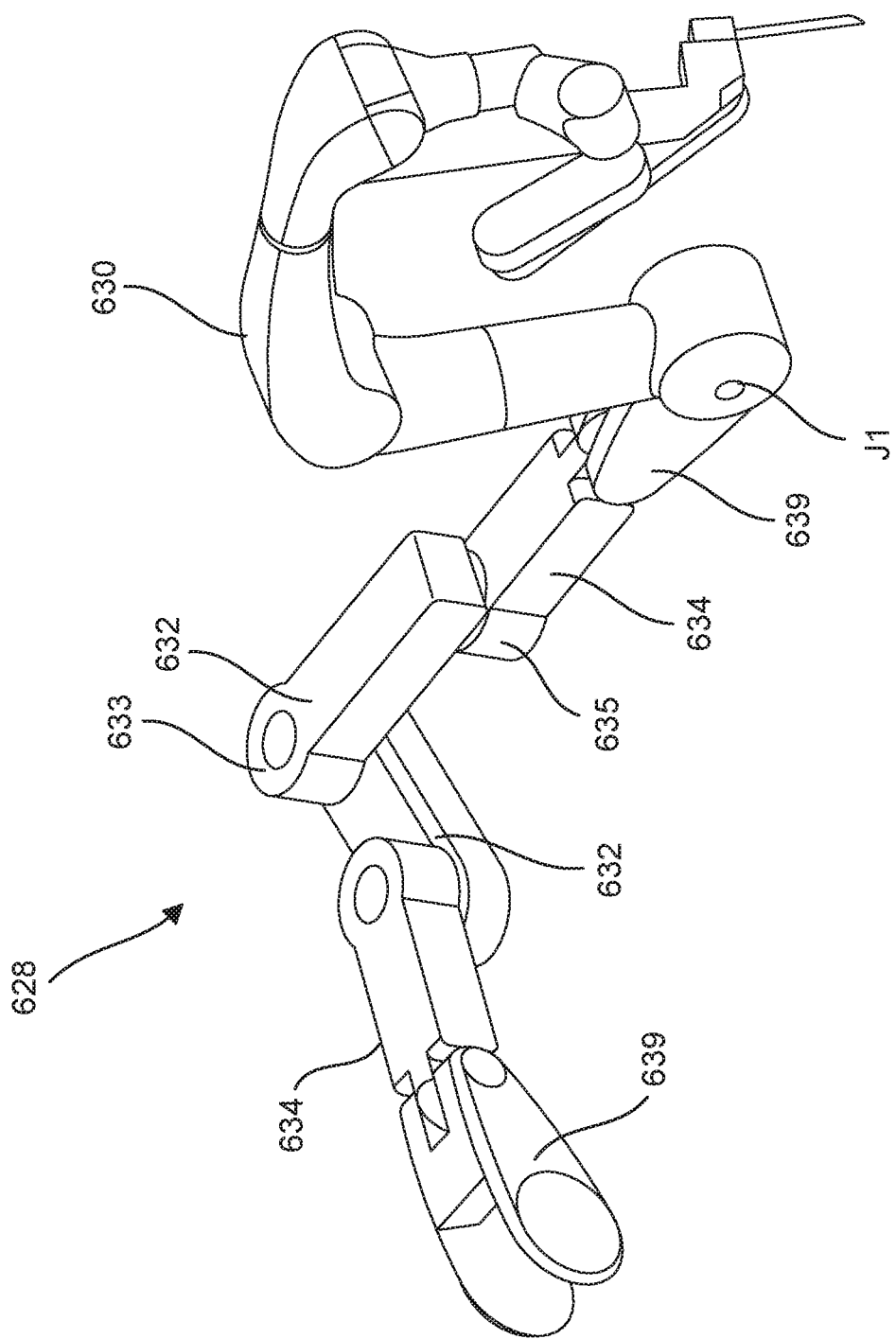
FIG. 17 is a perspective view of a portion of the adapter of FIGS. 12A and 12B with one robotic arm coupled thereto.

FIGS. 16A and 16B are schematic illustrations of the various degrees of freedom provided by the joints of the adapter 628 and robotic arm 630, and FIG. 16C is a table listing the type of degree of freedom (e.g., rotational, linear) associated therewith. As shown in FIGS. 16A and 16B, and as described above, the interface mechanism 640 is couple-able to the support 622 of the table 600 and the first link members 632 are pivotally coupled to the interface mechanism 640 at joint 633. The pivotal joint 633 of the first link members 632 to the interface mechanism 640 allows the first link members 632 to rotate about the z-axis and provide a first degree of freedom DOF 1 at joint 633, i.e., Z-axis rotation. The joint 635 between the first link member 632 and the second link member 634 is also a rotational or pivotal joint that can pivot about the z-axis and provide a second degree of freedom DOF 2 at joint 635, i.e., Z-axis rotation. In this embodiment, the adapter 628 includes a joint 645 between the second link member 634 and the coupling portion 639 that can pivot about a horizontal axis and provide a third degree of freedom DOF 3 (best shown in the side view illustration of FIG. 43B) that is X-Y plane rotation. Similarly, the joint J1 between the coupling portion 639 and the coupling portion 638 of the robotic arm 630 is also a pivotal joint that can pivot about a horizontal axis and provide a fourth degree of freedom DOF 4 (best shown in the side view illustration of FIG. 16B) that is X-Y plane rotation. Although not labeled in FIGS. 16A and 16B, the various joints between links 610 of the arm 630 and a medical instrument 615 disposed on the distal end of the robotic arm 630 can provide additional motion of the arm relative to a patient (e.g., a target treatment location on the patient) disposed on the table 600, and therefore, additional degrees of freedom.

Figure 18:
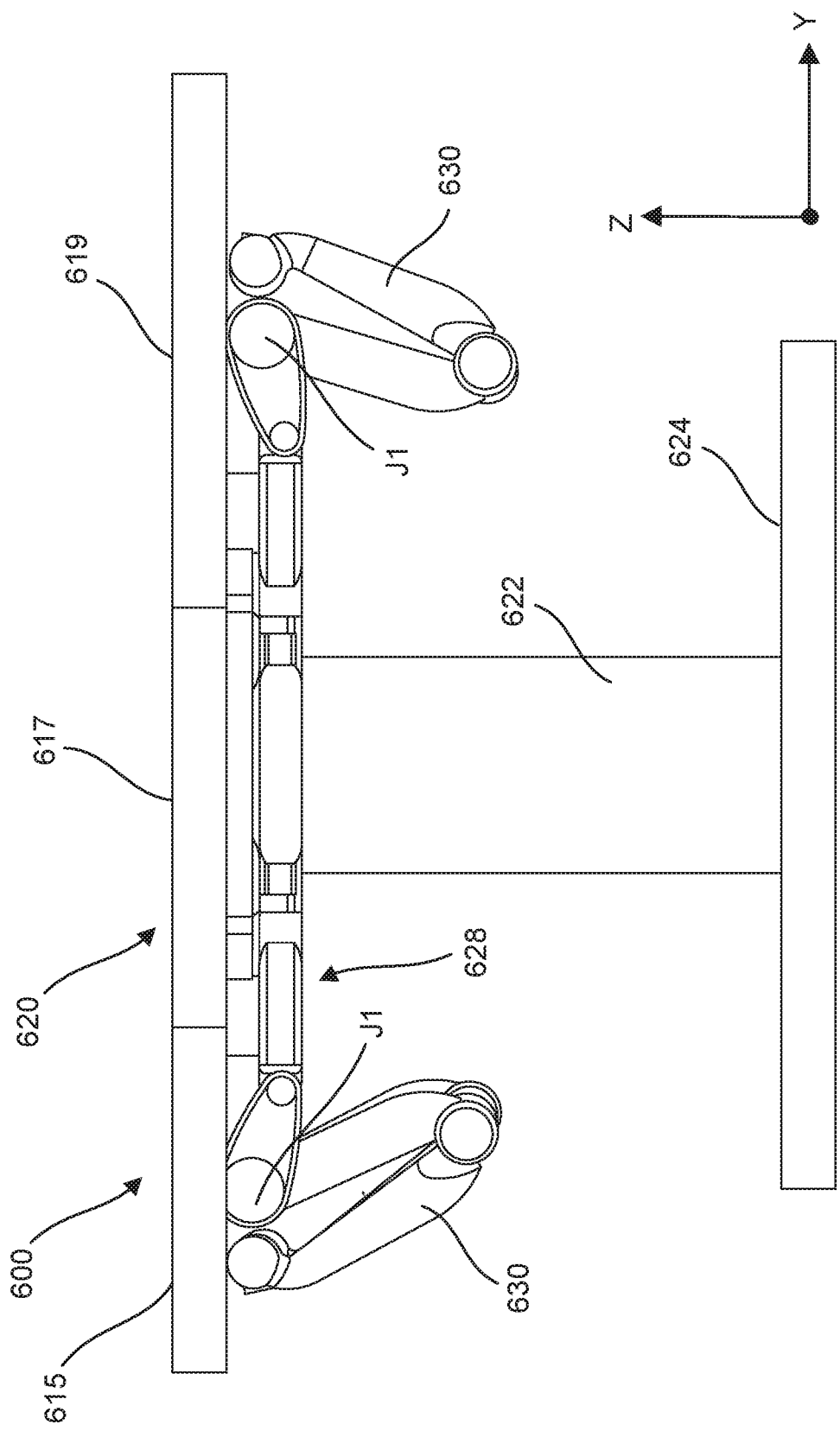
FIG. 18 is a side view of the surgical table and adapter of FIGS. 12A and 12B with two robotic arms coupled thereto and shown in a stowed position.
Figure 19:
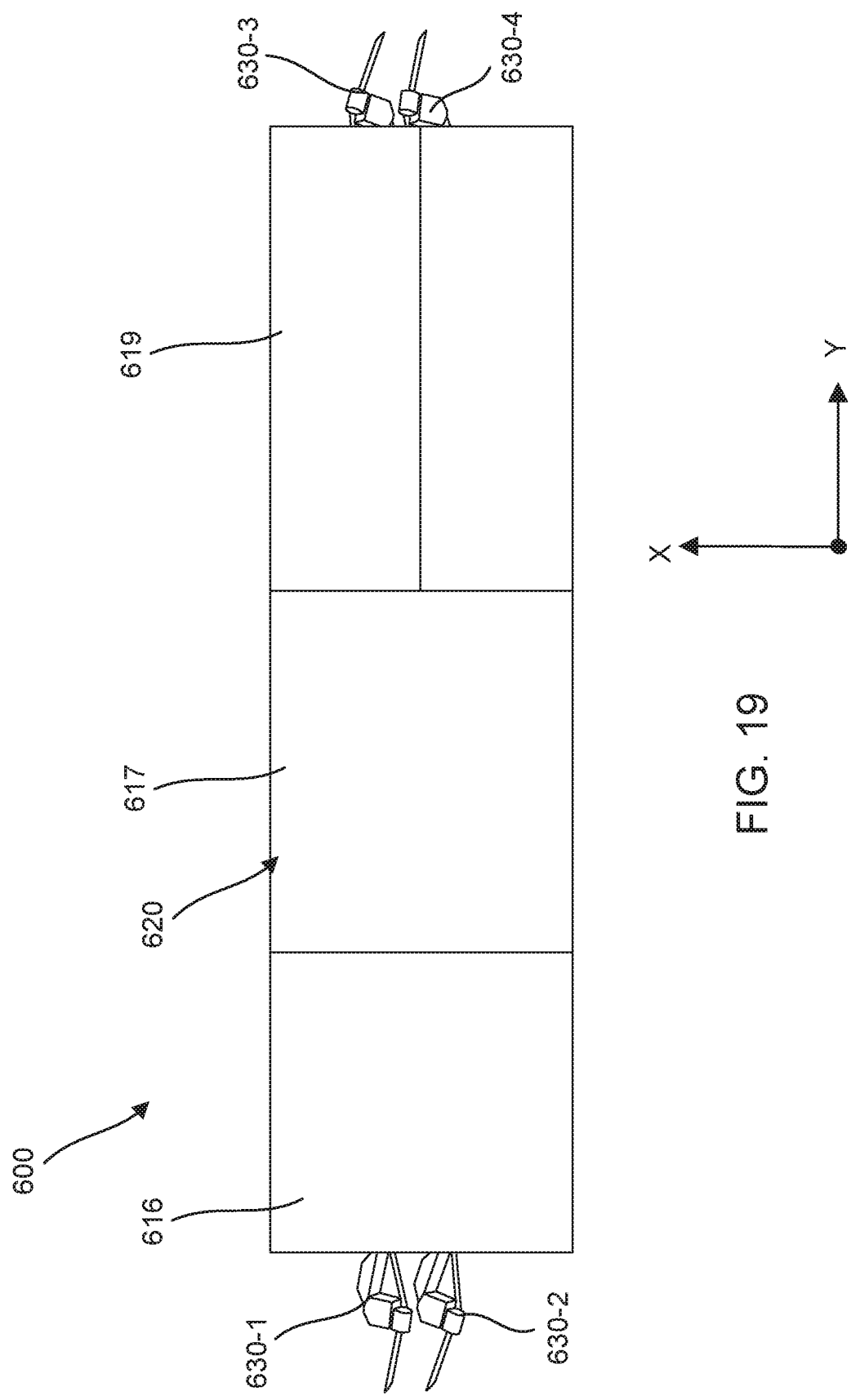
FIG. 19 is a top view of the surgical table and adapter with four robotic arms coupled thereto and shown in the stowed position.

The collective motion of the first link members 632, the second link members and the coupling portion 639 allows the adapter 628 and robotic arms 630 to move between a variety of different positions relative to the surgical table 600 during a surgical procedure. For example, adapter 628 and robotic arms 630 can be moved to a stowed position as shown, for example, in FIGS. 18 and 19. FIG. 18 illustrates one arm 630 disposed beneath the head section 616 and one arm 630 disposed beneath the leg section 619 of the table top 620. FIG. 19 illustrates two arms 630 disposed beneath the head section 616 and two arms 630 disposed beneath the leg section 619 of the table top 620.

As with the previous embodiment, the arms 630 and the link members 632 and 634 can be moved to the stowed position via the first joint 633 and the second joint 635. For example, the arms 630 and the second links 634 can be lowered via the second joint 635. The first links 632, second links 634 and the arms 630 can then be pivoted to the ends via the first joints 633. The arms 630 can be further folded via the joints between the links/segments of the arms 630. Similarly, the first link member 632 and the second link member 634 can be further folded or collapsed. The arms 630 and adapter 628 are thus in a folded or collapsed configuration in the stowed position.

Figure 20:
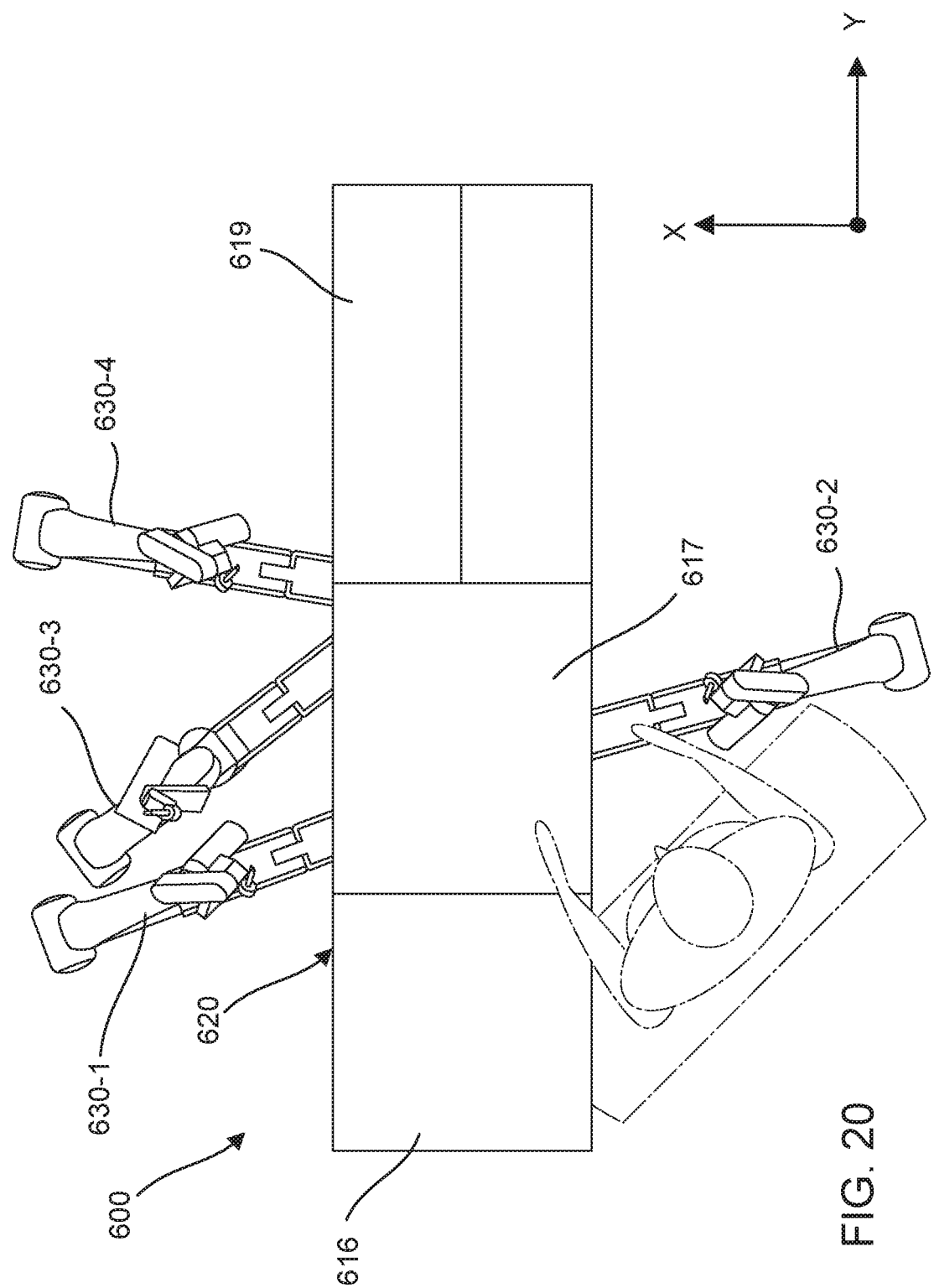

The adapter 628 and arms 630 can also be moved from the stowed position to various operating positions in a similar manner by moving the arms 630 via the first joints 633, the second joints 635 and the coupling joint 645. FIGS. 20-24 illustrate the robotic arms 630 and adapter 628 in various different operating positions for particular surgical procedures. FIG. 20 illustrates an example operating position that includes three arms 630 on one side of the table 600 and one arm 630 on the opposite side of the table 630. To achieve this configuration, a pair of arms 630 coupled to the adapter 628 on one end of the table 600 (arms 630-3 and 630-4 in FIG. 20) can be pivoted via the first joint 633 and/or by sliding the location of the first joint 633 laterally to position both arms 630 on one side of the table 600. The third arm 630 can be one of arms 630 (630-3) from the pair of arms 630 on the opposite end of the table 600 (arms 630-3 and 630-4 in FIG. 20). The other arm 630-4 can be moved to the opposite side of the table 600.

Figure 21:
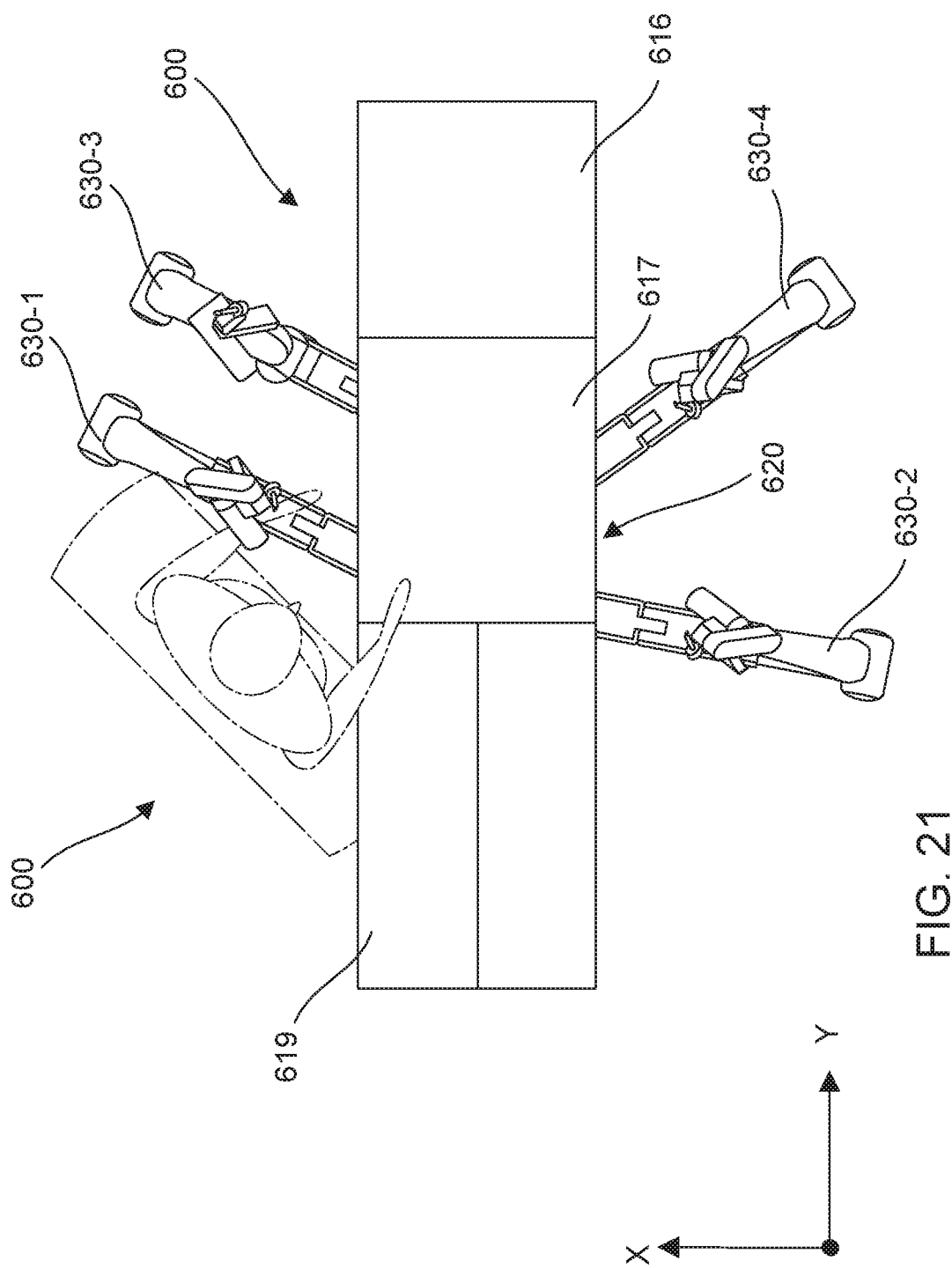
Figure 22:
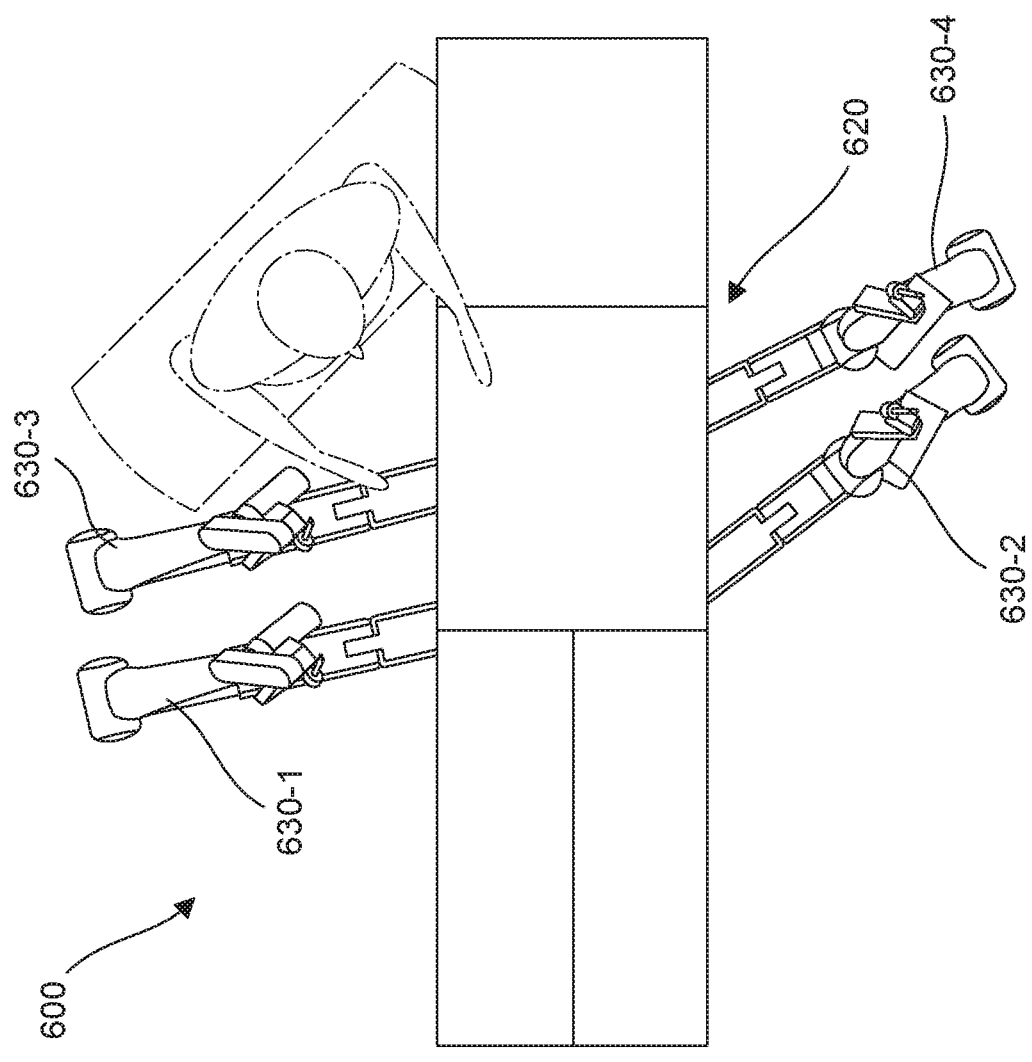
Figure 23:
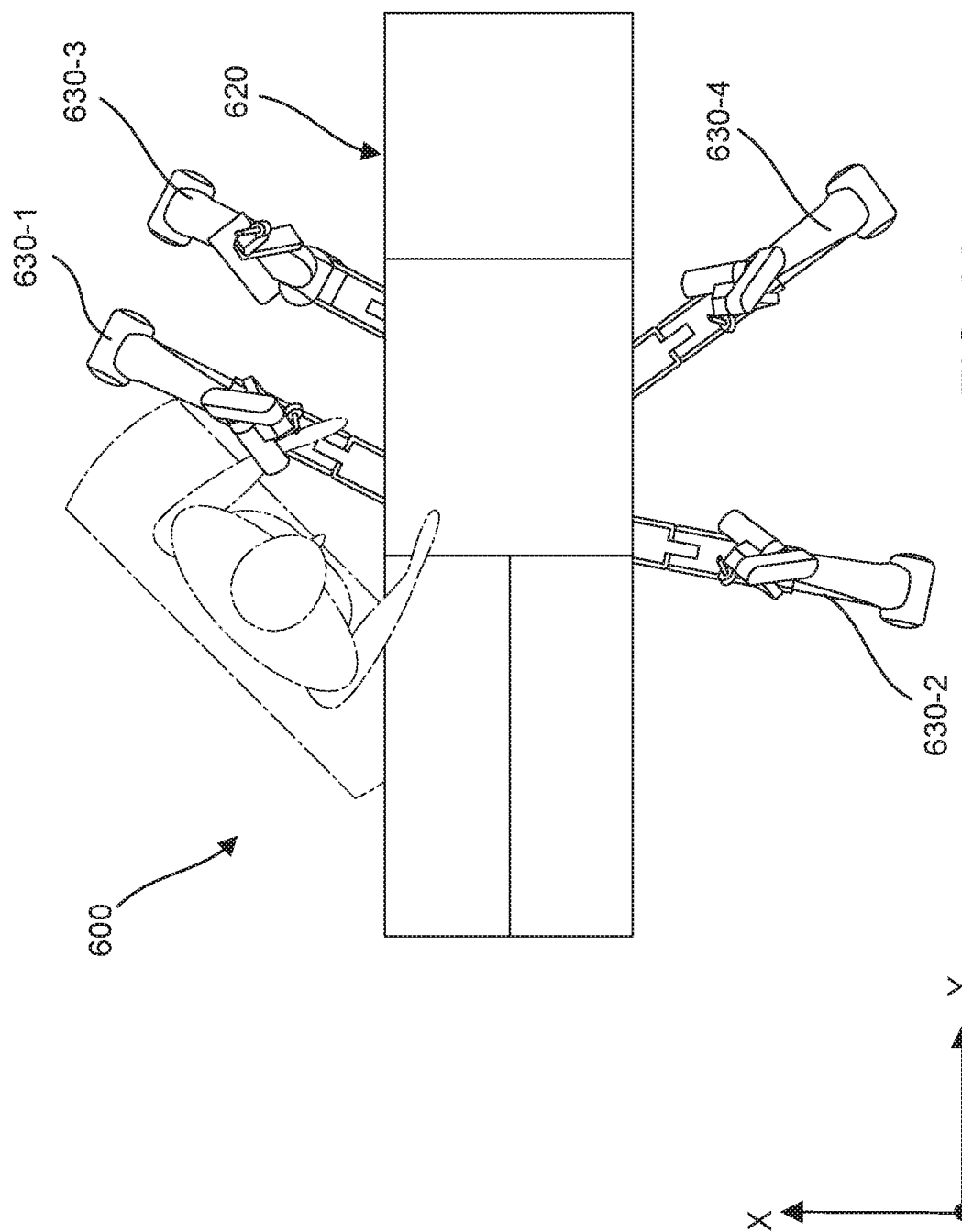

FIGS. 21-24 each illustrate an example operating position that includes two arms 630 on each side of the table 600. Such an operating position may be used to perform, for example, a LAR procedure, a lobectomy procedure, gastric bypass, prostatectomy or other surgical procedure. To achieve this configuration, one arm from each pair of arms 630 disposed at both ends of the table 600 can be moved (pivoted, slid) to a side of the table 600, and the other arm of each pair of arms can be moved (pivoted, slid) to the opposite side of the table 600. For example, as shown in FIG. 21, arms 630-1 and 630-2 are mounted to the adapter at the leg end 619 of the table 600 and arm 630-1 is moved to one side of the table 600 and arm 630-2 is moved to an opposite side of the table 600. Similarly, arms 630-3 and 630-4 are mounted to the adapter at the head end 616 of the table 600 and arm 630-3 is moved to one side of the table 600 and arm 630-4 is moved to an opposite side of the table 600. In each of the operating positions, the target joint J1 for each arm 630 is positioned at a target location relative to the table top 620 such that a distal end of the arm 630 (e.g., with medical instrument thereon) can be disposed in a desired treatment zone and can be maneuvered within a range of motion in a treatment region or zone.

Figure 26:
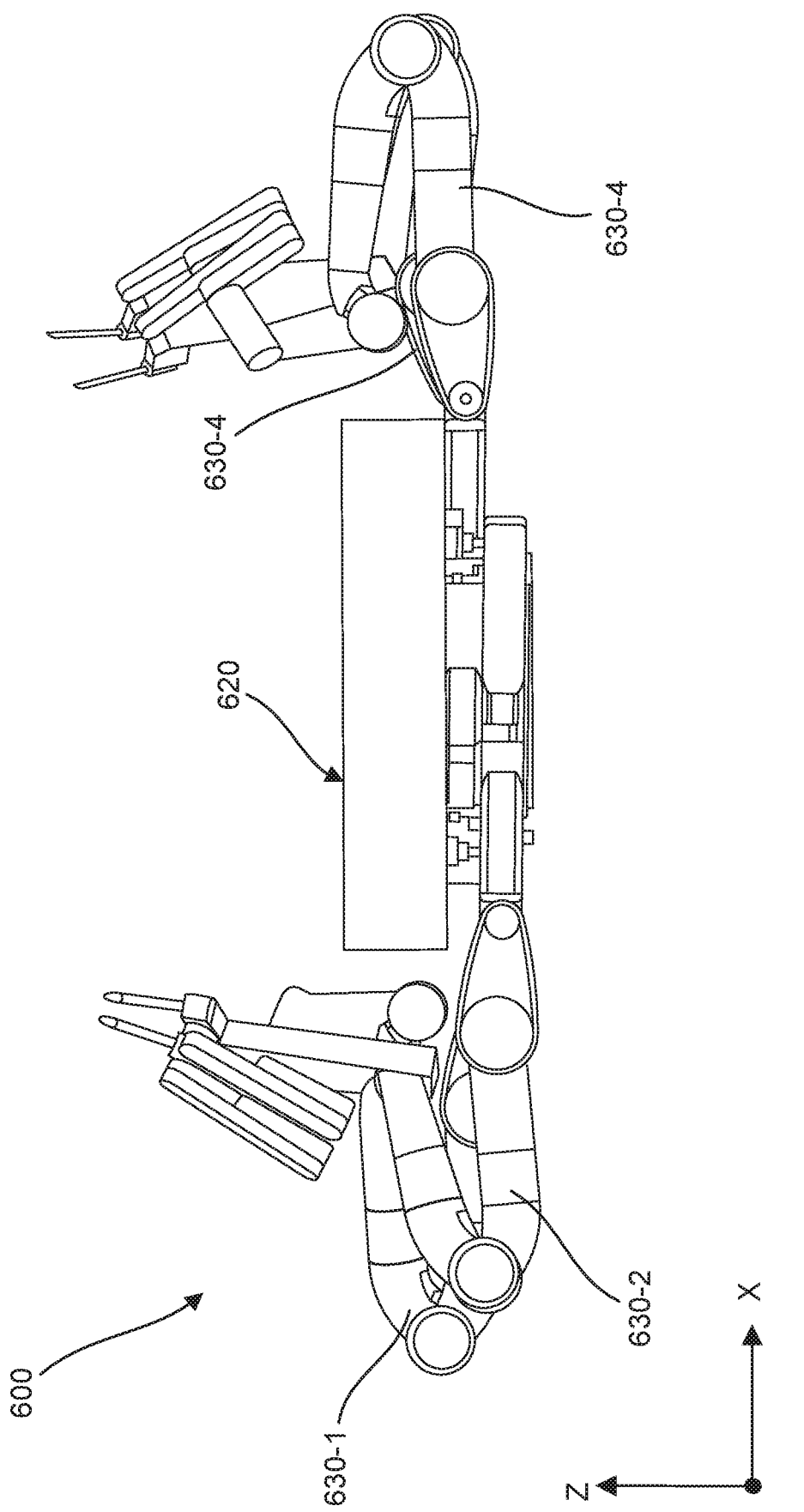
FIG. 26 is an end view of a portion of the surgical table (support and base not shown) and adapter of FIGS. 12A and 12B with four robotic arms coupled thereto and shown in a parked position.

As described above, during a surgical procedure, the adapter 628 and arms 630 can also be moved to a parked position to provide clearance, for example, for medical staff to access the patient or to provide clearance for other devices such as an imaging device. FIGS. 25 and 26 each illustrate an example parked position in which the arms 630-1, 630-2, 630-3, and 630-4 are disposed out of the way of the sides of the table 600 to provide clearance for medical personnel or other equipment. The arms 630 can be moved by pivoting and/or sliding the arms 630 as described above. When the need for the clearance has passed, the arms 630 can then be placed back into the operating position with the target joints J1 disposed at the target treatment locations relative to the table top 620.

FIGS. 27-30D illustrate a surgical table 700 and adapter 728 according to another embodiment. The surgical table 700 includes a table top 720, a support 722 (also referred to herein as pedestal) and a base 724 (shown in FIG. 29, which illustrates the base 724 and support 722 of the table 700 in an exploded view disposed spaced apart from the table top 720, and FIG. 30A, which includes a schematic illustration of the table 700). As described above for previous embodiments, the support 722 can be mounted to the base 724, which can be fixed to the floor of an operating room, or can be movable relative to the floor. The table top 720 includes a head section 716, a torso section 717 and a leg section 719. The table top 720 can also include an arm section(s) (not shown). The table top 720 has a top surface on which a patient can be disposed. The support 722 can provide for movement of the table top 720 in a desired number of degrees of freedom as described above for previous embodiments. Also as described above, movement of the table top 720 and/or its constituent sections may be performed manually, driven by motors, controlled remotely, etc. The surgical table 700 can also include a radio-translucent window (not shown) as described for previous embodiments.

Figure 27:
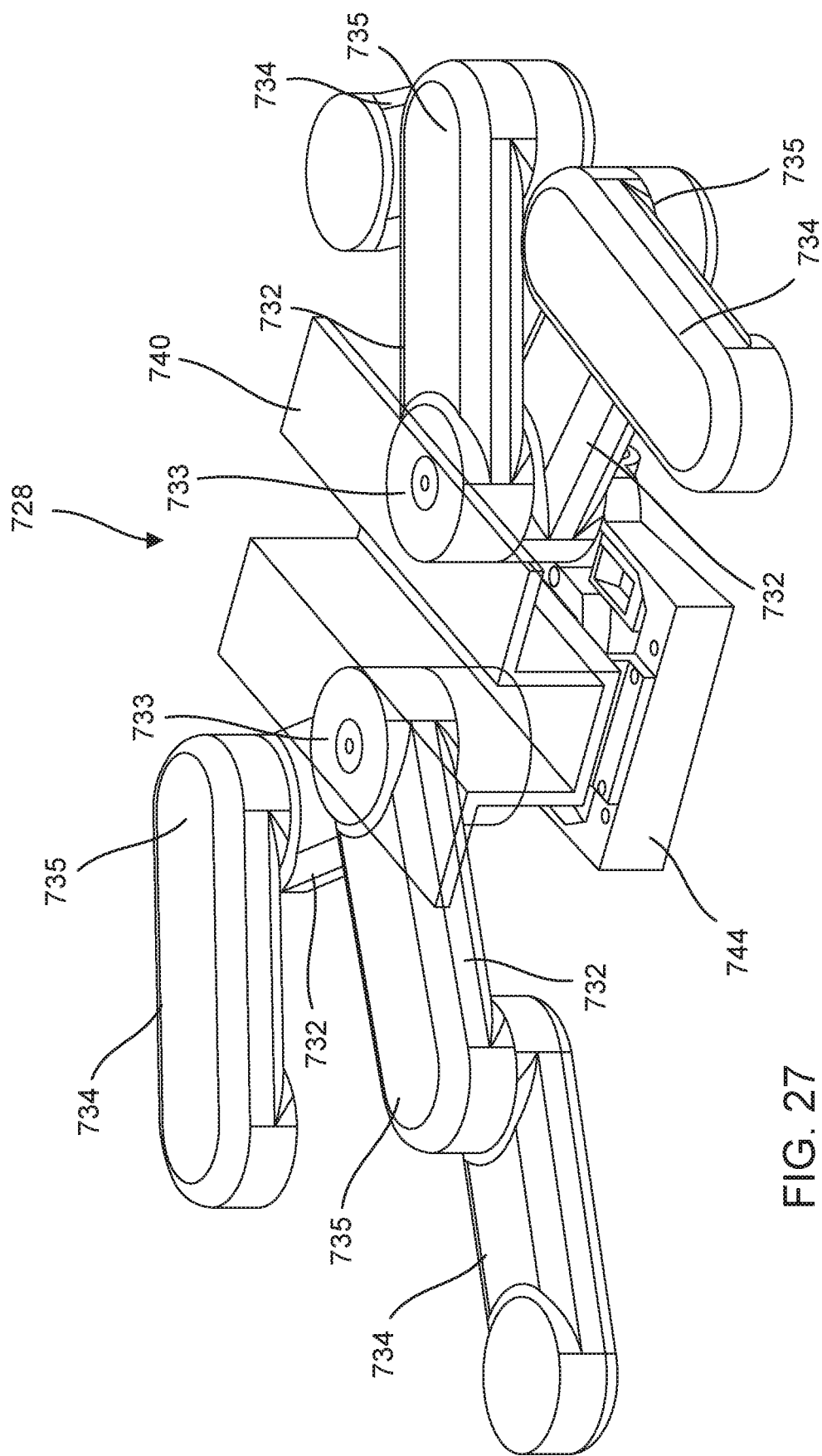
FIG. 27 is a perspective view of an adapter according to another embodiment.
Figure 28:
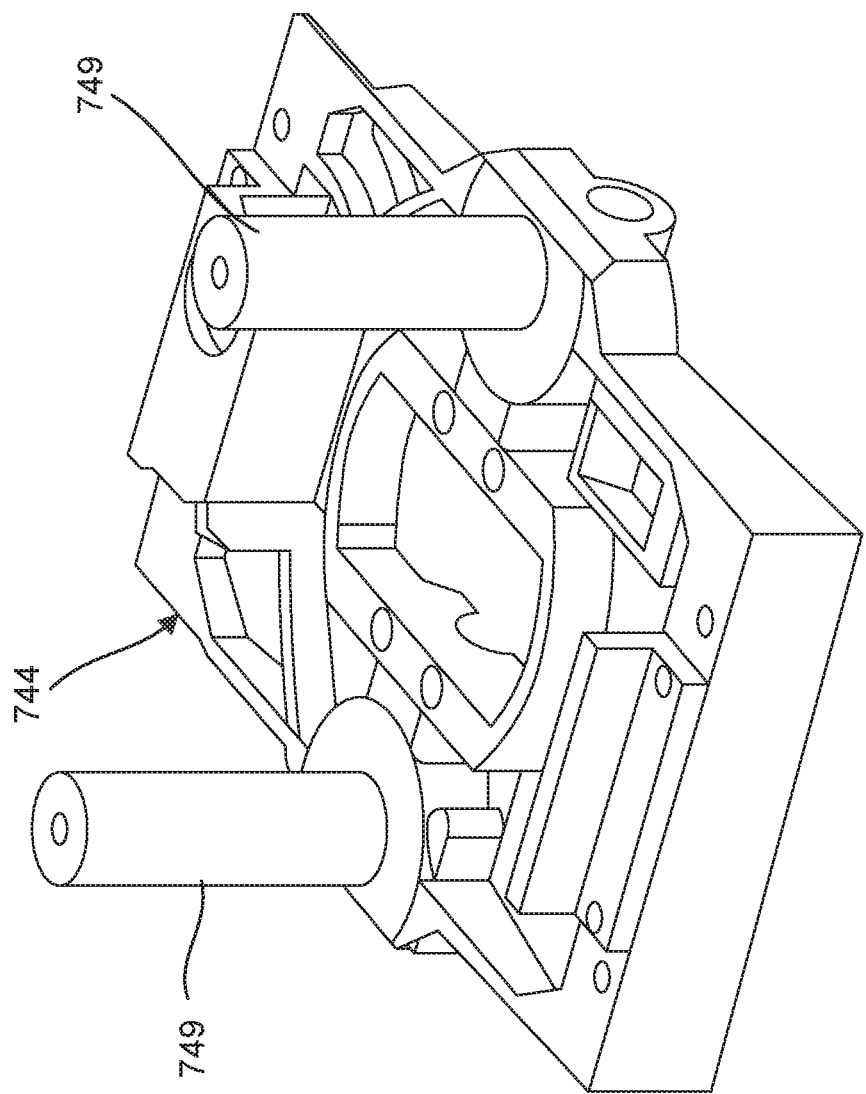
FIG. 28 is a perspective view of a mounting column for coupling the adapter of FIG. 27 to a surgical table, according to an embodiment.
Figure 29:
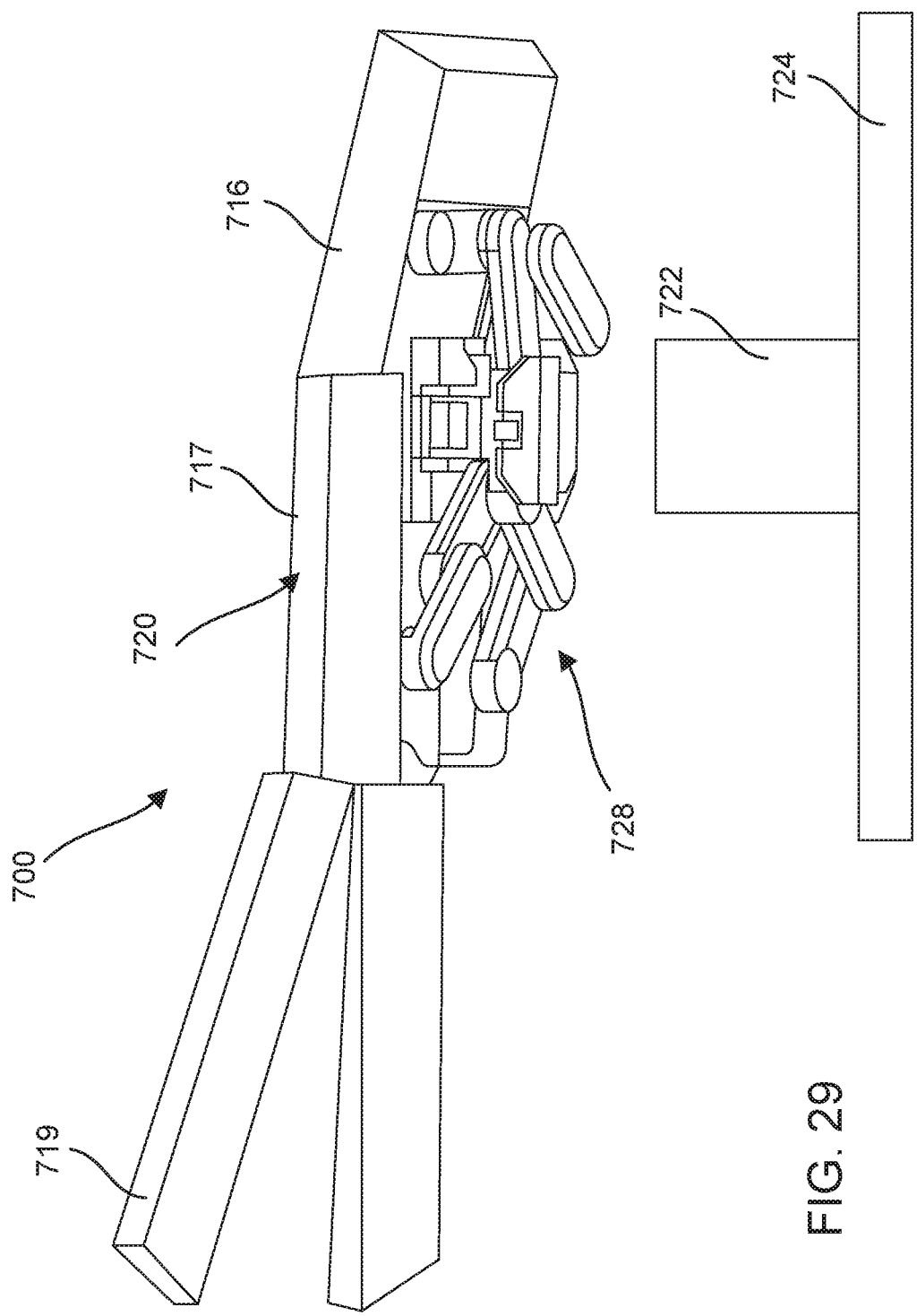
FIG. 29 is a partial exploded view of a surgical table with the adapter and mounting column of FIGS. 27 and 28 coupled thereto.

The adapter 728 can be coupled to the table 700 and is constructed similar to and can function the same as or similar to the adapter 628. As shown in FIG. 27, as with the previous embodiment, the table adapter 728 (also referred to herein as "adapter") can be coupled to the surgical table 700 via a column mount 744 (FIG. 28) that is coupled to the support 722. The adapter 728 includes a u-shaped table interface mechanism 740 (FIG. 27) that can be mounted to a pair of pivot mounts 749 coupled to or integrally formed with the column mount 744 as described in more detail below. The adapter 728 further includes multiple first link members 732 that are each pivotally coupled to the table interface mechanism 740 at one of the pivot mounts 749 as shown in FIG. 27. As with the previous embodiment, two first link members 732 are coupled to the interface mechanism 740 at a single shared first joint 733 on the pivot mounts 749 on each side of the interface mechanism 740. In this embodiment, the adapter 728 is coupled to the table 700 such that the shared first joints 733 are disposed at the ends of the table 700 beneath the head section 716 and the leg section 719.

The adapter 728 also includes multiple second link members 734 that are each coupled to one of the first link members 732 at a second joint 735. The second joint 735 provides the lift mechanism for moving the second link member 734 vertically. In this embodiment, the second joint 735 includes a pivotal coupling between the first link member 732 and the second link member 734. The first link members 732 and the second link members 734 can be moved between an extended configuration for use during a surgical procedure, and a folded or collapsed configuration for storage when not in use, in a similar manner as described above for adapter 628.

Figure 30A:
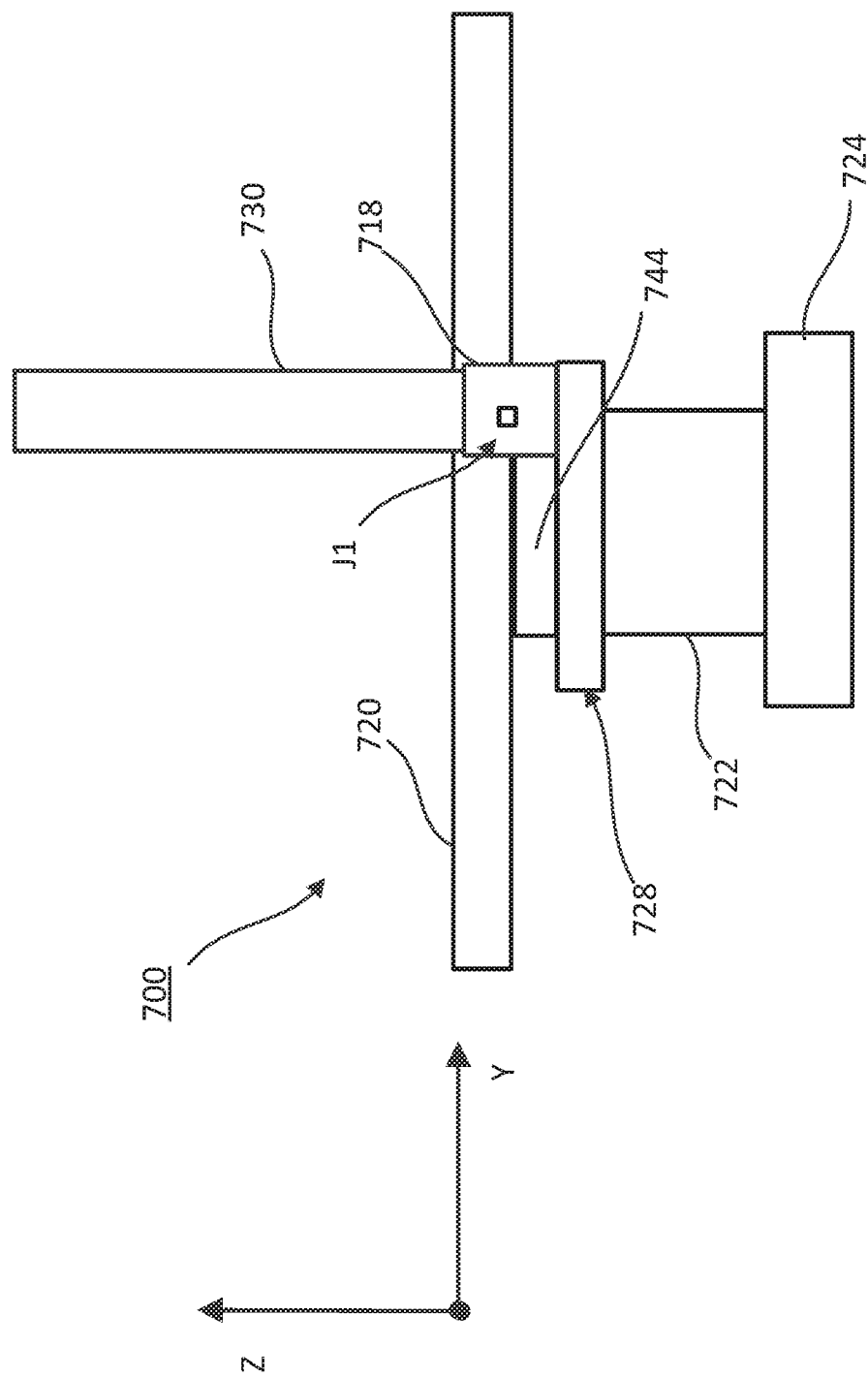
FIG. 30A is a schematic illustration of a side view off the surgical table, adapter and column mount of FIGS. 27-29 and a robotic arm coupled to the adapter.

Each of the second link members 734 can also be coupled to a robotic arm 730 (shown schematically in FIG. 30A) at a coupling 718 (FIG. 30A). The coupling 718 can include a coupling portion 739 (shown schematically in FIGS. 30B and 30C) disposed at a free end of the second link member 734 as described above for previous embodiments. In some embodiments, the adapter 728 can include a coupling portion 739 similar to the coupling portion 639 described above for adapter 628 that can be pivotally coupled to the second link member 734 at a coupling joint 718. In such an embodiment, the coupling portion 739 can be pivotally coupled to a coupling portion 738 (shown schematically in FIGS. 30B and 30C) at a mounting end of a robotic arm 730. As with the previous embodiment, in some embodiments, the target joint J1 of the robotic arm 730 coupled to the adapter 728 can be defined at the coupling 718 between the coupling portion of the adapter 728 and the coupling portion of the robotic arm 730. In some embodiments, the target joint J1 can be defined at a joint of the robotic arm 730. In this embodiment, the robotic arms 730 can be fixedly, semi-fixedly or releasably coupled to the adapter 728 and the adapter 728 can accommodate four arms. The robotic arms 730 can be configured the same as or similar to, and function the same as or similar to, the robotic arms 130 described above and thus, further details regarding the robotic arms are not discussed with respect to this embodiment. For example, as described above for robotic arms 130, robotic arms 730 can be coupled to the adapter 728 that can include multiple links or segments coupled together to allow the robotic arms to move between an extended configuration for use during a surgical procedure, and a folded or collapsed configuration for storage when not in use. In this embodiment, the movement of the first joint 733 and the second joint 735 (and in some cases, a coupling joint between the second link member 734 and a coupling portion (e.g., similar to coupling portion 639 described above) can provide for movement of a robotic arm 730 (and the target joint J1) coupled to the adapter 728 along and/or about the X, Y, and/or Z axes (see, e.g., FIG. 30A, with X-axis defined coming out of the page, FIG. 30B with Z-axis coming out of the page, and FIG. 30C with Y-axis coming out of the page) as described in more detail below.

More specifically, as with the previous embodiments, the first joint 733 can provide for rotational motion of the two first link members 732 coupled thereto relative to the table interface structure 740 (and table 700) about a vertical z-axis relative to a top surface of the table top 720 (e.g., the top surface of the torso section 717), and movement of the first link members 732 and second link members 734 in lateral and longitudinal directions (also referred to herein as x-direction and y-direction) relative to the top surface of the table top 720 of the surgical table 700. As described above, the second joint 735 can provide the lift mechanism to allow for vertical movement of the second link member 734 and the coupling between the second link member 734 and a robotic arm 730 coupled thereto. Thus, the motion of the first link member 732 and the second link member 734 of the adapter 728 can provide for movement of a robotic arm 730 coupled thereto along and/or about the X, Y, and/or Z axes to position the target joint J1 at a desired treatment location relative to the table top 720.

Figure 30B:
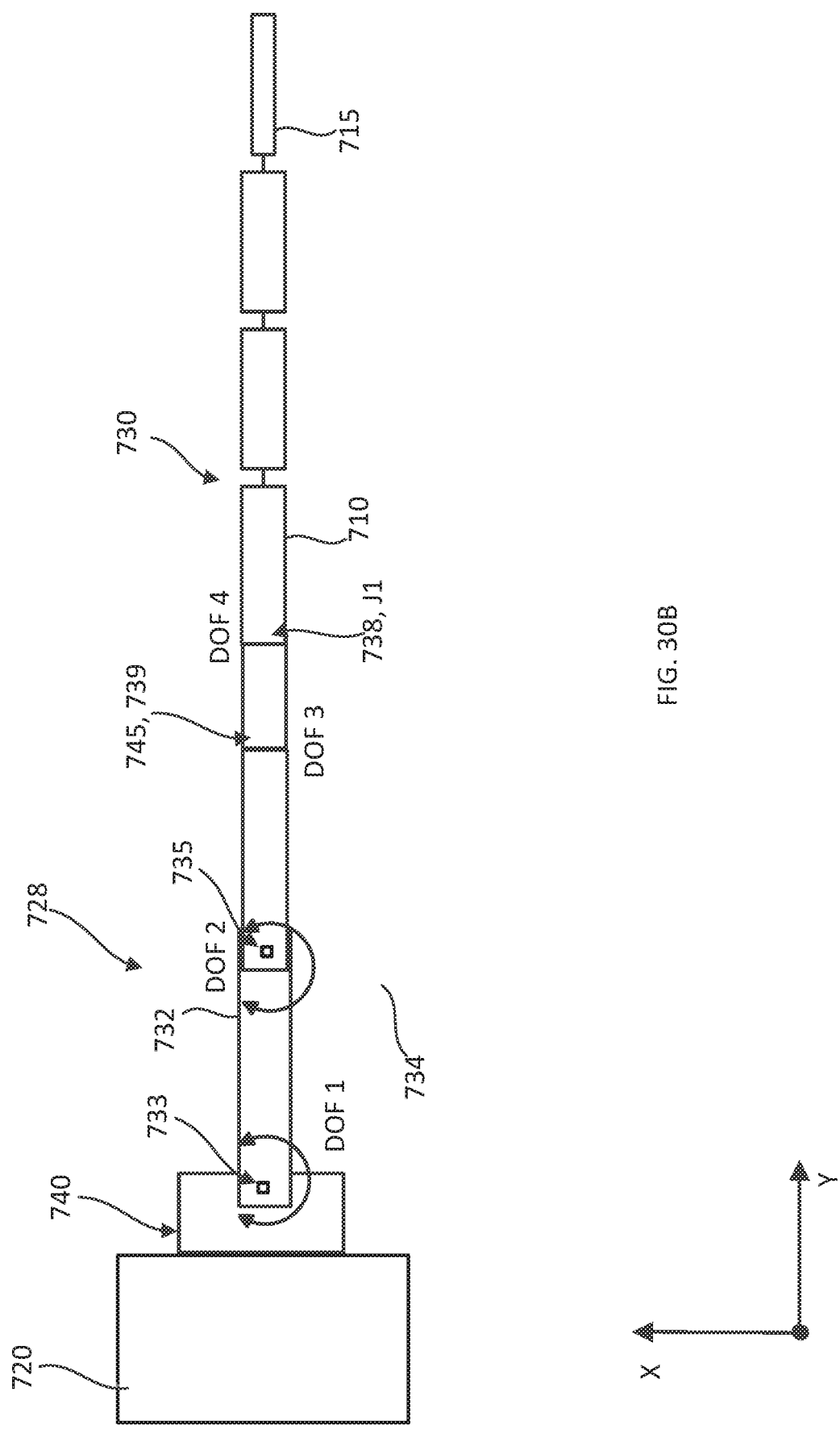
Figure 31:
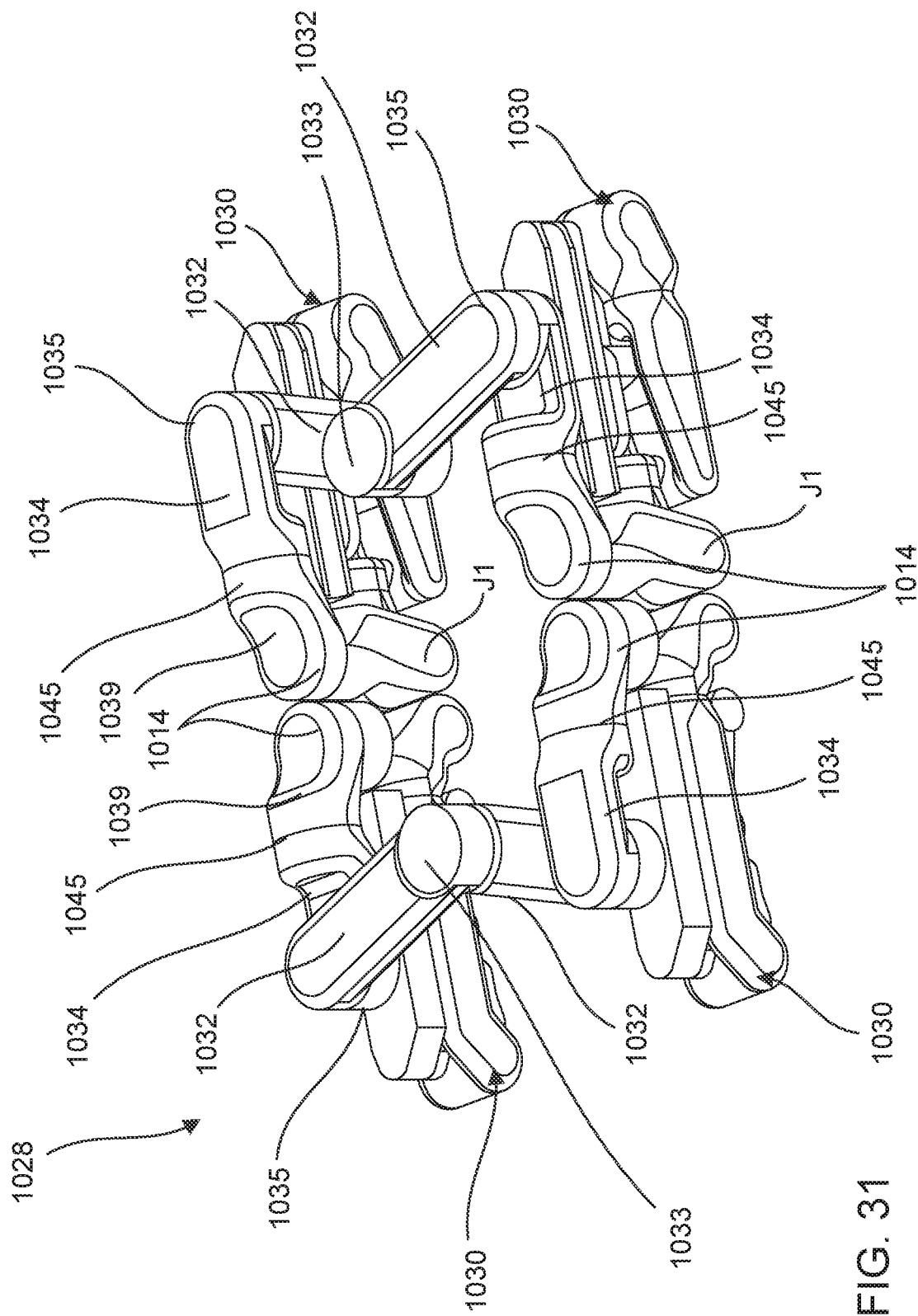
FIG. 31 is a side perspective view of an adapter according to another embodiment, and four robotic arms coupled thereto, with the adapter and robotic arms in a stowed or folded position.

FIGS. 30B and 30C are schematic illustrations of the various degrees of freedom provided by the joints of the adapter 728 and robotic arm 730, and FIG. 30D is a table listing the type of degree of freedom (e.g., rotational, linear) associated therewith. As shown in FIGS. 30B and 30C, and as described above, the interface mechanism 740 is coupleable to the support 722 of the table 700 and the first link members 732 are pivotally coupled to the interface mechanism 740 at joint 733. The pivotal joint 733 of the first link members 732 to the interface mechanism 740 allows the first link members 732 to rotate about the z-axis and provide a first degree of freedom DOF 1 at joint 733, i.e., Z-axis rotation. The joint 735 between the first link member 732 and the second link member 734 is also a rotational or pivotal joint that can pivot about the z-axis and provide a second degree of freedom DOF 2 at joint 735, i.e., Z-axis rotation. As described above, in this embodiment, the adapter 728 can also include a joint 745 (shown in FIGS. 30B and 30C) between the second link member 734 and a coupling portion 739 of the robotic arm 730 that can pivot about a horizontal axis and provide a third degree of freedom DOF 3 (best shown in the side view illustration of FIG. 30C) that is X-Y plane rotation. Similarly, the joint J1 between the coupling portion 739 and the coupling portion 738 of the robotic arm 730 is also a pivotal joint that can pivot about a horizontal axis and provide a fourth degree of freedom DOF 4 (best shown in the side view illustration of FIG. 30C) that is X-Y plane rotation. Although not labeled in FIGS. 30B and 30C, the various joints between links 710 of the arm 730 and a medical instrument 715 disposed on the distal end of the robotic arm 730 can provide additional motion of the arm relative to a patient (e.g., a target treatment location on the patient) disposed on the table 700, and therefore, additional degrees of freedom.

The collective motion of the first link members 732, the second link members 734 allows the adapter 728 and robotic arms 730 to move between a variety of different positions relative to the surgical table 700 during a surgical procedure. For example, as described above for previous embodiments, the adapter 728 and robotic arms 730 can be moved to a stowed position in a similar manner as described above for adapter 628 and arms 630. As with the previous embodiment, the arms 730 and the link members 732 and 734 can be moved to the stowed position via the first joint 733 and the second joint 735. For example, the arms 730 and the second links 734 can be lowered via the second joint 735. The first links 732, second links 734 and the arms 730 can then be pivoted to the ends via the first joints 733. The arms 730 can be further folded via the joints between the links/segments of the arms 730. Similarly, the first link members 732 and the second link members 734 can be further folded or collapsed. The arms 730 and adapter 728 are thus in a folded or collapsed configuration in the stowed position.

The adapter 728 and arms 730 coupled thereto can also be moved from the stowed position to various operating positions in a similar manner as described above for adapter 628, by moving the arms 730 via the first joints 733 and the second joints 735 (and in some cases via a coupling joint between the second link members 734 and a coupling portion). For example, the robotic arms 730 and adapter 728 can be moved to various different operating positions for particular surgical procedures. For example, as described above for adapter 628, the adapter 728 can have four arms 730 coupled thereto; two on each end of the table 700. The adapter 728 and arms 730 can be moved to an operating position that includes three arms 730 on one side of the table 700 and one arm 730 on the opposite side of the table 730. To achieve this configuration, a pair of arms 730 coupled to the adapter 728 on one end of the table 700 can be pivoted via the first joint 733 to position both arms 730 on one side of the table 700. The third arm 730 can be one of the arms 730 from the other pair of arms 730 on the opposite end of the table 700, which can be moved to the opposite side of the table 700.

As described above, during a surgical procedure, the adapter 728 and arms 730 can also be moved to a parked position to provide clearance, for example, for medical staff to access the patient or to provide clearance for other devices such as an imaging device. The adapter 728 and arms 730 can be moved to the parked position by pivoting the arms 730 as described above for movement of the adapter 728 and arms 730 between stowed and operating positions. When the need for the clearance has passed, the arms 730 can then be placed back into the operating position with the target joints J1 disposed at the target treatment locations relative to the table top 720.

Figure 33:
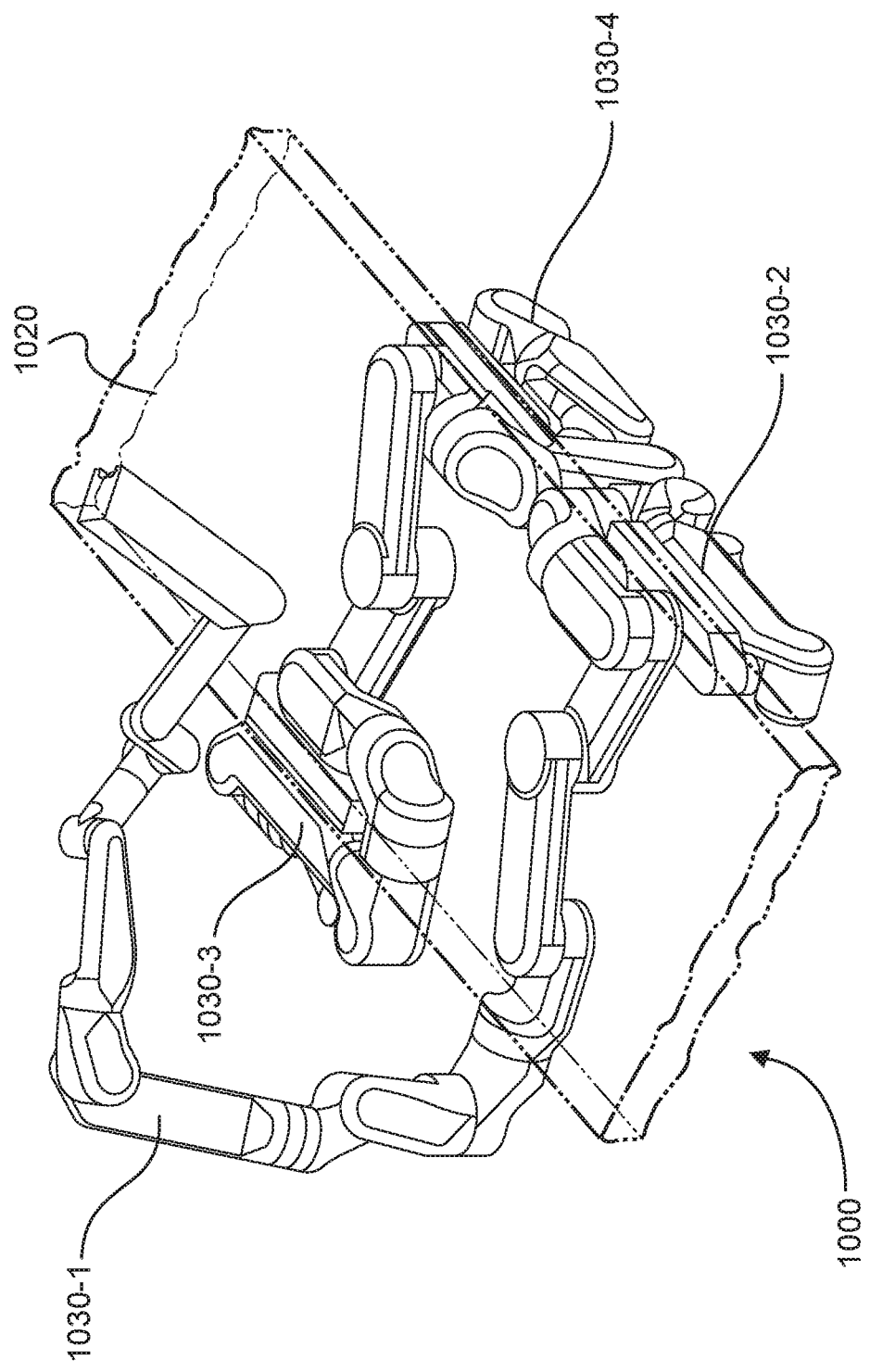
FIG. 33 is an end perspective view of the adapter and robotic arms of FIG. 31 shown disposed partially under a portion of a surgical table top (shown cut-away and transparent), with one of the robotic arms in an operating or extended position.

FIGS. 31-34C illustrate an adapter according to another embodiment. An adapter 1028 can be coupled to a surgical table 1000 (see FIG. 33) that includes a table top 1020 (a portion of the table top 1020 is shown in FIG. 33 and transparent for illustrative purposes), a support 1022 (shown schematically in FIG. 34A) and a base (not shown). The surgical table 1000 can include the same or similar components and function in the same or similar manner as the surgical tables described above, and therefore, is not described in detail with respect to this embodiment.

Figure 34A:
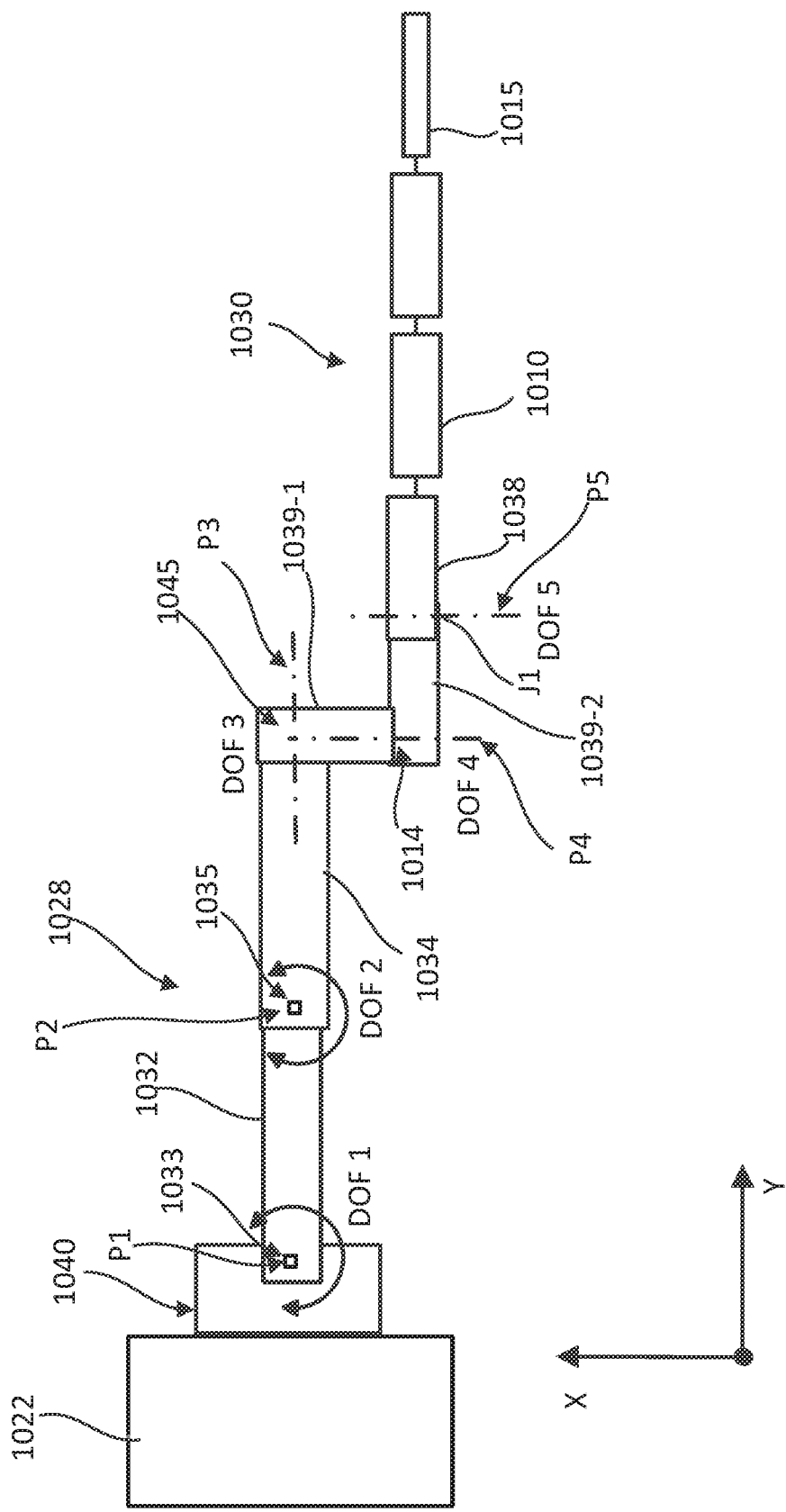
FIGS. 34A and 34B are a schematic top view and side view, respectively, of the adapter and a robotic arm of FIGS. 31-33, illustrating the degrees of freedom between the joints of the adapter and robotic arm.

The table adapter 1028 (also referred to herein as "adapter") includes a table interface mechanism 1040 (shown schematically in FIGS. 34A and 34B) that can be coupled to the support 1022 (FIG. 34A). The adapter 1028 further includes multiple first link members 1032 that are each pivotally coupled to the table interface mechanism 1040 at a single shared first joint 1033 such that the first link members 1032 can pivot about a pivot axis P1 as shown in the schematic illustration of FIG. 34B. Similar to the adapter 628, in this embodiment, the adapter 1028 can be coupled to the table 1000 such that the shared first joints 1033 are disposed at the ends of the table 1000 beneath the head section and the leg section of the table top.

Figures 34B, 34C:
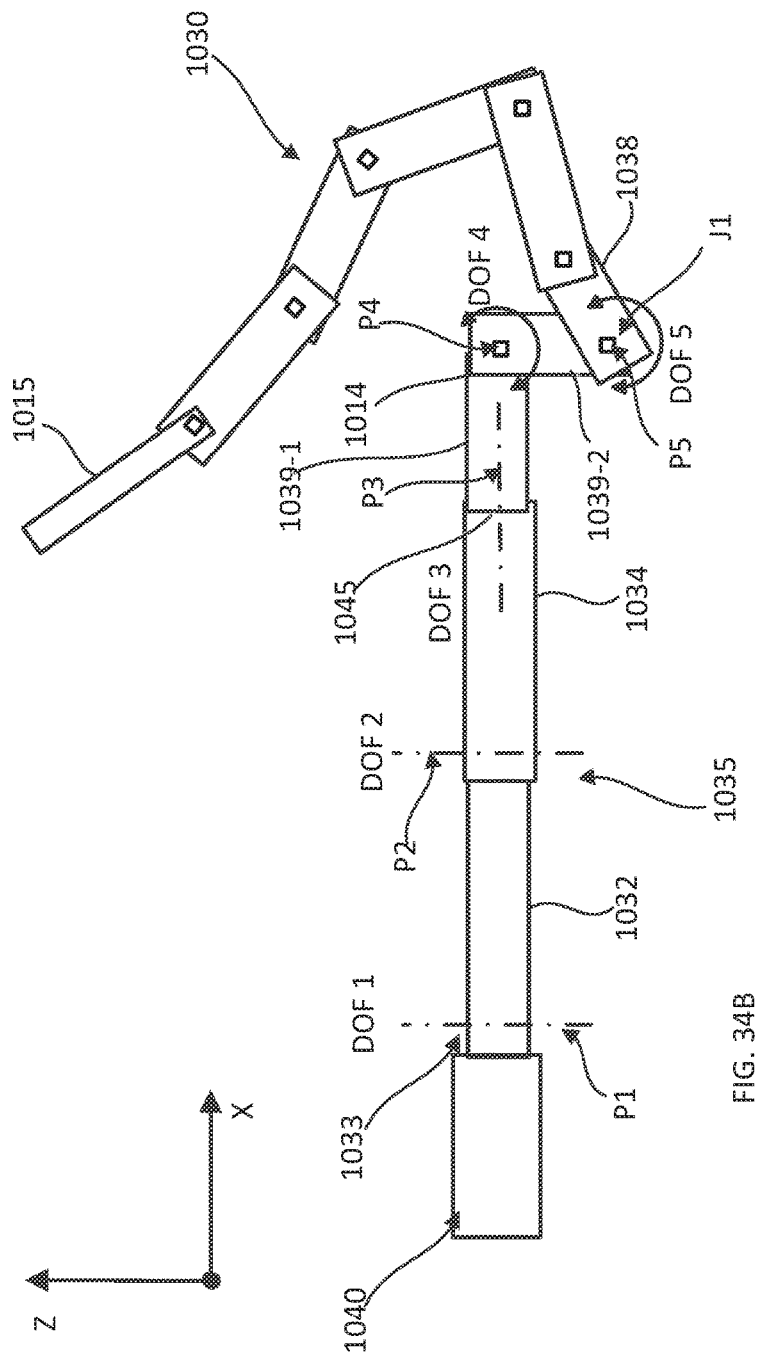
FIG. 34C is a table listing the type of degree of freedom of each of the joints.
Figure 35:
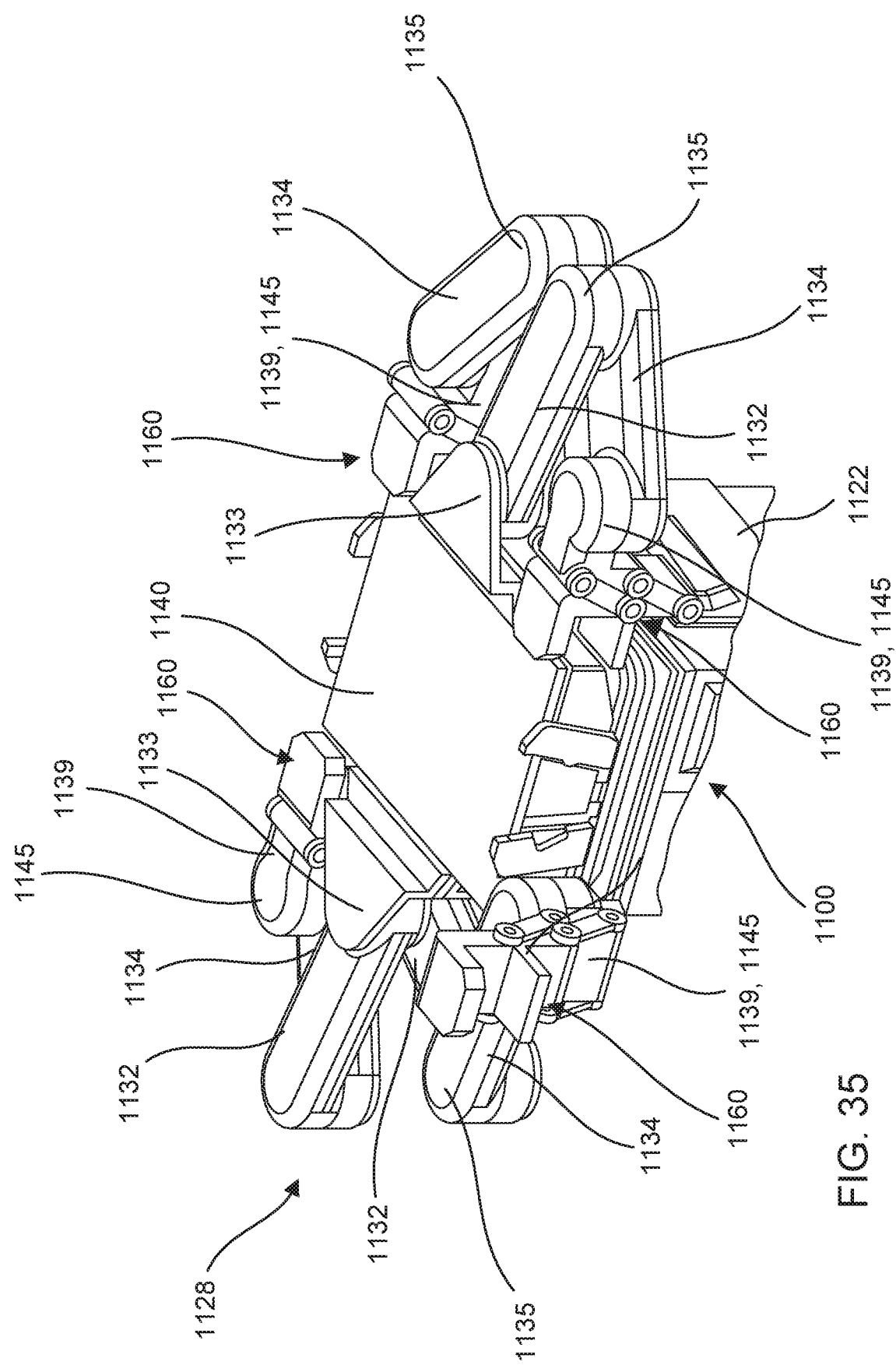
FIG. 35 is a side perspective view of an adapter according to another embodiment, shown coupled to a surgical table and in a stowed or folded position.
Figure 36:
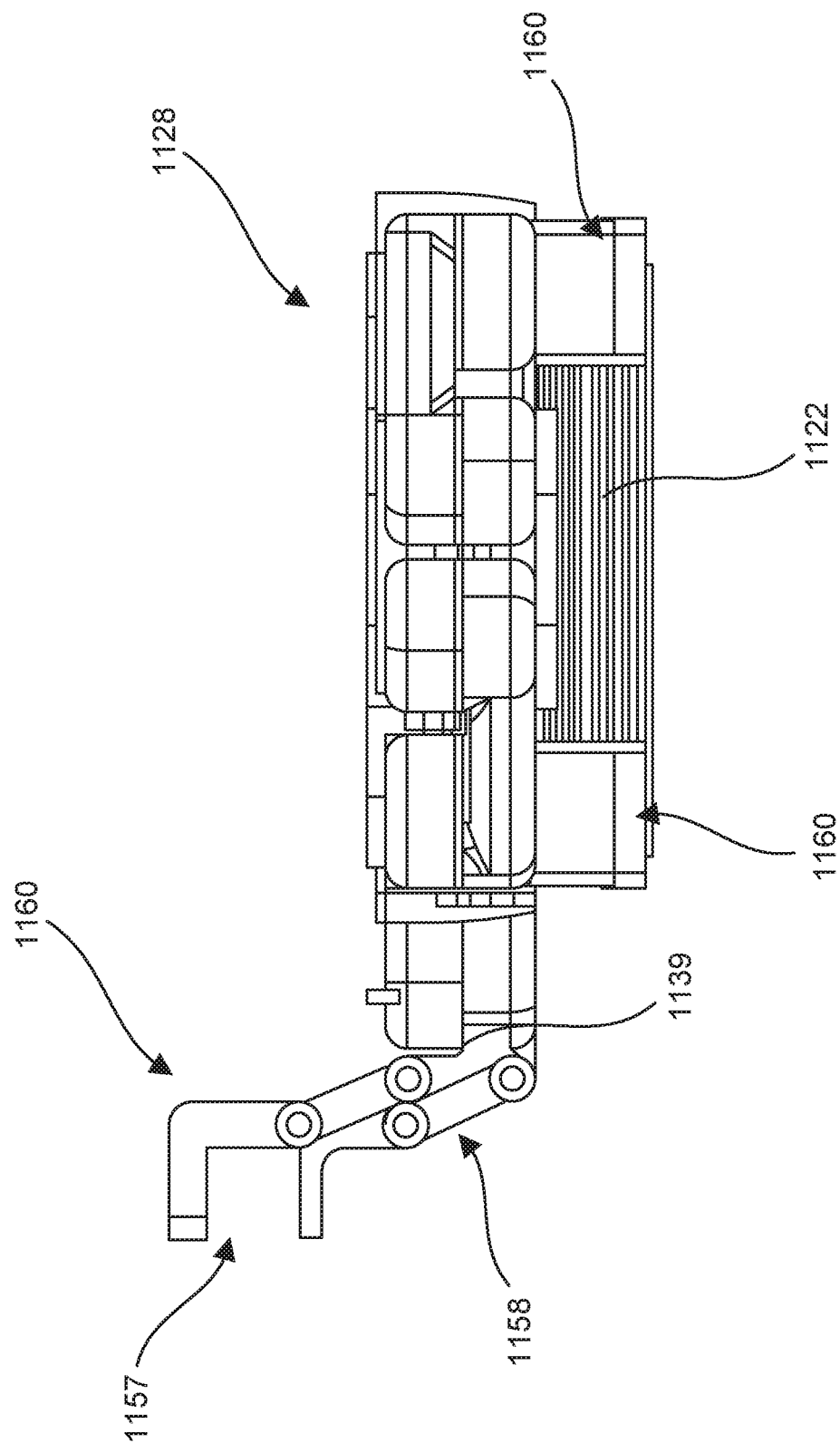
FIG. 36 is a side view of the adapter of FIG. 35, with a coupling portion of the adapter in an operating or extended position.

The adapter 1028 also includes multiple second link members 1034 that are each coupled to one of the first link members 1032 at a second joint 1035 such that the second link member 1034 can pivot about a second pivot axis P2 (see FIG. 34B). Each of the second link members 1034 can also pivotally coupled to a coupling portion 1039 at a joint 1045 and can pivot about a third pivot axis P3 (FIGS. 34A and 34B). The coupling portion 1039 includes a first portion 1039-1 and a second portion 1039-2 that are pivotally coupled to each other at a joint 1014 and can pivot about a fourth pivot axis P4. Each coupling portion 1039-2 is coupled to a coupling portion 1038 of a robotic arm 1030 at a pivotal coupling that includes the target joint J1. The target joint J1 is a pivotal joint that can allow the coupling portion 1038 of the robotic arm 1030 to pivot about a fifth pivot axis P5. The various coupling joints between interface mechanism 1040, the first link members 1032, second link members 1034, coupling portion 1039 and the robotic arm 1030 allow the adapter 1028 and robotic arm 1030 to be moved between an extended configuration for use during a surgical procedure, and a folded or collapsed configuration for storage when not in use.

As described above for previous embodiments, the robotic arm(s) 1030 can be used to perform a surgical procedure on a patient disposed on the surgical table 1000. Each robotic arm 1030 can be configured the same as or similar to, and function the same as or similar to, the robotic arms described above and thus, specific details regarding the robotic arms are not discussed with respect to this embodiment. For example, as described above for robotic arms 130, the robotic arms 1030 can include multiple links or segments and can be moved between an extended configuration for use during a surgical procedure, and a folded or collapsed configuration for storage when not in use. The various coupling joints of the adapter 1028 and the robotic arm 1030 allow the robotic arm 1030 to be moved along and/or about the X, Y, and/or Z axes as described in more detail below.

More specifically, the first joint 1033 can provide for rotational motion of the first link members 1032 relative to the interface structure 1040 (and table 1000) about a vertical z-axis (i.e., pivot axis P1 in FIGS. 34A and 34B) relative to the top surface of the table top (e.g., the top surface of the torso section of the table top). The second joint 1035 provides for movement of the second link members 1034 to rotate about the pivot axis P2 which is also a z-axis rotation. The joint 1045 provides for the coupling portion 1039-1 to rotate about the pivot axis P3 which is coextensive with a center line of the second link member 1034 and which axis of rotation can vary depending on the orientation of the second link member 1034. The joint 1014 between the first coupling portion 1039-1 and second coupling portion 1039-2 allows the second coupling portion 1039-2 to rotate about the axis P4 which axis of rotation can vary depending on the orientation of the first coupling portion 1039-1. The J1 joint rotates about the axis P5 which rotates within the X-Y plane. The joint 1045 and the joint 1014 collectively provide a lift mechanism to allow for vertical movement of the coupling portion 1039, and the robotic arm 1030 coupled thereto. Thus, the motion of the first link member 1032, the second link member 1034, and the coupling portion 1039 of the adapter 1028 can provide for movement of the robotic arm 1030 coupled thereto along and/or about the X, Y, and/or Z axes to position the target joint J1 at a desired treatment location relative to the top surface of the table top.

FIGS. 34A and 34B are schematic illustrations of the various degrees of freedom provided by the joints of the adapter 1028 and robotic arm 1030, and FIG. 34C is a table listing the type of degree of freedom (e.g., rotational, linear) associated therewith. As shown in FIGS. 34A and 34B, and as described above, the interface mechanism 1040 is coupleable to the support 1022 of the table 1000 and the first link members 1032 are pivotally coupled to the interface mechanism 1040 at joint 1033 and pivot about the pivot axis P1 to provide a first degree of freedom DOF 1 that is Z-axis rotation. The joint 1035 between the first link member 1032 and the second link member 1034 is also a rotational or pivotal joint that is also Z-axis rotation (i.e., pivot axis P2) and provide a second degree of freedom DOF 2. The joint 1045 between the second link member 1034 and the coupling portion 1039 is also a rotational or pivotal joint that can pivot about the axis P3 and provide a third degree of freedom DOF 3 that is rotation in a direction that varies depending on the orientation of the second link member 1034. Similarly, the joint 1014 between the first coupling portion 1039-1 and the second coupling portion 1039-2 is also a rotational or pivotal joint that can pivot about the axis P4 and provide a fourth degree of freedom DOF 4 that is rotation in a direction that varies depending on the orientation of the first coupling portion 1039-1. The joint J1 between the coupling portion 1039-2 and the coupling portion 1038 of the robotic arm 1030 is also a pivotal joint that can pivot about a horizontal axis and provide a fifth degree of freedom DOF 5 that is X-Y plane rotation. Although not labeled in FIGS. 34A and 34B, the various joints between links 1010 of the arm 1030 and a medical instrument 1015 disposed on the distal end of the robotic arm 1030 can provide additional motion of the arm relative to a patient (e.g., a target treatment location on the patient) disposed on the table 1000, and therefore, additional degrees of freedom.

As described above for previous embodiments, the collective motion of the various components of the adapter 1028 allow the robotic arms 1030 to move between a variety of different positions relative to the surgical table 1000 during a surgical procedure. For example, adapter 1028 and robotic arms 1030 can be moved to a stowed or folded position to provide clearance or access to the table top (not shown). In the stowed position, the arms 1030 and adapter 1028 are each in a folded or collapsed configuration. To move the adapter 1028 and arms 1030 to the stowed position, the arms 1030 can be rotated via the joints 1033 and 1035 to a position at an end of the table, for example, beneath the table top. In the stowed position, the adapter 1028 and arms 1030 are in a position which provides clearance along the sides of the table 1000 to, for example, move a patient from a gurney onto the table top, or for anesthetic to be administered, as described above for previous embodiments.

The adapter 1028 and arms 1030 can also be disposed in a parked position (not shown) and various operating positions (not shown). In an operating position, the target joints J1 are disposed at a desired target treatment location relative to the table top to accommodate a particular surgical procedure to be performed. For example, as described for previous embodiments, the arms 1030 can be positioned with two arms on each side of the table 1000, or with one arm 1030 on one side and three arms on an opposite side of the table.

The parked position is used when access to the patient is needed, and the robotic arms 1030 are moved to a clearance position relative to the table top. In this embodiment, the robotic arms 1030 can be moved/rotated (i.e., via the movement of the link members 1032, 1034 to a position outside of a treatment zone to provide space for a medical professional to tend to the patient. When the need for the clearance has passed, the arms 1030 can then be placed back into an operating position with the target joints J1 disposed at the desired target treatment locations relative to the table top.

FIGS. 35-40C illustrate an adapter according to another embodiment. An adapter 1128 can be coupled to a surgical table 1100 (see FIG. 35) that includes a table top (not shown), a support 1122 and a base (not shown). The surgical table 1100 can include the same or similar components and function in the same or similar manner as the surgical tables described above, and therefore, is not described in detail with respect to this embodiment.

The table adapter 1128 (also referred to herein as "adapter") includes a table interface mechanism 1140 that can be coupled to the support 1122 of the table 1100. The adapter 1128 further includes multiple first link members 1132 that are each pivotally coupled to the table interface mechanism 1140 at a single shared first joint 1133 such that the first link members 1132 can pivot about a pivot axis P1 as shown in the schematic illustrations of FIGS. 40A and 40B. The adapter 1128 can be coupled to the table 1100 such that the shared first joints 1133 are disposed at the ends of the table 1100 beneath the head section and the leg section of the table top.

Figure 40A:
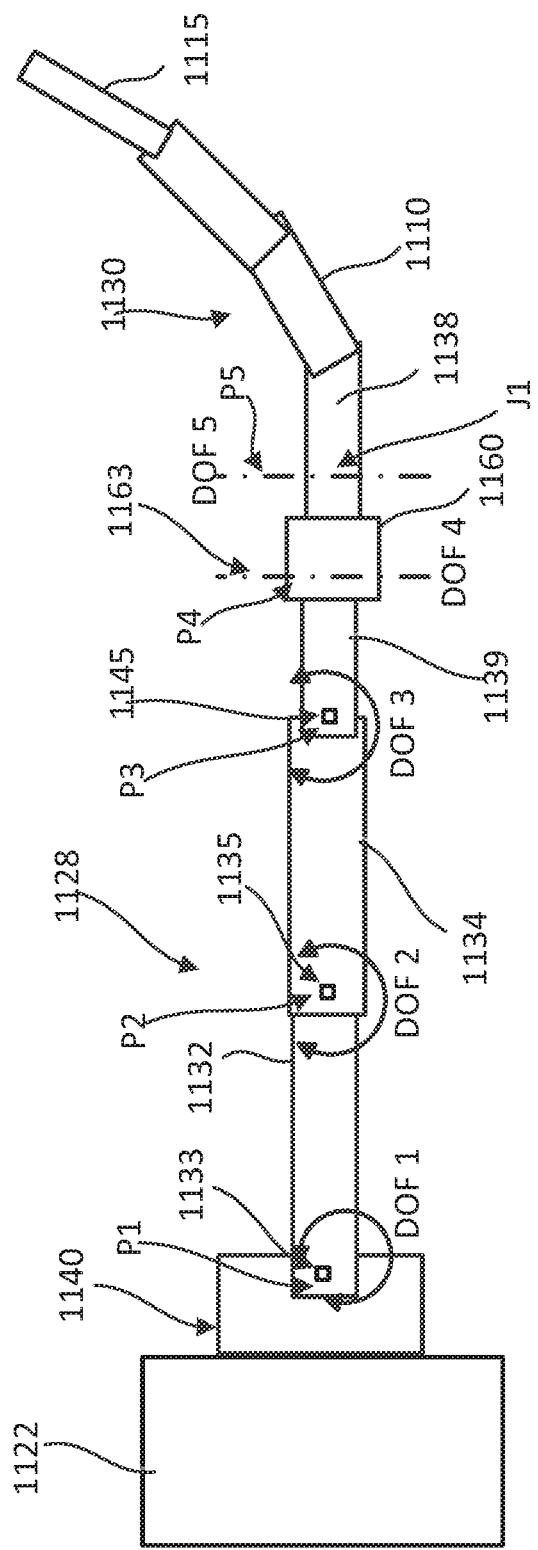
FIGS. 40A and 40B are a schematic top view and side view, respectively, of the adapter and a robotic arm of FIGS. 35-39, illustrating the degrees of freedom between the joints of the adapter and robotic arm.
Figures 40B, 40C:
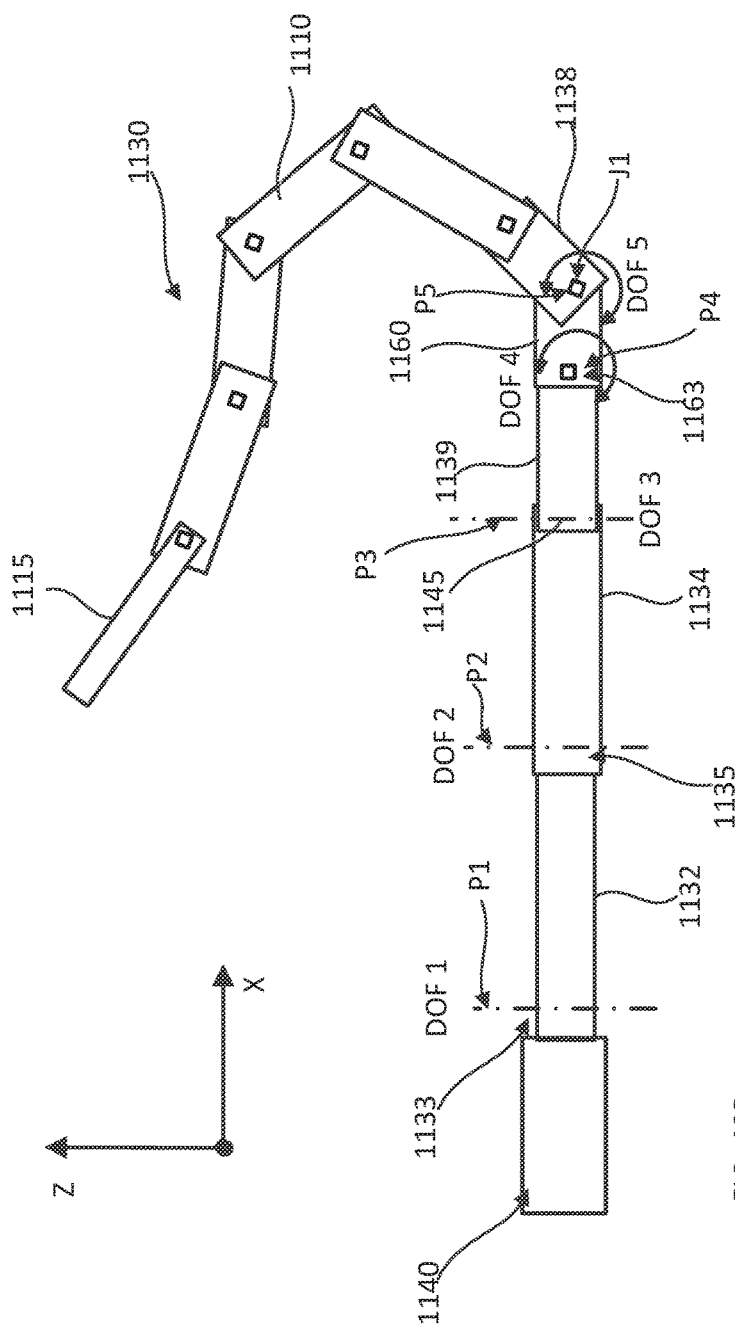
FIG. 40C is a table listing the type of degree of freedom of each of the joints.
Figure 41:
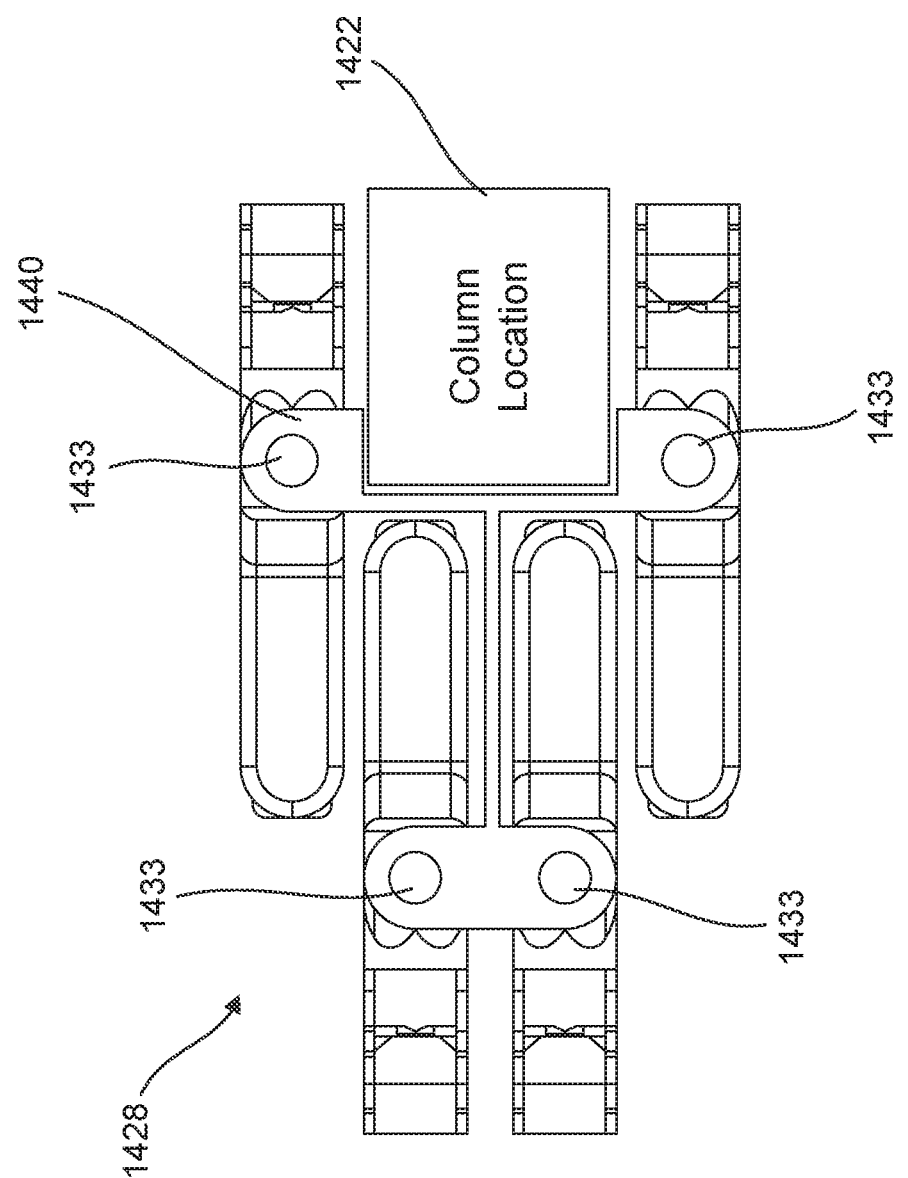
FIG. 41 is a top view of an adapter according to another embodiment, shown in a folded position.
Figure 42:
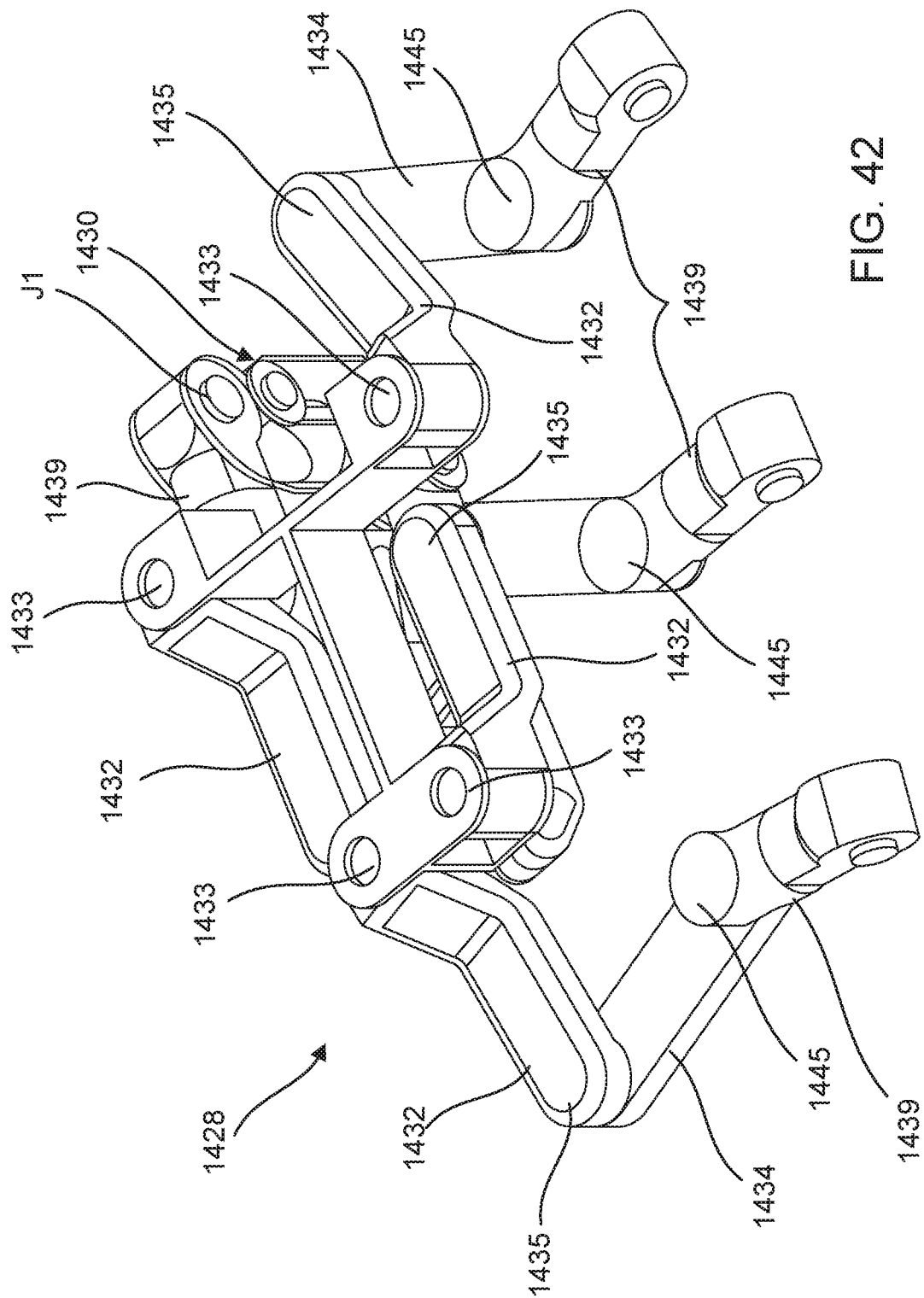
FIG. 42 is a side perspective view of the adapter of FIG. 41 with one robotic arm coupled thereto, and the adapter in an extended position.
Figure 43:
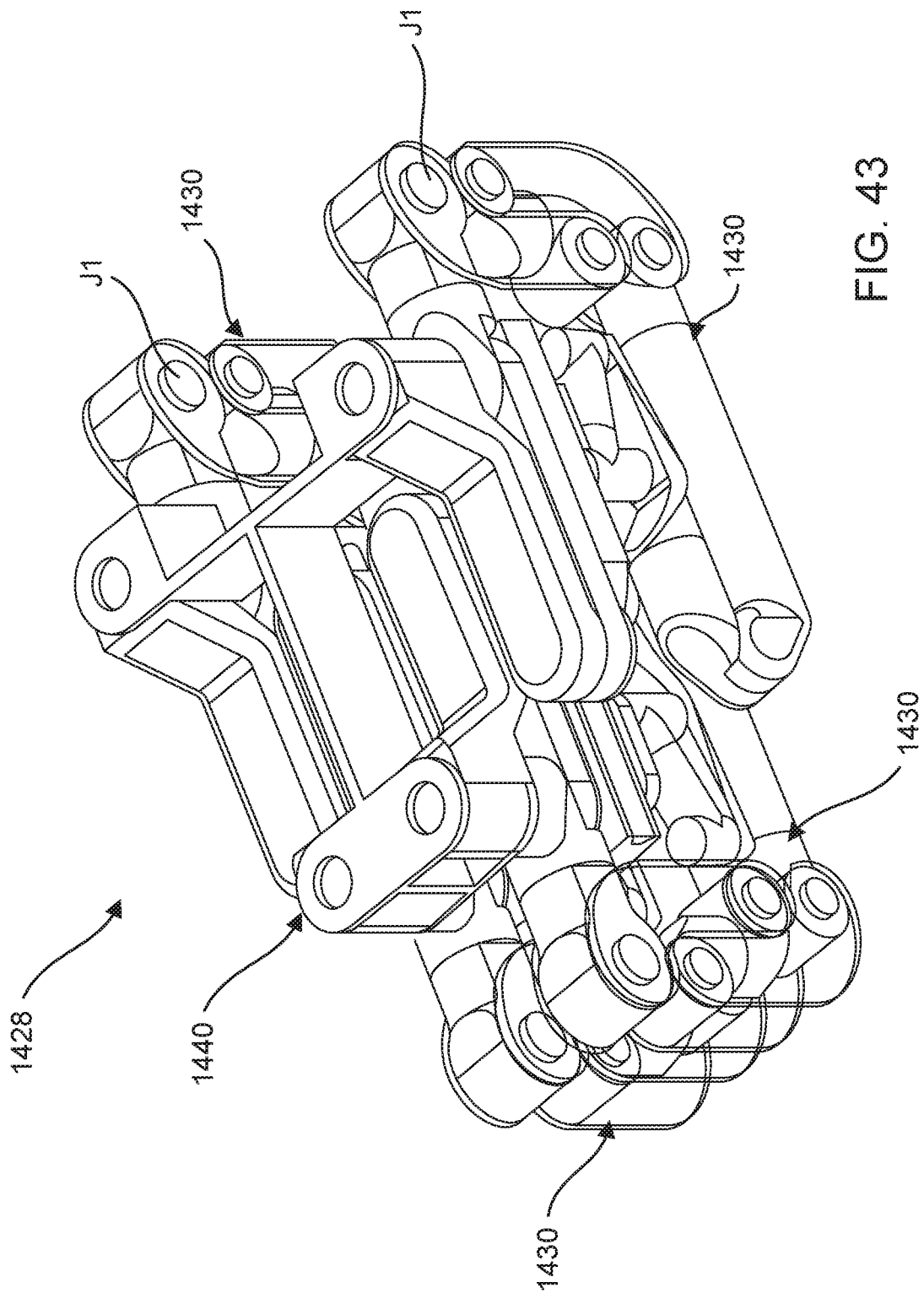
FIG. 43 is a side perspective view of the adapter of FIG. 41 with four robotic arms coupled thereto, and the adapter and robotic arms in a folded position.
Figure 44:
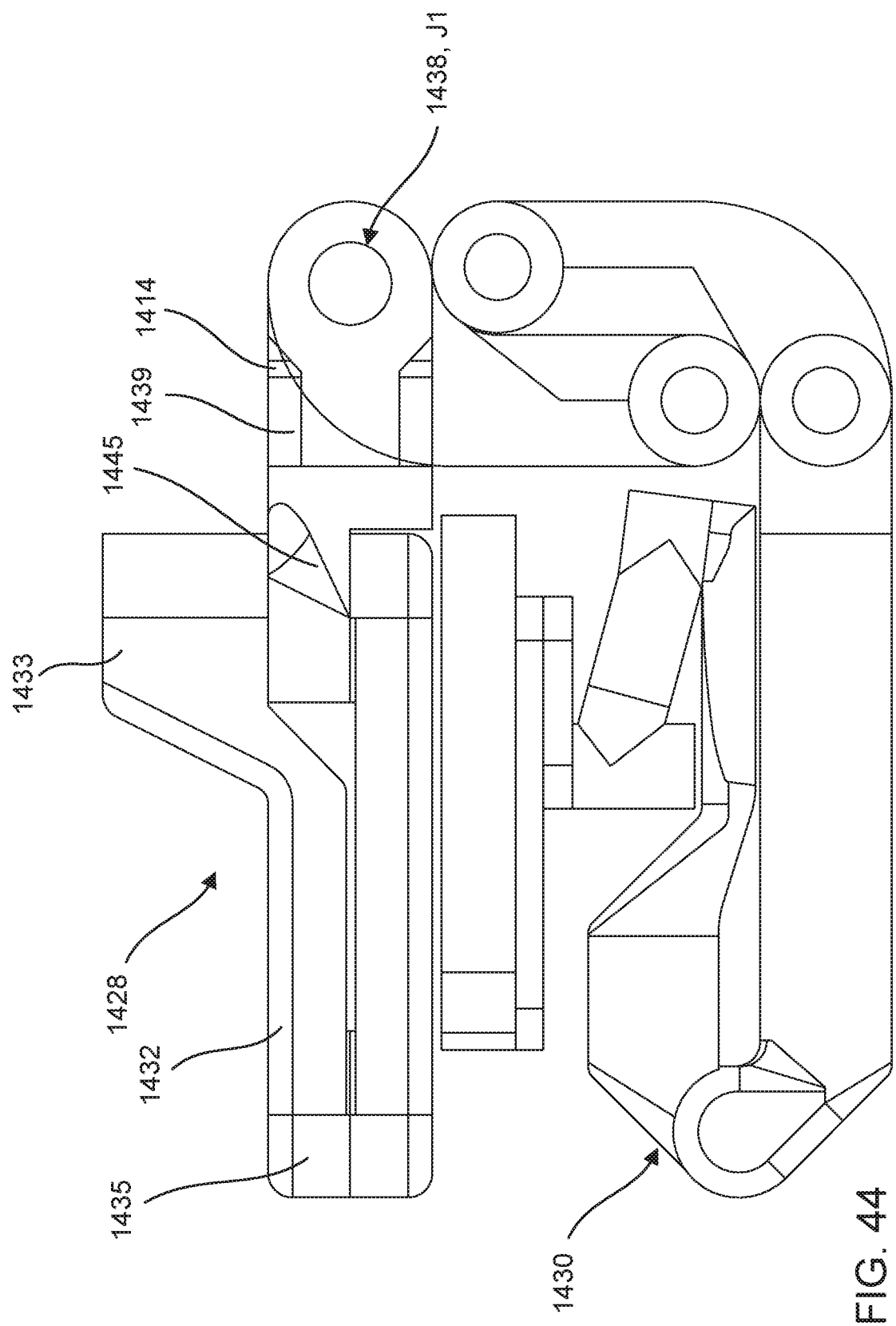
FIG. 44 is a side perspective view of a portion of the adapter of FIG. 41 with one robotic arm coupled thereto, and the adapter and robotic arm in a folded position.
Figure 45:
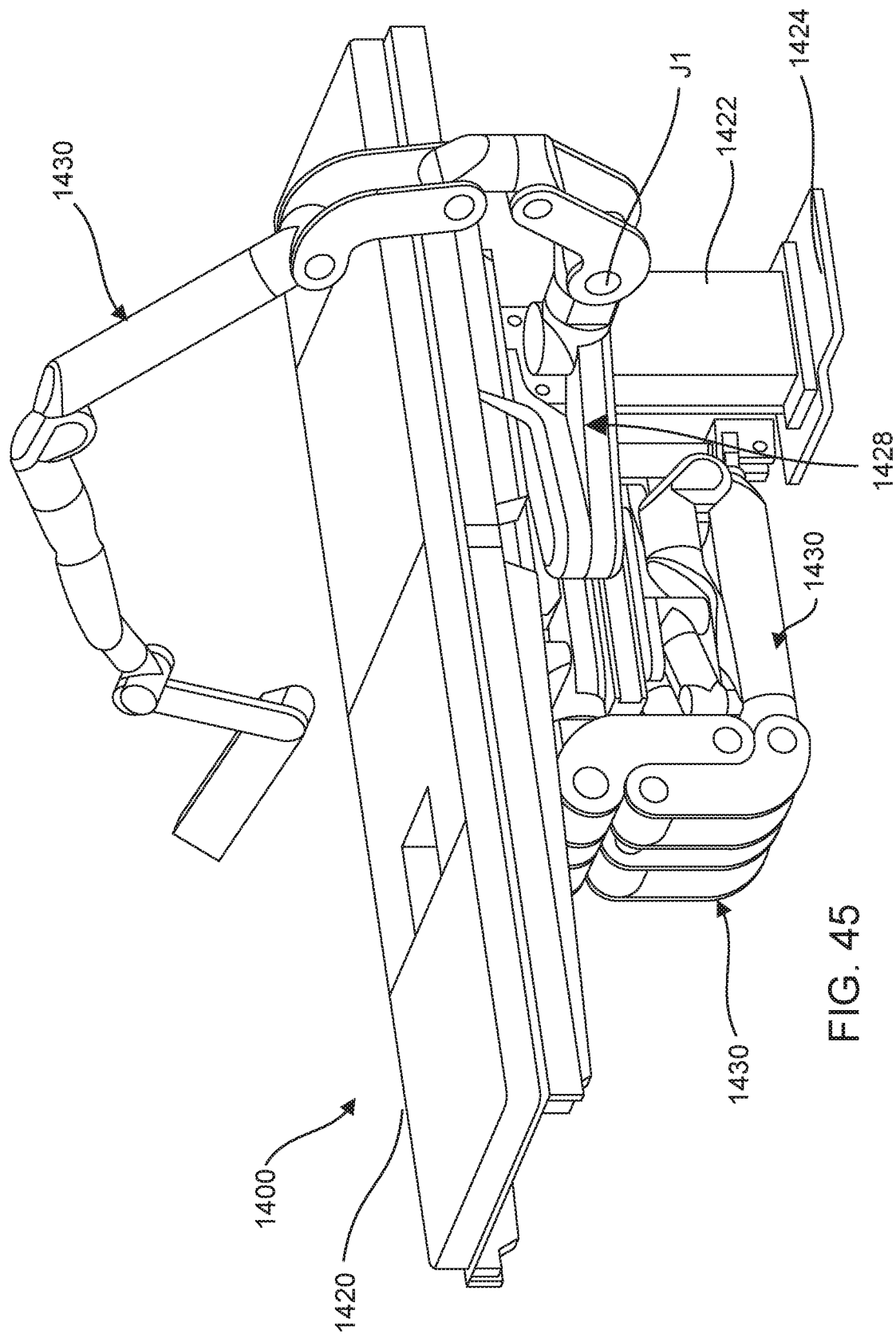
FIG. 45 is a side perspective view of the adapter and robotic arms of FIG. 43 shown coupled to a surgical table, and one robotic arm in an operating or extended position.

The adapter 1128 also includes multiple second link members 1134 that are each coupled to one of the first link members 1132 at a second joint 1135 such that the second link member 1134 can pivot about a second pivot axis P2 (see FIGS. 40A and 40B). Each of the second link members 1134 are also pivotally coupled to a coupling portion 1139 at a joint 1145 and can pivot about a third pivot axis P3 (FIGS. 40A and 40B). The coupling portion 1139 is coupled to a linkage coupler 1160 at joint 1163. The linkage coupler 1160 includes a set of linkages 1158 and a coupler 1157. The set of linkages 1158 includes four pivot links connected at one end to the coupling portion 1145 and connected at an opposite end to the coupler 1157. The pivotal motion of the four pivot links collectively define the joint 1163, with each pivoting about an axis P4 (labeled as a single axis P4 in FIGS. 40A and 40B). The coupler 1157 is coupleable to a coupling portion 1138 of a robotic arm 1130 that includes the target joint J1, as shown schematically in FIGS. 40A and 40B. The target joint J1 is a pivotal joint that can allow the coupling portion 1138 of the robotic arm 1130 to pivot about a fifth pivot axis P5. The various coupling joints of the adapter 1128 and the robotic arm 1130 allow the adapter 1128 and robotic arm 1130 to be moved between an extended configuration for use during a surgical procedure, and a folded or collapsed configuration for storage when not in use.

As described above for previous embodiments, the robotic arm(s) 1130 can be used to perform a surgical procedure on a patient disposed on the surgical table 1100. Each robotic arm 1130 can be configured the same as or similar to, and function the same as or similar to, the robotic arms described above and thus, specific details regarding the robotic arms are not discussed with respect to this embodiment. For example, as described above for robotic arms 130, the robotic arms 1130 can include multiple links or segments and can be moved between an extended configuration for use during a surgical procedure, and a folded or collapsed configuration for storage when not in use. The various coupling joints (e.g., first joint 1133, second joint 1135, joint 1145, and joint J1) can provide for movement of the robotic arm 1130 along and/or about the X, Y, and/or Z axes as described in more detail below.

More specifically, the first joint 1133 can provide for rotational motion of the first link members 1132 relative to the interface structure 1140 (and table 1100) about a vertical z-axis (i.e., pivot axis P1) relative to the top surface of the table top (e.g., the top surface of the torso section of the table top). The second joint 1135 provides for movement of the second link members 1134 to rotate about the pivot axis P2 which is also a z-axis rotation. The joint 1145 provides for the coupling portion 1139 to rotate about the pivot axis P3 which is also a z-axis rotation and the joint 1163 provides rotational movement of the linkage coupler 1160 about the pivot axes P4. The J1 joint rotates about the axis P5 which rotates within the X-Y plane. The joint 1163 provides a lift mechanism to allow for vertical movement of the linkage coupler 1160 and a robotic arm 1130 coupled thereto. Thus, the motion of the first link member 1132, the second link member 1134, and the coupling portion 1139 and the linkage coupler 1160 can provide for movement of the robotic arm 1130 coupled thereto along and/or about the X, Y, and/or Z axes to position the target joint J1 at a desired treatment location relative to the top surface of the table top.

FIGS. 40A and 40B are schematic illustrations of the various degrees of freedom provided by the joints of the adapter 1128 and robotic arm 1130, and FIG. 40C is a table listing the type of degree of freedom (e.g., rotational, linear) associated therewith. As shown in FIGS. 40A and 40B, and as described above, the interface mechanism 1140 is coupleable to the support 1122 of the table 1100 and the first link members 1132 are pivotally coupled to the interface mechanism 1140 at joint 1133 and pivot about the pivot axis P1 to provide a first degree of freedom DOF 1 that is Z-axis rotation. The joint 1135 between the first link member 1132 and the second link member 1134 is also a rotational or pivotal joint that is a Z-axis rotation (i.e., pivot axis P2) and provide a second degree of freedom DOF 2. The joint 1145 between the second link member 1134 and the coupling portion 1139 is also a rotational or pivotal joint that can pivot about the axis P3 and provide a third degree of freedom DOF 3. The joint 1163 is a rotational or pivotal joint that can pivot about a horizontal axis and provide a fourth degree of freedom DOF 4 that is X-Y plane rotation, and the joint J1 is a pivotal joint that can pivot about a horizontal axis and provide a fifth degree of freedom DOF 5 that is X-Y plane rotation. Although not labeled in FIGS. 40A and 40B, the various joints between links 1110 of the arm 1130 and a medical instrument 1015 disposed on the distal end of the robotic arm 1130 can provide additional motion of the arm relative to a patient (e.g., a target treatment location on the patient) disposed on the table 1100, and therefore, additional degrees of freedom.

As described above for previous embodiments, the collective motion of the various components of the adapter 1128 allow the robotic arms 1130 to move between a variety of different positions relative to the surgical table 1100 during a surgical procedure. For example, adapter 1128 and robotic arms 1130 can be moved to a stowed or folded position to provide clearance or access to the table top (not shown). In the stowed position, the arms 1130 and adapter 1128 are each in a folded or collapsed configuration. To move the adapter 1128 and arms 1130 to the stowed position, the arms 1130 can be rotated and/or pivoted via the joints 1133, 1135 and 1145 to a position at an end of the table, for example, beneath the table top. In the stowed position, the adapter 1128 and arms 1130 are in a position which provides clearance along the sides of the table 1100 to, for example, move a patient from a gurney onto the table top, or for anesthetic to be administered, as described above for previous embodiments.

The adapter 1128 and arms 1130 can also be disposed in a parked position (not shown) and various operating positions (not shown). In an operating position, the target joints J1 are disposed at a desired target treatment location relative to the table top to accommodate a particular surgical procedure to be performed. For example, as described for previous embodiments, the arms 1130 can be positioned with two arms on each side of the table 1100, or with one arm 1130 on one side and three arms on an opposite side of the table.

The parked position is used when access to the patient is needed, and the robotic arms 1130 are moved to a clearance position relative to the table top. In this embodiment, the robotic arms 1130 can be moved/rotated (e.g., via the movement of the link members 1132, 1134 and coupling portion 1139) to a position outside of a treatment zone to provide space for a medical professional to tend to the patient. When the need for the clearance has passed, the arms 1130 can then be placed back into an operating position with the target joints J1 disposed at the desired target treatment locations relative to the table top.

FIGS. 41-46C illustrate an adapter according to another embodiment. An adapter 1428 can be coupled to a surgical table 1400 (see FIG. 45) that includes a table top 1420, a support 1422 and a base 1424. The surgical table 1400 can include the same or similar components and function in the same or similar manner as the surgical tables described above, and therefore, is not described in detail with respect to this embodiment.

The table adapter 1428 (also referred to herein as "adapter") includes a table interface mechanism 1440 that can be coupled to the support 1422 of the table 1400. The adapter 1428 further includes multiple first link members 1432 that in this embodiment are each pivotally coupled to the table interface mechanism 1440 at a separate first joint 1433 such that the first link members 1432 can each pivot about a pivot axis P1 as shown in the schematic illustrations of FIGS. 46A and 46B. The adapter 1428 can be coupled to the table 1400 such that the first joints 1433 are disposed at the ends of the table 1400 beneath the head section and the leg section of the table top.

Figure 46A:
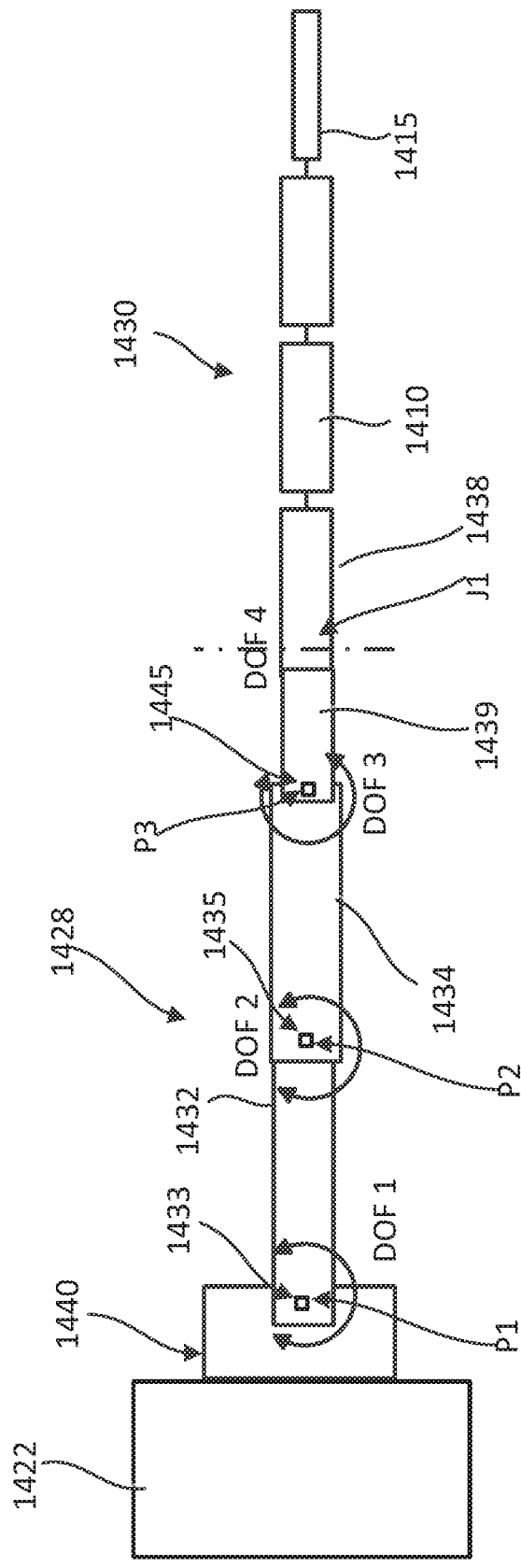
Figure 46C:
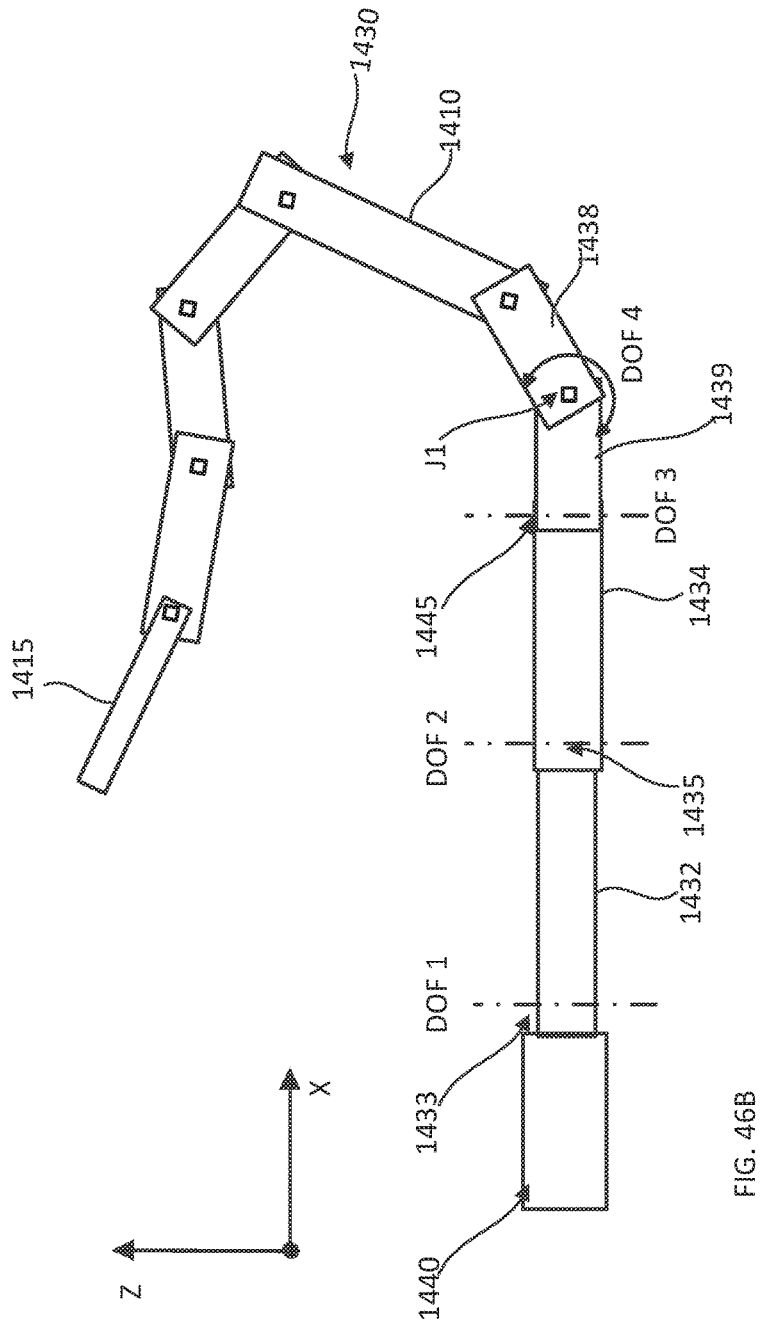
FIG. 46C is a table listing the type of degree of freedom of each of the joints.

The adapter 1428 also includes multiple second link members 1434 that are each coupled to one of the first link members 1432 at a second joint 1435 such that the second link member 1434 can pivot about a second pivot axis P2 (see FIGS. 46A and 46B). Each of the second link members 1134 are also pivotally coupled to a coupling portion 1439 at a joint 1445 and can pivot about a third pivot axis P3 (FIGS. 46A and 46B). The coupling portion 1439 is couple-able to a coupling portion 1438 of a robotic arm 1430 that includes the target joint J1, as shown schematically in FIGS. 46A and 46B. The target joint J1 is a pivotal joint that can allow the coupling portion 1438 of the robotic arm 1430 to pivot about a fourth pivot axis P4. The various coupling joints of the adapter 1428 and the robotic arm 1430 allow the adapter 1428 and robotic arm 1430 to be moved between an extended configuration for use during a surgical procedure, and a folded or collapsed configuration for storage when not in use.

As described above for previous embodiments, the robotic arm(s) 1430 can be used to perform a surgical procedure on a patient disposed on the surgical table 1400. Each robotic arm 1430 can be configured the same as or similar to, and function the same as or similar to, the robotic arms described above and thus, specific details regarding the robotic arms are not discussed with respect to this embodiment. For example, as described above for robotic arms 130, the robotic arms 1430 can include multiple links or segments and can be moved between an extended configuration for use during a surgical procedure, and a folded or collapsed configuration for storage when not in use. The various coupling joints (e.g., first joint 1433, second joint 1435, joint 1445, and joint J1) can provide for movement of the robotic arm 1430 along and/or about the X, Y, and/or Z axes as described in more detail below.

More specifically, as shown in FIGS. 46A and 46B, the first joint 1433 can provide for rotational motion of the first link members 1432 relative to the interface structure 1440 (and table 1400) about a vertical z-axis (i.e., pivot axis P1) relative to the top surface of the table top (e.g., the top surface of the torso section of the table top) and provide a first degree of freedom DOF 1. The second joint 1435 provides for movement of the second link member 1434 to rotate about the pivot axis P2 which is also a z-axis rotation, and provides a second degree of freedom DOF 2. The joint 1445 provides for the coupling portion 1439 to rotate about the pivot axis P3 which is also a z-axis rotation and provide a third degree of freedom DOF 3, and the J1 joint rotates about the axis P4 which rotates within the X-Y plane, and provides a fourth degree of freedom DOF 4. The J1 joint provides a lift mechanism to allow for vertical movement of the robotic arm 1430. The various motions of the first link member 1432, the second link member 1434, and the coupling portion 1439 can provide for movement of the robotic arm 1430 coupled along and/or about the X, Y, and/or Z axes to position the target joint J1 at a desired treatment location relative to the top surface of the table top. Although not labeled in FIGS. 46A and 102B, the various joints between links 1410 of the arm 1430 and a medical instrument 1415 disposed on the distal end of the robotic arm 1430 can provide additional motion of the arm 1430 relative to a patient (e.g., a target treatment location on the patient) disposed on the table 1400, and therefore, additional degrees of freedom.

As described above for previous embodiments, the collective motion of the various components of the adapter 1428 allow the robotic arms 1430 to move between a variety of different positions relative to the surgical table 1400 during a surgical procedure. For example, adapter 1428 and robotic arms 1430 can be moved to a stowed or folded position (see FIG. 45 which illustrates two robotic arms 1430 disposed in a stowed position). In the stowed position, the arms 1140 and adapter 1428 are each in a folded or collapsed configuration. The adapter 1428 and arms 1430 can also be disposed in a parked position (not shown) and various operating positions (see FIG. 45 which shows one robotic arm 1430 in an operating position). In an operating position, the target joints J1 are disposed at a desired target treatment location relative to the table top to accommodate a particular surgical procedure to be performed. For example, as described for previous embodiments, the arms 1430 can be positioned with two arms on each side of the table 1400, or with one arm 1430 on one side and three arms on an opposite side of the table.

The adapter 1428 and arms 1430 can be moved to a parked position when access to the patient is needed. When the need for the clearance has passed, the arms 1430 can then be placed back into an operating position with the target joints J1 disposed at the desired target treatment locations relative to the table top.

FIGS. 47-48C illustrate another embodiment of an adapter where the adapter is configured similar to the previous embodiment, except the first joints where the first link members are coupled to the interface mechanism are disposed at a spaced distance from each other in a longitudinal direction (i.e., y-axis direction). More specifically, an adapter 1528 can be coupled to a surgical table 1500 that includes a table top 1520, a support 1522 and a base 1524. The surgical table 1500 can include the same or similar components and function in the same or similar manner as the surgical tables described above, and therefore, is not described in detail with respect to this embodiment.

Figure 48A:
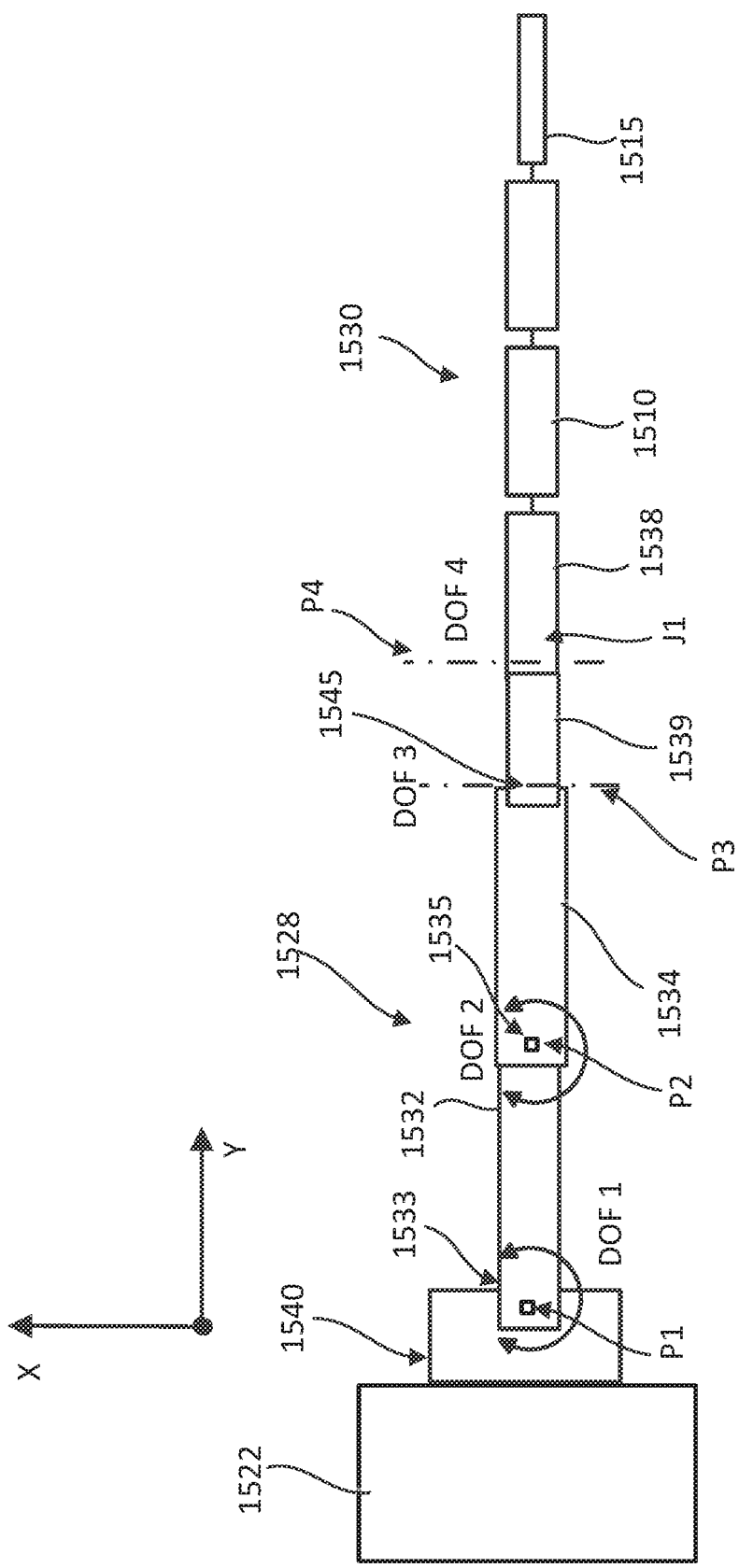

As shown schematically in FIGS. 48A and 48B, the table adapter 1528 (also referred to herein as "adapter") includes a table interface mechanism 1540 that can be coupled to the support 1522 of the table 1500. The adapter 1528 further includes multiple first link members 1532 that are each pivotally coupled to the table interface mechanism 1540 at a first joint 1533 such that the first link members 1532 can pivot about a pivot axis P1 as shown in the schematic illustrations of FIGS. 48A and 48B. In this embodiment, the adapter 1528 can be coupled to the table 1500 such that the first joints 1533 are disposed beneath the table top 1520 at a spaced distance from each other such that robotic arms 1530 coupled to the adapter 1528 are folded inward in the same direction on each side of the table 1500.

The adapter 1558 also includes multiple second link members 1534 that are each coupled to one of the first link members 1532 at a second joint 1535 such that the second link member 1534 can pivot about a second pivot axis P2 (see FIGS. 48A and 48B). Each of the second link members 1534 are also pivotally coupled to a coupling portion 1539 at a joint 1545 and can pivot about a third pivot axis P3 (FIGS. 48A and 48B). The coupling portion 1539 is coupleable to a coupling portion 1538 of a robotic arm 1530 that includes the target joint J1, as shown schematically in FIGS. 48A and 48B. The target joint J1 is a pivotal joint that can allow the coupling portion 1538 of the robotic arm 1530 to pivot about a fourth pivot axis P4. The various coupling joints of the adapter 1528 and the robotic arm 1530 allow the adapter 1528 and robotic arm 1530 to be moved between an extended configuration for use during a surgical procedure, and a folded or collapsed configuration for storage when not in use.

As described above for previous embodiments, the robotic arm(s) 1530 can be used to perform a surgical procedure on a patient disposed on the surgical table 1500. Each robotic arm 1530 can be configured the same as or similar to, and function the same as or similar to, the robotic arms described above and thus, specific details regarding the robotic arms are not discussed with respect to this embodiment. For example, as described above for robotic arms 130, the robotic arms 1530 can include multiple links or segments and can be moved between an extended configuration for use during a surgical procedure, and a folded or collapsed configuration for storage when not in use. The various coupling joints (e.g., first joint 1533, second joint 1535, joint 1545, and joint J1) can provide for movement of the robotic arm 1530 along and/or about the X, Y, and/or Z axes as described in more detail below.

More specifically, as shown in FIGS. 48A and 48B, the first joint 1533 can provide for rotational motion of the first link members 1532 relative to the interface structure 1540 (and table 1500) about a vertical z-axis (i.e., pivot axis P1) relative to the top surface of the table top (e.g., the top surface of the torso section of the table top) and provide a first degree of freedom DOF 1. The second joint 1535 provides for movement of the second link member 1534 to rotate about the pivot axis P2 which is also a z-axis rotation, and provides a second degree of freedom DOF 2. The joint 1545 provides for the coupling portion 1539 to rotate about the pivot axis P3 which is also a z-axis rotation and provide a third degree of freedom DOF 3, and the J1 joint rotates about the axis P4 which rotates within the X-Y plane, and provides a fourth degree of freedom DOF 4. The J1 joint provides a lift mechanism to allow for vertical movement of the robotic arm 1530. The various motions of the first link member 1532, the second link member 1534, and the coupling portion 1539 can provide for movement of the robotic arm 1430 coupled along and/or about the X, Y, and/or Z axes to position the target joint J1 at a desired treatment location relative to the top surface of the table top. Although not labeled in FIGS. 48A and 48B, the various joints between links 1510 of the arm 1430 and a medical instrument 1515 disposed on the distal end of the robotic arm 1530 can provide additional motion of the arm 1530 relative to a patient (e.g., a target treatment location on the patient) disposed on the table 1500, and therefore, additional degrees of freedom.

As described above for previous embodiments, the collective motion of the various components of the adapter 1528 allow the robotic arms 1530 to move between a variety of different positions relative to the surgical table 1500 during a surgical procedure. For example, adapter 1528 and robotic arms 1530 can be moved to a stowed or folded position (see FIG. 47). In the stowed position, the arms 1540 and adapter 1528 are each in a folded or collapsed configuration. The adapter 1528 and arms 1530 can also be disposed in a parked position (not shown) and various operating positions (not shown). In an operating position, the target joints J1 are disposed at a desired target treatment location relative to the table top to accommodate a particular surgical procedure to be performed. For example, as described for previous embodiments, the arms 1530 can be positioned with two arms on each side of the table 1500, or with one arm 1530 on one side and three arms on an opposite side of the table.

The adapter 1528 and arms 1530 can be moved to a parked position when access to the patient is needed. When the need for the clearance has passed, the arms 1530 can then be placed back into an operating position with the target joints J1 disposed at the desired target treatment locations relative to the table top.

Figure 49A:
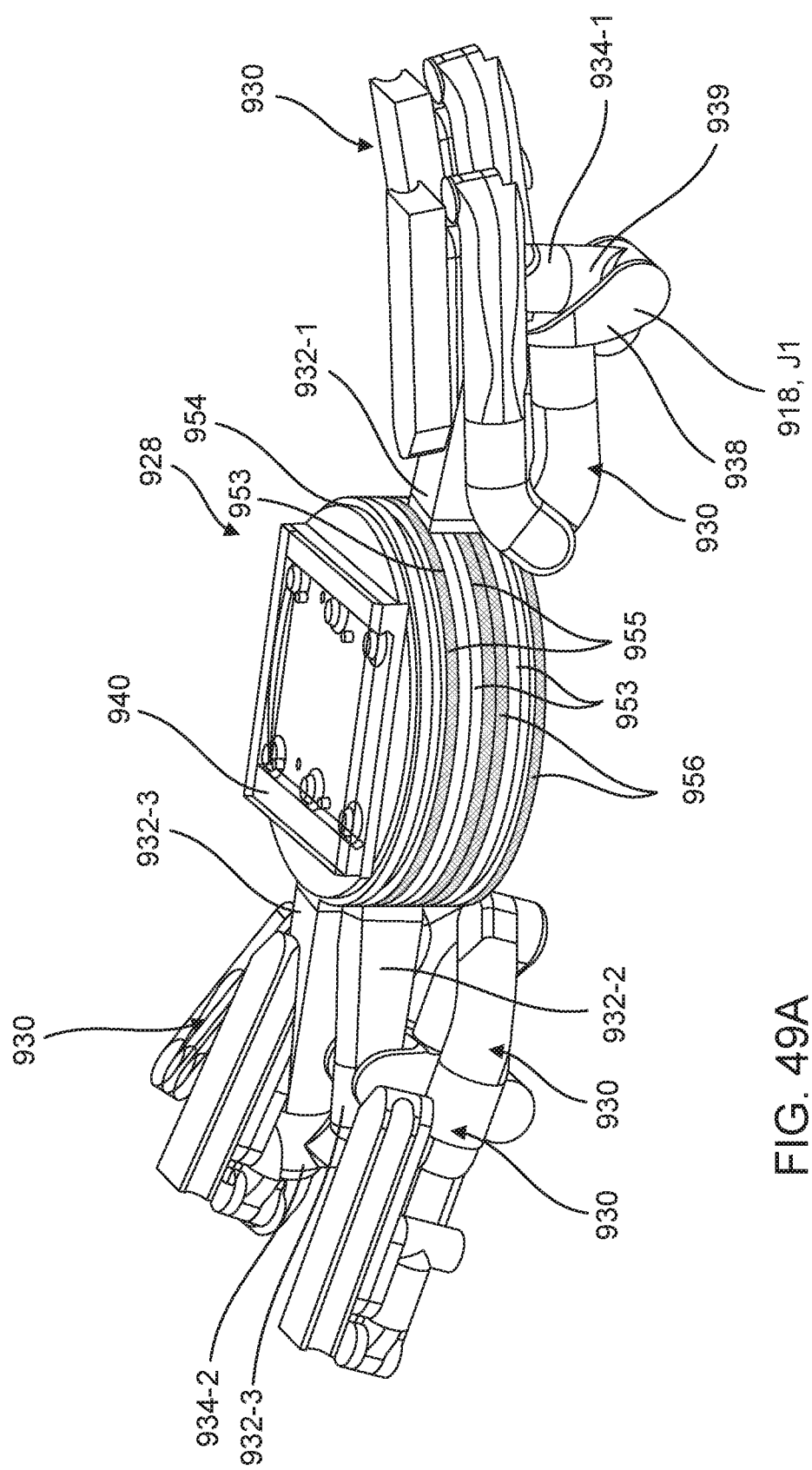
FIG. 49A is a side perspective view of an adapter according to another embodiment, and four robotic arms coupled thereto.
Figure 49B:
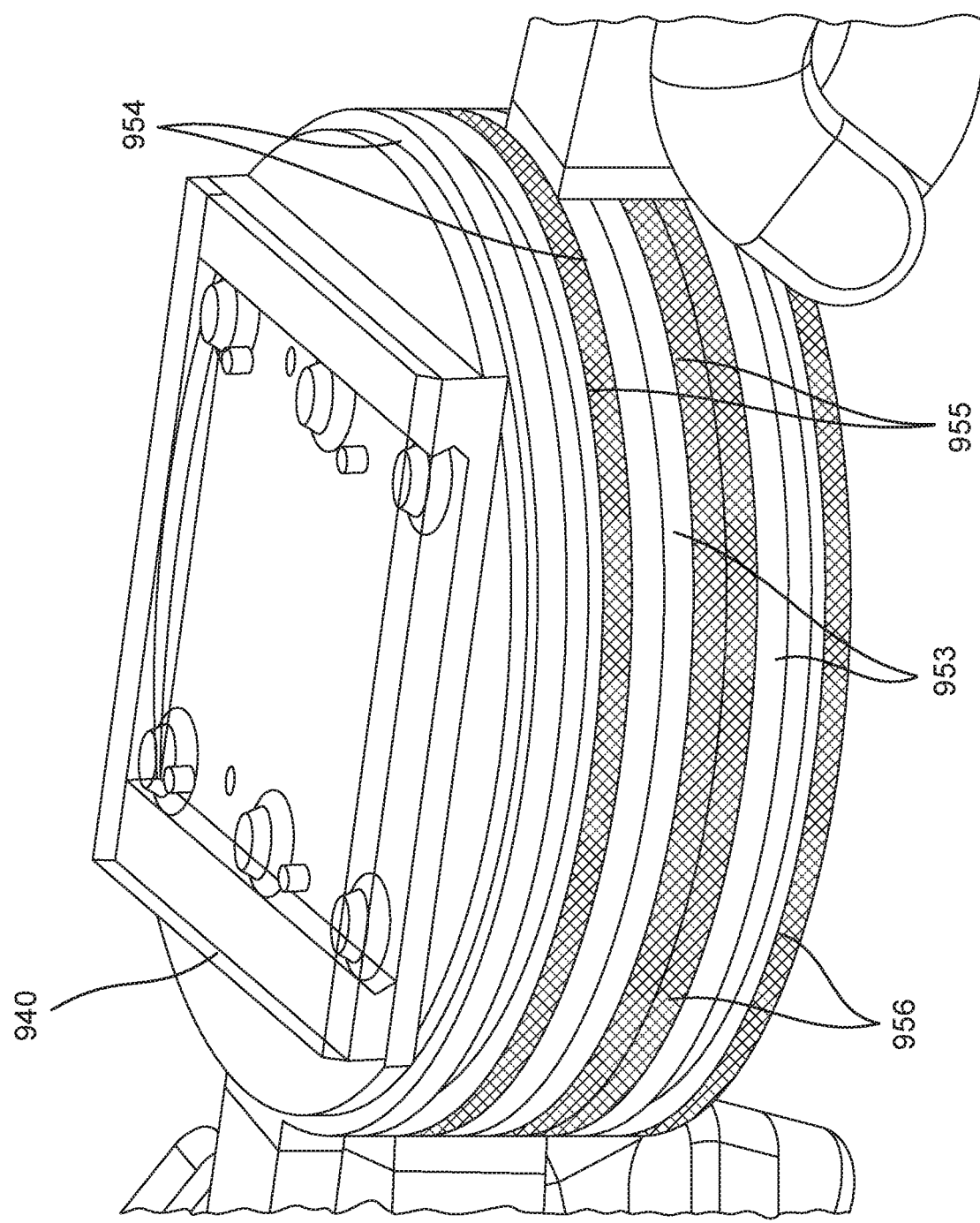
FIG. 49B is an enlarged view of a portion of the adapter of FIG. 49A.
Figure 50:
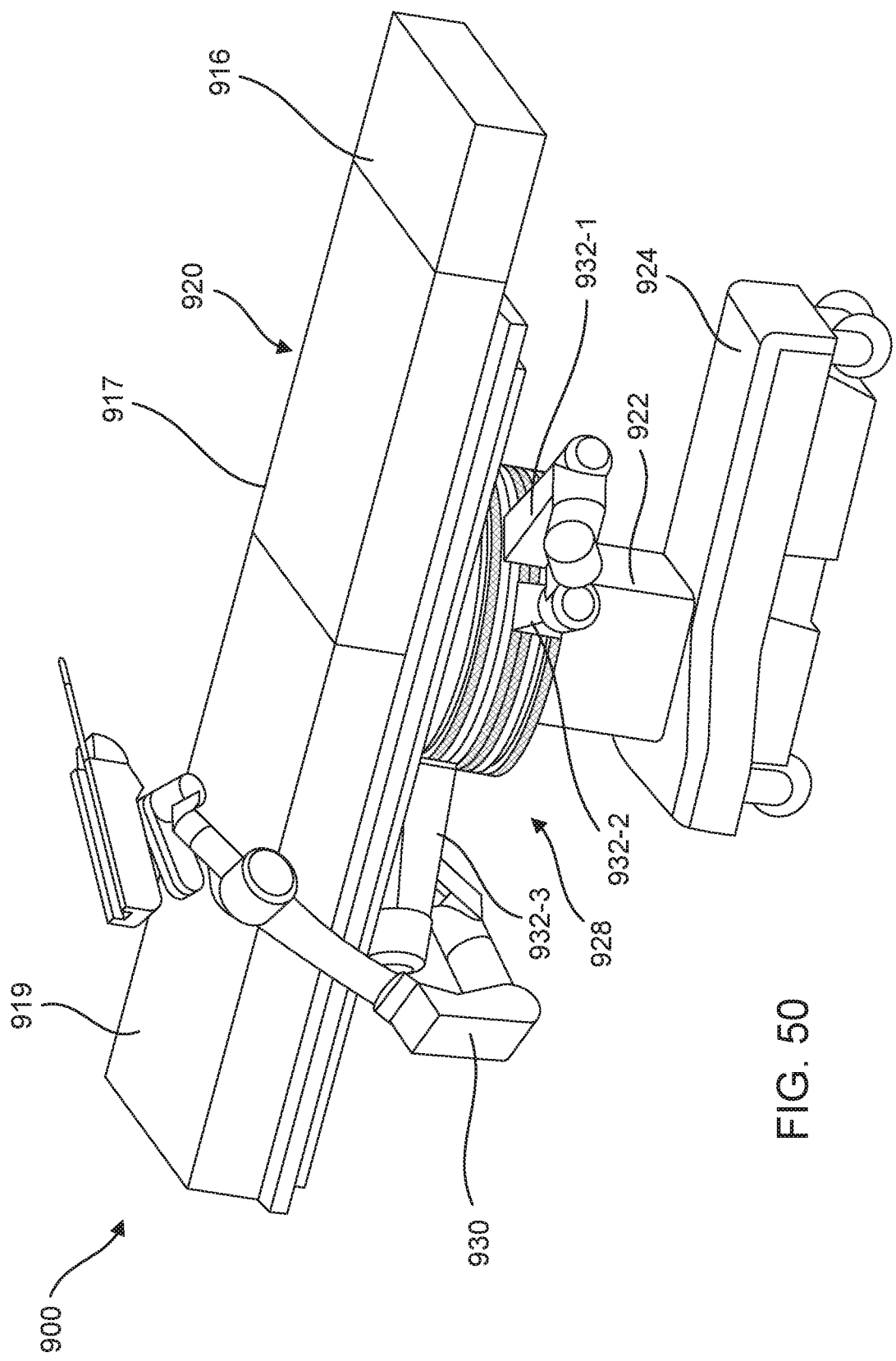
FIG. 50 is a side perspective view of the adapter and robotic arms of FIG. 49A coupled to a surgical table.

FIGS. 49A-49C illustrate a surgical table and adapter according to another embodiment. As shown in FIG. 50, a surgical table 900 includes a table top 920, a support 922 (also referred to herein as pedestal) and a base 924. The surgical table 900 can include the same or similar components and function in the same or similar manner as the surgical tables described above, and therefore, is not described in detail with respect to this embodiment. As shown in FIG. 50, a table adapter 928 (also referred to herein as "adapter") can be coupled to the surgical table 900. As best shown in FIGS. 49A and 49B, the adapter 928 includes a table interface mechanism 940 coupleable to the support 922 of the table 900. The table interface mechanism 940 includes four ring pairs 953, 954, 955, 956 with each pair coupled to a first link member 932. More specifically, there are four first link members 932-1, 932-2, 932-3 and 932-4 (not visible in FIGS. 49A and 49B) (collectively referred to as link members 932) coupled to the ring pair 953, 954, 955 and 956 respectively. The ring pairs can rotate about a circular base portion of the interface mechanism 940. The adapter 928 is also shown supporting four robotic arms 930 (only one robotic arm 930 is shown coupled to adapter 928 in FIG. 50).

Figure 51A:
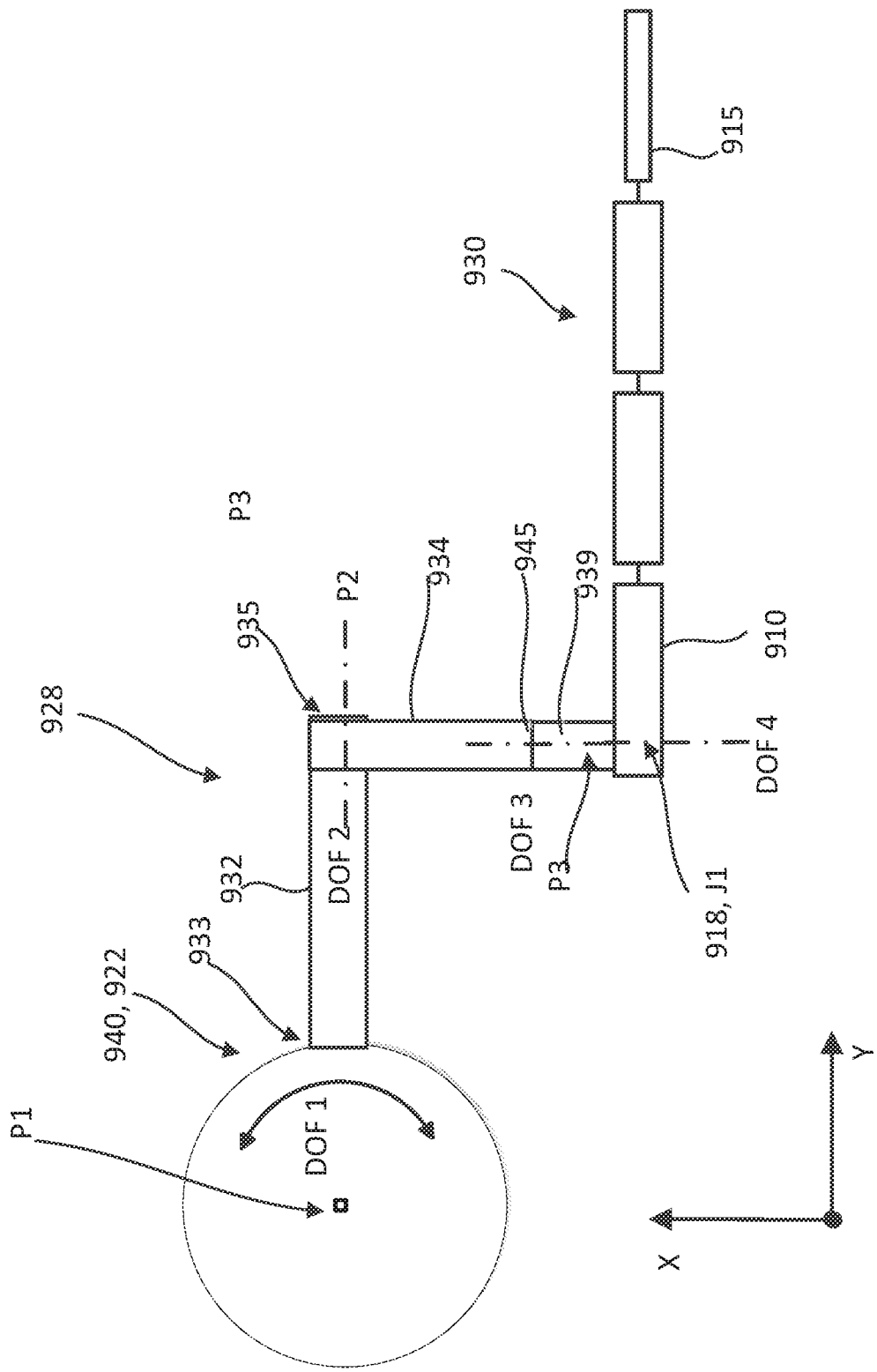
FIGS. 51A and 51B are a schematic top view and side view, respectively, of the adapter and a robotic arm of FIGS. 49A-50, illustrating the degrees of freedom between the joints of the adapter and robotic arm.

The four first link members 932 are each pivotally coupled to the interface mechanism 940 at a first joint 933 and can pivot about a pivot axis P1 as shown in the schematic illustration of FIG. 51A. The firs link members 932 are each pivotally coupled to a second link member 934 at a second joint 935 such that the second link member 934 can pivot about a second pivot axis P2. Each of the second link members 934 can also pivotally coupled to a coupling portion 939 at a joint 945 and can pivot about a third pivot axis P3. Each coupling portion 939 is coupled to a coupling portion 938 of a robotic arm 930 at a coupling 918. In this embodiment, the coupling 918 includes a pivotal coupling joint between the coupling portion 939 and the coupling portion 938 on the robotic arm 930 that includes the target joint J1. As described for previous embodiments, the target joint J1 is a pivotal joint that can allow the coupling portion 938 of the robotic arm 930 to pivot about a fourth pivot axis P4 (shown in FIGS. 51B and 51C). The various coupling joints between interface mechanism 940, the first link members 932, second link members 934 and the robotic arm 930 allow the adapter 928 and robotic arm 930 to be moved between an extended configuration for use during a surgical procedure, and a folded or collapsed configuration for storage when not in use.

As described above for previous embodiments, the robotic arm(s) 930 can be used to perform a surgical procedure on a patient disposed on the surgical table 900. Each robotic arm 930 can be configured the same as or similar to, and function the same as or similar to, the robotic arms described above and thus, specific details regarding the robotic arms are not discussed with respect to this embodiment. For example, as described above for robotic arms 130, the robotic arms 930 can include multiple links or segments and can be moved between an extended configuration for use during a surgical procedure, and a folded or collapsed configuration for storage when not in use. The various coupling joints of the adapter 928 and the robotic arm 930 can provide for movement of the robotic arm 930 along and/or about the X, Y, and/or Z axes as described in more detail below.

More specifically, the first joint 933 can provide for rotational motion of the first link members 932 relative to the interface structure 940 (and table 900) about a vertical z-axis (i.e., pivot axis P1 in FIGS. 51A and 51B) relative to the top surface of the table top 920 (e.g., the top surface of the torso section of the table top). The second joint 935 provides for movement of the second link members to rotate about the pivot axis P2 which is coextensive with a center line of the first link members 932 and allows the second link members 934 to rotate in lateral and longitudinal directions (also referred to herein as x-direction and y-direction, see X-Y axes in, e.g., FIGS. 51A and 51B) relative to the table top 920 of the surgical table 900. The joint 945 provides for movement of the coupling portion 939 to rotate about the pivot axis P3 which is coextensive with the pivot axis P2. The second joint 935 and the joint 945 collectively provide a lift mechanism to allow for vertical movement of the second link member 934 and coupling portion 939, and the robotic arm 930 coupled thereto. Thus, the motion of the first link member 932, the second link member 934, and the coupling portion 939 of the adapter 928 can provide for movement of the coupling 918 and therefore, movement of a robotic arm 930 coupled thereto along and/or about the X, Y, and/or Z axes to position the target joint J1 at a desired treatment location relative to the top surface of the table top 920.

Figures 51B, 51C:
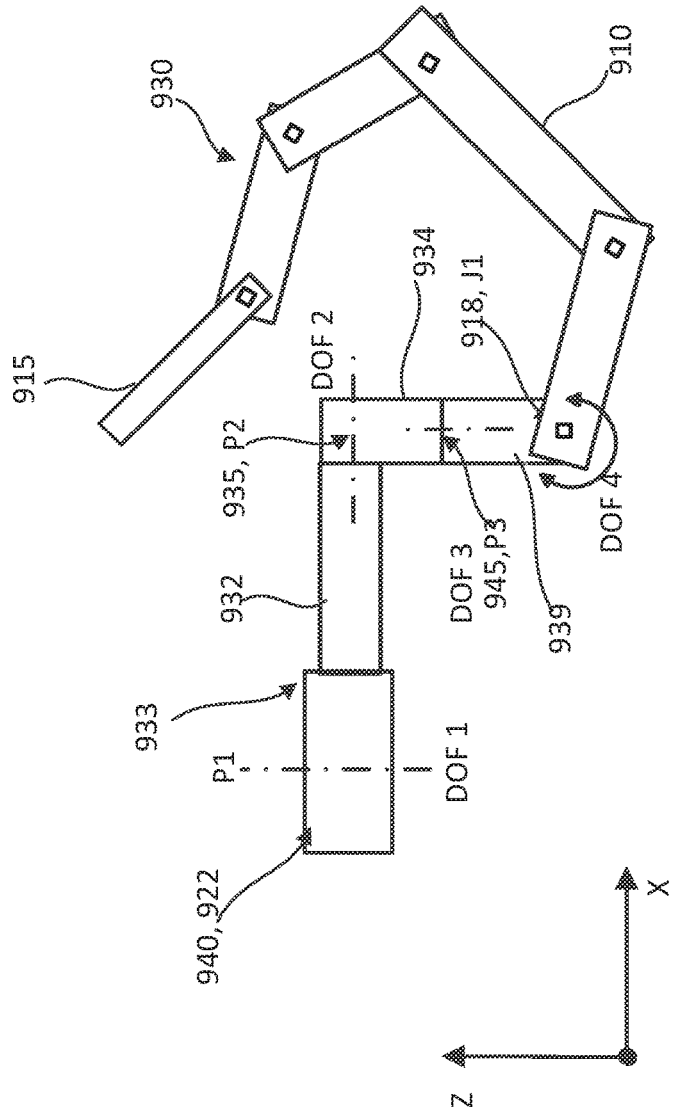
FIG. 51C is a table listing the type of degree of freedom of each of the joints.

FIGS. 51A and 51B are schematic illustrations of the various degrees of freedom provided by the joints of the adapter 928 and robotic arm 930, and FIG. 51C is a table listing the type of degree of freedom (e.g., rotational, linear) associated therewith. As shown in FIGS. 51A and 51B, and as described above, the interface mechanism 940 is coupleable to the support 922 of the table 900 and the first link members 932 are pivotally coupled to the interface mechanism 940 at joint 933 and pivot about the pivot axis P1 to provide a first degree of freedom DOF 1 that Z-axis rotation. The joint 935 between the first link member 932 and the second link member 934 is also a rotational or pivotal joint that can pivot about a horizontal axis (i.e., pivot axis P2) and provide a second degree of freedom DOF 2 (best shown in the side view illustration of FIG. 51B) that is X-Y plane rotation. The joint 945 between the second link member 934 and the coupling portion 939 is also a rotational or pivotal joint that can pivot about the axis P3 and provide a third degree of freedom DOF 3 that is rotation in a direction that varies depending on the orientation of the second link member 934. The joint J1 between the coupling portion 939 of the adapter 928 and the coupling portion 938 of the robotic arm 930 is also a pivotal joint that can pivot about a horizontal axis and provide a fourth degree of freedom DOF 4 (best shown in the side view illustration of FIG. 51B) that is X-Y plane rotation. Although not labeled in FIGS. 51A and 51B, the various joints between links 910 of the arm 930 and a medical instrument 915 disposed on the distal end of the robotic arm 930 can provide additional motion of the arm relative to a patient (e.g., a target treatment location on the patient) disposed on the table 900, and therefore, additional degrees of freedom.

As described above for previous embodiments, the collective motion of the various components of the adapter 928 allow the robotic arms 930 to move between a variety of different positions relative to the surgical table 900 during a surgical procedure. For example, adapter 928 and robotic arms 930 can be moved to a stowed or folded position (not shown). In the stowed position, the arms 930 and adapter 928 are each in a folded or collapsed configuration to provide clearance or access to the table top 920. To move the adapter 928 and arms 930 to the stowed position, the arms 930 can be slidably moved about the interface structure 940 via the ring pairs coupled to the first link members 932. In the stowed position, the adapter 928 and arms 930 are in a position which provides clearance along the sides of the table 900 to, for example, move a patient from a gurney onto the table top 920, or for anesthetic to be administered, as described above for previous embodiments.

The adapter 928 and arms 930 can also be disposed in a parked position (not shown) and various operating positons (as shown, e.g., in FIG. 50). In an operating position, the target joints J1 are disposed at a desired target treatment location relative to the table top 920 to accommodate a particular surgical procedure to be performed. For example, as described for previous embodiments, the arms 930 can be positioned with two arms on each side of the table 900, or with one arm 930 on one side and three arms on an opposite side of the table.

The parked position is used when access to the patient is needed, and the robotic arms 930 are moved to a clearance position relative to the table top 920. In this embodiment, the robotic arms 930 can be moved/rotated (i.e., via the movement of first link member 932 and corresponding ring pair about the interface mechanism 940) to a position outside of a treatment zone to provide space for a medical professional to tend to the patient. When the need for the clearance has passed, the arms 930 can then be placed back into an operating position with the target joints J1 disposed at the desired target treatment locations relative to the table top 920.

FIGS. 52-59C illustrate an adapter according to another embodiment. An adapter 1228 can be coupled to a surgical table 1200 (see, e.g., FIGS. 54-58) that includes a table top 1220, a support 1222 and a base 1224. The surgical table 1200 can include the same or similar components and function in the same or similar manner as the surgical tables described above, and therefore, is not described in detail with respect to this embodiment.

Figure 52:
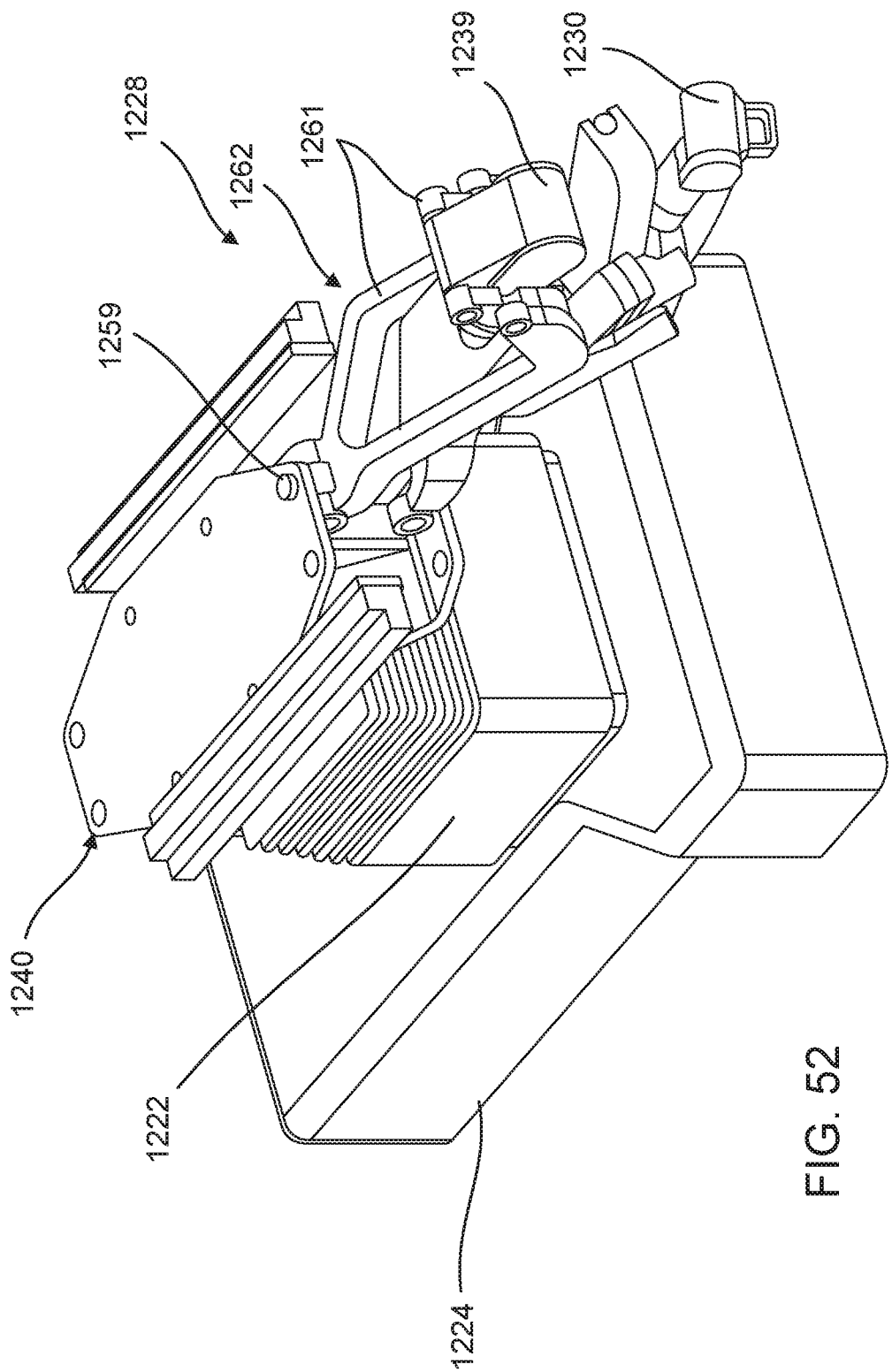
FIG. 52 is an end perspective view of an adapter according to another embodiment and a robotic arm coupled thereto, with the adapter and robotic arm shown coupled to a surgical table and in a stowed or folded position.
Figure 53:
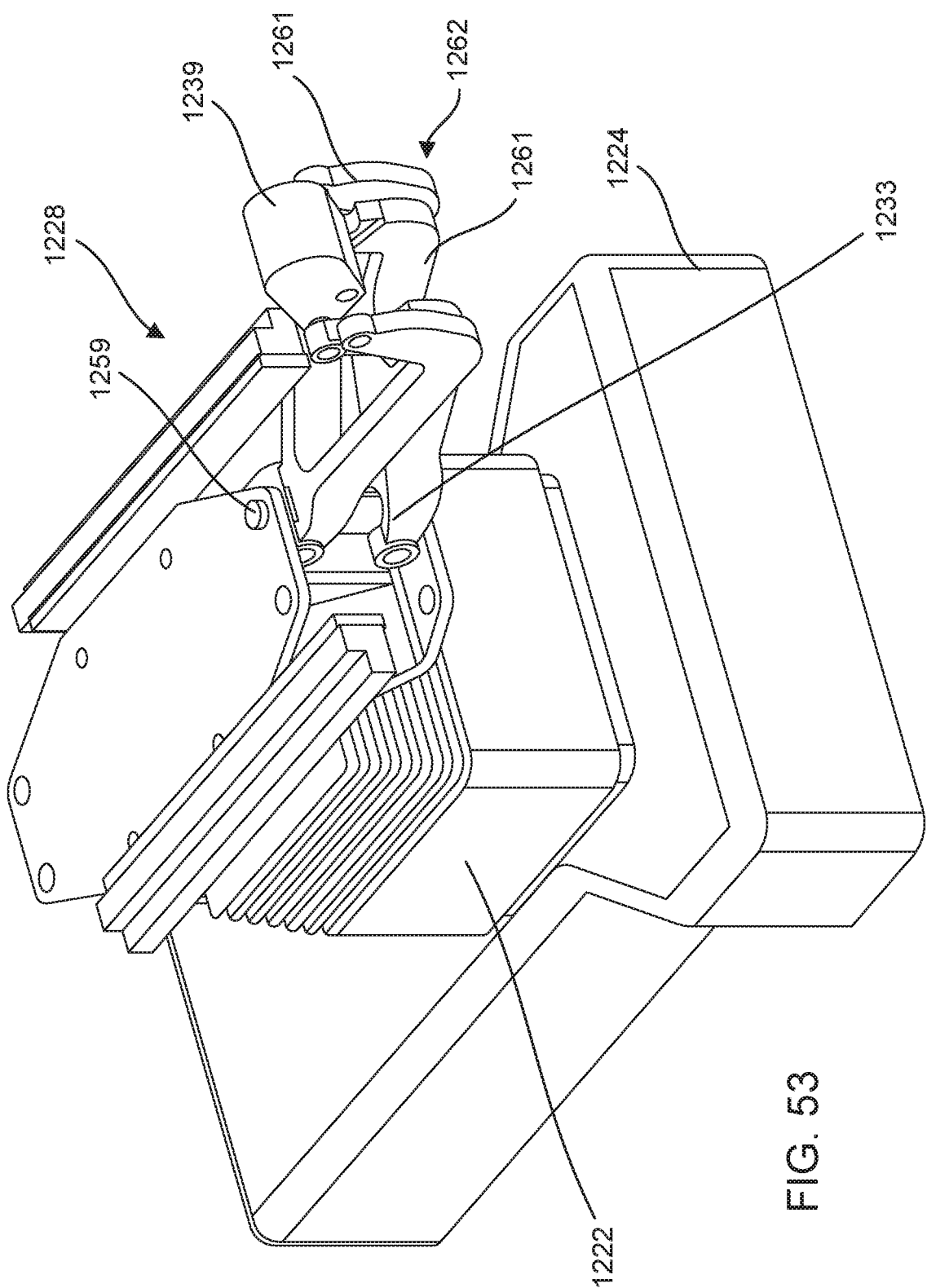
FIG. 53 is an end perspective view of the adapter of FIG. 52 without the robotic arm coupled thereto, and shown coupled to a surgical table and in a stowed or folded position.
Figure 54:
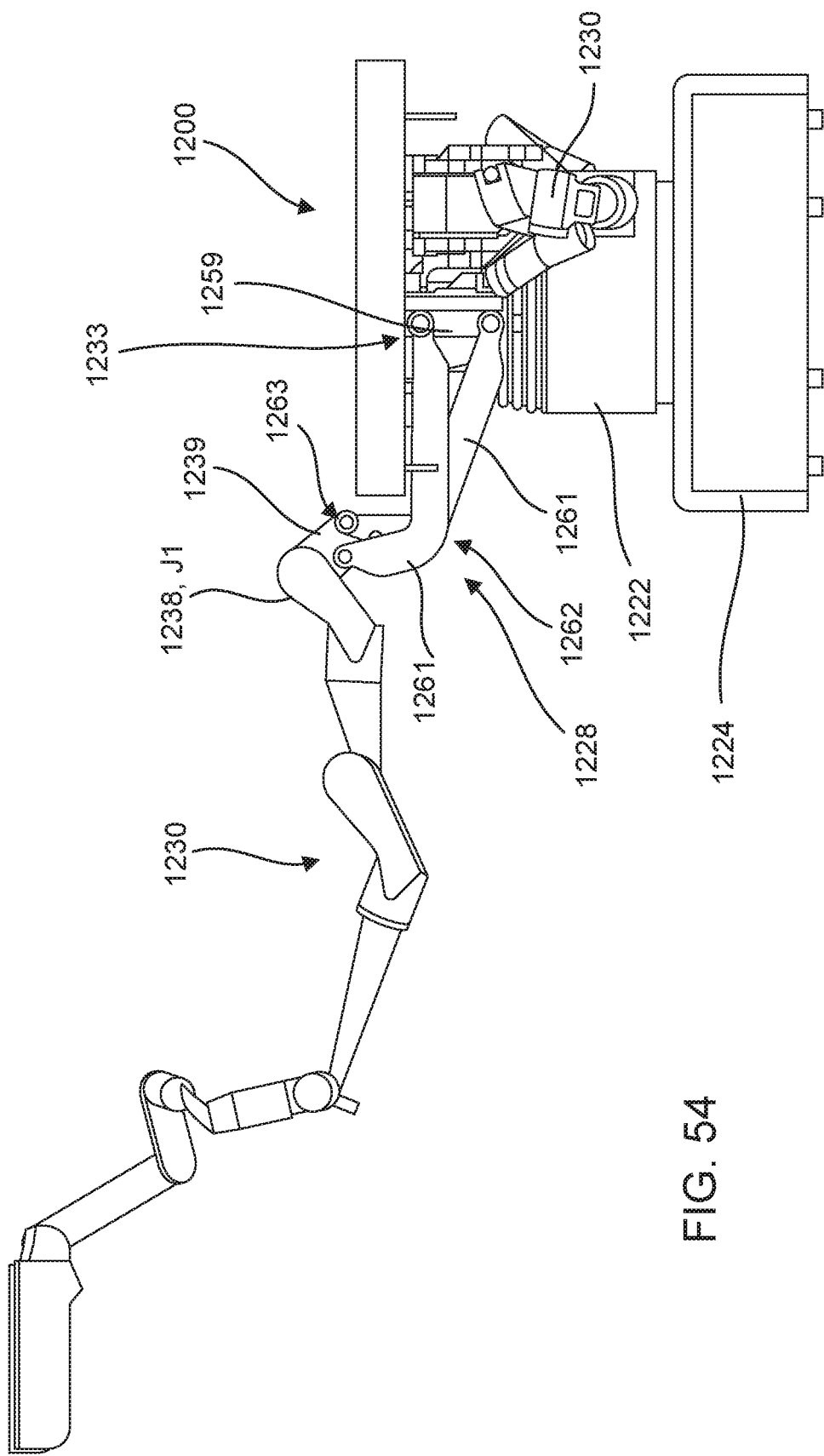
FIG. 54 is an end view of the adapter and surgical table of FIG. 52 with two robotic arms shown coupled to the adapter, and with one of the robotic arms in an operating or extended position.
Figure 55:
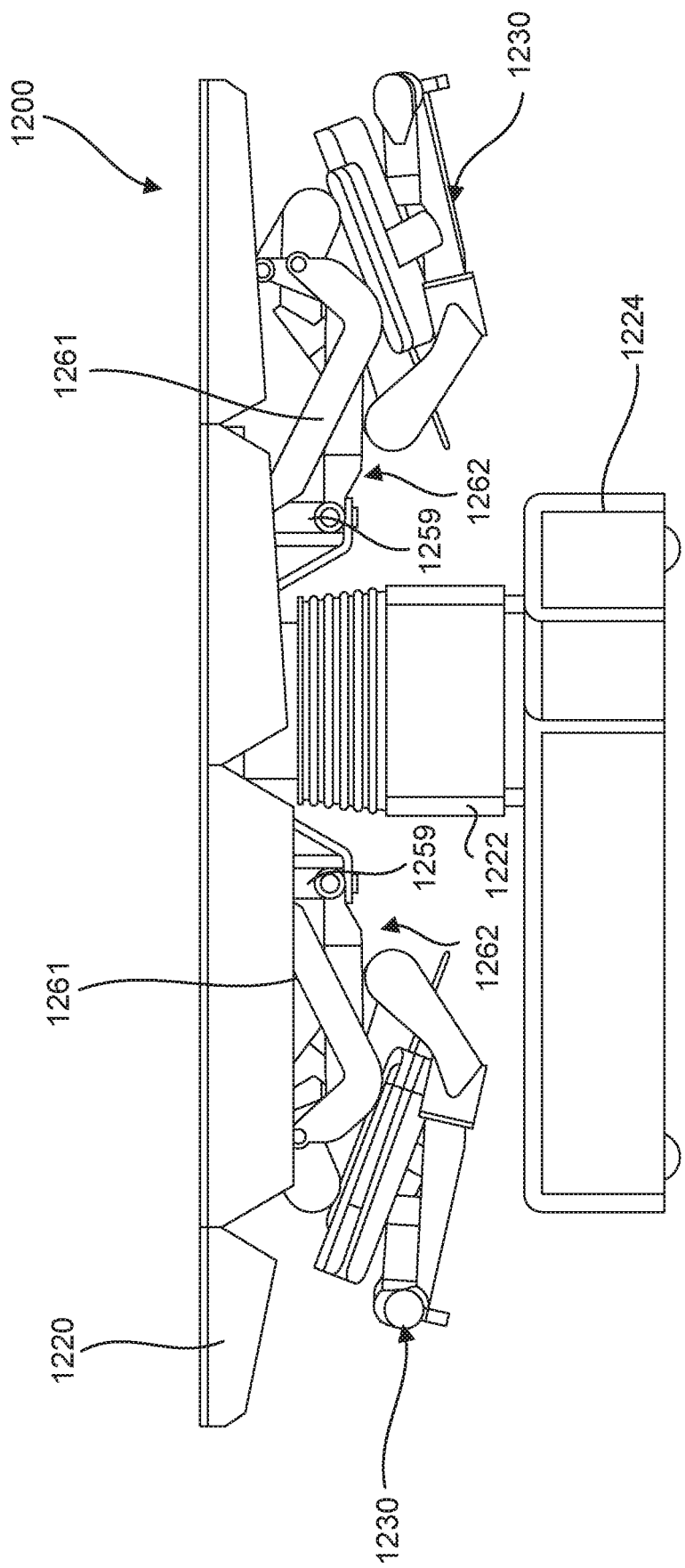
FIG. 55 is a side view of the adapter and surgical table of FIG. 52 with two robotic arms shown coupled to the adapter, and with the robotic arms in a stowed or folded position.

The table adapter 1228 (also referred to herein as "adapter") includes a table interface mechanism 1240 that can be coupled to the support 1222 of the table 1200. The adapter 1228 further includes four four-bar linkage assemblies 1262 (each also referred to as "linkage assembly") that are each coupleable to the interface mechanism 1240 via a rod coupler 1259 (only one four-bar linkage assembly is shown in FIGS. 52 and 53. The four-bar linkage assemblies 1262 each include two two-bar link members 1261 that are each pivotally coupled to the table interface mechanism 1240 via the rod coupler 1259 at a first joint 1133 such that the two-bar link members 1161 can pivot about a pivot axis P1 and also a pivot axis P2, as shown in the schematic illustrations of FIGS. 59A and 59B, and as described in more detail below. The two bar link members 1261 are each also pivotally coupled to a coupling portion 1239 at a coupling joint 1263. The pivotal motion of the two two-bar link members 1261 of a given linkage assembly 1262 collectively define the joint 1263 and each can pivot about a pivot axis P3. The coupling portion 1239 is coupled to a coupling portion 1238 of a robotic arm 1230 that includes the target joint J1. The target joint J1 is a pivotal joint that can allow the coupling portion 1238 of the robotic arm 1230 to pivot about a pivot axis P4.

As described above for previous embodiments, the robotic arm(s) 1230 can be used to perform a surgical procedure on a patient disposed on the surgical table 1200. Each robotic arm 1230 can be configured the same as or similar to, and function the same as or similar to, the robotic arms described above and thus, specific details regarding the robotic arms are not discussed with respect to this embodiment. For example, as described above for robotic arms 130, the robotic arms 1230 can include multiple links or segments and can be moved between an extended configuration for use during a surgical procedure, and a folded or collapsed configuration for storage when not in use. The various coupling joints of the adapter 1228 and the robotic arm 1230 can provide for movement of the robotic arm 1230 along and/or about the X, Y, and/or Z axes as described in more detail below.

More specifically, the first joint 1233 can provide for rotational motion of the linkage assembly 1262 relative to the interface structure 1240 (and table 1200) about a vertical z-axis (i.e., pivot axis P1) relative to the top surface of the table top 1220 (e.g., the top surface of the torso section of the table top) and also with the X-Y plane via the pivot axis P2. The joint 1263 provides for movement of the coupling portion 1239 to rotate about the pivot axis P3 which is also an X-Y plane rotation. The joint J1 provides for rotation of the coupling portion 1238 about the axis P4 which also rotates within the X-Y plane. The joint 1233 and the joint 1263 collectively provide a lift mechanism to allow for vertical movement of the coupling portion 1238 of the robotic arm 1230 coupled thereto. Thus, the motion provided by the various joints of the adapter 1228 can provide for movement of the robotic arm 1230 coupled thereto along and/or about the X, Y, and/or Z axes to position the target joint J1 at a desired treatment location relative to the top surface of the table top.

Figure 59A:
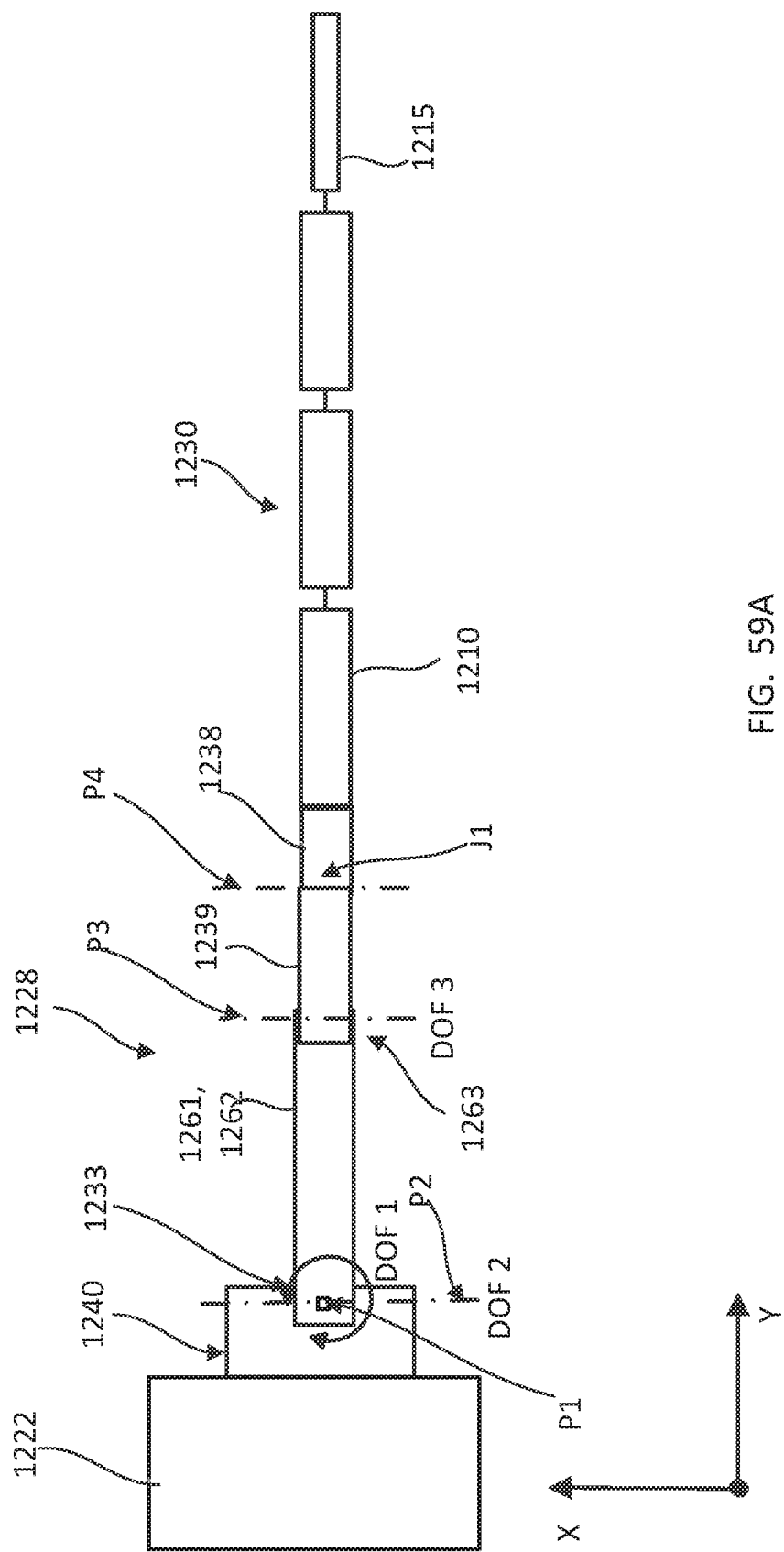
FIGS. 59A and 59B are a schematic top view and side view, respectively, of the adapter and a robotic arm of FIGS. 52-58, illustrating the degrees of freedom between the joints of the adapter and robotic arm.
Figures 59B, 59C:
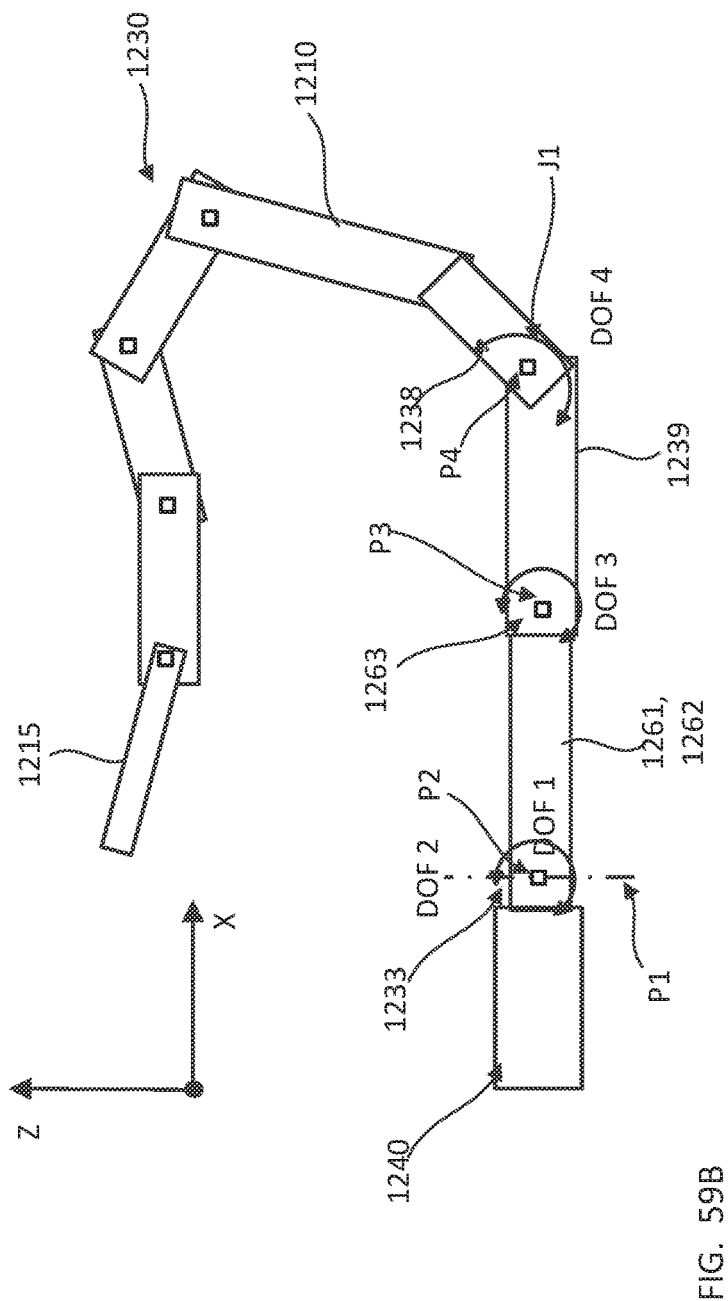
FIG. 59C is a table listing the type of degree of freedom of each of the joints.

FIGS. 59A and 59B are schematic illustrations of the various degrees of freedom provided by the joints of the adapter 1228 and robotic arm 1230, and FIG. 59C is a table listing the type of degree of freedom (e.g., rotational, linear) associated therewith. As shown in FIGS. 959A and 59B, the joint 1233 provides for rotation about the pivot axis P1 to provide a first degree of freedom DOF 1 that is Z-axis rotation and for rotation about the pivot axis P2 to provide a second degree of freedom DOF 2 that is X-Y plane rotation. The joint 1263 between the first link member 1132 and the second link member 1134 is also a rotational or pivotal joint that provides a third degree of freedom DOF 3 that is X-Y plane rotation. The joint J1 is a pivotal joint that can pivot about a horizontal axis and provide a fourth degree of freedom DOF 4 that is X-Y plane rotation. Although not labeled in FIGS. 59A and 59B, the various joints between links 1210 of the arm 1230 and a medical instrument 1215 disposed on the distal end of the robotic arm 1230 can provide additional motion of the arm 1230 relative to a patient (e.g., a target treatment location on the patient) disposed on the table 1200, and therefore, additional degrees of freedom.

As described above for previous embodiments, the collective motion of the various components of the adapter 1228 allow the robotic arms 1230 to move between a variety of different positions relative to the surgical table 1200 during a surgical procedure, such as stowed, parked and operating positions. For example, adapter 1228 and robotic arms 1230 can be moved to a stowed or folded position, as shown, for example, in FIG. 55. In the stowed position, the adapter 1228 and arms 1230 are in a position which provides clearance along the sides of the table 1200 to, for example, move a patient from a gurney onto the table top 1220, or for anesthetic to be administered, as described above for previous embodiments. The adapter 1128 and arms 1130 can also be disposed in a parked position (not shown) and various operating positions (not shown). In an operating position, the target joints J1 are disposed at a desired target treatment location relative to the table top to accommodate a particular surgical procedure to be performed.

Figure 56:
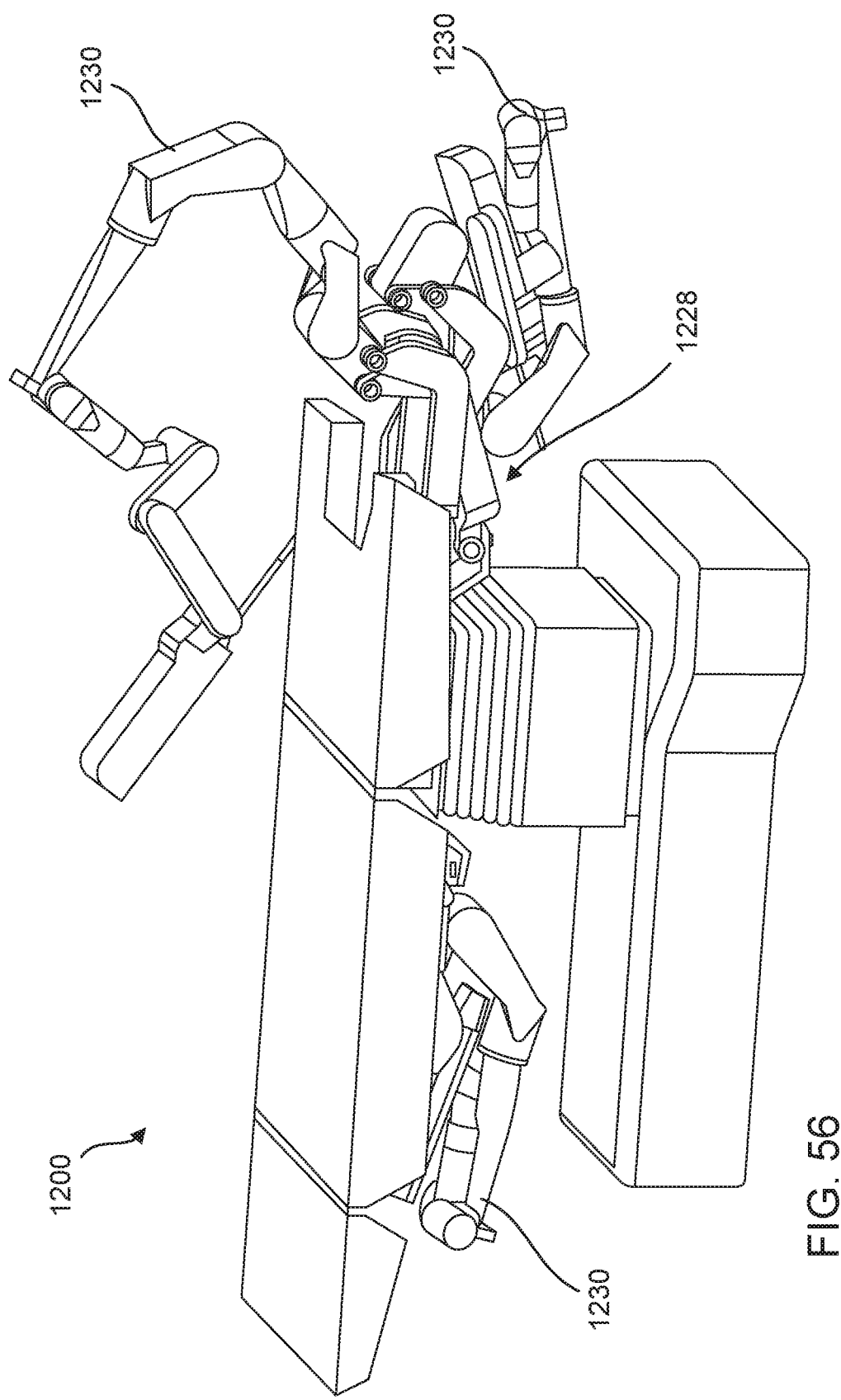
FIG. 56 is a side perspective view of the adapter and surgical table of FIG. 52 with three robotic arms shown coupled to the adapter, and with one of the robotic arms in an operating or extended position.
Figure 57:
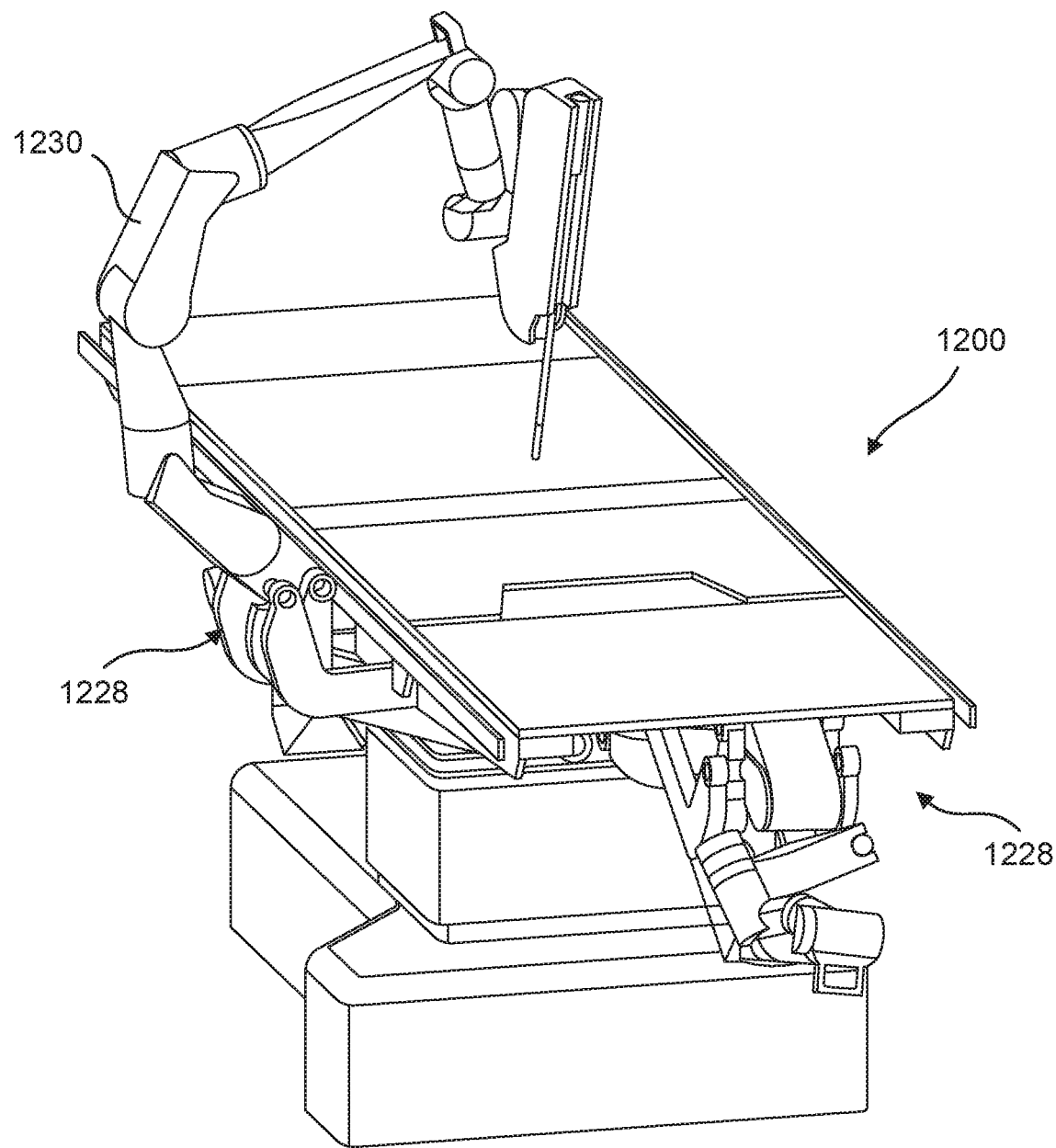
FIG. 57 is an end perspective view of the adapter and surgical table of FIG. 52 showing two robotic arms coupled to the adapter, and with one of the robotic arms in an operating or extended position.
Figure 58:
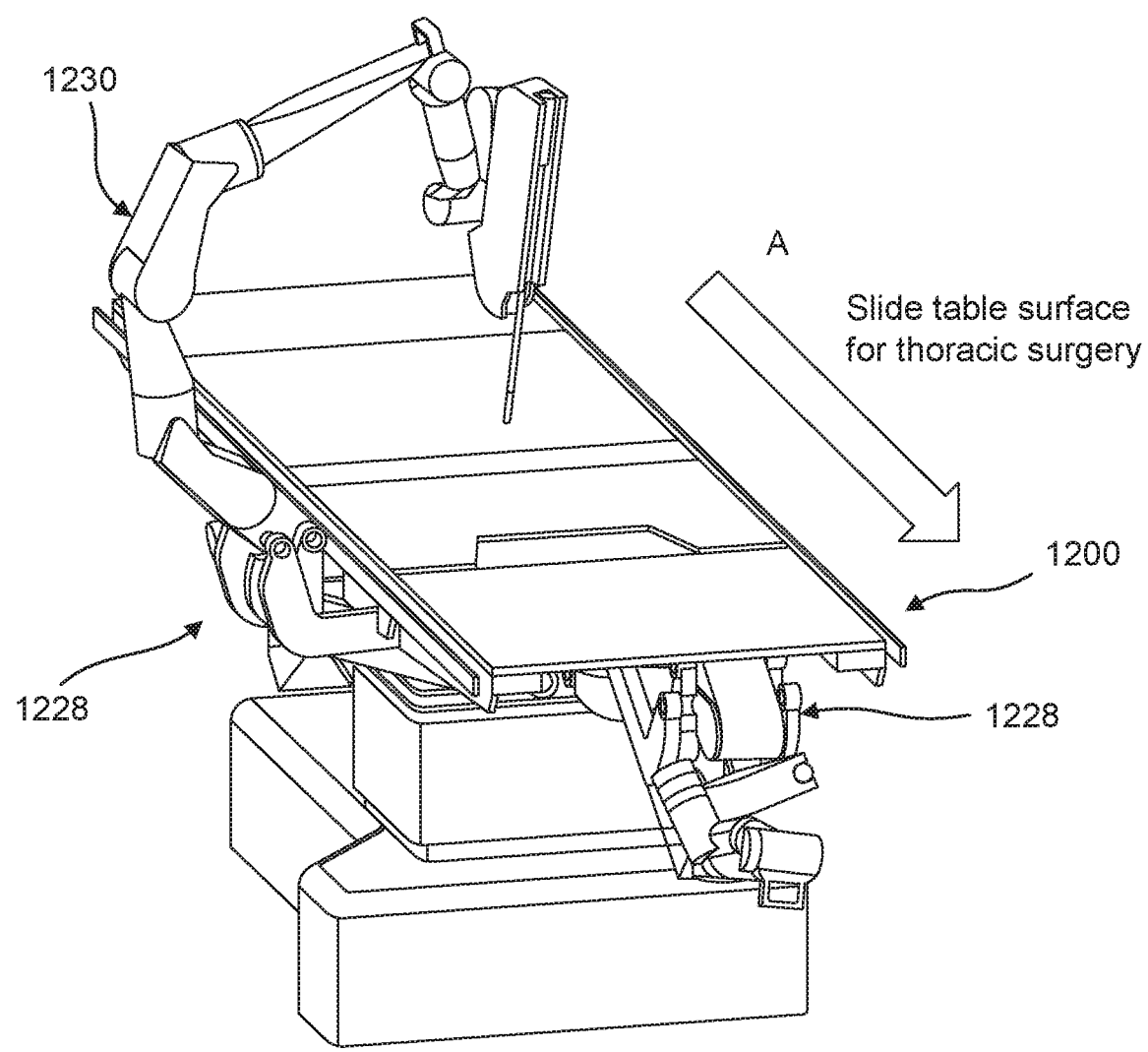
FIG. 58 is an end perspective view of the adapter, surgical table and robotic arms of FIG. 57 showing the surgical table moved in a Y-axis direction to accommodate a thoracic surgical procedure.

FIGS. 56-58 illustrate example operating positions for the adapter 1228 and robotic arms 1230. FIG. 56 illustrates an example operating position for performing a pelvic surgery where a leg section of the table top 1220 has been removed such that a robotic arm 1230 can be positioned at an end of the table 1200. FIG. 57 illustrates an example operating position to perform an abdominal surgery and FIG. 58 illustrates an example operating position to perform a thoracic surgery in which the table top 1220 is slid relative to the base 1224 in the direction of arrow A.

As described above, the parked position (not shown) is used when access to the patient is needed, and the robotic arms 1230 are moved to a clearance position relative to the table top to a location outside of a treatment zone to provide space for a medical professional to tend to the patient. When the need for the clearance has passed, the arms 1230 can then be placed back into an operating position with the target joints J1 disposed at the desired target treatment locations relative to the table top.

Figure 60:
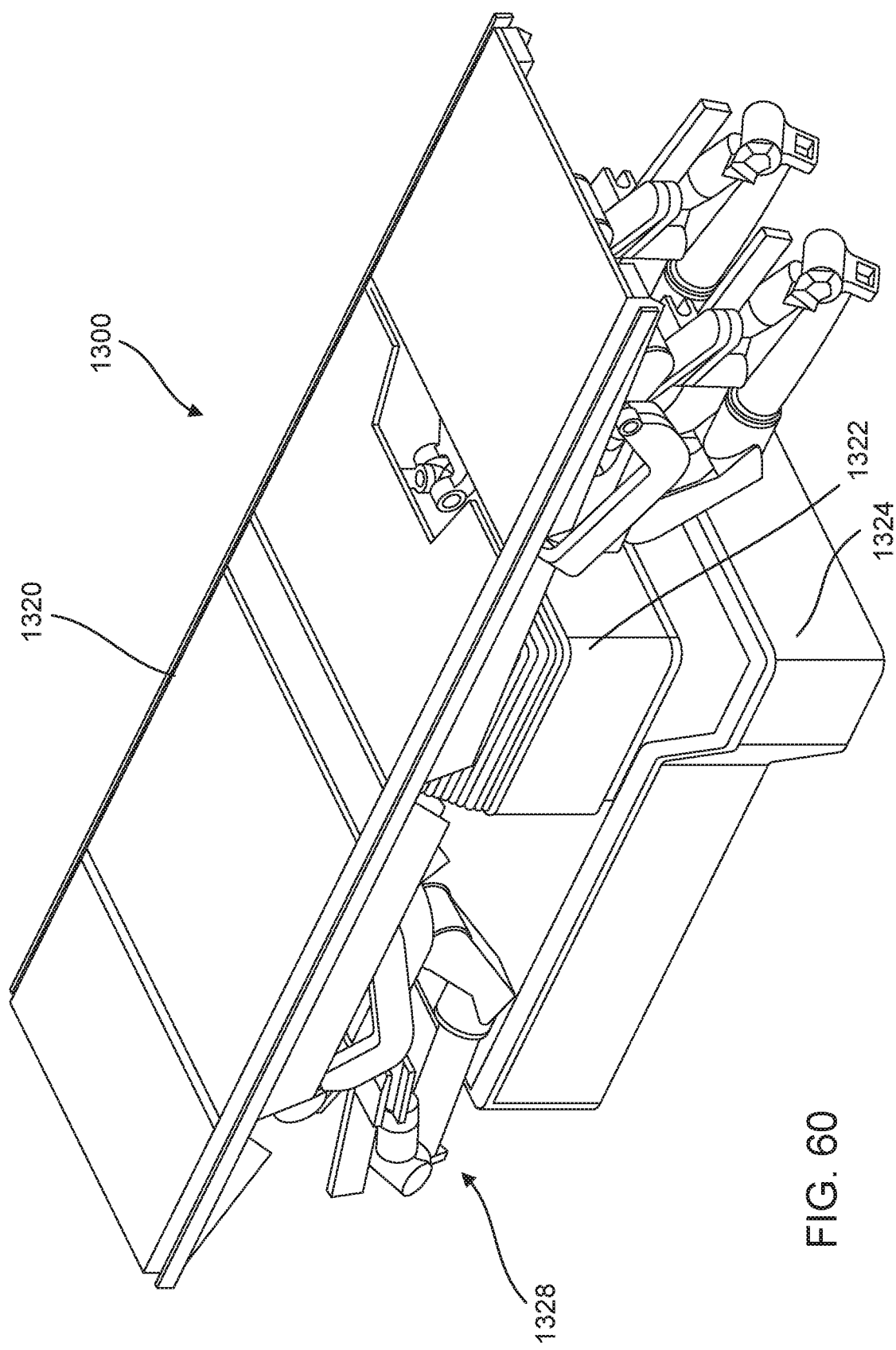
FIG. 60 is a side perspective view of an adapter according to another embodiment coupled to a surgical table and with four robotic arms coupled thereto and in a stowed or folded position.
Figure 61:
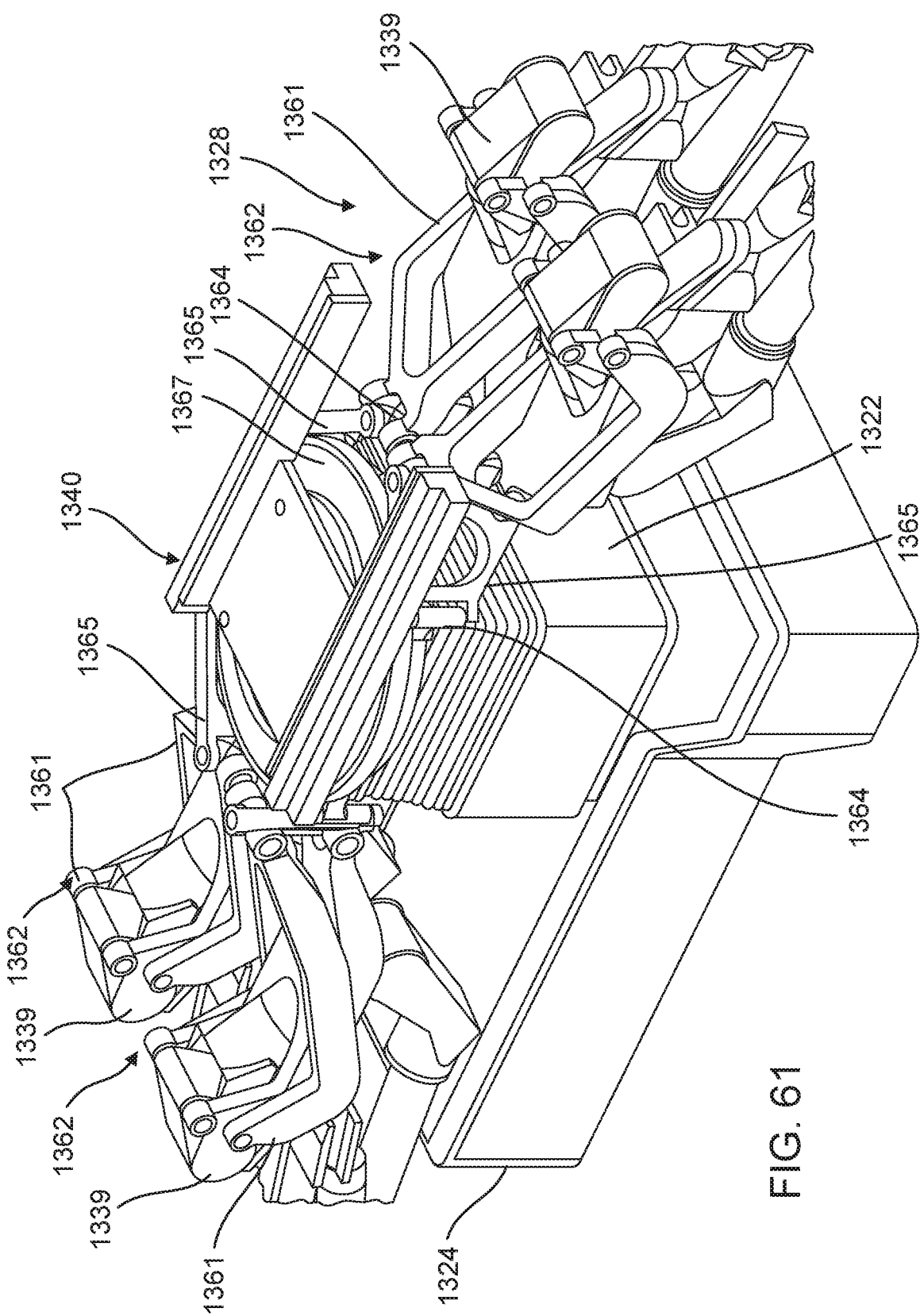
FIG. 61 is a side perspective view of the adapter, robotic arms and surgical table of FIG. 60 with the table top removed from the surgical table.
Figure 62:
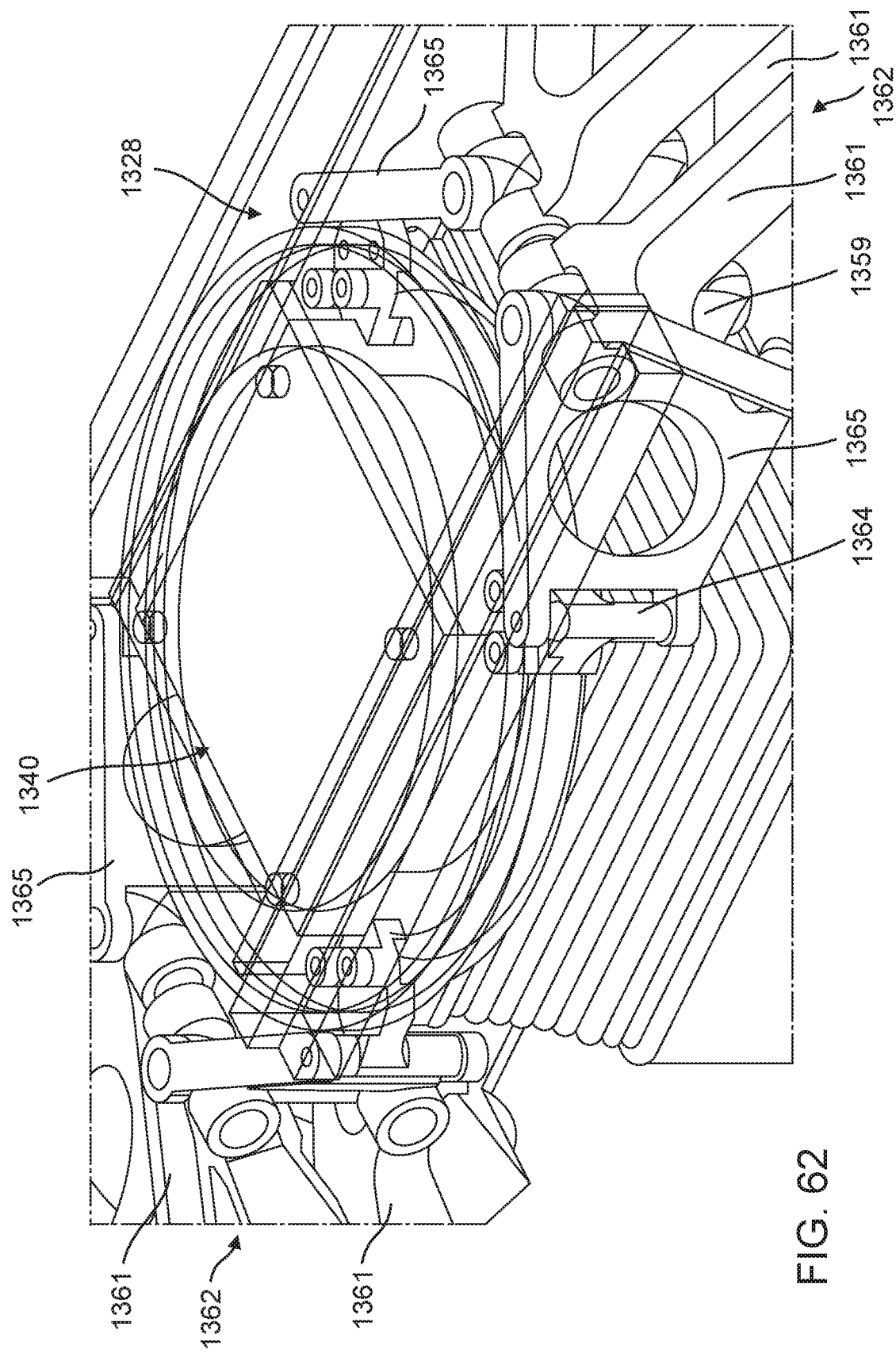
FIG. 62 is an enlarged view of a portion of the adapter of FIG. 61.

FIGS. 60-61 illustrate an adapter according to another embodiment. An adapter 1328 can be coupled to a surgical table 1300 (see, e.g., FIG. 60) that includes a table top 1320, a support 1322 and a base 1324. The surgical table 1300 can include the same or similar components and function in the same or similar manner as the surgical tables described above, and therefore, is not described in detail with respect to this embodiment.

The table adapter 1328 (also referred to herein as "adapter") includes a table interface mechanism 1340 that can be coupled to the support 1322 of the table 1300. The interface mechanism 1340 is similar to the interface mechanisms 840 and 940 in that it includes a track 1367 that provides for 360 degree rotation around the table 1300. The adapter 1328 also includes four four-bar linkage assemblies 1362 (each also referred to as "linkage assembly") that are each coupled to a rod coupler 1359, but in this embodiment, the rod coupling 1359 is coupled to the interface mechanism 1340 via a bracket 1365 and a track coupler 1364 as described in more detail below.

As with the previous embodiment, each four-bar linkage assembly 1362 includes two two-bar link members 1361 that are each pivotally coupled to the rod coupler 1359 at a first joint 1333 such that the two-bar link members 1361 can pivot about a pivot axis P3 and also a pivot axis P4, as shown in the schematic illustrations of FIGS. 64A and 64B, and as described in more detail below. The track coupler 1364 is coupled to the track 1367 of the interface mechanism 1340 at a joint 1369 and can rotate around the table 1300 about an axis P1. The track coupler 1364 is also pivotally coupled to the bracket 1365 at a joint 1368 and can pivot about an axis P2. The bracket 1365 is also coupled to the two bar assembly 1362 at the joint 1333. The two bar link members 1361 are each also pivotally coupled to a coupling portion 1339 at a coupling joint 1363. The pivotal motion of the two two-bar link members 1361 of a given linkage assembly 1362 collectively define the joint 1363 and each can pivot about a pivot axis P5. The coupling portion 1339 is coupled to a coupling portion 1338 of a robotic arm 1330 that includes the target joint J1. The target joint J1 is a pivotal joint that can allow the coupling portion 1338 of the robotic arm 1330 to pivot about a pivot axis P5.

As described above for previous embodiments, the robotic arm(s) 1330 can be used to perform a surgical procedure on a patient disposed on the surgical table 1300. Each robotic arm 1330 can be configured the same as or similar to, and function the same as or similar to, the robotic arms described above and thus, specific details regarding the robotic arms are not discussed with respect to this embodiment. For example, as described above for robotic arms 130, the robotic arms 1330 can include multiple links or segments and can be moved between an extended configuration for use during a surgical procedure, and a folded or collapsed configuration for storage when not in use. The various coupling joints of the adapter 1328 and the robotic arm 1330 can provide for movement of the robotic arm 1330 along and/or about the X, Y, and/or Z axes as described in more detail below.

Figure 64A:
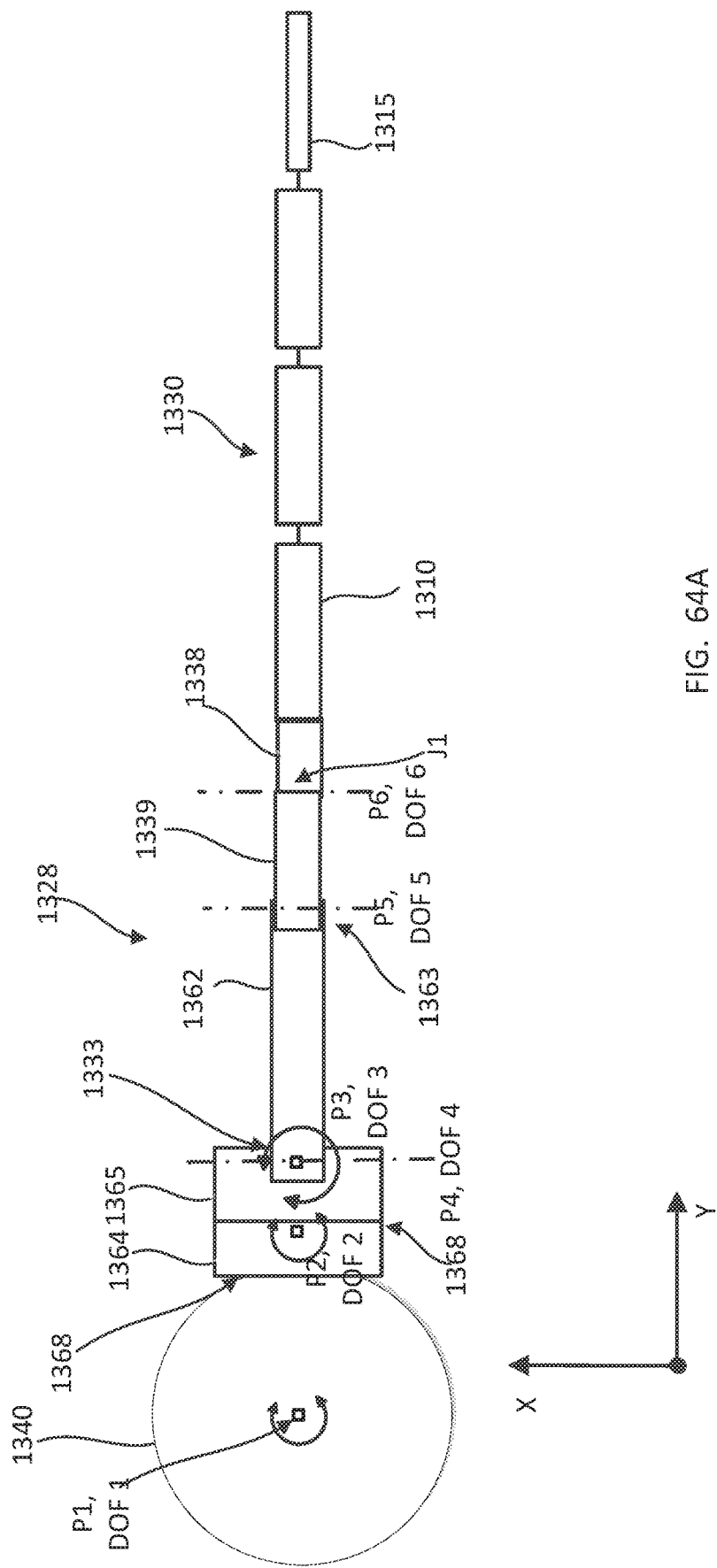
FIGS. 64A and 64B are a schematic top view and side view, respectively, of the adapter and a robotic arm of FIGS. 60-63, illustrating the degrees of freedom between the joints of the adapter and robotic arm.
Figures 64B, 64C:
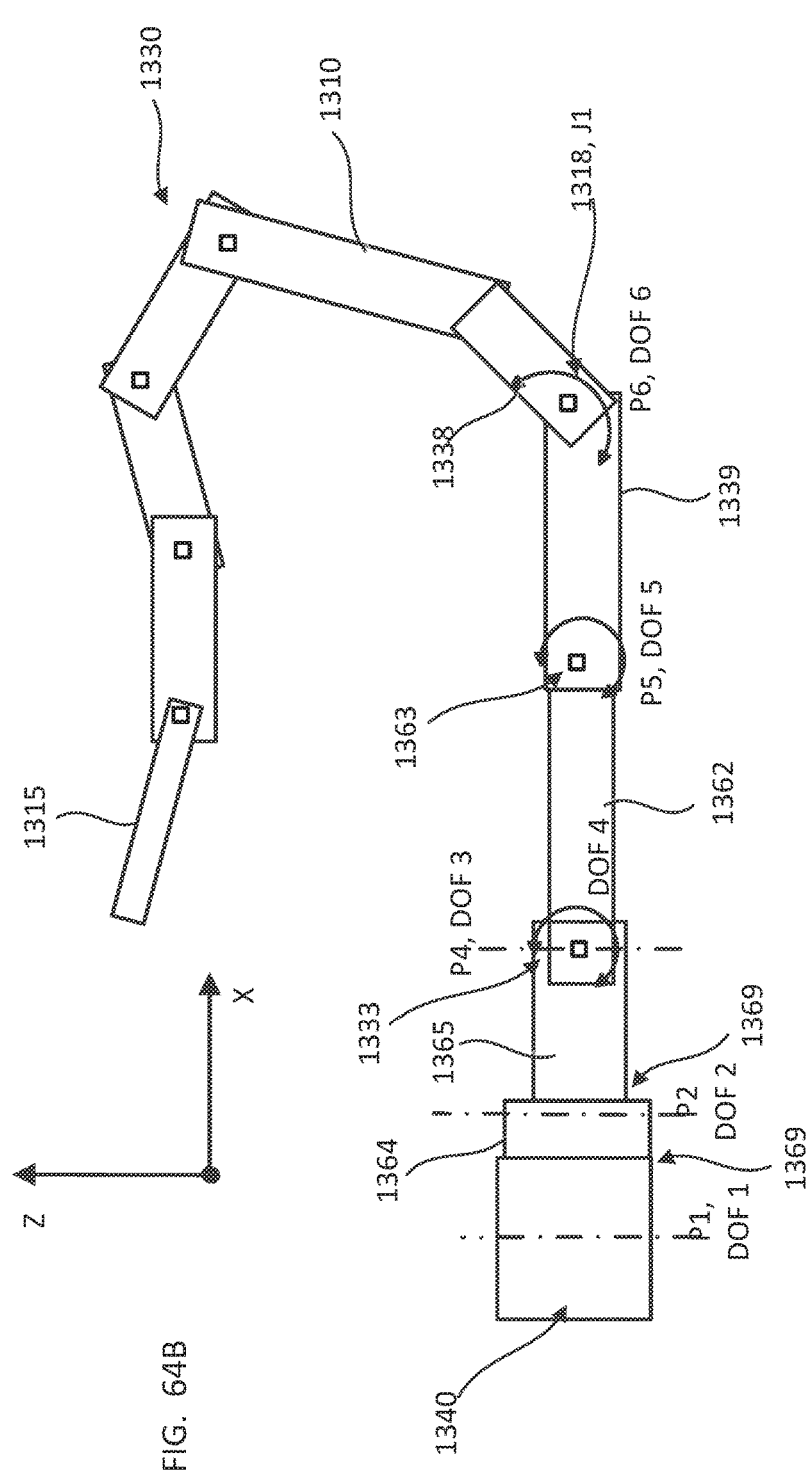
FIG. 64C is a table listing the type of degree of freedom of each of the joints.
Figure 66:
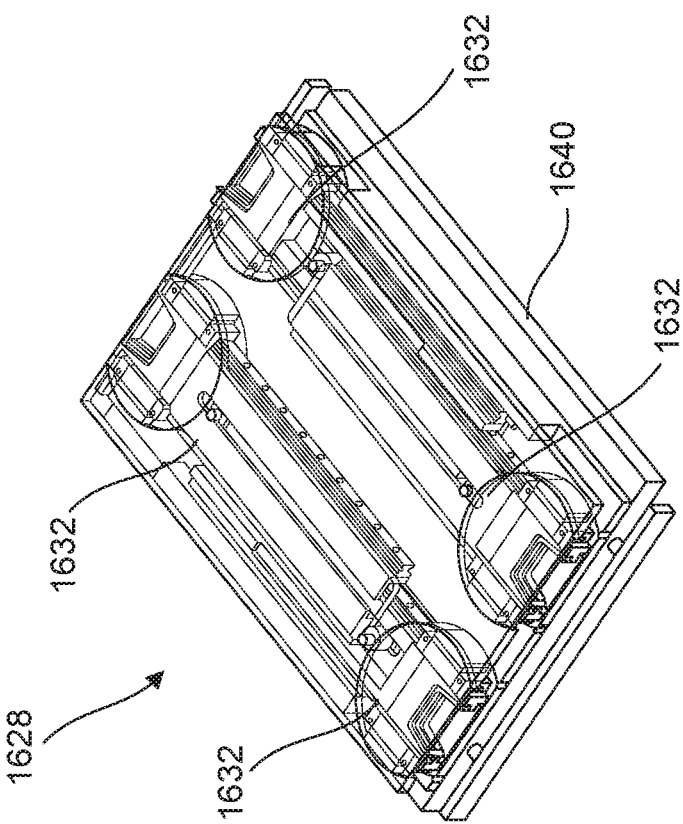
FIG. 66 is a top perspective view of the adapter of FIG. 65 with a top plate of the adapter shown transparent.
Figure 65:
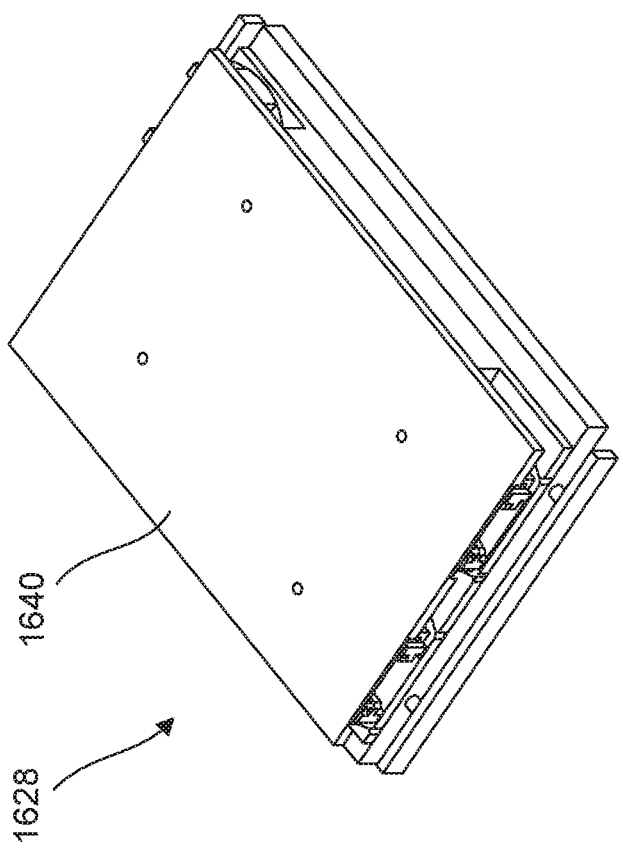
FIG. 65 is a top perspective view of an adapter according to another embodiment.

More specifically, the joint 1369 can provide for rotational motion of the track coupler 1364 relative to the interface structure 1340 about a vertical z-axis (i.e., the pivot axis P1) and relative to the top surface of the table top 1320 (e.g., the top surface of the torso section of the table top) and provide a first degree of freedom DOF 1 as shown in the schematic illustrations of FIGS. 64A and 64B. The joint 1368 can provide for rotational motion between the bracket 165 and the track coupler 1364 about the z-axis (i.e., the pivot axis P2) and provide a second degree of freedom DOF 2. The joint 1333 can provide for rotational motion of the two bar link members 1361 relative to the rod coupler 1359 about a vertical z-axis (i.e., pivot axis P1) relative to the top surface of the table top 1320 (e.g., the top surface of the torso section of the table top) and provide a third degree of freedom DOF 3, and also within the X-Y plane via the pivot axis P4 to provide a fourth degree of freedom DOF 4.

The joint 1363 provides for movement of the coupling portion 1339 to rotate about the pivot axis P5 which is also a X-Y plane rotation and provides a fifth degree of freedom DOF 5 and the joint J1 provides for rotation of the coupling portion 1338 about the axis P6 which also rotates within the X-Y plane to provide a sixth degree of freedom DOF 6. The joint 1333 and the joint 1263 collectively provide a lift mechanism to allow for vertical movement of the coupling portion 1338 of the robotic arm 1330 coupled thereto. Thus, the motion provided by the various joints of the adapter 1328 can provide for movement of the robotic arm 1330 coupled thereto along and/or about the X, Y, and/or Z axes to position the target joint J1 at a desired treatment location relative to the top surface of the table top. Although not labeled in FIGS. 64A and 64B, the various joints between links 1310 of the arm 1330 and a medical instrument 1315 disposed on the distal end of the robotic arm 1330 can provide additional motion of the arm 1330 relative to a patient (e.g., a target treatment location on the patient) disposed on the table 1300, and therefore, additional degrees of freedom.

Figure 63:
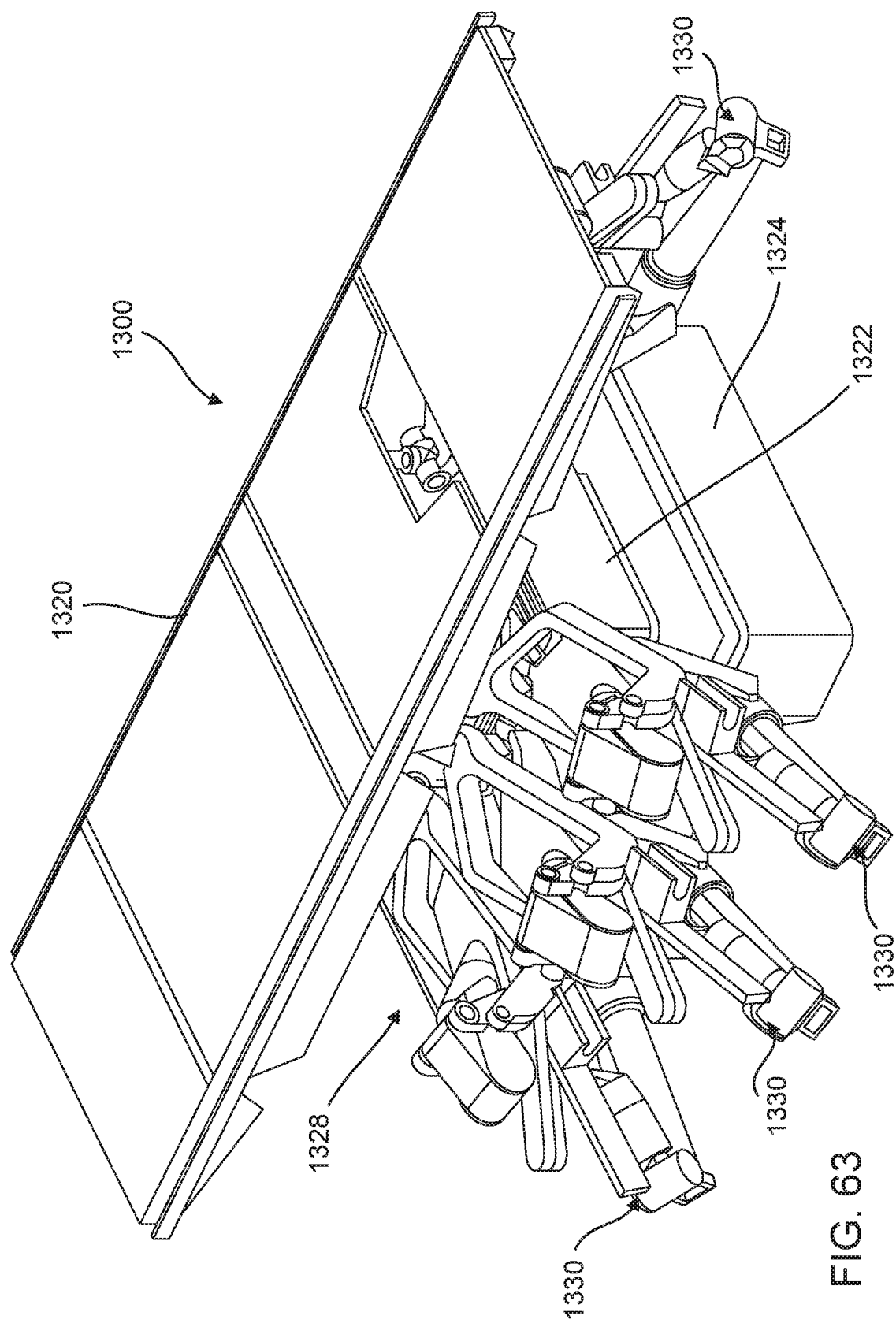
FIG. 63 is a side perspective view of the adapter, robotic arms and surgical table of FIG. 60 with three of the robotic arms positioned outside the perimeter of the table top.

As described above for previous embodiments, the collective motion of the various components of the adapter 1328 allow the robotic arms 1330 to move between a variety of different positions relative to the surgical table 1300 during a surgical procedure, such as stowed, parked and operating positions. For example, adapter 1328 and robotic arms 1330 can be moved to a stowed or folded position, as shown, for example, in FIGS. 60 and 61. The adapter 1328 and arms 1330 can also be disposed in a parked position (not shown) and various operating positions (see, e.g., FIG. 63). In an operating position, the target joints J1 are disposed at a desired target treatment location relative to the table top to accommodate a particular surgical procedure to be performed. As described above, the parked position (not shown) is used when access to the patient is needed, and the robotic arms 1330 are moved to a clearance position relative to the table top to a location outside of a treatment zone to provide space for a medical professional to tend to the patient. When the need for the clearance has passed, the arms 1330 can then be placed back into an operating position with the target joints J1 disposed at the desired target treatment locations relative to the table top.

FIGS. 65-71C illustrate another embodiment of an adapter 1628 that can be coupled to a surgical table (not shown) that can include the same or similar components and function in the same or similar manner as the surgical tables described above, and therefore, is not described in detail with respect to this embodiment.

Figure 67:
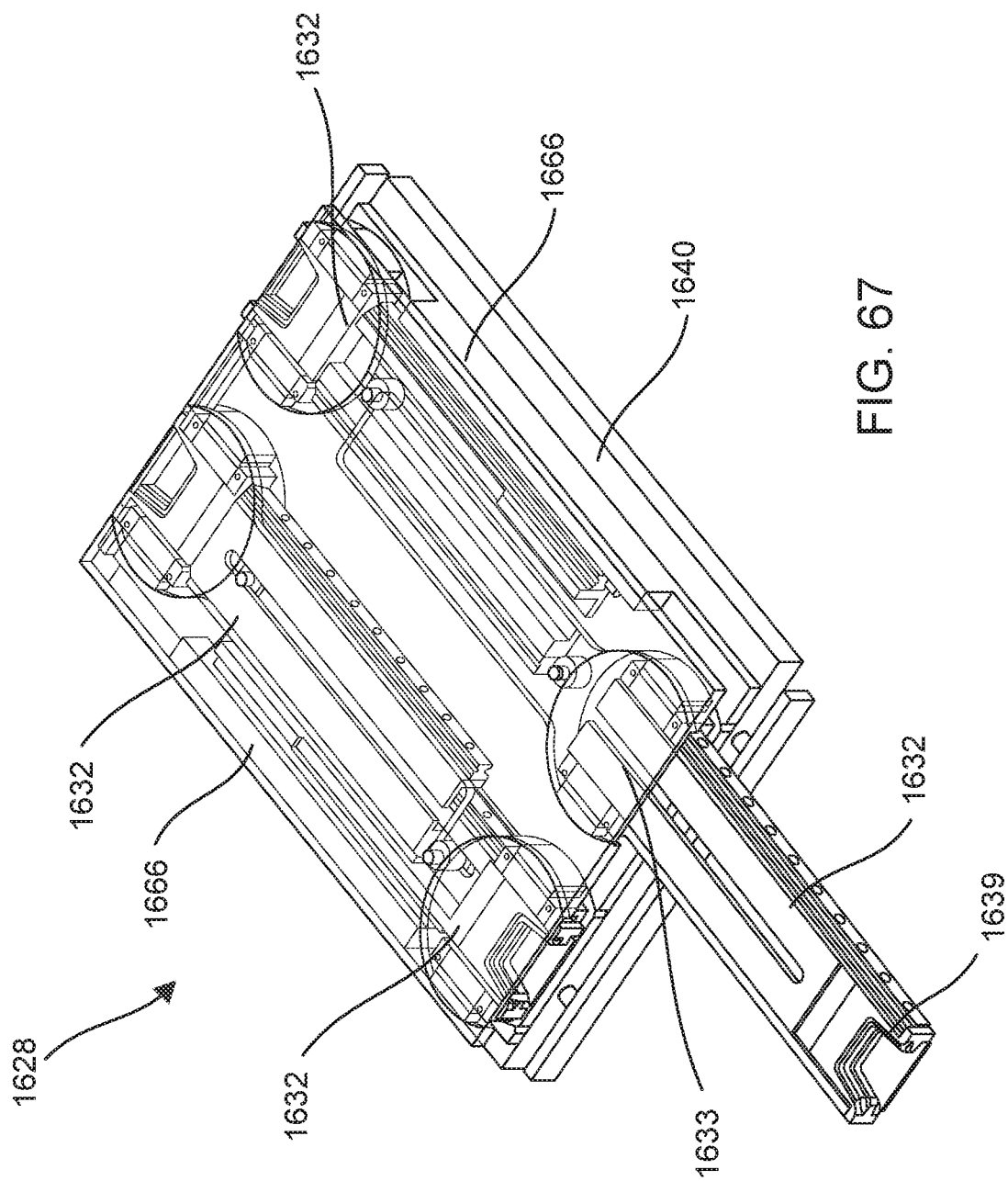
FIG. 67 is a top perspective view of the adapter of FIG. 66 with a link member in an extended position.
Figure 68:
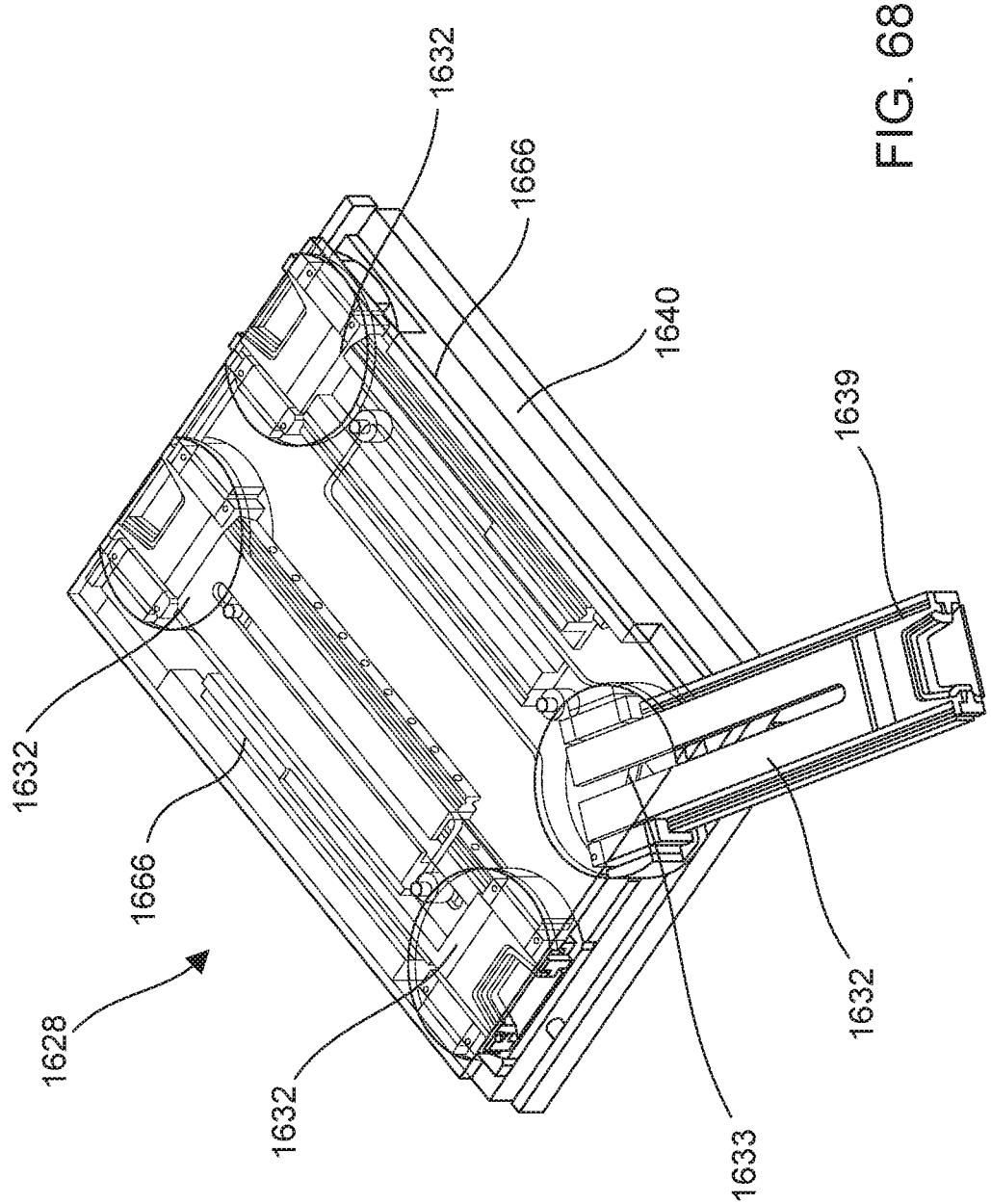
FIG. 68 is a top perspective view of the adapter of FIG. 67 with the link member in an extended and rotated position.
Figure 69:
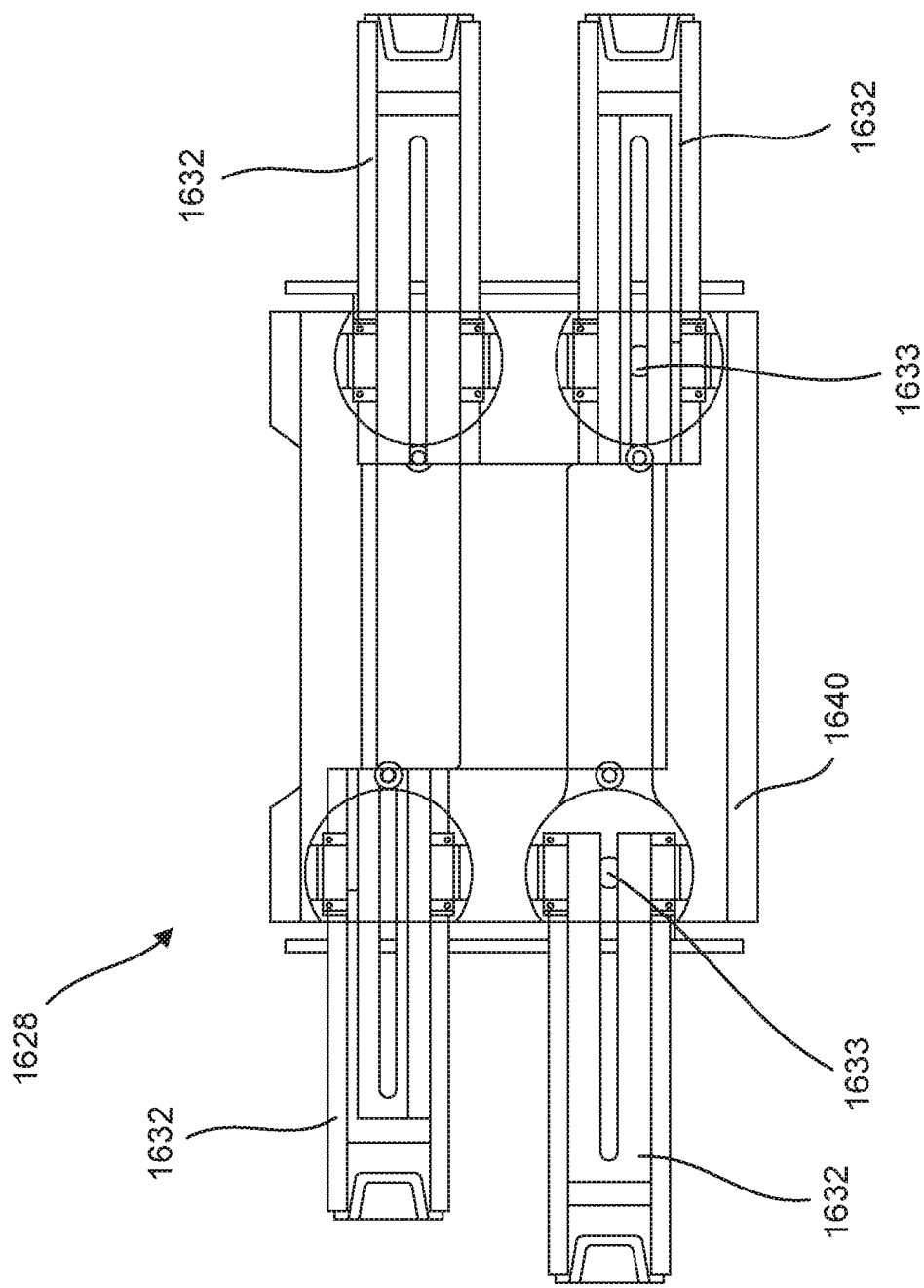
FIG. 69 is a top view of the adapter of FIG. 65 with four link members in an extended position.

The table adapter 1628 (also referred to herein as "adapter") includes a table interface mechanism 1640 that can be coupled to the support (not shown) of the surgical table and multiple first link members 1632. In this embodiment, the first link members 1632 are slidably received within a track 1666 such that the first link members 1632 can be moved between a stowed positon within the interface mechanism 1640 (as shown for example, in FIGS. 105 and 106) and an extended position extended or slid outwardly from the interface mechanism 1640 (as shown for example in FIGS. 69 and 70). FIGS. 67 and 68 illustrate one of the first link members 1632 in the extended position. When in a fully extended position, the first members 1632 can be locked into position at the joint 1633 such that the first link members 1632 can pivot relative to the interface mechanism 1640, as shown for example, in FIG. 168, about a pivot axis P1 (see FIGS. 71A and 71B). The first link members 1632 also include a coupling portion 1639 that can be releasably coupled to a coupling portion 1638 of a robotic arm 1630 (see FIGS. 71A and 71B). The coupling portion 1638 can include the target joint J1, which can provide for rotation about a pivot axis P2.

As described above for previous embodiments, the robotic arm(s) 1630 can be used to perform a surgical procedure on a patient disposed on the surgical table. Each robotic arm 1630 can be configured the same as or similar to, and function the same as or similar to, the robotic arms described above and thus, specific details regarding the robotic arms are not discussed with respect to this embodiment. For example, as described above for robotic arms 130, the robotic arms 1630 can include multiple links or segments and can be moved between an extended configuration for use during a surgical procedure, and a folded or collapsed configuration for storage when not in use. The motion provided by the various coupling joints can provide for movement of the robotic arm 1630 along and/or about the X, Y, and/or Z axes as described in more detail below.

Figure 71A:
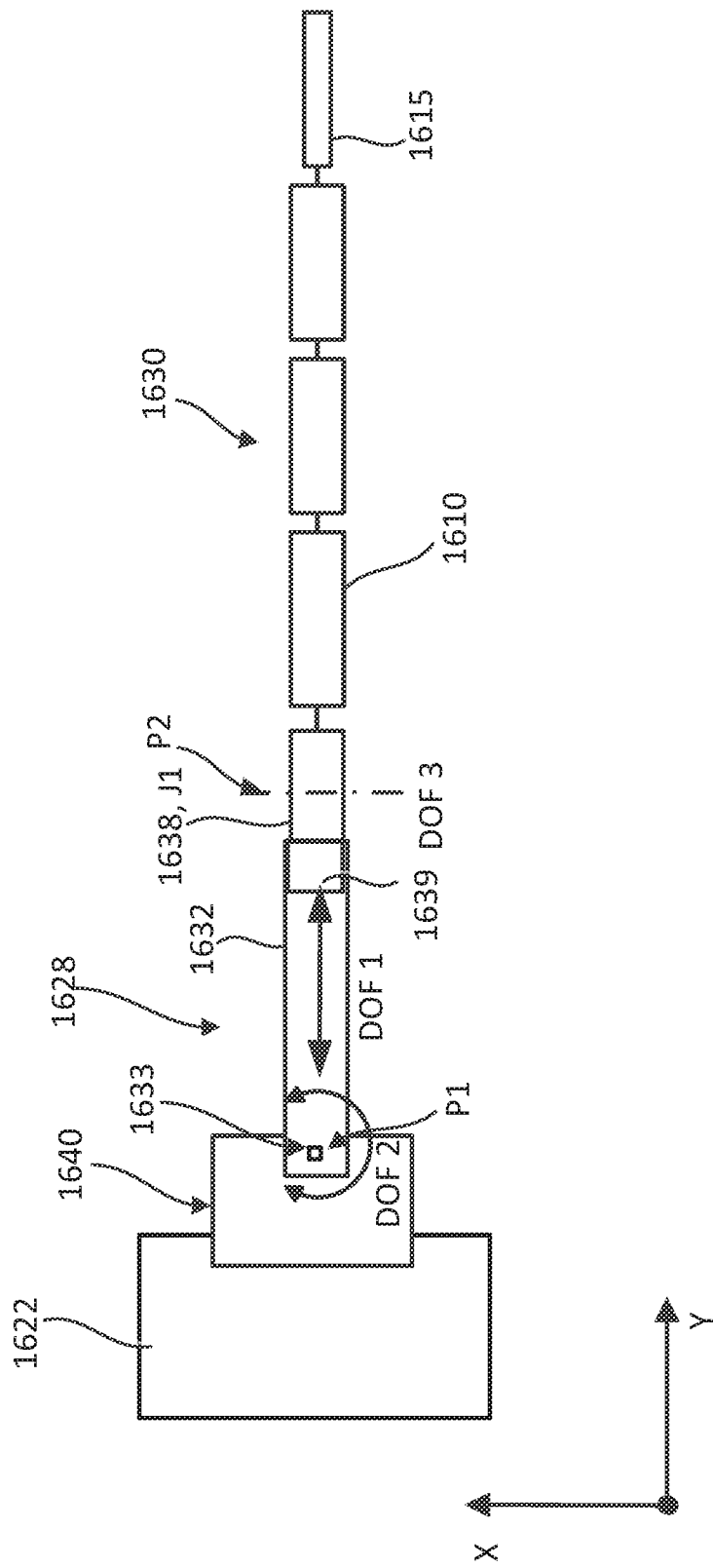

More specifically, as shown in FIGS. 71A and 71B, the linear slidable coupling of the first link members 1632 to the interface mechanism provides a linear first degree of freedom DOF 1 in the x-axis direction. The joint 1633 can provide for rotational motion of the first link members 1632 relative to the interface structure 1640 (and table 1600) about a vertical z-axis (i.e., pivot axis P1) relative to the top surface of the table top (e.g., the top surface of the torso section of the table top) and provide a second degree of freedom DOF 2. The target joint J1 provides rotation about the axis P2 which rotates within the X-Y plane, and provides a third degree of freedom DOF 3. The J1 joint provides a lift mechanism to allow for vertical movement of the robotic arm 1630. The various motions of the first link member 1632 together with the joint J1 can provide for movement of the robotic arm 1630 along and/or about the X, Y, and/or Z axes to position the target joint J1 at a desired treatment location relative to the top surface of the table top. Although not labeled in FIGS. 71A and 71B, the various joints between links 1610 of the arm 1630 and a medical instrument 1615 disposed on the distal end of the robotic arm 1630 can provide additional motion of the arm 1630 relative to a patient (e.g., a target treatment location on the patient) disposed on the table and therefore, additional degrees of freedom.

The adapter 1628 and robotic arms 1630 can be moved between a variety of different positions relative to the surgical table during a surgical procedure. For example, the robotic arms 16309 can be removed from the adapter 1628 and the adapter 1628 can be moved to a stowed or folded position (see, e.g., FIGS. 65 and 66). The adapter 1628 and arms 1630 can also be disposed in a parked position (not shown) and various operating positions (not shown). In an operating position, the target joints J1 are disposed at a desired target treatment location relative to the table top to accommodate a particular surgical procedure to be performed as described above for previous embodiments.

Although not described for all embodiments, any of the embodiments of an adapter can be manually controlled or motor driven. For example, some or all of the motion of the various constituent components of an adapter can be operatively coupled to a drive motor that can be controlled and operated by a user (e.g., medical professional). Further, any of the embodiments can be operatively coupled to a computer system configured to operate and control the movement of the various components of an adapter as well as movement of the robotic arms coupled thereto. Although not all features of each embodiment of an adapter were described for all embodiments, it should be understood that any of the various features described herein can be included or added to any embodiment.

In addition, although not necessarily described for each embodiment, any of the embodiments described herein can include an adapter with more than two link members or only one link member. The various embodiments of a robotic surgical system described herein can include a table top on which a patient can be disposed, an adapter, and one or more link members. As described above, in some embodiments, the robotic arm can be incorporated into the adapter (e.g., an adapter/robotic arm assembly) and be coupled to a surgical table or be coupleable to a surgical table. The adapters and the robotic arms (or in the case of an adapter/robotic arm assembly) can include one or more links or link members to allow for movement of the adapter and/or arms about and/or along the X, Y, and/or Z axes, to a desired location relative to the table top and/or relative to a patient disposed thereon.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:
1. An apparatus, comprising:
a surgical table having a table top, a support coupled to the table top, and a base coupled to the support; and
an adapter coupled to, and supported by, the surgical table, the adapter including an interface structure that is fixedly attached to the surgical table between the table top and the support of the surgical table,
the adapter including a first link member coupled to the interface structure, the first link member pivotally coupled to the interface structure such that the first link member can rotate about a first pivot axis defined in a vertical direction relative to the table top, the first link member configured to be coupled to a first robotic arm and provide for movement of the first robotic arm about the first pivot axis,
the adapter including a second link member coupled to the interface structure, the second link member pivotally coupled to the interface structure such that the second link member can rotate about a second pivot axis different than the first pivot axis and defined in a vertical direction relative to the table top, the second link member configured to be coupled to a second robotic arm and provide for movement of the second robotic arm about the second pivot axis,
the adapter including a first coupling with a first coupling portion that is configured to be coupled to the first link member and to the first robotic arm at a mounting end of the first robotic arm, the first coupling portion having a first joint that provides for rotation of the first robotic arm about a third pivot axis, and
the adapter including a second coupling with a second coupling portion that is configured to be coupled to second link member and to the second robotic arm at a mounting end of the second robotic arm, the second coupling portion having a second joint that provides for rotation of the second robotic arm about a fourth pivot axis.

2. The apparatus of claim 1, wherein the first link member is coupled to the interface structure on a first side of the table top, and the second link member is coupled to the interface structure on a second side of the table top opposite the first side of the table top.

3. The apparatus of claim 1, wherein the first link member and the second link member are each coupled to the interface structure on the same side of the table top.

4. The apparatus of claim 1, wherein the first link member is slidably coupled to the interface structure such that the first link member can move in a lateral direction relative to the table top.

5. The apparatus of claim 1, further comprising:
a column mount coupled to the support of the surgical table, the adapter being configured to be slidably received within a track defined by the column mount.

6. The apparatus of claim 1, wherein the first link member can rotate about the first pivot axis such that the first link member can rotate about the interface structure, and
the second link member can rotate about the second pivot axis such that the second link member can rotate about the interface structure.

7. The apparatus of claim 1, wherein the first link member and the second link member each include a bar link member.

8. The apparatus of claim 1, wherein the adapter is coupled to the support of the surgical table.

9. The apparatus of claim 1, wherein the adapter is coupleable to the surgical table above the base.

10. The apparatus of claim 1, wherein the first joint is a first target joint configured to be positioned at a first target location relative to the table top such that a distal end of the first robotic arm can be disposed in a desired first treatment zone and can be maneuvered within a prescribed range of motion in the first treatment zone.

11. The apparatus of claim 10, wherein the second joint is a second target joint configured to be positioned at a second target location relative to the table top such that a distal end of the second robotic arm can be disposed in a desired second treatment zone and can be maneuvered within a prescribed range of motion in the second treatment zone.

12. The apparatus of claim 1, wherein the third pivot axis and the fourth pivot axis are transverse to the first pivot axis and the second pivot axis.

13. The apparatus of claim 1, wherein the first link member is slidably received within a track such that the first link members is movable between a stowed positon at least partially within the interface mechanism and an extended position extended or slid outwardly from the interface mechanism.

14. The apparatus of claim 13, wherein the second link member is slidably received within a track such that the second link members is movable between a stowed positon at least partially within the interface mechanism and an extended position extended or slid outwardly from the interface mechanism.

15. An apparatus, comprising:
a surgical table having a table top, a support coupled to the table top, and a base coupled to the support; and
an adapter coupled to, and supported by, the surgical table, the adapter including an interface structure that is fixedly coupled to the table top or the support of the surgical table,
the adapter including a plurality of link members, each link member directly pivotally coupled to the interface structure at a different joint that rotates about a different, respective pivot axis that is defined in a vertical direction relative to the table top and extends through the interface structure and the table top,
the adapter including plurality of couplings, each coupling of the plurality of coupling being configured to couple respective link members of the plurality of link members to corresponding robotic arms of a plurality of robot arms, such that each link member is configured to provide for movement of a corresponding robotic arm in at least one of a lateral, a longitudinal or a vertical direction relative to the table top, each coupling including a coupling portion that is coupled to the corresponding robotic arm at a mounting end thereof, each coupling portion having a joint that provides for rotation of the corresponding robotic arm about an additional pivot axis.

16. The apparatus of claim 15, wherein the joint is a target joint configured to be positioned at a target location relative to the table top such that a distal end of the corresponding robotic arm can be disposed in a desired treatment zone and can be maneuvered within a prescribed range of motion in the treatment zone.

17. The apparatus of claim 15, wherein at least one link member of the plurality of link members is coupled to the interface structure on a first side of the table top, and at least one link member of the plurality of link members is coupled to the interface structure on an opposing, second side of the table top.

18. The apparatus of claim 15, wherein two or more link members of the plurality of link members are coupled to the interface structure along one side of the table top.

19. The apparatus of claim 18, wherein at least one additional link member of the plurality of link members is coupled to the interface structure on a side that is opposite the table top to the one side.

20. The apparatus of claim 15, wherein each link member of the plurality of link members is slidably coupled to the interface structure such that each link member can move in a lateral direction relative to the table top.

21. The apparatus of claim 15, wherein each link member of the plurality of link members includes a bar link member.

22. The apparatus of claim 15, wherein the adapter is coupleable to the surgical table above the base.

23. The apparatus of claim 15, wherein interface structure is fixedly coupled to the surgical table between the table top and the support such that a top side of the interface structure is joined to the bottom side of the table top and a bottom side of the interface structure is joined to a top side of the support, and wherein the interface structure includes a plurality of corners and each of the plurality of link members are coupled to the interface structure at or adjacent a respective corner of the plurality of corners.

24. An apparatus, comprising:
a surgical table having a table top, a support coupled to the table top, and a base coupled to the support; and
an adapter coupled to, and supported by, the surgical table, the adapter including an interface structure fixedly coupled to the support of the surgical table such that the interface structure remains fixated to the support during use of the adapter,
the adapter including a plurality of link members pivotally coupled to the interface structure, such that each link member each link member can rotate about a different, respective pivot axis defined in a vertical direction relative to the table top, each link member of the plurality of link members being slidably received within a track such that each link member is movable between a stowed positon at least partially within the interface mechanism and an extended position extended or slid outwardly from the interface mechanism,
the adapter including plurality of couplings, each coupling of the plurality of coupling being configured to couple respective link members of the plurality of link members to corresponding robotic arms of a plurality of robot arms, such that each link member is configured to provide for movement of a corresponding robotic arm in at least one of a lateral, a longitudinal or a vertical direction relative to the table top, each coupling including a coupling portion that is coupled to the corresponding robotic arm at a mounting end thereof, each coupling portion having a joint that provides for rotation of the corresponding robotic arm about an additional pivot axis.

* * * * *